US011931198B2

(12) United States Patent
Patriciu et al.

(10) Patent No.: US 11,931,198 B2
(45) Date of Patent: Mar. 19, 2024

(54) X-RAY CALIBRATION FOR DISPLAY OVERLAYS ONTO X-RAY IMAGES

(71) Applicant: KONINKLIJKE PHILIPS N.V., Eindhoven (NL)

(72) Inventors: Alexandru Patriciu, Belmont, MA (US); Alyssa Torjesen, Charlstown, MA (US); Jan Rongen, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 366 days.

(21) Appl. No.: 17/378,975

(22) Filed: Jul. 19, 2021

(65) Prior Publication Data

US 2021/0369230 A1    Dec. 2, 2021

Related U.S. Application Data

(63) Continuation-in-part of application No. 17/421,029, filed as application No. PCT/EP2020/053927 on Feb.
(Continued)

(51) Int. Cl.
*A61B 5/05*    (2021.01)
*A61B 6/00*    (2006.01)

(52) U.S. Cl.
CPC ............ *A61B 6/584* (2013.01); *A61B 6/4441* (2013.01); *A61B 6/463* (2013.01); *A61B 6/5205* (2013.01); *A61B 6/54* (2013.01)

(58) Field of Classification Search
None
See application file for complete search history.

(56) References Cited

U.S. PATENT DOCUMENTS 5,442,674 A      8/1995  Picard
6,856,827 B2 *   2/2005  Seeley ............... A61B 6/547
                                                250/362
(Continued)

FOREIGN PATENT DOCUMENTS

CN    112168357 A    1/2021
WO    2018078445 A2  5/2018
(Continued)

OTHER PUBLICATIONS

International Search Report and Written Opinion of PCT/EP2020/053927, dated May 12, 2020.
(Continued)

*Primary Examiner* — Hoon K Song

(57) ABSTRACT

Various embodiments of an X-ray imaging system employ a C-arm (60) and an X-ray overlay controller (410). In a planning overlay display mode, the controller (410) processes a planning X-ray image (420) and a reference planning X-ray image (421), both illustrative of the planning X-ray calibration device (400) and further processes a base X-ray image (424, 425) (422) illustrative of a base X-ray calibration device to control a display of a planned tool trajectory overlay (412) and a tracked tool position overlay (413) onto the planning X-ray image (420). In a guiding overlay display mode, the controller (410) processes a pair of interventional X-ray images (424, 425) and a guiding X-ray image (426), all illustrative of a guiding X-ray calibration device (402), to control a display of a guidance tool trajectory overlay (414) and a racked tool position overlay (415) onto the guiding X-ray image (426).

15 Claims, 68 Drawing Sheets

Related U.S. Application Data 14, 2020, application No. 17/378,975 is a continuation-in-part of application No. 17/423,921, filed as application No. PCT/EP2020/058278 on Mar. 25, 2020.

(60) Provisional application No. 62/806,005, filed on Feb. 15, 2019, provisional application No. 62/823,190, filed on Mar. 25, 2019.

(56) References Cited

U.S. PATENT DOCUMENTS

| | | | |
|---|---|---|---|
| 10,206,645 B2 | 2/2019 | Claus | |
| 10,893,842 B2 | 1/2021 | Barak | |
| 2001/0022834 A1* | 9/2001 | Graumann | A61B 6/466 378/197 |
| 2004/0082854 A1* | 4/2004 | Essenreiter | A61B 34/20 600/429 |
| 2008/0285724 A1 | 11/2008 | Dehler | |
| 2010/0284601 A1 | 11/2010 | Rubner | |
| 2011/0164721 A1* | 7/2011 | Jank | A61B 6/466 378/4 |
| 2012/0281808 A1 | 11/2012 | Graumann | |
| 2016/0045269 A1 | 2/2016 | Elhawary | |
| 2016/0106338 A1 | 4/2016 | Kruger | |
| 2017/0035382 A1 | 2/2017 | Zhang | |
| 2017/0258418 A1 | 9/2017 | Averbuch | |
| 2017/0296136 A1* | 10/2017 | Rai | A61B 34/20 |
| 2019/0029623 A1 | 1/2019 | Kunio | |

FOREIGN PATENT DOCUMENTS

| | | |
|---|---|---|
| WO | 2019023375 A2 | 1/2019 |
| WO | 2020159984 A1 | 8/2020 |
| WO | 2020165422 A1 | 8/2020 |
| WO | 2020185048 A2 | 9/2020 |

OTHER PUBLICATIONS

Steger, Tenna et al "Marker Detection Evaluation by Phantom and Cadaver Experiments for C-arm Pose Estimation Pattern", SPIE—International Society for Optical Engineering, vol. 8671, Mar. 2012.

Calvet, Lilian et al "Detection and Accurate Localization of Circular Fiducials under Highly Challenging Conditions", 2016 IEEE Conference on Computer Vision and Pattern Recognition, pp. 562-570 Jun. 27, 2016.

Kainz, Bernhard et al "Fast Marker Based C-Arm Pose Estimation", International Conference on Financial Cryptography and Data Security, Sep. 6, 2008, pp. 652-659.

* cited by examiner

FLOWCHART 80

S82: IDENTIFY RIPPLE MARKER/68ATTERN IN X-RAY IMAGE

S84: DERIVE TRANSFORMATION PARAMETER(S) FROM RIPPLE PATTERN

S86: REGISTER X-RAY RIPPLE MARKER AND X-RAY C-ARM

S88: REMOVE X-RAY RIPPLE MARKER FROM X-RAY IMAGE

TERMINATE

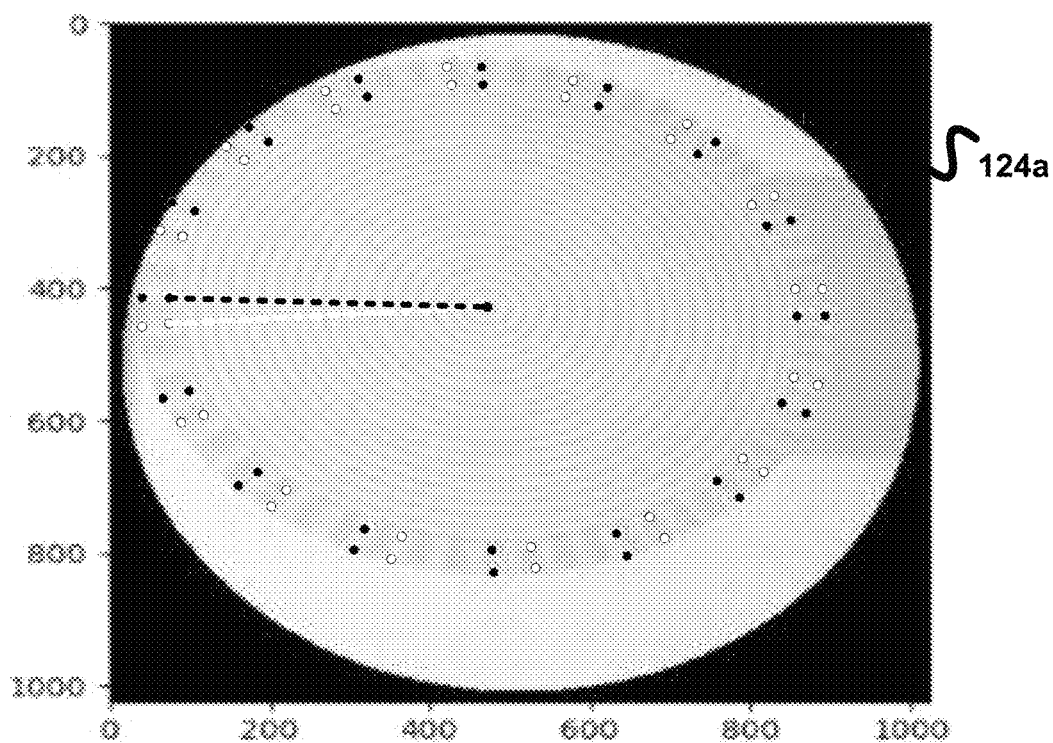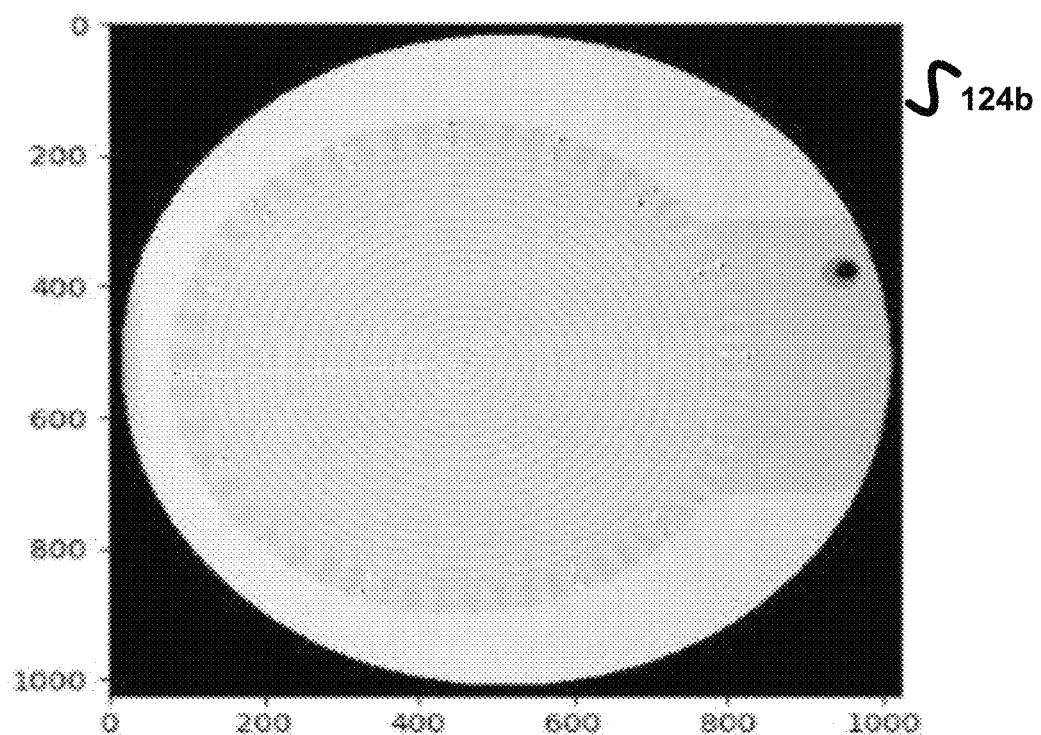
FIG. 11A

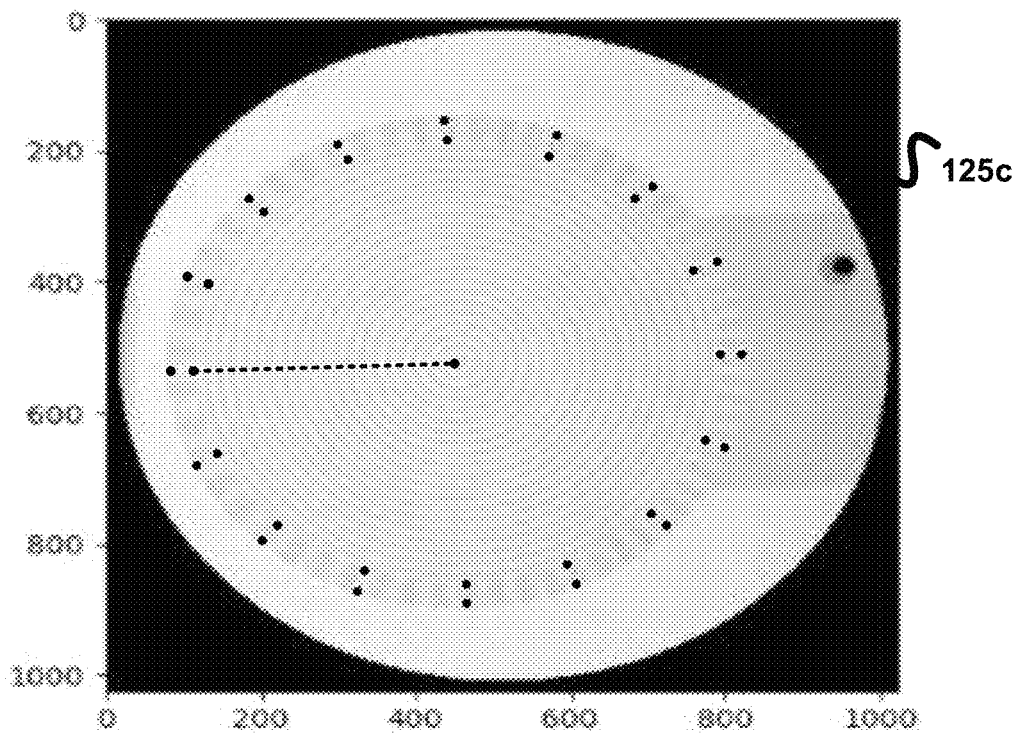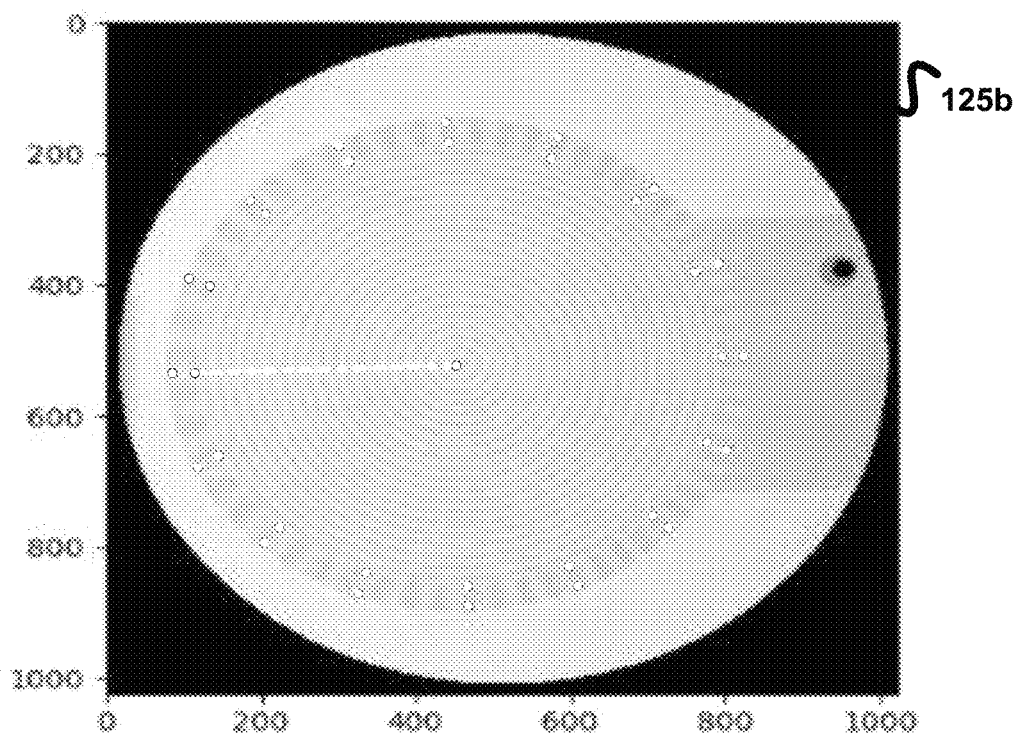
FIG. 11B

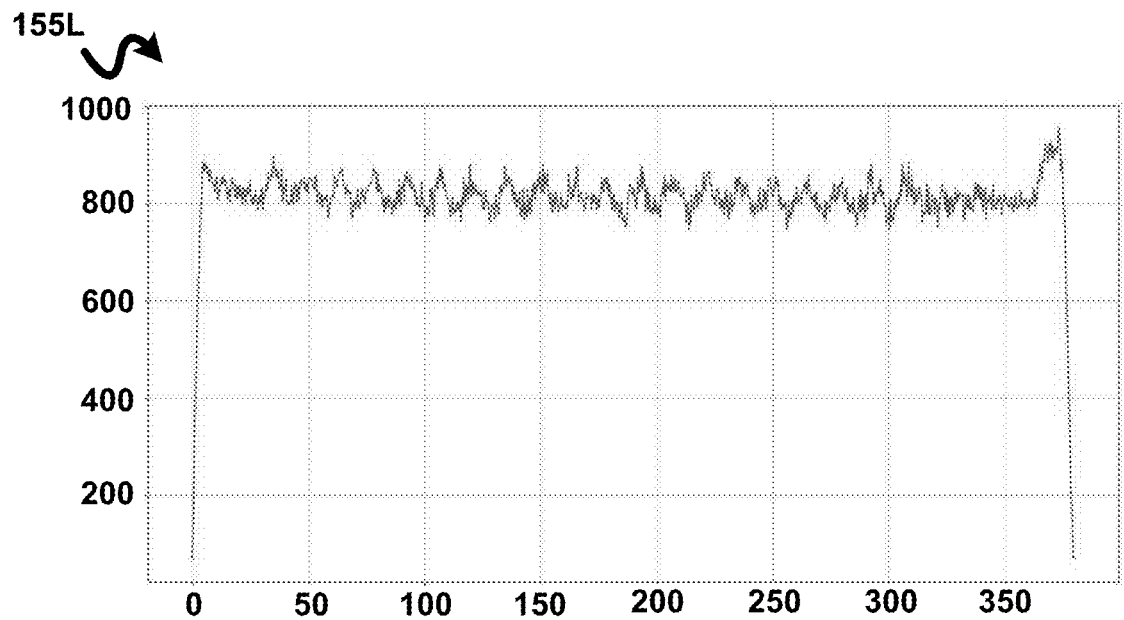
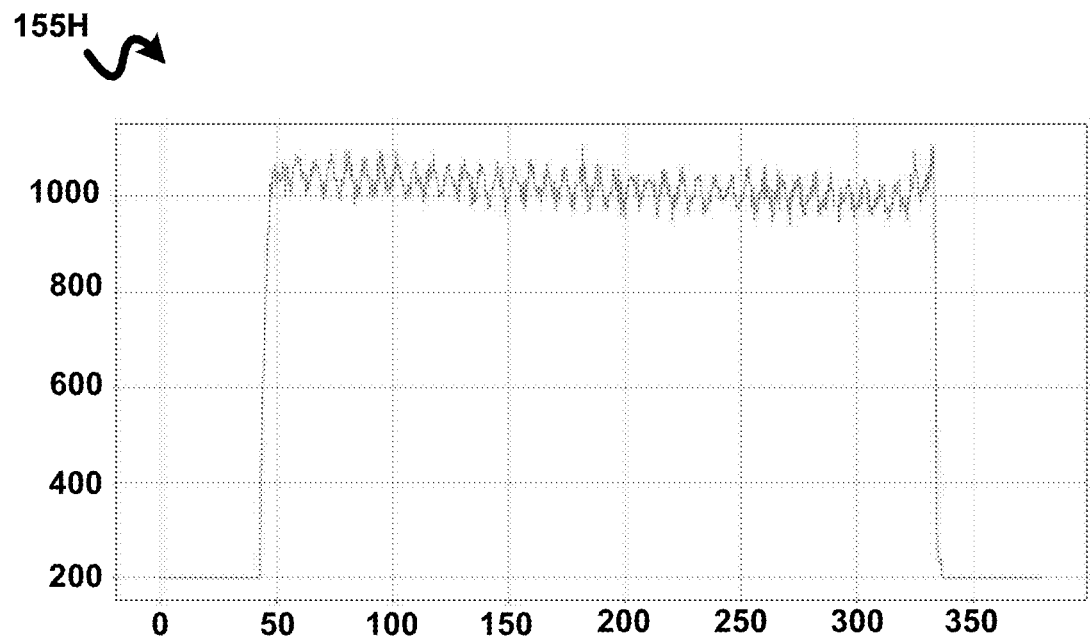
FIG. 16B

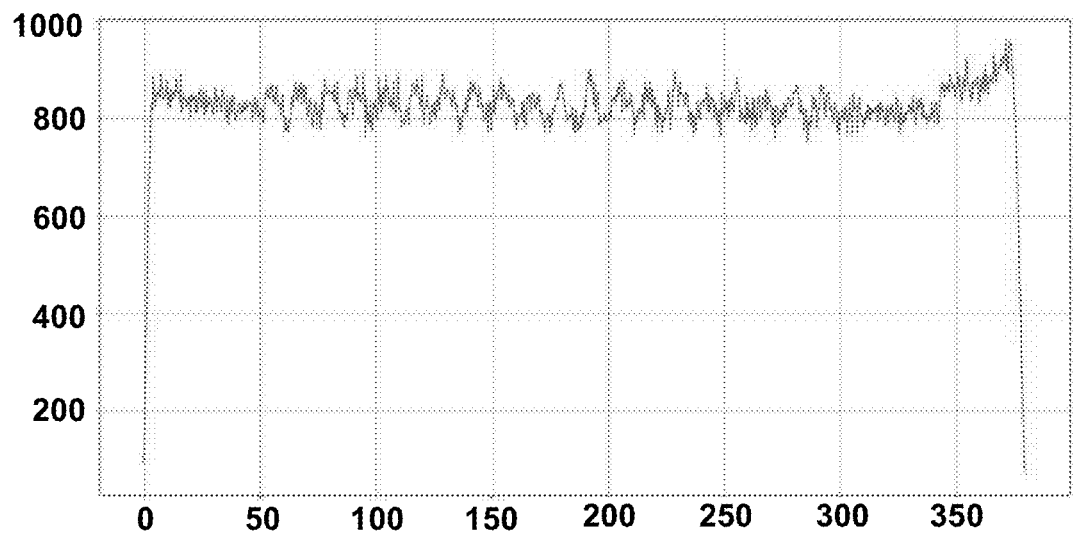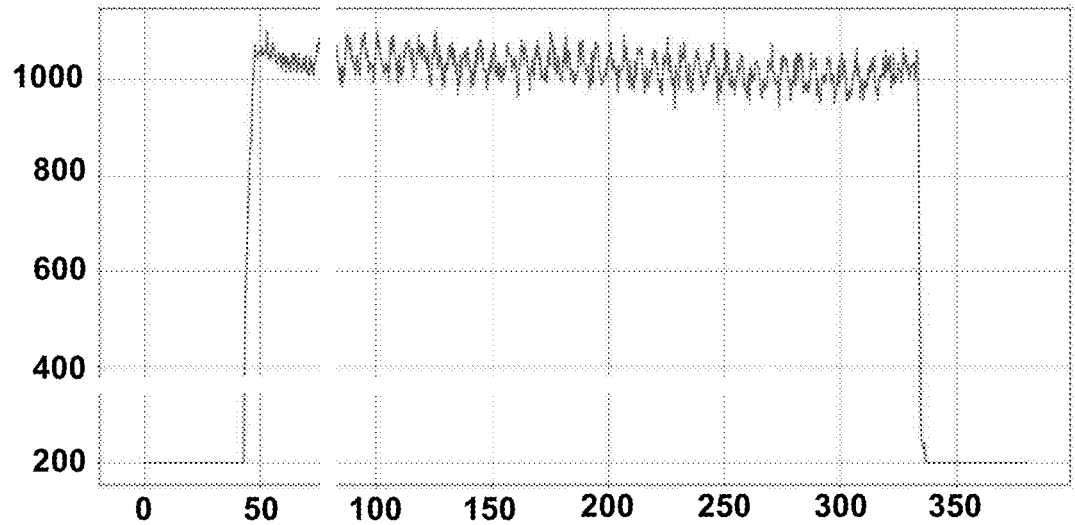
FIG. 17B

```
                    ┌─────────────────────┐
                    │   FLOWCHART 280     │
                    └──────────┬──────────┘
                               ▼
    ┌──────────────────────────────────────────────────────┐
    │  S282:  BASELINE X-RAY IMAGE ACQUISITION             │
    └──────────────────────────┬───────────────────────────┘
                               ▼
    ┌──────────────────────────────────────────────────────┐
    │  S284:  BASELINE POSITION/TWIST PARAMETER DERIVATIONS (FIG. 32) │
    └──────────────────────────┬───────────────────────────┘
                               ▼
    ┌──────────────────────────────────────────────────────┐
    │  S286:  TARGET X-RAY IMAGE ACQUISITION               │
    └──────────────────────────┬───────────────────────────┘
                               ▼
    ┌──────────────────────────────────────────────────────┐
    │  S288:  TARGET POSITION/TWIST PARAMETER DERIVATIONS (FIG. 32) │
    └──────────────────────────┬───────────────────────────┘
                               ▼
                    ┌─────────────────────┐
                    │     TERMINATE       │
                    └─────────────────────┘
```

FIG. 31

```
                    ┌─────────────────────┐
                    │   FLOWCHART 290     │
                    └──────────┬──────────┘
                               ▼
    ┌──────────────────────────────────────────────────────┐
    │  S292:  COMPUTE MARKER CENTER POINT ON X-RAY DETECTOR │
    └──────────────────────────┬───────────────────────────┘
                               ▼
    ┌──────────────────────────────────────────────────────┐
    │  S294:  COMPUTE BASELINE/TARGETPOSITION PARAMETERS $t_Z, t_Y, t_Z, \Theta_X, \Theta_{Z1}$ │
    └──────────────────────────┬───────────────────────────┘
                               ▼
    ┌──────────────────────────────────────────────────────┐
    │  S296:  COMPUTE BASELINE/TARGET TWIST PARAMETER $\Theta_{Z2}$ │
    └──────────────────────────┬───────────────────────────┘
                               ▼
    ┌──────────────────────────────────────────────────────┐
    │  S298:  OPTIMIZE BASELINE/TARGET PARAMETERS $t_Z, t_Y, t_Z, \Theta_X, \Theta_{Z1}, \Theta_{Z2}$ │
    └──────────────────────────┬───────────────────────────┘
                               ▼
                    ┌─────────────────────┐
                    │     TERMINATE       │
                    └─────────────────────┘
```

FIG. 32

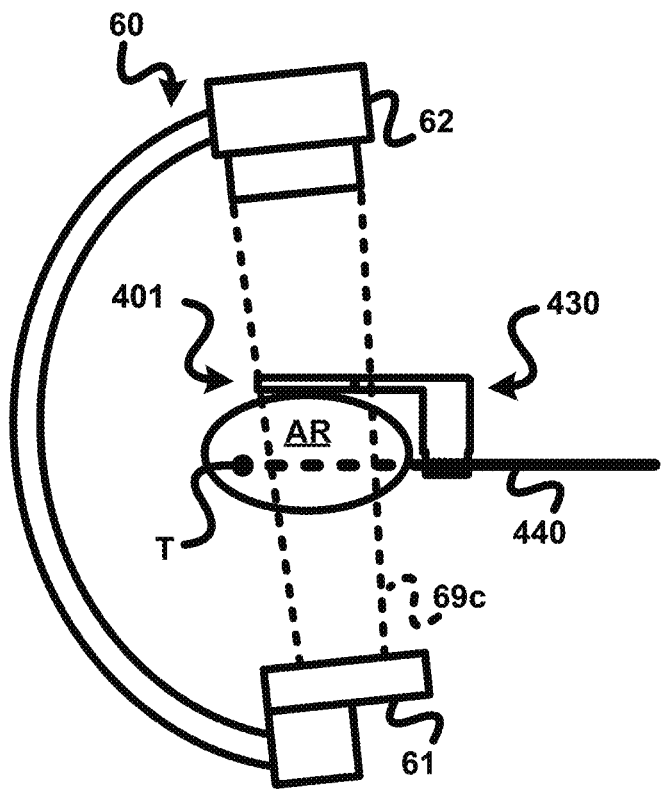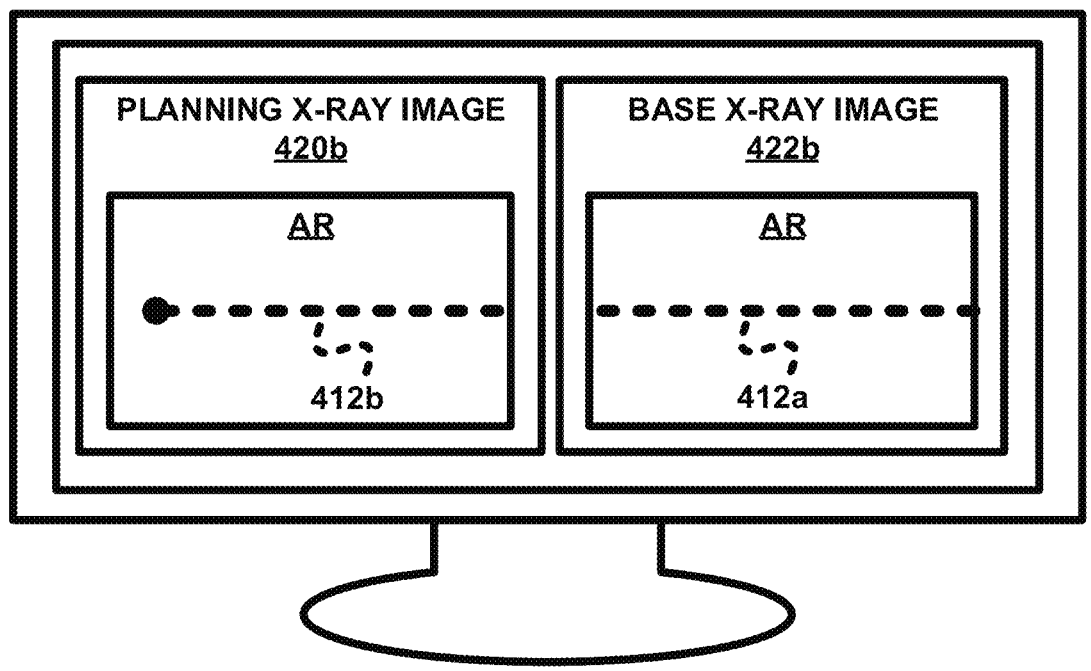
FIG. 42A

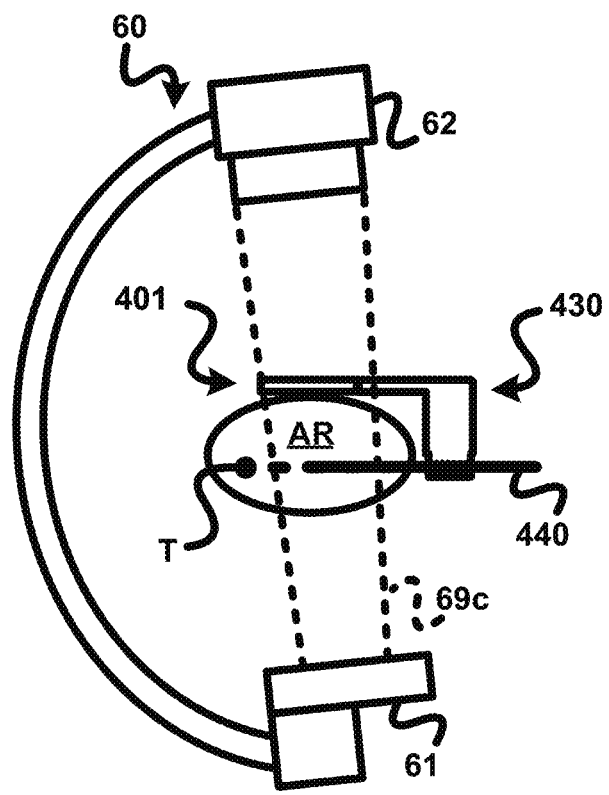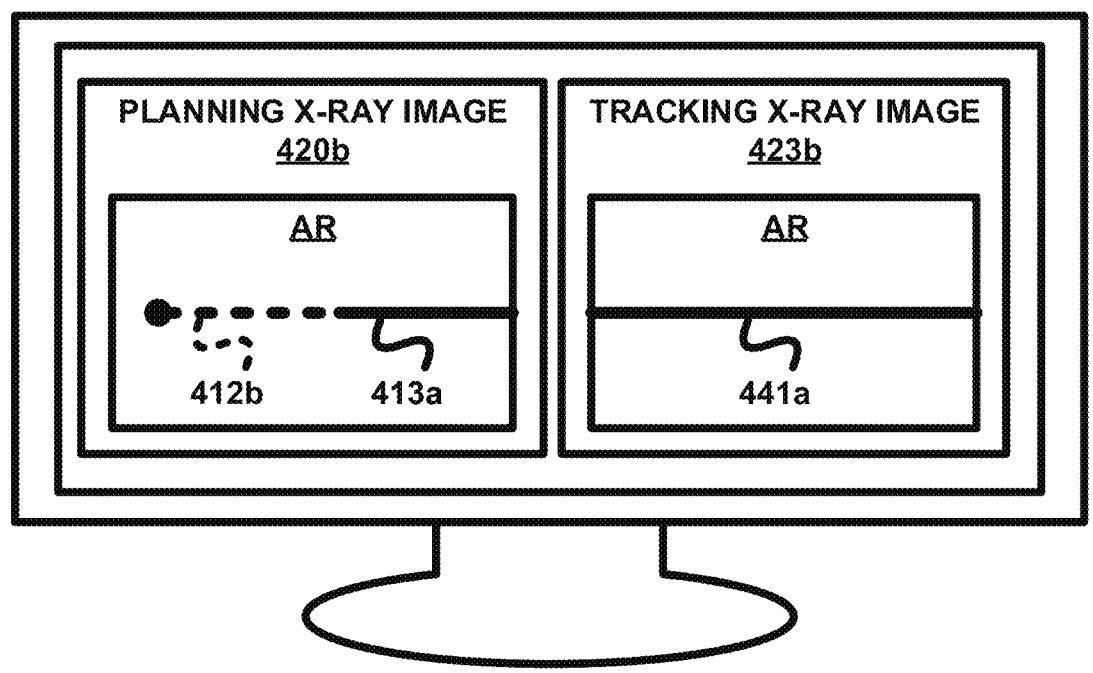
FIG. 42B

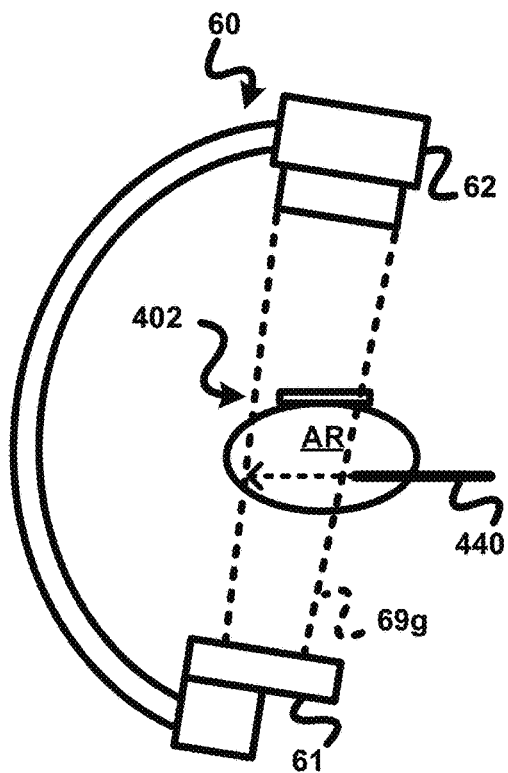
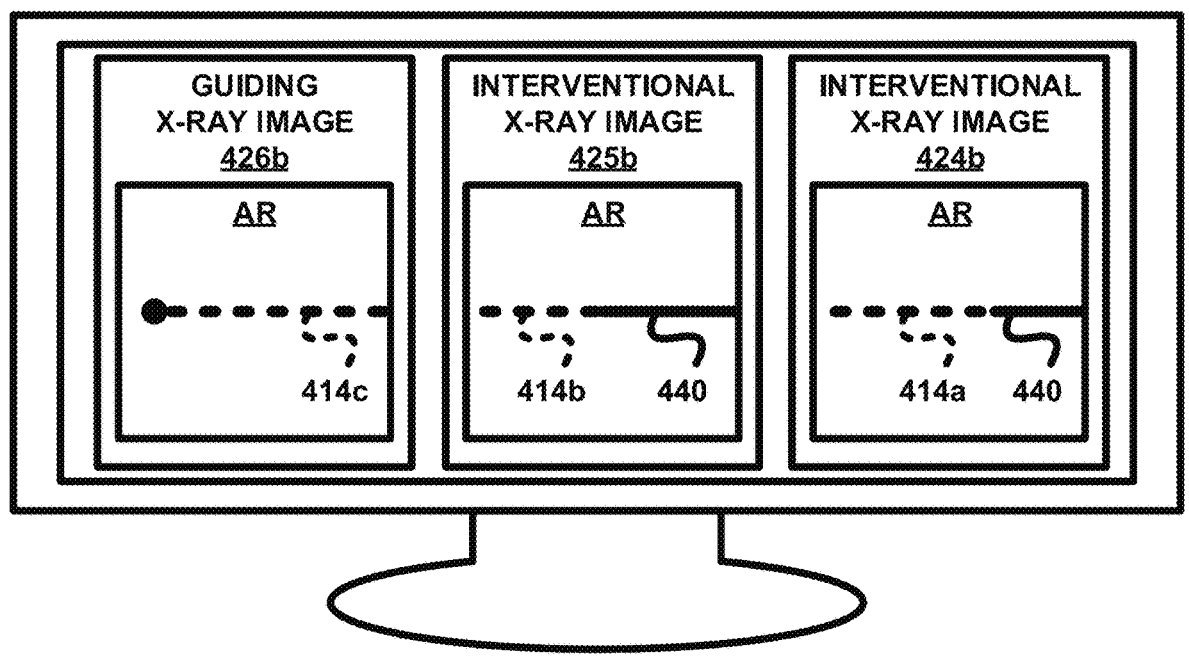
FIG. 51A

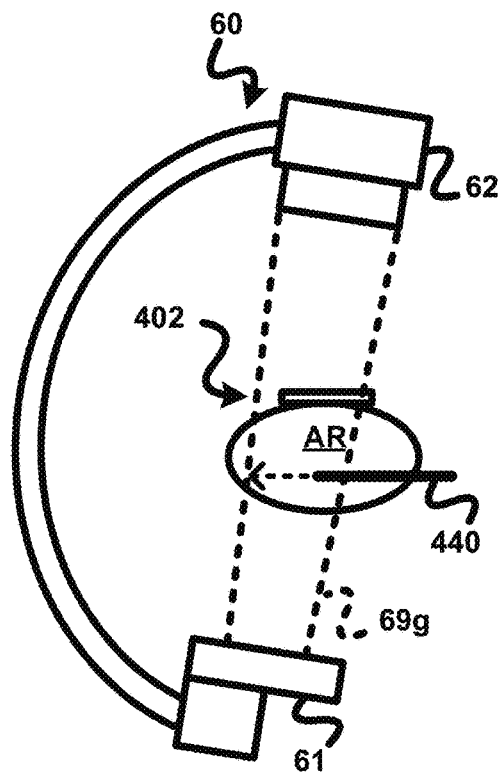
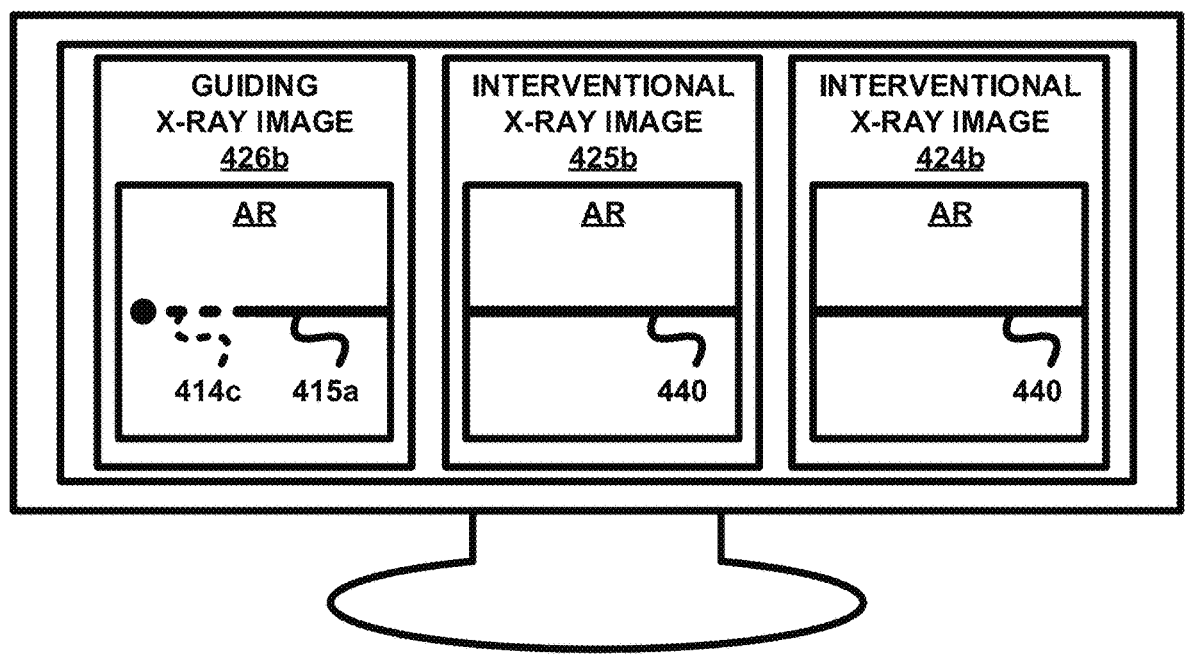
FIG. 51B

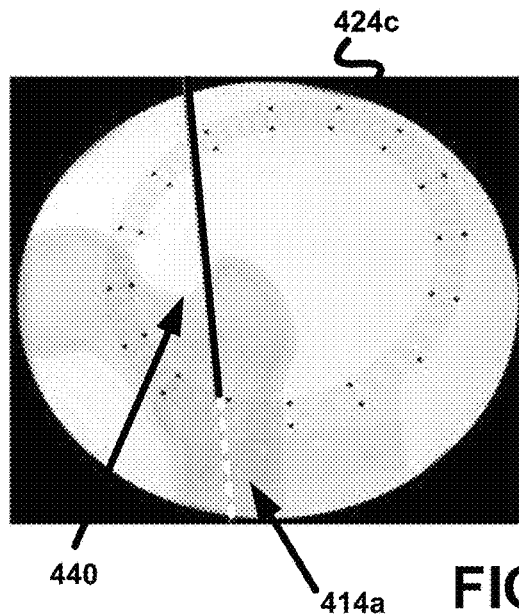
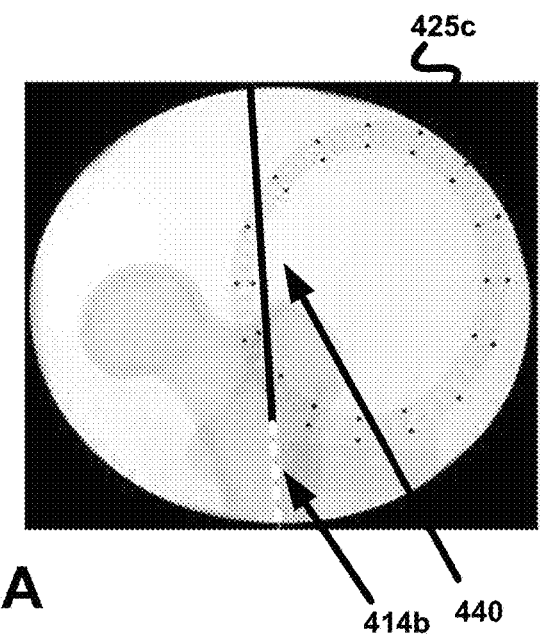
FIG. 54A
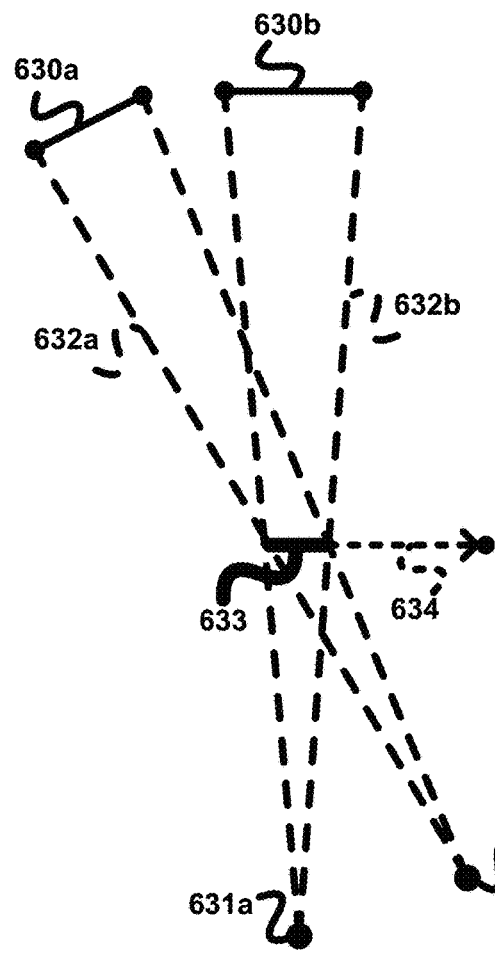
FIG. 55A

X-RAY CALIBRATION FOR DISPLAY OVERLAYS ONTO X-RAY IMAGES

CROSS-REFERENCE TO PRIOR APPLICATIONS

This application is a Continuation-in-part of U.S. application Ser. No. 17/421,029, filed Jul. 7, 2021 which is U.S. National Phase application under 35 U.S.C. § 371 of International Application No. PCT/EP2020/053927, filed on Feb. 14, 2020, which claims the benefit of U.S. Provisional Patent Application Ser. No. 62/806,005, filed Feb. 15, 2019. This application is also a Continuation-in-part of U.S. application Ser. No. 17/423,921, filed Jul. 19, 2021 which is U.S. National Phase application under 35 U.S.C. § 371 of International Application No. PCT/EP2020/058278, filed on Mar. 25, 2020, which claims the benefit of U.S. Provisional Patent Application Ser. No. 62/823,190, filed Mar. 25, 2019. These applications are hereby incorporated by reference herein.

FIELD OF THE INVENTION

The present disclosure generally relates to X-ray calibration. The present disclosure specifically relates to an imaging of an X-ray calibration marker for interventional tool position overlays and interventional tool trajectory overlays onto X-ray images.

BACKGROUND OF THE INVENTION

X-ray C-arm systems are frequently used in minimally invasive surgical procedures (e.g., orthopedic procedures, vascular interventions, etc.) for enabling surgeons to see inside a patient body by taking X-ray images from arbitrary directions. More particularly, a mobile C-arm usually has wheels to provide mobility around the room and once positioned, the mobile C-arm allows the user to adjust the position of the C-arm in five (5) directions. While this provides flexibility in the execution of minimally invasive surgical procedures, the exact position and angle of the X-ray projection is not known. This precludes the user from employing advanced tools including making true three-dimensional ("3D") measurements, large field of view imaging, dynamic overlay of pre-operative or intraoperative information, and target localization for image guided intervention. Thus, after a positioning of the mobile C-arm with respect to the patient body, there has been a need to compute a pose of the X-ray projection with respect to a fixed coordinate system, which is conventionally called C-arm registration. Specifically, a mobile C-arm position is computed with respect to a fixed coordinate system and described by a homogeneous transformation composed of a translation vector ($t \in R^3$) and a rotation matrix ($R \in SO(3)$). Therefore, the task has been to compute the pair ($t, R$) that accurately describes the position of the mobile C-arm with respect to the fixed coordinate system.

One historic approach for solving the C-arm registration required an installation of hardware on the C-arm (e.g., optical tracking markers, inertial markers, etc.). This approach requires the addition of multiple components to the room and often negatively impacts the workflow for the procedure.

A current practice for C-arm registration is to provide a marker having a fixed position in the operating space (e.g., a marker attached to a robot or an operating table), and to generate an X-ray image of features of the marker to perform the C-arm registration (e.g., steel balls or features of a known geometry). For such markers, there are cost-benefit tradeoffs with respect to a required registration accuracy, the number of opaque features on the marker, size of the marker, impact to the workflow, and impact to the x-ray image.

Also as known in the art of the present disclosure, mobile x-ray fluoroscopy is widely used in minimally invasive interventions in fields such as orthopedics, orthopedic trauma, vascular and spine. Mobile x-ray systems are commonly used because of their relatively small footprint compared to fixed x-ray systems, their maneuverability and reduced cost. However, given that mobile X-ray systems are typically not position-encoded, it can be difficult to implement advanced tools that rely on the precise orientation of the C-arm. For example, mobile X-ray systems have a limited field of view, and given that the translational position is not encoded, it is not trivial to stitch images together to increase the field of view.

Many mobile C-arm procedures require precise positioning of tools or anatomy. In orthopedic-trauma, for example, fracture reduction is a common procedure, which requires clinicians to realign bone fragments and deploy nails or screws at specific locations and angles. In femoral fracture reduction, an intramedullary nail may be inserted from the proximal end of the femur to the distal end. Aligning the nail correctly at the proximal end such that it maintains proper positioning at the distal end can be challenging, given that the distal end is outside of the field of view. Similarly, in pelvic fracture reduction, a screw may be placed through the sacroiliac joint. The placement of the sacroiliac screw is particularly challenging, given that there is a small target area for the screw to land and it is important to avoid damaging critical structures in the spine. Furthermore, typically, the target landing area for the screw is not visible in the same X-ray field of view as the starting point.

SUMMARY OF THE INVENTION

The present disclosure provides image-based navigation methods for X-ray imaging systems to localize an interventional tool in three-dimensional (3D) space that facilitates a display of a tool position and/or a tool trajectory both inside and outside of the field of view of the X-ray imaging system to thereby improve tool insertion outcomes with minimal effect on procedure time.

One embodiment of the present disclosure is an X-ray imaging system employing a C-arm and an X-ray overlay controller.

The C-arm is configured to acquire a plurality of X-ray images at different X-ray imaging poses of the C-arm.

The X-ray overlay controller is configured in a planning overlay display mode to:
  (a) process a planning X-ray image acquired by the C-arm at a planning X-ray imaging pose of the C-arm, the planning X-ray image being illustrative of a planning X-ray calibration device and non-illustrative of an interventional tool;
  (b) process a reference planning X-ray image acquired by the C-arm at a reference X-ray imaging pose of the C-arm, the reference planning X-ray image being illustrative of the planning X-ray calibration device and non-illustrative of the interventional tool;
  (c) compute a rigid body transformation between the C-arm at the planning X-ray imaging pose and the C-arm at the reference X-ray imaging pose based on the illustrations of the planning X-ray calibration device in the planning X-ray image and in the reference planning X-ray image;

(d) process a base X-ray image acquired by the C-arm at the reference X-ray imaging pose of the C-arm, the base X-ray image being illustrative of a base X-ray calibration device and non-illustrative of the interventional tool, the base X-ray calibration device being registered to a tool guide;

(e) compute a rigid body transformation between the C-arm at the planning X-ray imaging pose and a tool guide based on a computation of the rigid body transformation between the C-arm at the planning X-ray imaging pose and the C-arm at the reference X-ray imaging pose and further based on the registration of the base X-ray calibration device to the tool guide; and (f) control a display of a planned tool trajectory overlay onto the planning X-ray image based on a computation of the rigid body transformation between the C-arm at the planning X-ray imaging pose and a tool guide.

A second embodiment of the present disclosure is an X-ray overlay controller, employing one or more processors operable in a planning overlay display mode, and a non-transitory machine-readable storage medium encoded in the planning overlay display mode with instructions executable by the at least one processor to:

(a) process a planning X-ray image acquired by the C-arm at a planning X-ray imaging pose of the C-arm, the planning X-ray image being illustrative of a planning X-ray calibration device and non-illustrative of an interventional tool;

(b) process a reference planning X-ray image acquired by the C-arm at a reference X-ray imaging pose of the C-arm, the reference planning X-ray image being illustrative of the planning X-ray calibration device and non-illustrative of the interventional tool;

(c) compute a rigid body transformation between the C-arm at the planning X-ray imaging pose and the C-arm at the reference X-ray imaging pose based on the illustrations of the planning X-ray calibration device in the planning X-ray image and in the reference planning X-ray image;

(d) process a base X-ray image acquired by the C-arm at the reference X-ray imaging pose of the C-arm, the base X-ray image being illustrative of a base X-ray calibration device and non-illustrative of the interventional tool, the base X-ray calibration device being registered to a tool guide;

(e) compute a rigid body transformation between the C-arm at the planning X-ray imaging pose and a tool guide based on a computation of the rigid body transformation between the C-arm at the planning X-ray imaging pose and the C-arm at the reference X-ray imaging pose and further based on the registration of the base X-ray calibration device to the tool guide; and (f) control a display of a planned tool trajectory overlay onto the planning X-ray image based on a computation of the rigid body transformation between the C-arm at the planning X-ray imaging pose and a tool guide.

A third embodiment of the present disclosure is an X-ray overlay display method involving an execution, by an X-ray overlay controller, of a planning overlay display mode including:

(a) processing, by the X-ray overlay controller, a planning X-ray image acquired by the C-arm at a planning X-ray imaging pose of the C-arm, the planning X-ray image being illustrative of a planning X-ray calibration device and non-illustrative of an interventional tool;

(b) processing, by the X-ray overlay controller, reference planning X-ray image acquired by the C-arm at a reference X-ray imaging pose of the C-arm, the reference planning X-ray image being illustrative of the planning X-ray calibration device and non-illustrative of the interventional tool;

(c) computing, by the X-ray overlay controller, a rigid body transformation between the C-arm at the planning X-ray imaging pose and the C-arm at the reference X-ray imaging pose based on the illustrations of the planning X-ray calibration device in the planning X-ray image and in the reference planning X-ray image;

(d) processing, by the X-ray overlay controller, a base X-ray image acquired by the C-arm at the reference X-ray imaging pose of the C-arm, the planning X-ray image being illustrative of a base X-ray calibration device and non-illustrative of the interventional tool, the base X-ray calibration device being registered to a tool guide;

(e) computing, by the X-ray overlay controller, a rigid body transformation between the C-arm at the planning X-ray imaging pose and a tool guide based on a computation of the rigid body transformation between the C-arm at the planning X-ray imaging pose and the C-arm at the reference X-ray imaging pose and further based on the registration of the base X-ray calibration device to the tool guide; and (f) controlling, by the X-ray overlay controller, a display of a planned tool trajectory overlay onto the planning X-ray image based on a computation of the rigid body transformation between the C-arm at the planning X-ray imaging pose and a tool guide.

For purposes of the description and claims of the present disclosure:

(1) terms of the art including, but not limited to, "marker", "X-ray", "X-ray image", "C-arm", "X-ray source", "X-ray detector", "X-ray projection", "interventional tool", "overlay", "process" and tenses thereof, "register" and tenses thereof, "calibration" and tenses thereof, "robot", "transformation parameter", "intervention", "landmark", "chirp", "annular", "parameter", "parametrize" and "derive" are to be interpreted as known in the art of the present disclosure and as exemplary described in the present disclosure;

(2) the term "X-ray ripple marker" broadly encompasses a marker incorporating a ripple pattern radially extending from a fixed point of the marker for creating X-ray imaged wave(s) with characteristics that are a function of a position of an X-ray projection by a C-arm with respect to the X-ray ripple marker in accordance with various aspects of the present disclosure as exemplary described herein;

(3) the term "wave" includes broadly encompasses a frequency signal of any type including, but not limited to, a fixed frequency signal and a swept frequency signals (e.g., chirps).

(4) the term "ripple pattern" broadly encompasses an arrangement one or more circular ripples and/or one or more arc ripples radially extending from a fixed point of the X-ray ripple marker whereby a frequency, a phase and/or an amplitude of the circular/arc ripple(s) serve to create the X-ray imaged wave(s) in accordance with various aspects of the present disclosure as exemplary described herein;

(5) the term "chirp pattern" broadly encompasses an arrangement of one or more chirps to generate a chirp signal representative of an additional dimension of freedom of the transformation of the X-ray projection by the C-arm with respect to the X-ray ripple marker;

(6) the term "landmark pattern" broadly encompasses an arrangement of one or more landmarks disposed on the X-ray ripple marker to find one or more points on the X-ray ripple marker (e.g., a center point of the X-ray ripple marker);

(7) the term "X-ray ring marker" broadly encompasses, as exemplary shown in the present disclosure and hereinafter conceived, a coaxial construction of a centric ring and a chirp ring;

(8) the term "centric ring" broadly encompasses, as exemplary shown in the present disclosure and hereinafter conceived, a X-ray imagable annular structure embodying a center of the X-ray ring marker, such as, for example, a X-ray imagable circular shaped ring or a X-ray imagable elliptical shaped ring embodying a center a X-ray ring marker defined by a spatial arrangement of protrusions formed in a X-ray imagable annular base, a spatial arrangement of indentations formed in the a X-ray imagable annular base, and/or a spatial arrangement of X-ray imagable objects disposed onto/into an annular base (e.g., cooper balls, brass balls, etc.);

(9) the term "chirp ring" broadly encompasses, as exemplary shown in the present disclosure and hereinafter conceived, a X-ray imagable annular structure embodying a chirp signal, such as, for example, a X-ray imagable circular shaped ring or a X-ray imagable elliptical shaped ring embodying a chirp signal defined by a spatial arrangement of protrusions formed in a X-ray imagable annular base, a spatial arrangement of indentations formed in a X-ray imagable annular base, and/or a spatial arrangement of X-ray imagable objects disposed onto/into an annular base (e.g., cooper balls, brass balls, etc.);

(10) the term "coaxial construction" broadly encompasses a permanent formation/disposal or a transient disposal of the centric ring and the chirp ring on the annular base including a concentric axial alignment or an eccentric axial alignment of the centers of the centric ring and the chirp ring;

(11) the terms "baseline" and "target" are used in the present disclosure as labels for distinguishing various X-ray images, X-ray projections and imaging poses and do not limit the scope of X-ray images, X-ray projections and imaging poses;

(12) the term "co-register" and tenses thereof broadly encompasses a correlation of X-ray calibration marker(s) as illustrated in X-ray images as a basis for generating overlays onto the X-ray image(s);

(13) the term "controller" broadly encompasses all structural configurations, as understood in the art of the present disclosure and as exemplary described in the present disclosure, of main circuit board or integrated circuit for controlling an application of various aspects of the present disclosure as exemplary described in the present disclosure. The structural configuration of the controller may include, but is not limited to, processor(s), computer-usable/computer readable storage medium(s), an operating system, application module(s), peripheral device controller(s), slot(s) and port(s). A controller may be housed within or linked to a workstation. Examples of a "workstation" include, but are not limited to, an assembly of one or more computing devices, a display/monitor, and one or more input devices (e.g., a keyboard, joysticks and mouse) in the form of a standalone computing system, a client computer of a server system, a desktop or a tablet;

(14) the term "application module" broadly encompasses an application incorporated within or accessible by a controller consisting of an electronic circuit (e.g., electronic components and/or hardware) and/or an executable program (e.g., executable software stored on non-transitory computer readable medium(s) and/or firmware) for executing a specific application; and

(15) the terms "data" and "signal" broadly encompasses all forms of a detectable physical quantity or impulse (e.g., voltage, current, or magnetic field strength) as understood in the art of the present disclosure and as exemplary described in the present disclosure for transmitting information and/or instructions in support of applying various aspects of the present disclosure as subsequently described in the present disclosure. Data/signal communication components of the present disclosure may involve any communication method as known in the art of the present disclosure including, but not limited to, data/signal transmission/reception over any type of wired or wireless datalink/signal link and a reading of data/signal uploaded to a computer-usable/computer readable storage medium.

The foregoing embodiments and other embodiments of the inventions of the present disclosure as well as various structures and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

BRIEF DESCRIPTION OF THE DRAWINGS

FIGS. 11A and 11D illustrate an exemplary marker position approximation/refinement of FIG. 9 in accordance with various aspects of the present disclosure.

FIGS. 16A and 16B illustrate an exemplary transformation parameter generation of an X-ray ripple marker of FIG. 15A in a first position in accordance with various aspects of the present disclosure.

FIGS. 17A and 17B illustrate an exemplary transformation parameter generation of an X-ray ripple marker of FIG. 15A in a second position in accordance with various aspects of the present disclosure.

FIG. 31 illustrates a flowchart representative of an exemplary embodiment of a C-arm→X-ray ring marker registration method in accordance with various aspects of the present disclosure.

FIG. 32 illustrates a flowchart representative of an exemplary embodiment of a registration parameter computation method in accordance with various aspects of the present disclosure.

FIGS. 42A and 42B illustrate a first exemplary displayed navigation of an interventional tool in accordance the various aspects of the planned overlay display mode of the present disclosure.

FIGS. 51A and 51B illustrate a first exemplary displayed navigation of an interventional tool in accordance the various aspects of the guidance overlay display mode of the present disclosure.

FIGS. 54A, 54B, and 54C illustrate a second exemplary displayed navigation of an interventional tool in accordance the various aspects of the guidance overlay display mode of the present disclosure.

FIGS. 55A and 55B illustrate exemplary virtual planar X-ray projections in accordance the various aspects of the guidance overlay display mode of the present disclosure.

DETAILED DESCRIPTION OF THE PREFERRED EMBODIMENTS

To facilitate an understanding of various inventive aspects of the present disclosure, the following description of FIGS. 1-4D teaches embodiments of an X-ray ripple marker of the present disclosure. From this description, those having ordinary skill in the art will appreciate how to apply the various aspects of the present disclosure for making and using additional embodiments of X-ray ripple markers of the present disclosure.

Figure 1:
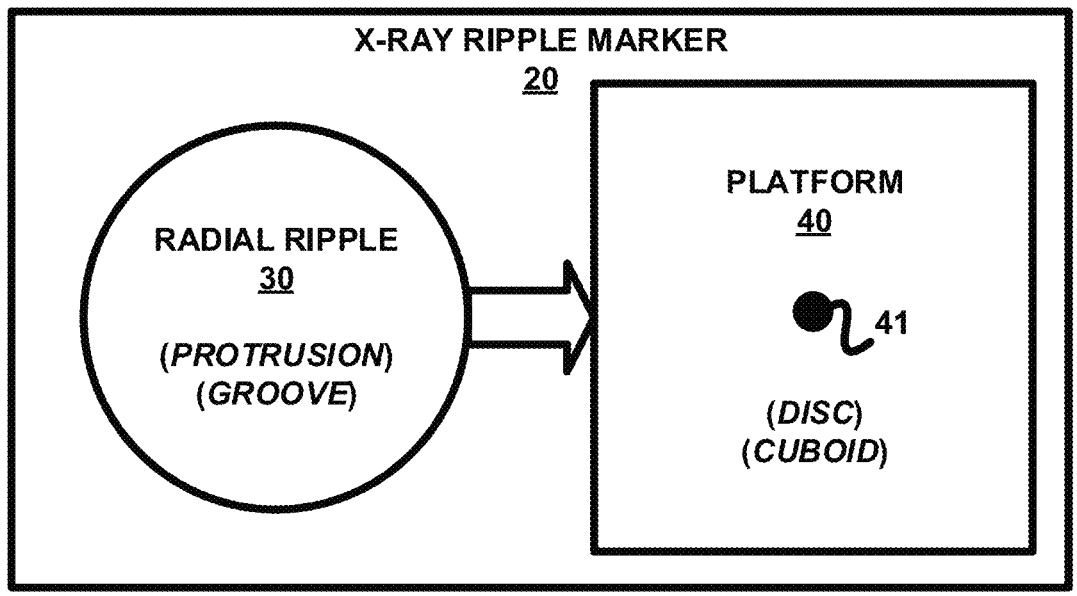
FIG. 1 illustrates an exemplary embodiment of an X-ray ripple marker in accordance with various aspects of the present disclosure.

Referring to FIG. 1, an X-ray ripple marker 20 of the present disclosure employs one or more radial ripples 30 integrated within a platform 40 and radially extending from a fixed point 41 of platform 40 (e.g., a center point of platform 40).

In practice, platform 40 may have any size and shape that facilitates an X-ray imaging of radial ripple(s) 30 radially extending from fixed point 41 of platform 40. For example, platform 40 may have a disc shape or a cuboid shape with radial ripple(s) 30 integrated onto a same side surface of the disc or the cuboid, and radially extending from any fixed point on that side surface of the disc or the cuboid (e.g., a center of the disc or the cuboid). The size of the disc and cuboid is not limited by the X-ray imaging space of one or particular types of X-ray imaging systems or generic to all X-ray imaging systems.

Figure 2A:
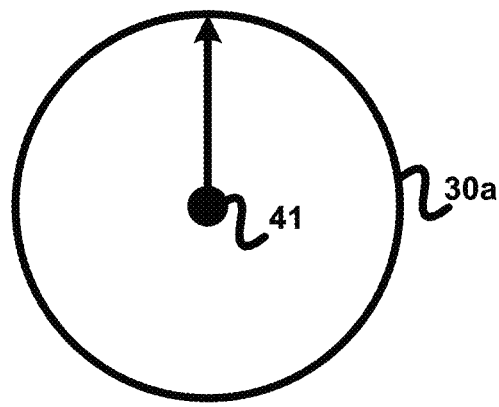
FIGS. 2A-2D illustrate exemplary embodiments of radial ripples in accordance with various aspects of the present disclosure.
Figure 2B:
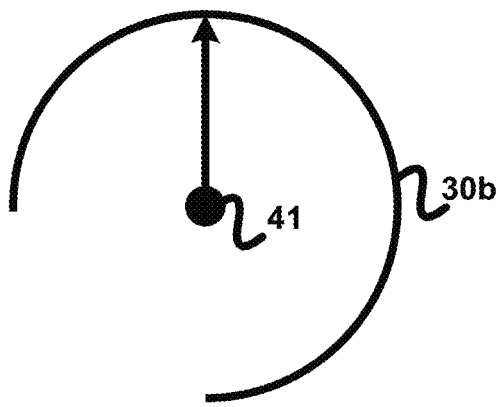
Figure 2C:
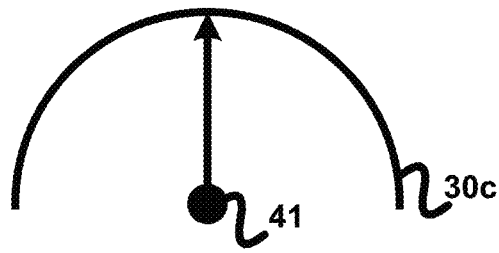
Figure 2D:
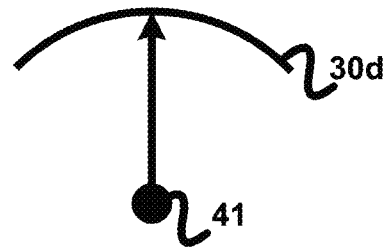

Also in practice, a radial ripple 30 may have any shape and dimensions that partially or fully encircles the fixed point. For example, FIG. 2A shows a radial ripple 30a as a circle fully encircling a fixed point 41 of platform 40, FIG. 2B shows a radial ripple 30b as a 270° arc partially encircling the fixed point 41 of platform 40, FIG. 2C shows a radial ripple 30c as a 180° arc partially encircling the fixed point 41 of platform 40 and FIG. 2D shows a radial ripple 30d as a 90° arc partially encircling the fixed point 41 of platform 40.

Figure 3A:
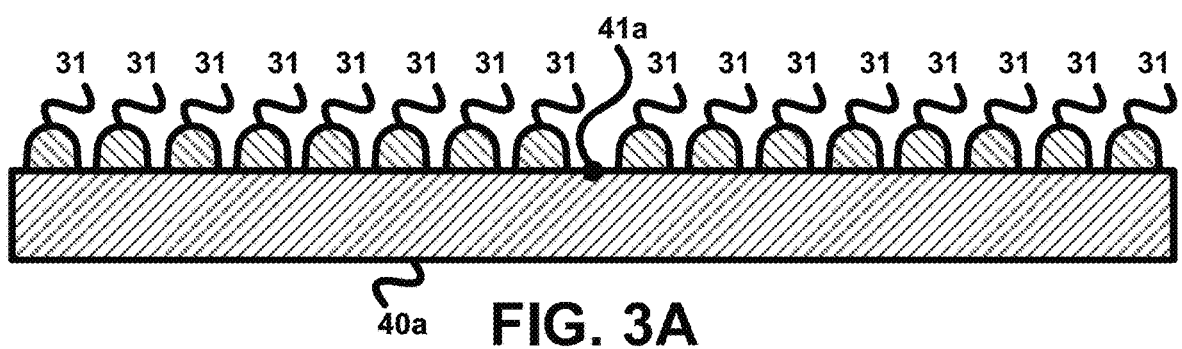
FIGS. 3A and 3B illustrate exemplary embodiments of platforms in accordance with various aspects of the present disclosure.
Figure 3B:
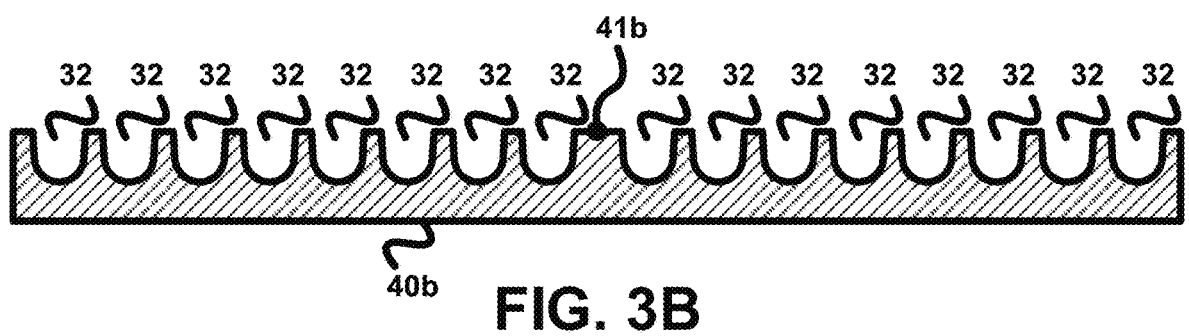

Further in practice, a radial ripple 30 may be integrated into platform 40 in any manner than facilitates an X-ray imaging of X-ray ripple marker 20 that distinguishes the radial ripple(s) 30 from the platform 40 within the X-ray image. For example, FIG. 3A shows a cross-section of a platform 40a having a plurality of radial ripples 30 as protrusions 31 upwardly extending from a top surface of platform 40a relative to a fixed point 41a, and FIG. 3B shows a cross-section of a platform 40b having a plurality of radial ripples as grooves 32 downwardly extending into a top surface of platform 40b relative to a fixed point 41b. Also by example, an X-ray ripple marker 20 may employ one or more radial ripples 30 as protrusions and one or more additional radial ripples 30 as grooves.

Referring back to FIG. 1, for C-arm registration purposes, radial ripple(s) 30 are integrated onto platform 40 to form a ripple pattern that create(s) X-ray imaged wave(s) with characteristics that are a function of a position of an X-ray projection of a C-arm with respect to the X-ray ripple marker 20 as will be further described in the present disclosure with the C-arm registration description of FIGS. 5-18.

Figure 4A:
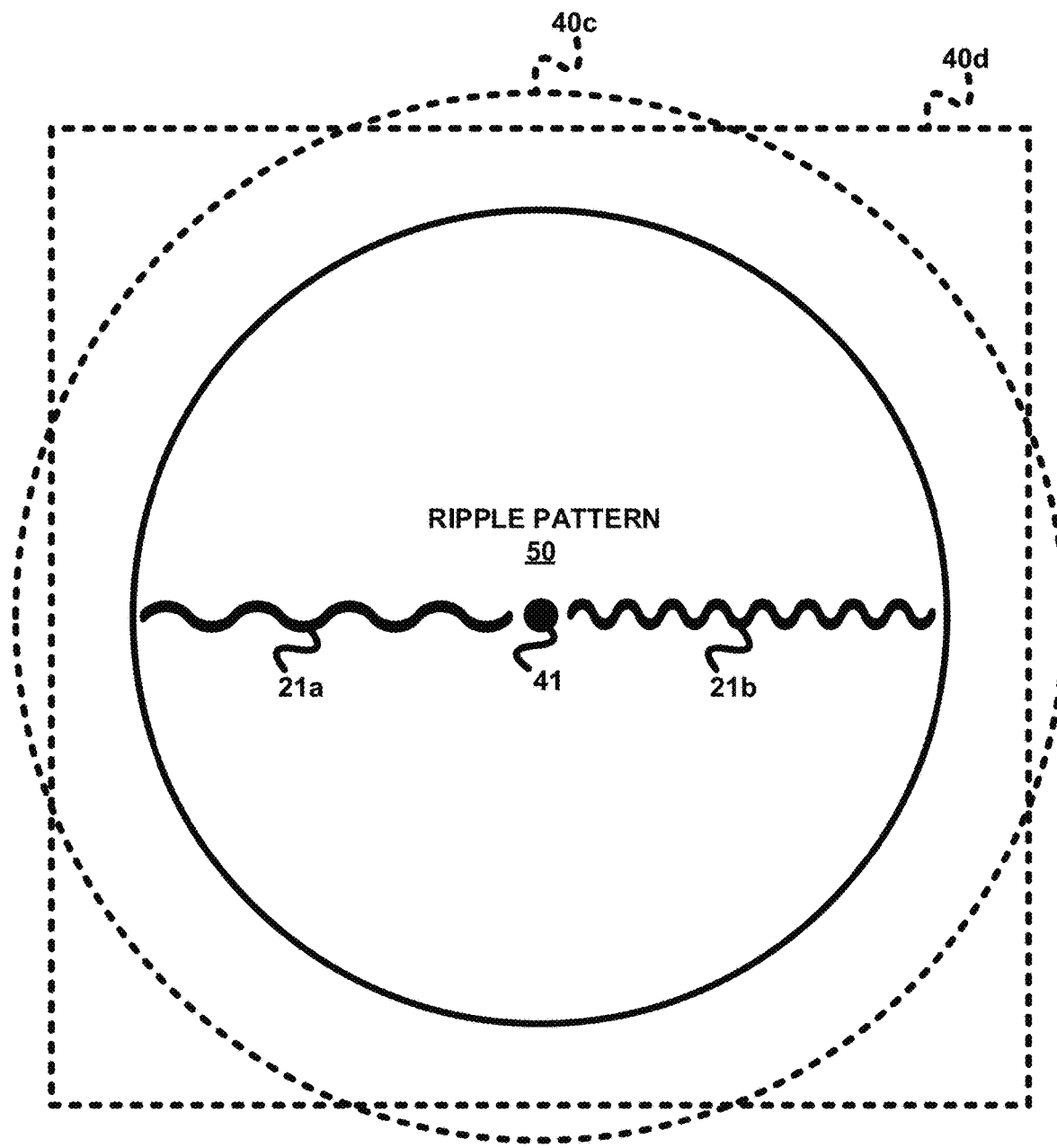
FIGS. 4A-4G illustrates exemplary embodiments of the X-ray ripple marker of FIG. 1 in accordance with various aspects of the present disclosure.

For example, FIG. 4A illustrates a radial pattern 50 of radial ripple(s) 30 being integrable onto a surface of a disc 40c or a platform 40b for creating X-ray imaged wave(s) as symbolically shown by waves 21a and 21b.

In practice, a frequency, a phase and/or an amplitude of an X-ray imaged wave may be the characteristic(s) that is(are) a function of a position of an X-ray projection of a C-arm with respect to the X-ray ripple marker 20.

Further in practice, relative frequencies, relative phases and/or relative amplitudes of two or more X-ray imaged wave(s) may be the characteristics that is(are) a function of a position of an X-ray projection of a C-arm with respect to the X-ray ripple marker 20.

Figure 4B:
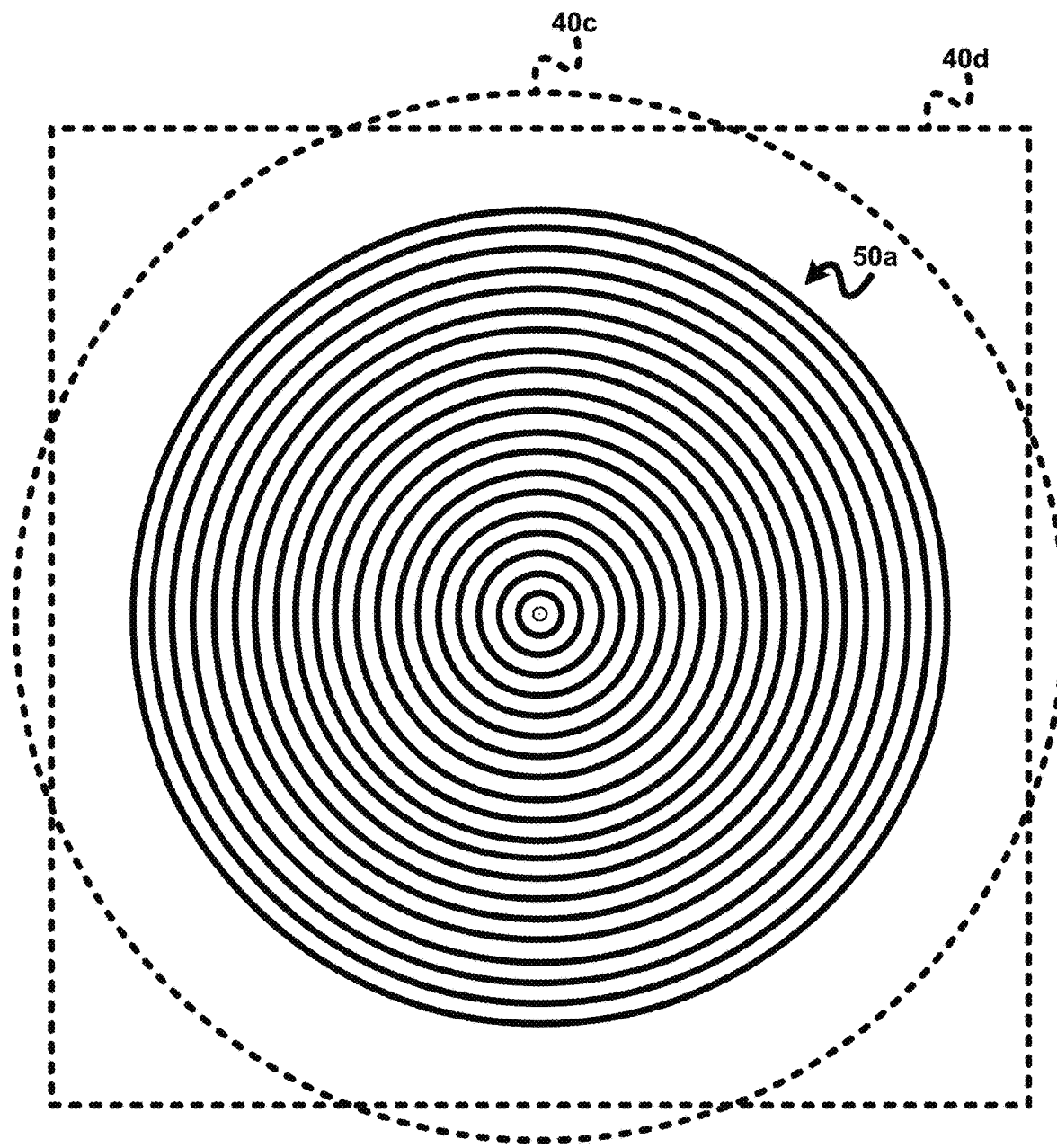

In one embodiment of ripple pattern 50 as shown in FIG. 4B, a ripple pattern 50a of twenty (20) concentric circular radial ripples as integrated on disc 40c or cuboid 40d, which provides a five (5) degree of freedom transformation of an X-ray projection of a C-arm to the coordinate system associated with the marker using a single X-ray image.

Figure 4C:
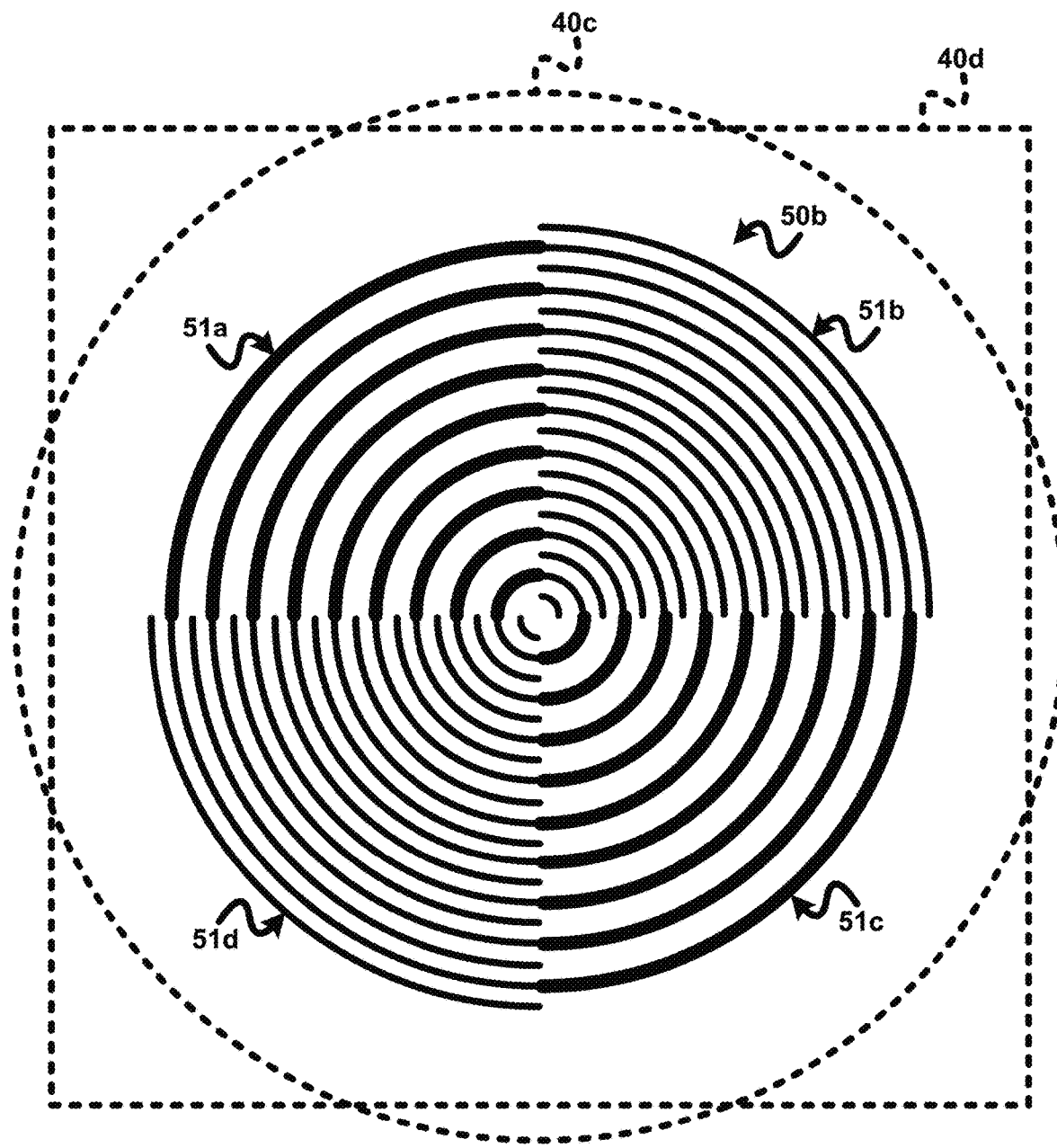

In a second embodiment of ripple pattern 50 as shown in FIG. 4C, a ripple pattern 50b includes a series 51a of nine (9) concentric 90° arc radial ripples, a series 51b of seventeen (17) concentric 90° arc radial ripples, a series 51c of nine (9) concentric 90° arc radial ripples and a series 51d of seventeen (17) concentric 90° arc radial ripples. Ripple pattern 50b also provides a five (5) degree of freedom transformation of an X-ray projection of a C-arm to the coordinate system associated with the marker using a single X-ray image.

Still referring to FIG. 4C, in practice of a ripple pattern 50 having a plurality of arc series, an arc series may be identical to one or more other arc series in terms of frequency, phase and amplitude, or the arc series may be dissimilar to one or more other arc series in terms of frequency, phase and/or amplitude.

For example, arc series 51a and arc series 51c are identical to each other in terms of frequency, phase and amplitude. Arc series 51a and arc series 51c are identical to arc series 51b and 51d in terms of phase, but dissimilar to arc series 51b and arc series 51d in terms of frequency and amplitude.

Figure 4D:
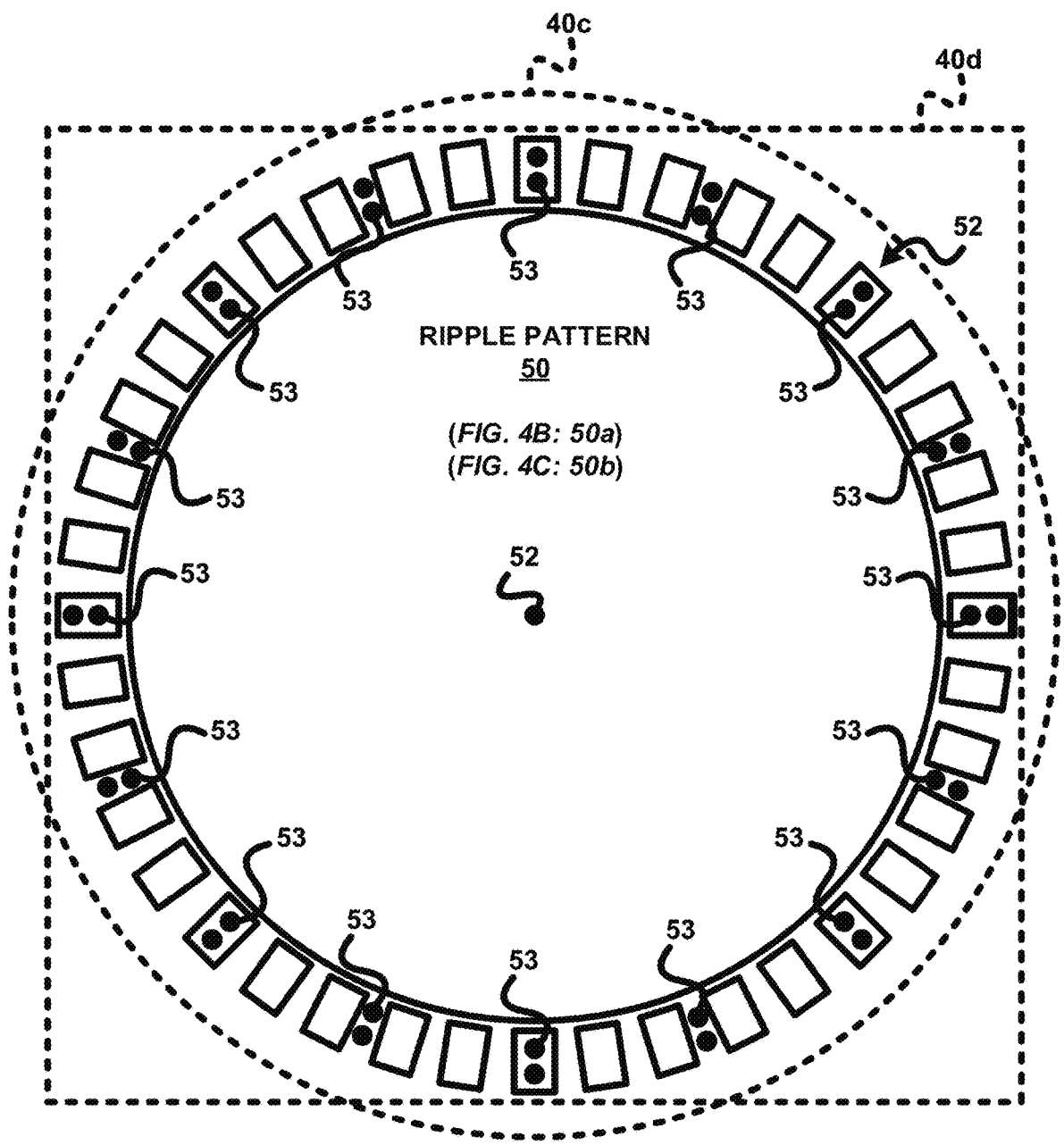

For any embodiment of ripple pattern 50 (e.g., ripple pattern 50a of FIG. 4A and ripple pattern 50b of FIG. 4B), a chirp pattern of chirps (e.g., protrusions and/or grooves) may be axially aligned with a ripple pattern 50 to provide a sixth degree of freedom transformation of an X-ray projection of a C-arm to the coordinate system associated with the marker using a single X-ray image. For example, FIG. 4D shows a circular chirp pattern 52 of forty (40) chirps encircling a perimeter of ripple pattern 50.

In practice, a chirp may be disposed on the same side surface of the platform as ripple pattern 50, and/or a chirp may be disposed on a side surface of the platform opposing the ripple pattern 50.

For any embodiment of ripple pattern 50 (e.g., ripple pattern 50a of FIG. 4A and ripple pattern 50b of FIG. 4B), a landmark pattern (e.g., a pattern of copper balls) may be axially aligned with the ripple pattern 50 to facilitate a finding of the fixed point of the platform and/or for C-arm registration computations including, but not limited to, a final optimization and registration error estimation. For example, FIG. 4D shows a landmark pattern of a series of sixteen (16) pairings of copper balls 53 encircling a perimeter of ripple pattern 50.

In practice, the landmark pattern may be disposed on the same side surface of the platform as ripple pattern 50, and/or the landmark pattern may be disposed on a side surface of the platform opposing the ripple pattern 50.

From the description of FIGS. 4A-4D, those having ordinary skill in the art will appreciate the broad scope of embodiments of X-ray ripple markers of the present disclosure.

Figure 4E:
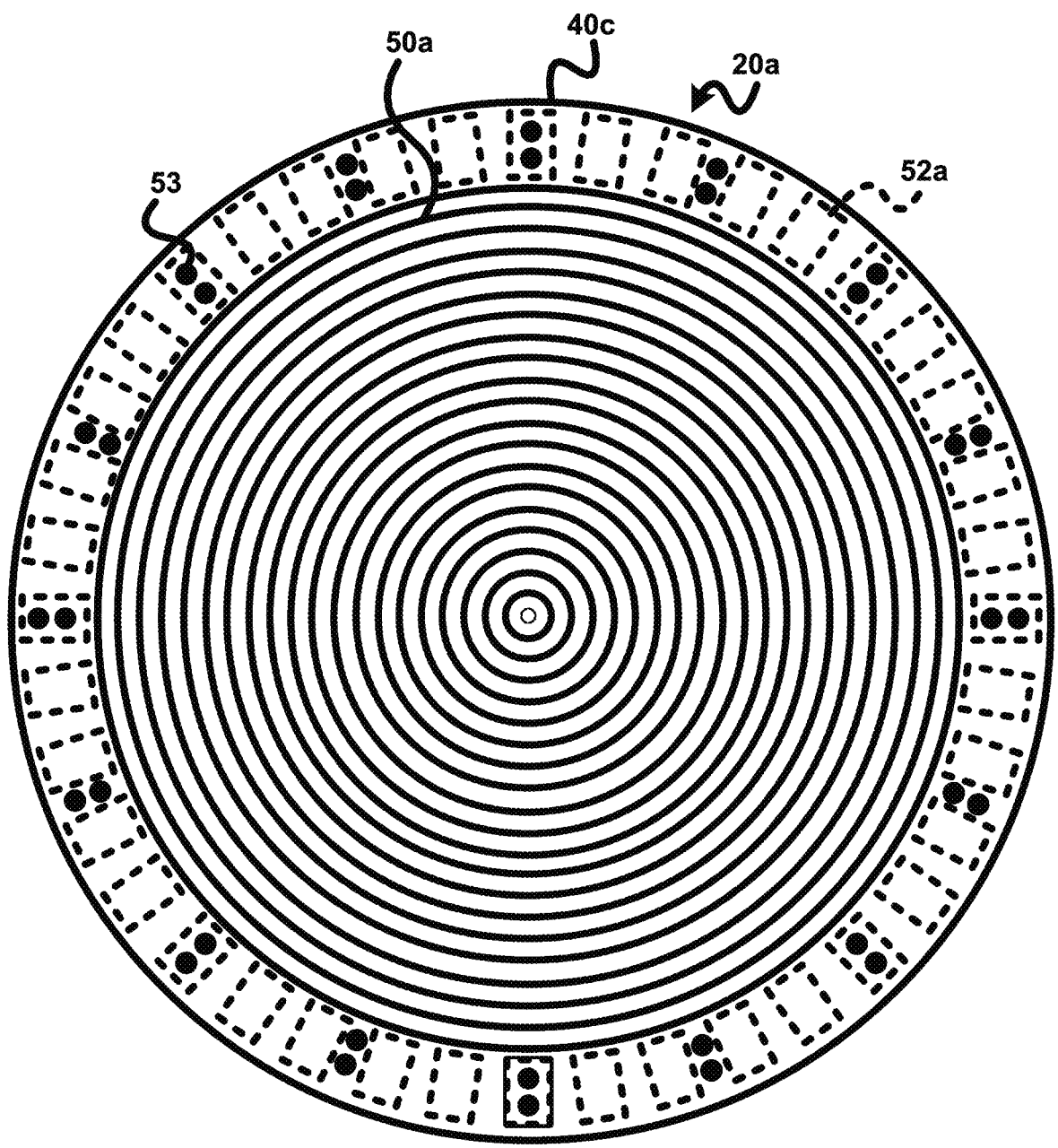

For example, FIG. 4E shows an exemplary X-ray ripple marker 20a incorporating a protrusion embodiment 31 of ripple pattern 50a (FIG. 4B) integrated on disc 40c, a protrusion embodiment 52a of circular chirp pattern 52 (FIG. 4D) disposed on a same side surface or an opposite side surface of disc 40c as ripple pattern 50a, and the landmark pattern of copper balls 53 of FIG. 4D encircling a perimeter of ripple pattern 50.

Figure 4F:
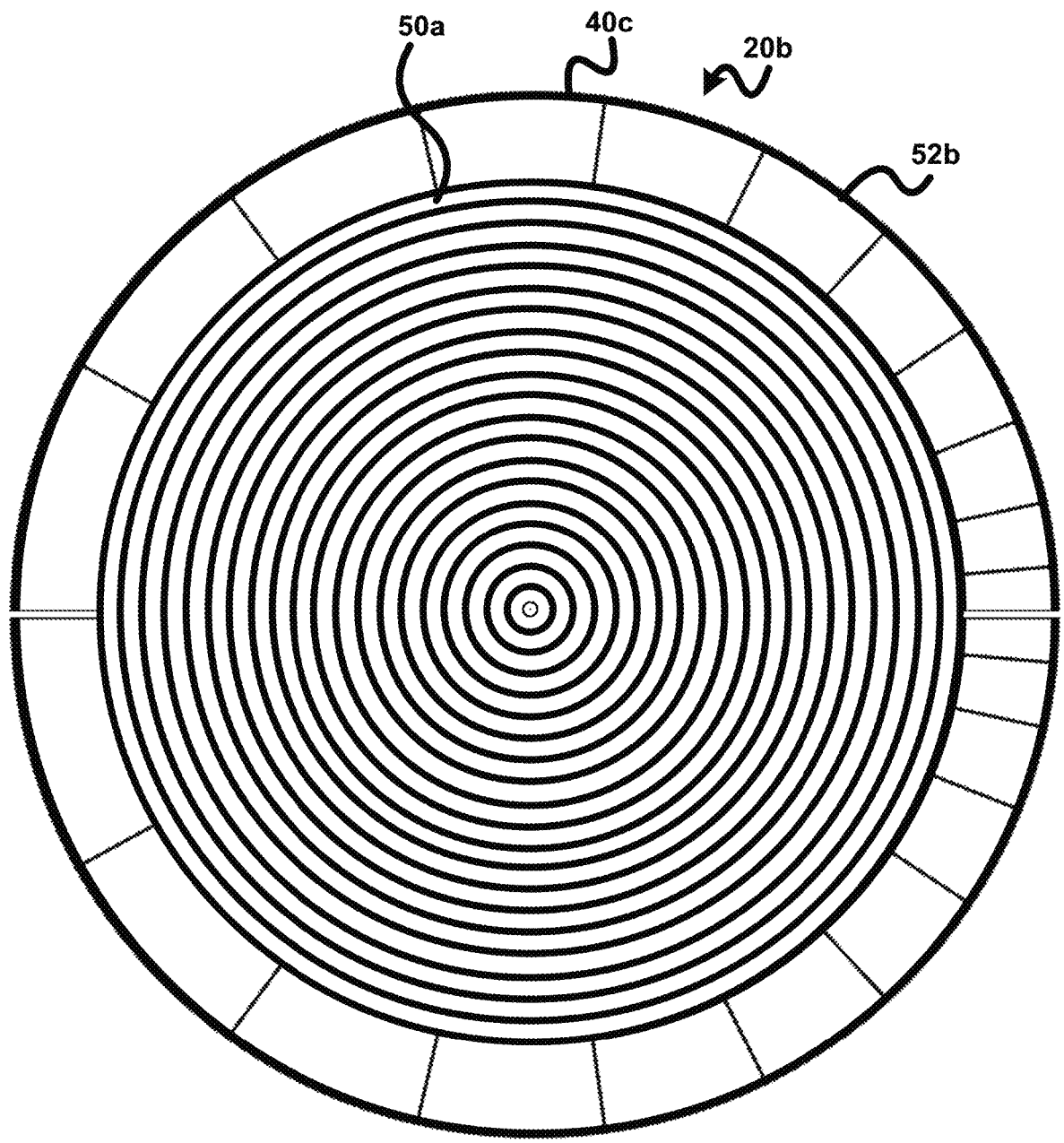

By additional example, FIG. 4F shows an exemplary X-ray ripple marker 20b incorporating a protrusion embodiment 31 of ripple pattern 50a (FIG. 4B) integrated on disc 40c, and a progressive spacing protrusion embodiment 52b of circular chirp pattern 52 (FIG. 4D) disposed on the same side surface or the opposite side surface of disc 40c as ripple pattern 50a.

Figure 4G:
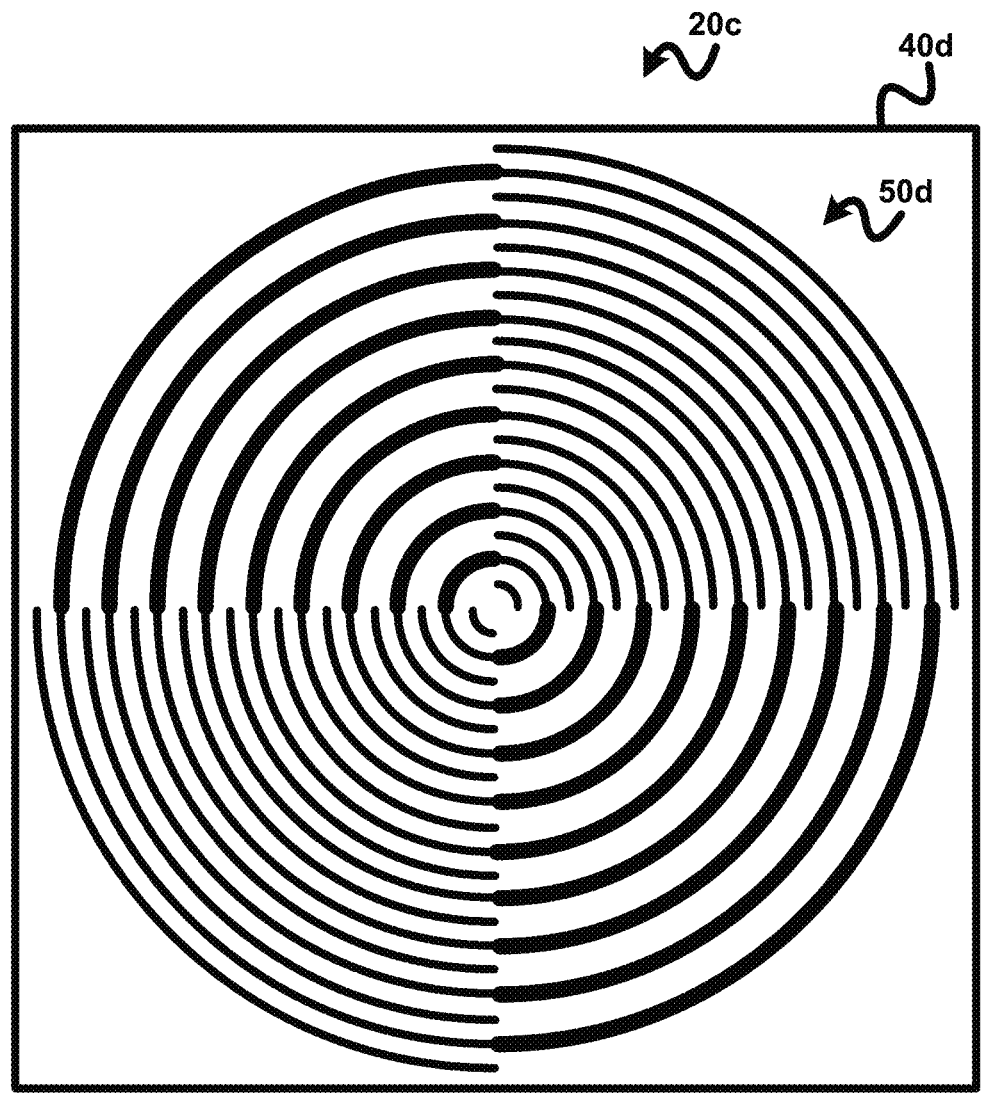

By further example, FIG. 4G shows an exemplary X-ray ripple marker 20c incorporating a protrusion embodiment 50d of ripple pattern 50b (FIG. 4C) integrated on cuboid 40d.

To further facilitate an understanding of various aspects of the present disclosure, the following description of FIGS. 5-18B teaches embodiments of a C-arm registration of the present disclosure. From this description, those having ordinary skill in the art will appreciate how to apply various aspects of the present disclosure for making and using additional embodiments of C-arm registrations of the present disclosure.

While X-ray ripple marker 20a of FIG. 4D and X-ray ripple marker 20b of FIG. 4E will be utilized for purposes of describing embodiments of a C-arm registration of the present disclosure, those having ordinary skill in the art will appreciate how to apply various aspects of the present disclosure for executing a C-arm registration of the present disclosure using any embodiment of an X-ray ripple marker of the present disclosure.

Figure 5A:
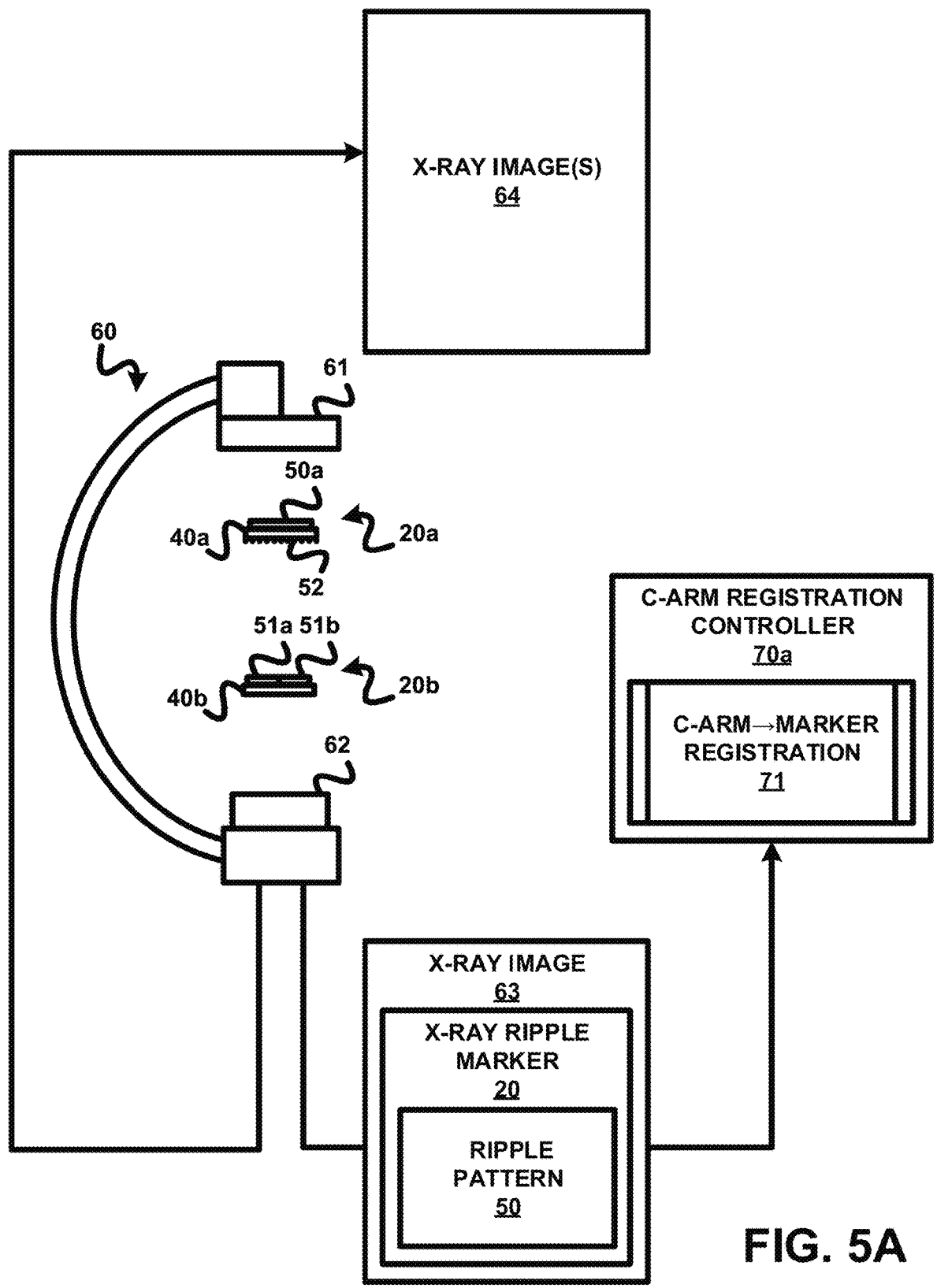
FIGS. 5A and 5B illustrate exemplary embodiments of an C-arm registration in accordance with various aspects of the present disclosure.
Figure 5B:
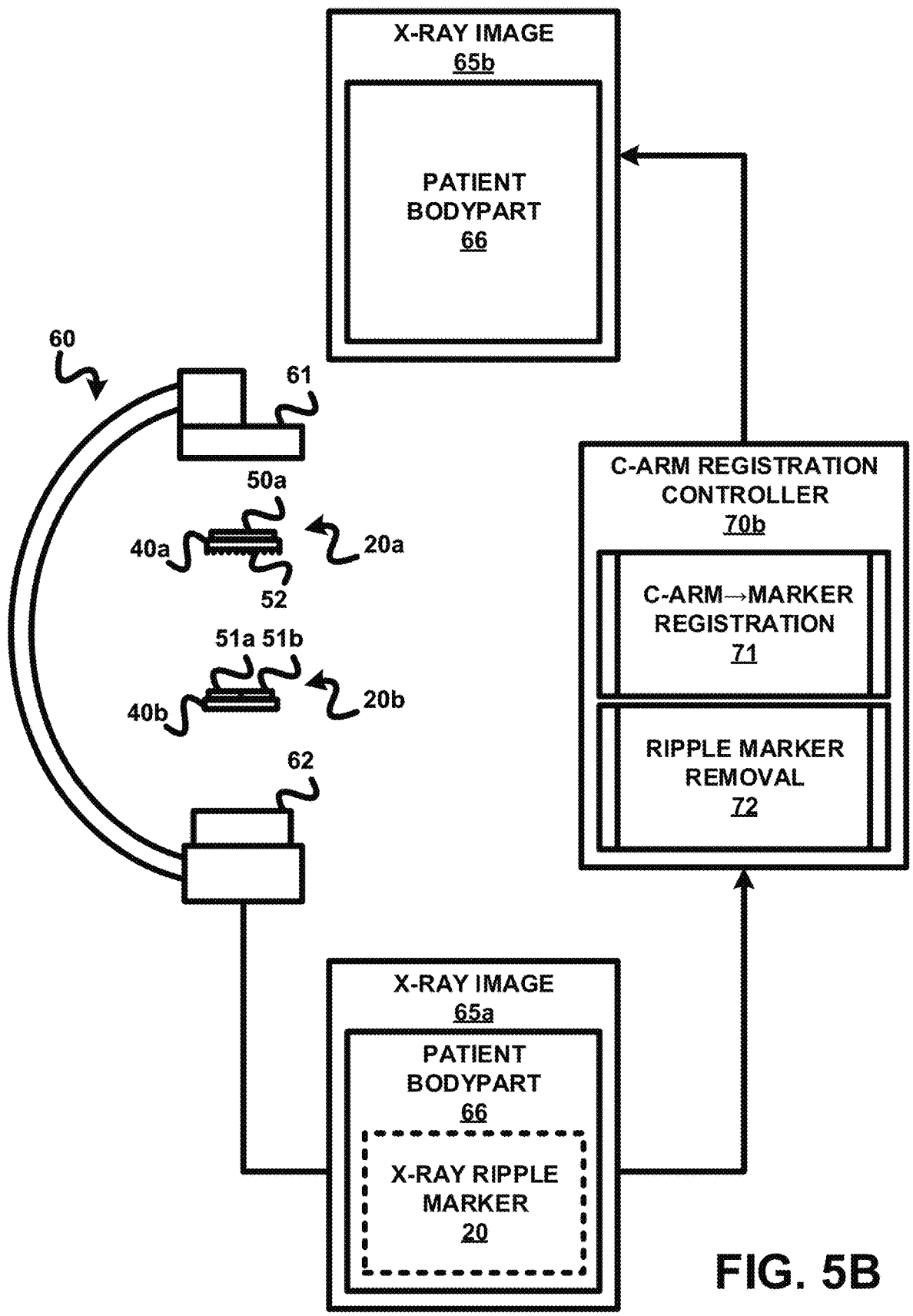

Referring to FIGS. 5A and 5B, a C-arm registration of the present disclosure is implemented in a patient-less mode and a patient mode, respectively.

Generally in the patient-less mode as shown in FIG. 5A, an X-ray ripple marker 20 (e.g., X-ray ripple marker 20a of FIG. 4E or X-ray ripple marker 20b of FIG. 4F as shown) has a fixed position within an intervention space (e.g., an attachment to an operating table, a rail, a drape, or an intervention robot). An X-ray source 61 and an X-ray detector 62 of a C-arm 60 are translated and/or rotated to a position to generate an X-ray image 63 of a ripple pattern 50 of X-ray ripple marker 20. A C-arm registration controller 70 acquires X-ray image 63 and executes a C-arm to marker registration 71 of the present disclosure delineating a position of an X-ray projection by C-arm 60 with respect to the X-ray ripple marker 20 as will be further described in the present disclosure. Subsequently, X-ray ripple marker 20 is removed from an imaging space of C-arm 60 whereby a patient may be positioned within the imaging space of C-arm 60 to thereby perform an intervention based on the C-arm registration involving a generation of X-ray image(s) 64.

Generally in the patient mode as shown in FIG. 5B, an X-ray ripple marker 20 (e.g., X-ray ripple marker 20a of FIG. 4E or X-ray ripple marker 20b of FIG. 4F as shown) has a fixed position within an intervention space (e.g., an attachment to an operating table or an intervention robot) and a body part of interest of a patient is positioned above and adjacent X-ray ripple marker 20 (body part not shown for clarity of the marker). The X-ray source 61 and the X-ray detector 62 of C-arm 60 are translated and/or rotated to a position to generate an X-ray image 63 of a ripple pattern 50 of X-ray ripple marker 20 relative to a body part 66. A C-arm registration controller 70 acquires X-ray image 65a and executes a C-arm to marker registration 71 of the present disclosure delineating a position of an X-ray projection by C-arm 60 with respect to the X-ray ripple marker 20 as will be further described in the present disclosure. C-arm registration controller 70 may additionally executes a ripple marker removal 72 of the present disclosure removing X-ray ripple marker 20 (or at least the ripple pattern 50) from X-ray image 65a to render an X-ray image 65b illustrating body part 66 for display during an intervention based on the C-arm registration of the present disclosure.

Figures 6, 7:
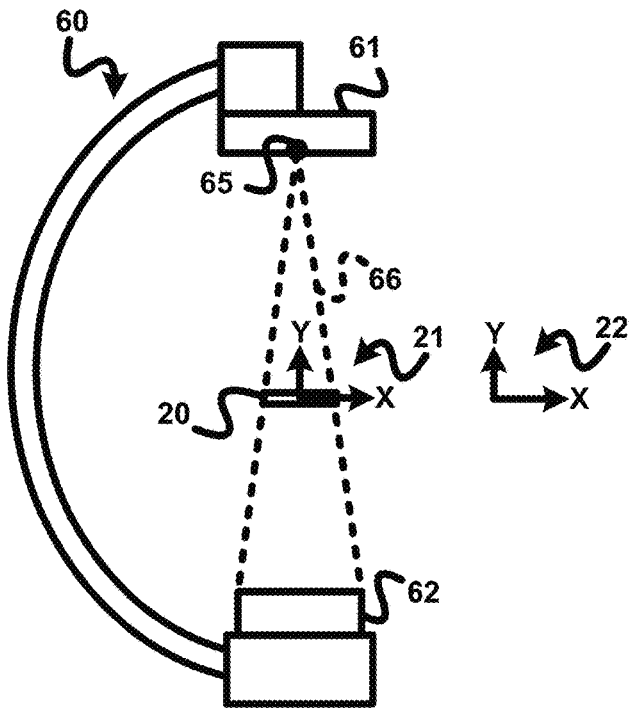
FIG. 6 illustrates a first exemplary embodiment of an X-ray projection by a C-arm in accordance with the various aspects of the present disclosure.
FIG. 7 illustrates a flowchart representative of a first exemplary embodiment of an C-arm registration of FIG. 5 in accordance with various aspects of the present disclosure.

More particularly to both the patient-less mode and the patient mode, as shown in FIG. 6, the C-arm to marker registration 71 involves registering a position of an X-ray projection relative to an X-ray ripple marker 20 of the present disclosure within a 3D coordinate system 21 or a 3D coordinate system 22 (only the Y-axis and the X-axis are shown, the Z-axis is not shown).

In practice, the X-ray projection may originate at any point of the X-ray source 61, such as, for example, a focal spot 65 as shown in FIG. 6.

In practice, X-ray ripple marker 20 may establish coordinate system 21 having a fixed point of the X-ray ripple marker 20 as the origin of coordinate system 21, or alternatively, X-ray ripple marker 20 may be calibrated with a coordinate system 22 of an intervention device (e.g., an intervention robot system having the X-ray ripple marker 20 attached thereto).

FIG. 7 illustrates a flowchart 80 representative of a C-arm to X-ray ripple marker registration executable by controller 70.

Referring to FIG. 7, a stage S82 of flowchart 80 encompasses controller 70 identifying a signature and a ripple pattern 50 of X-ray ripple marker 20 in the X-ray image 63 in the patient-less mode of FIG. 5A or in the X-ray image 65a of the patient mode of FIG. 5B. The identification of ripple pattern 50 within the X-ray image is characteristic of a position of the X-ray projection by the C-arm 60 (e.g., focal spot 65) relative to the X-ray ripple marker 20, meaning a location and/or an orientation the X-ray projection within coordinate system 21 or coordinate system 22 is characterized by ripple pattern 50 as illustrated within the X-ray image.

In practice, knowing the geometry of X-ray ripple marker 20 may serve as a basis for identifying X-ray maker 20 within the X-ray image when an entirety of X-ray ripple marker 20 is illustrated within the X-ray image, or the utilization of a landmark pattern (e.g., landmark pattern of copper balls 53) may serve as a basis for identifying X-ray maker 20 within the X-ray image when a portion of X-ray ripple marker 20 is illustrated within the X-ray image.

For example, in the patient-less mode, X-ray ripple marker 20 may be aligned between focal spot 65 and X-ray detector 62 whereby an entirety of X-ray ripple marker 20 may be illustrated within X-ray image 63 (FIG. 5A).

By further example, in the patient mode, a landmark pattern of copper balls 53 (FIG. 4D) may be utilized to find the fixed point of X-ray ripple marker 20 (e.g., the center point), particularly when a portion of the X-ray ripple marker 20 is illustrated within X-ray image 65a (FIG. 5B).

A stage S84 of flowchart 80 involves a derivation of transformation parameter(s) from the ripple pattern 50 identified in stage S82 to thereby register X-ray ripple marker 20 and X-ray C-arm 60 during a stage S86 of flowchart 80.

In practice, stage S84 involves a generation of transformation signal(s) from frequency(ies), phase(s) and/or amplitude(s) of the radial ripples of ripple pattern 50 identified in stage 82. The transformation signal(s) may be analyzed during stage S84 to derive transformation parameter(s) that define the position of the X-ray projection by the C-arm 60 (e.g., focal spot 65) relative to the X-ray ripple marker 20, meaning a location and/or an orientation of the X-ray projection within coordinate system 21 or coordinate system 22 may now be determined from the transformation parameter(s) during stage S86.

In one embodiment of stages 84 and 86, particularly for embodiments of ripple pattern 50 having an arrangement of radial ripples of the same frequency, phase and amplitude, a pose of X-ray ripple marker 20 in the C-arm space is described by a rigid body transformation composed of a rotation R and a translation t. The rotation is parameterized using ZXZ Euler angles as in accordance with the following equation [1]:

$$R(\theta_{z1},\theta_x,\theta_{z2}) = R_z(\theta_{z1})R_x(\theta_x)R_z(\theta_{z2}) \quad [1]$$

where $R_z(\theta)$ is a rotation around z axis with angle $\theta$.

The translation vector t is composed of elementary displacements along axes as shown in the following equation [2]:

$$t(t_x, t_y, t_z) = \begin{pmatrix} t_x \\ t_y \\ t_z \end{pmatrix} \quad [2]$$

Any point $p^{Marker} \in R^3$ in marker space 21 or 22 may be converted in C-arm space (e.g., having focal spot 65 as an origin) in accordance with the following equation [3]:

$$p^{C-arm} = R(\theta_{z1},\theta_x,\theta_{z2})p^{Marker} + t(t_x,t_y,t_z) \quad [3]$$

Similarly, a position of any point in C-arm space— $p^{C-arm}$—can be translated in marker space 21 or 22 in accordance with the following equation [4]:

$$p^{Marker} = R(\theta_{z1},\theta_x,\theta_{z2})^T p^{C-arm} - R(\theta_{z1},\theta_x,\theta_{z2})^T t(t_x,t_y,t_z) \quad [4]$$

In a second embodiment of stages S84 and S86, particularly for embodiments of ripple pattern 50 having an arrangement of a first series radial ripples and a second series of radial ripples having a frequency, a phase and/or an amplitude dissimilar from the first series of radial ripples, a distance from the focal spot 65 to the fixed point of the X-ray ripple marker 20 may be determined from the dissimilar frequencies, dissimilar phases and/or dissimilar amplitudes as will be exemplary described in the present disclosure with the description of FIGS. 13-18B.

Still referring to FIG. 7, for the patient mode only, a stage S88 of flowchart 80 involves a removal of X-ray ripple marker 20 from X-ray image 65a (FIG. 5B) to render X-ray image 65b (FIG. 5B). In practice, any technique may be used to remove the X-ray ripple marker 20 in a manner that minimizes, if not impedes, artifacts and/or affect the illustration of the patient body part in a same spatial frequency ranges as X-ray ripple marker 20.

In one embodiment, a frequency-based filtering technique may be utilized during stage S88.

In a second embodiment, image subtraction technique may be utilized involving a transformation of a model of X-ray ripple marker 20 to an actual location and orientation of X-ray ripple marker 20 in the X-ray image 65a to thereby subtract the X-ray ripple marker in the X-ray image 65a with minimal effect on image quality as will be exemplary described in the present disclosure with the description of FIGS. 12A-12F.

Figure 8A:
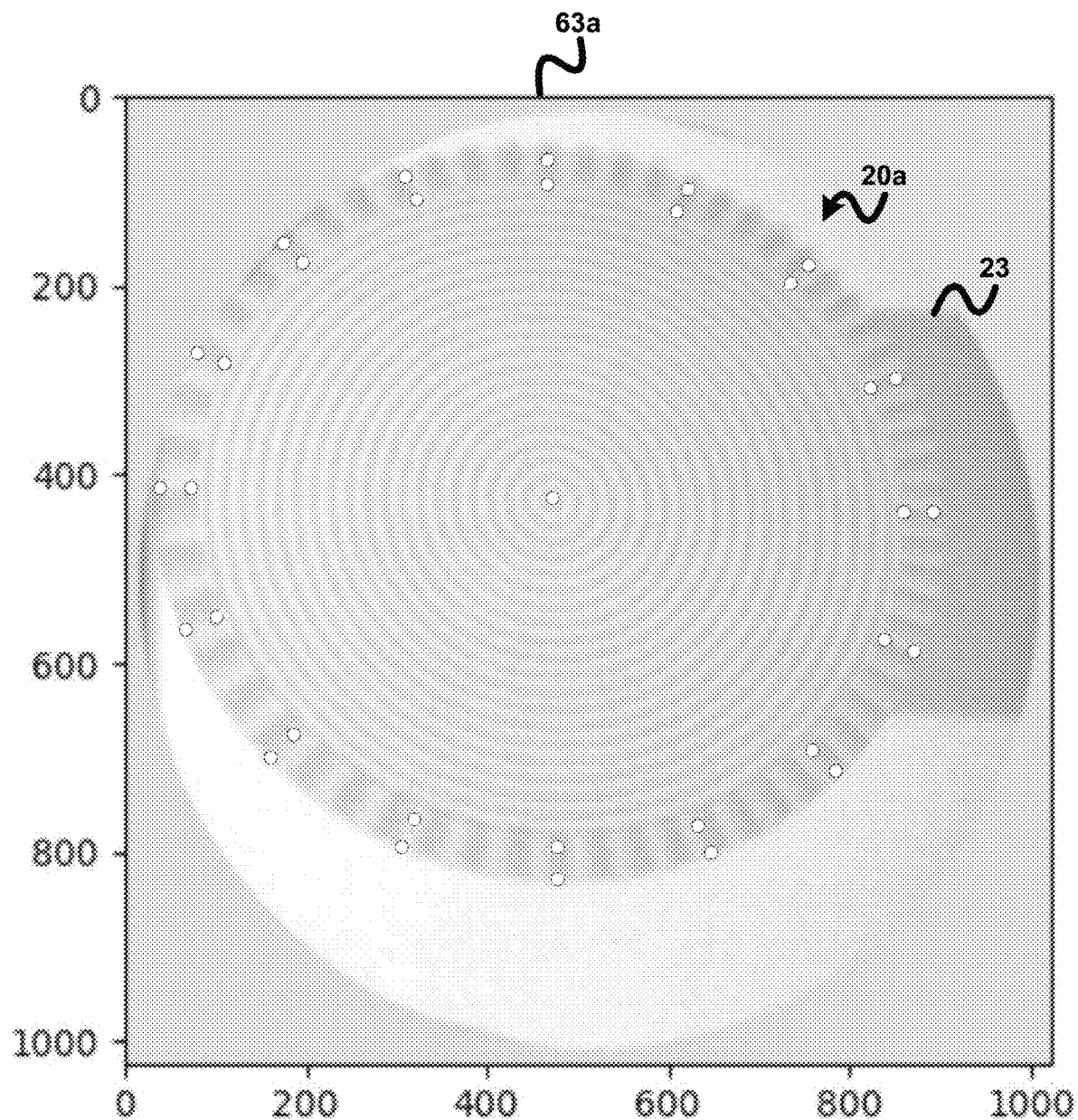
FIGS. 8A and 8B illustrate an exemplary sinusoidal signal transformation in accordance with various aspects of the present disclosure.

The following is a description of one embodiment of a patient mode of C-arm registration controller 70 (FIG. 5B) in the context of an X-ray image 63a of an X-ray ripple marker 20a being held by an arm 23 (e.g., a robot extension or C-arm extension) as shown in FIG. 8A. In practice, where the ripple pattern 50 of X-ray ripple marker 20a is passed through a perspective transformation, the pattern 50 will change into a chirp signal whereby the following equation [5] will become the following equation [6] whereby wave projection parameters $c_1$ and $c_2$ are a function of the perspective transformation parameters:

$$s(r) = A\exp(2\pi j f_m r) \quad [5]$$

$$s_p(r) = A_1 \exp\left(2\pi j f_m \frac{c_1 r}{1 + rc_2}\right) \quad [6]$$

where s(r) is the model sinusoidal pattern, A is the amplitude, $f_m$ is the frequency, and $s_p(s)$ is the projective geometry transformed pattern of s(r).

Figure 8B:
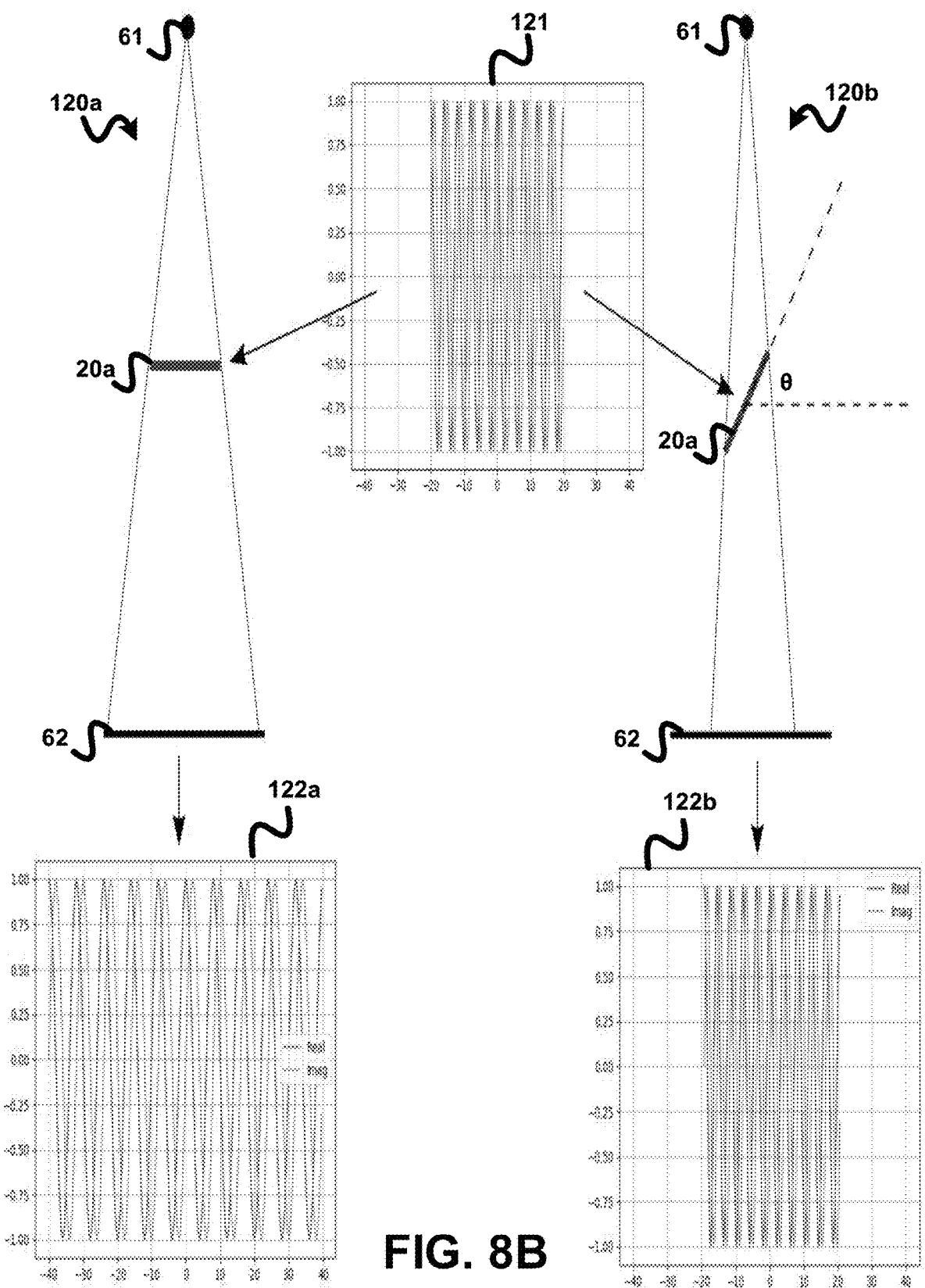

FIG. 8B shows the transformation of the sinusoidal signal of X-ray ripple marker 20 through a perspective projection. If the marker 20 is parallel with X-ray detector 62 and at a midpoint of an X-ray projection 120a as shown, then an original sinusoidal signal 121 of marker 20 is stretched into sinusoidal signal 122a whereby $c_1=0.5$ and $c_2=0.0$. If the marker 20 is tilted with respect to X-ray detector 62 and at a midpoint of an X-ray projection 120b as shown, the $c_2>0$, resulting in a chirp signal 122b (e.g., $c_1=1.0$ and $c_2=0.002$). Thus, the signal along each diagonal of the marker is transformed through the perspective transformation into wave projection parameters $c_1$ and $c_2$.

Figure 9:
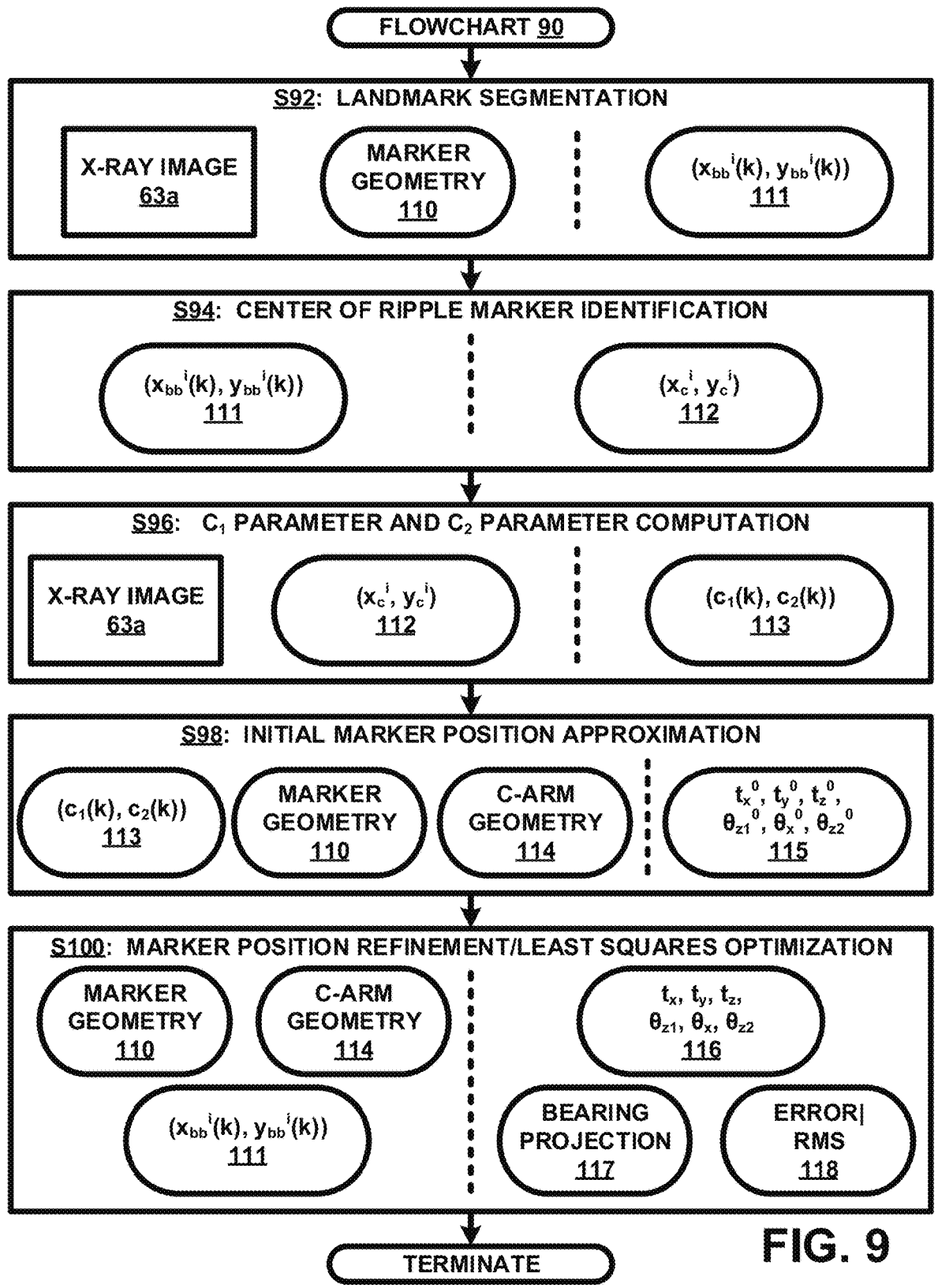
FIG. 9 illustrates a flowchart representative of a first exemplary embodiment of transformation parameter generation method in accordance with various aspects of the present disclosure.

FIG. 9 illustrates a flowchart 90 representative of a transformation generation method for X-ray ripple marker 20a shown in FIG. 8A.

Referring to FIG. 9, a stage S92 of flowchart 90 encompasses controller 70 processing an acquired X-ray image 63a and a stored marker geometry 110 to compute $(x_{bb}^i(k), y_{bb}^i(k))$ coordinates 111 for each ball bearing landmark of X-ray ripple marker 20a to thereby find $(x_c^i, y_c^i)$ coordinates 112 for the center point of X-ray ripple marker 20a during a stage S94 of flowchart 90.

A stage S96 of flowchart 90 encompasses controller 70 processing acquired X-ray image 63a and computed center point $(x_c^i, y_c^i)$ coordinates 112 to compute wave projection parameters $c_1$ and $c_2$.

A stage S98 of flowchart 90 encompasses controller 70 processing acquired X-ray image 63a, wave projection parameters $c_1$ and $c_2$ and stored marker geometry 110 and C-arm geometry to obtain an initial approximation of transformation parameters $(t_x^o, t_y^o, t_z^o, \Theta_x^o, \Theta_y^o, \Theta_z^o)$ 115.

A stage S100 of flowchart 90 encompasses controller 70 processing transformation parameters $(t_x^o, t_y^o, t_z^o, \Theta_x^o, \Theta_y^o, \Theta_z^o)$ 115, $(x_{bb}^i(k), y_{bb}^i(k))$ coordinates 111 for each ball bearing landmark and stored marker geometry 110 and C-arm geometry to obtain a refinement/least square optimization of transformation parameters $(t_x, t_y, t_z, \Theta_x, \Theta_y, \Theta_z)$ 116, bearing projection 117 and error/rms 118.

Figure 10A:
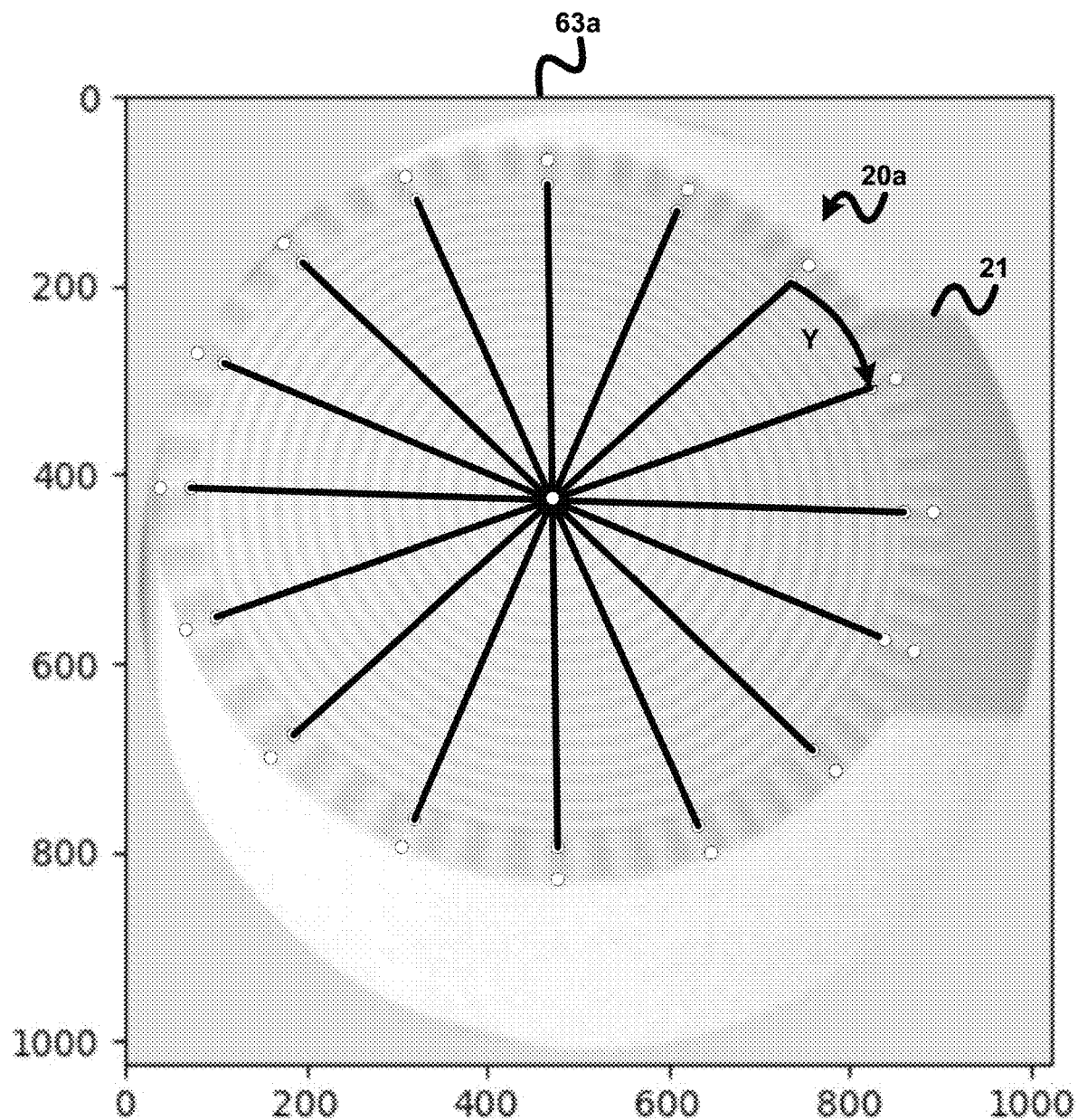
FIGS. 10A-10E illustrate an exemplary transformation parameter generation of FIG. 9 in accordance with various aspects of the present disclosure.

More particularly, in one embodiment of stages S92 and S94, a marker geometry 110 is such that a connection of the closet two (2) ball bearings defines lines that will intersect in the marker center as shown in FIG. 10A. Therefore, the projection of center of X-ray ripple marker 20a is identified by segmenting the BBs in the image 63a and grouping them to define rays as shown in FIG. 10A. The intersection of these rays defines the center of X-ray ripple marker 20a in image space.

The center of the ball bearings is computed using simple thresholding or more advanced algorithms, such as, for example, adaptive thresholding or Otsu thresholding. The ball bearing pairs are formed by simple clustering since the radial neighbor which is of interest is much closer than the lateral ones. After segmentation, blobs that are too small or too large are filtered out. Then, the intersection of the rays is computed using a linear least squares approach.

Figure 10B:
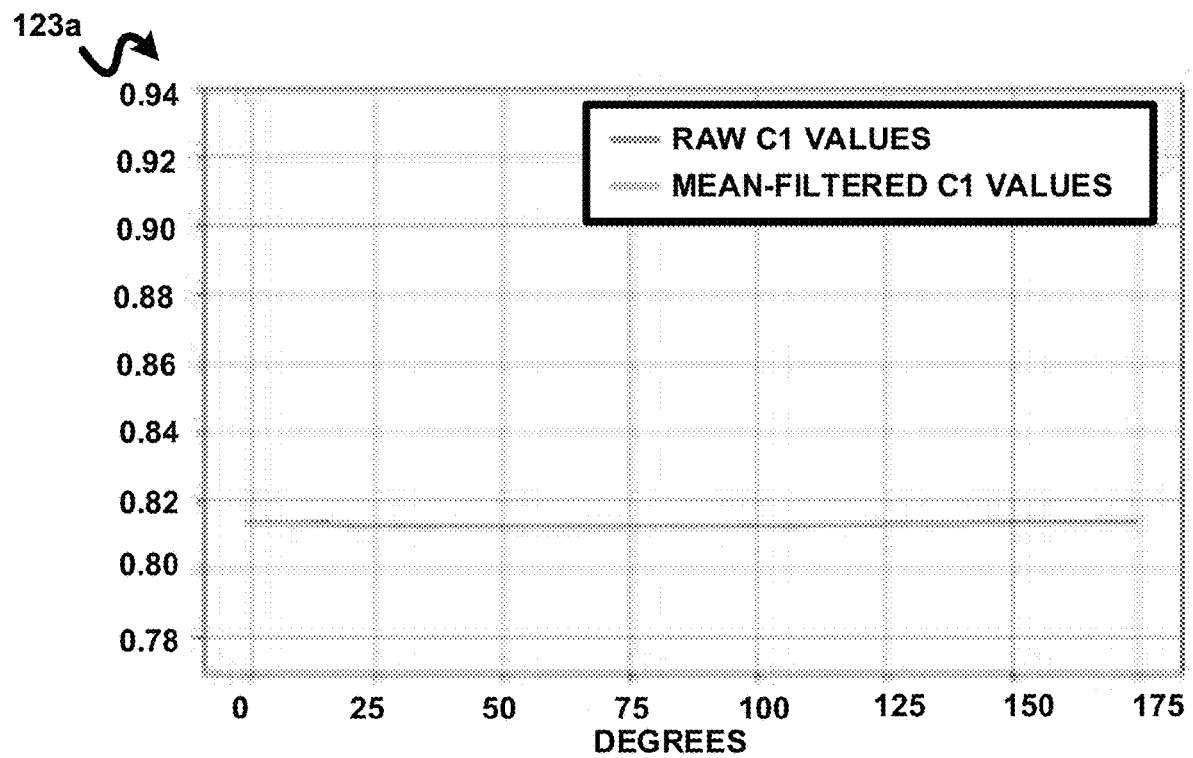
Figure 10C:
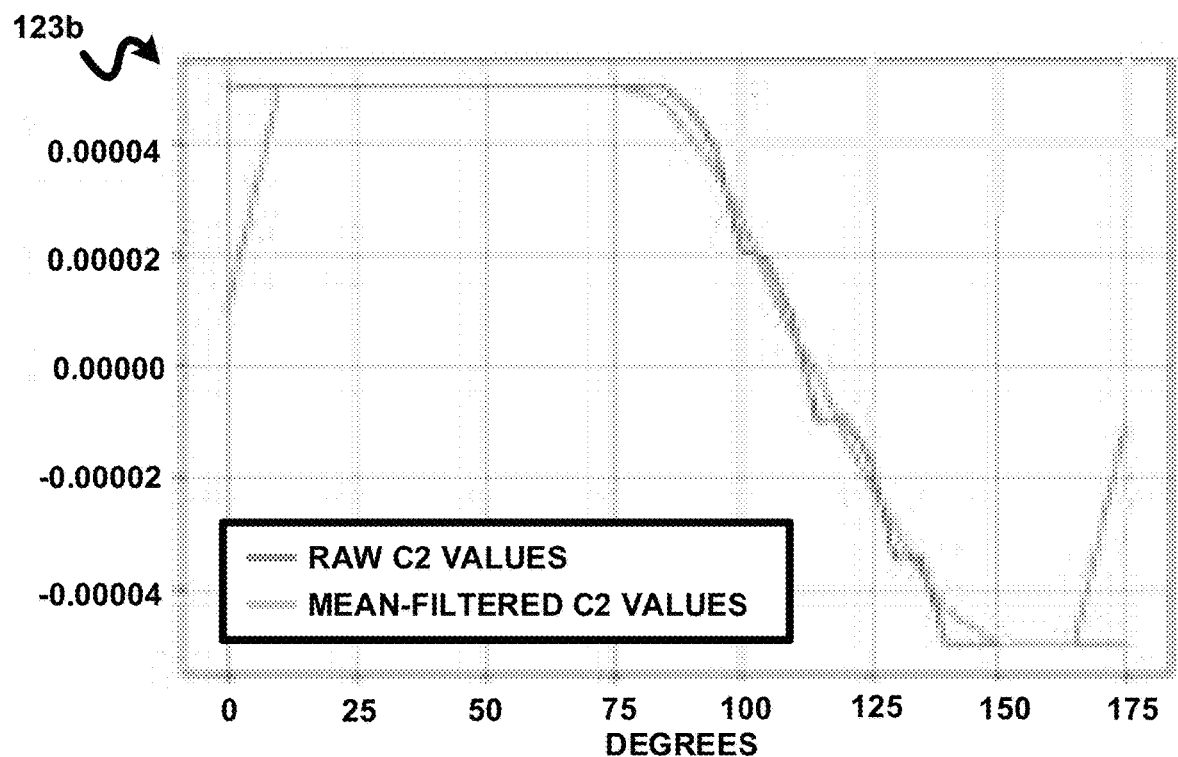
Figure 10D:
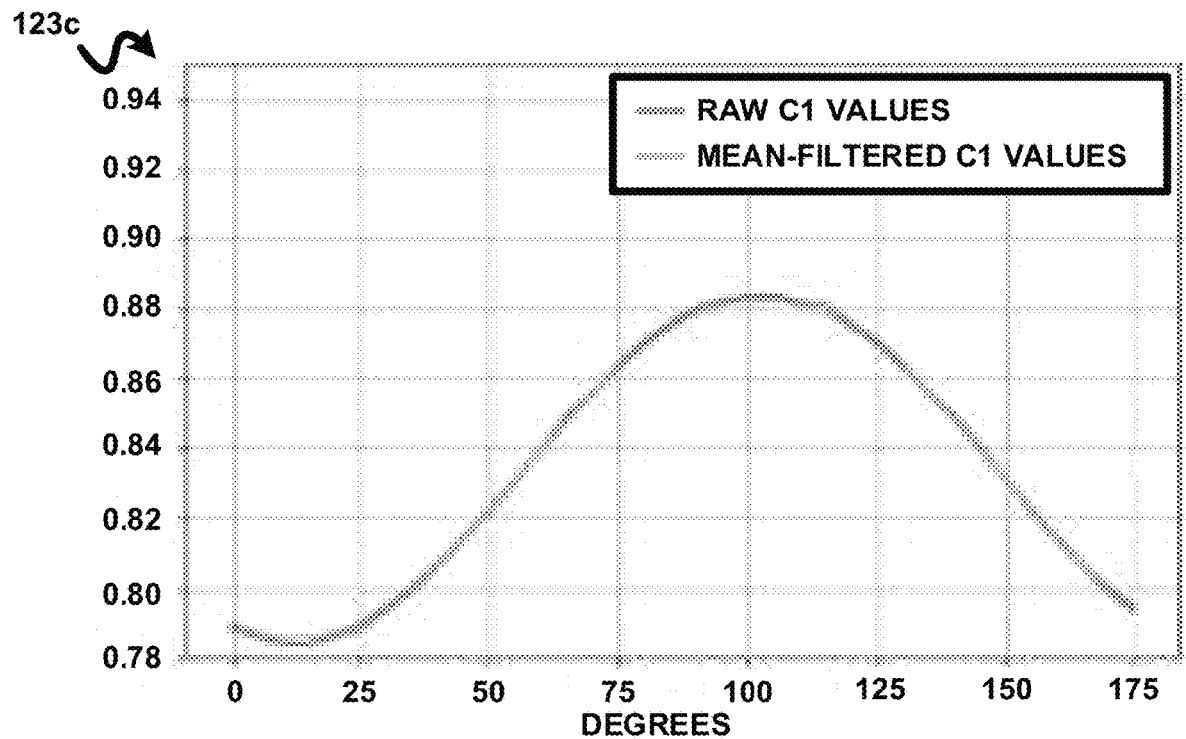
Figure 10E:
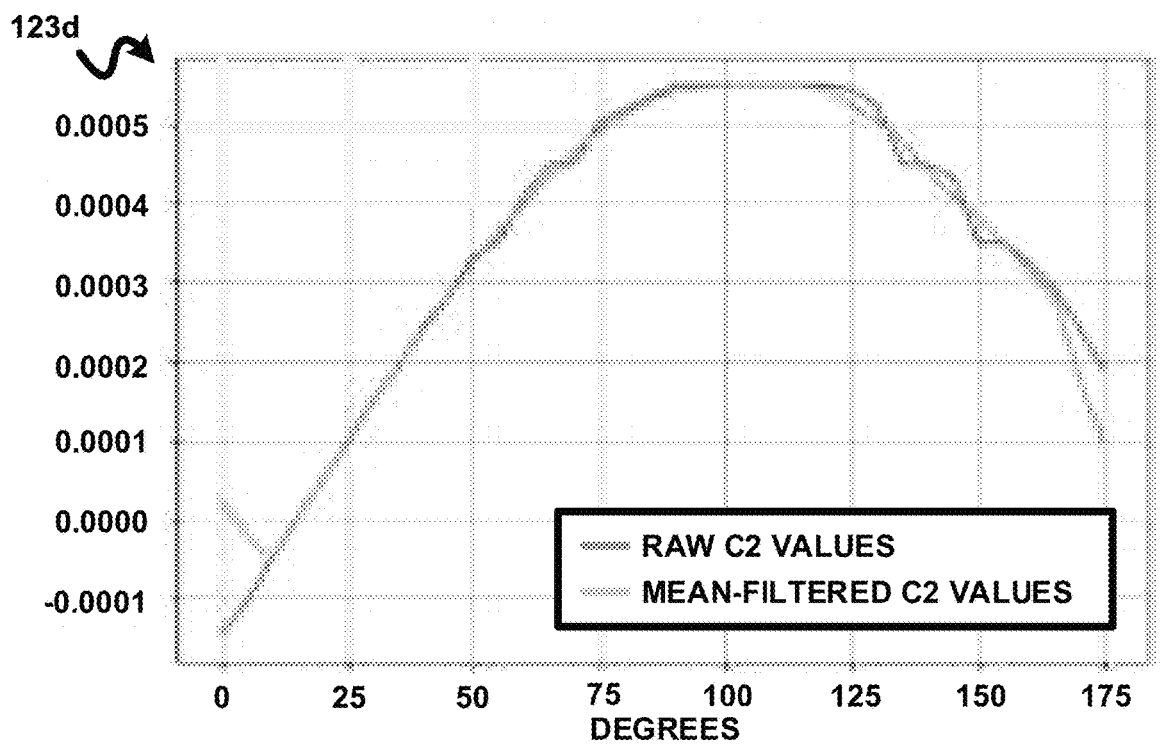

In one embodiment of stage S96, FIG. 10B illustrates a plot 123a of wave projection parameter $c_1$ and FIG. 10C illustrates a plot 123b of wave projection parameter $c_2$ for two marker positions for X-ray ripple marker 20a being parallel with X-ray detector 62 and at a midpoint of an X-ray projection 120a as shown in FIG. 8B. FIG. 10D illustrates a plot 123c of wave projection parameter $c_1$ and FIG. 10E illustrates a plot 123d of wave projection parameter $c_2$ for X-ray ripple marker 20a is tilted with respect to X-ray detector 62 and at a midpoint of an X-ray projection 120b as shown in FIG. 8B. The computation of wave projection parameters $c_1$ and $c_2$ for a diagonal is performed by maximizing the convolution of the image signal along that diagonal with the chirp signal windowed with a Gaussian function.

In one embodiment of stage S98, $c_1$, $c_2$, and a range of $\gamma$ values are then used to compute the position of X-ray ripple marker 20a down to the twist around the axis of the X-ray ripple marker 20a. An initial approximation of the marker position in the image space comprises five (5) degrees of freedom computed from wave projection parameters $c_1$ and $c_2$ and one (1) degree of freedom which is twisted around z axis angle $\Theta_{z2}$. The angle $\Theta_{z2}$ is the one that maximizes the normalized cross correlation between the image signal retrieved at the coordinates corresponding to the projection of the rim chirp using the 5DOF initial position approximation and y twist angle and the model chirp pattern in accordance with the following equation [7]:

$$Twist_{chirp}(\gamma) = 40 * \gamma * \left(1.0 + \frac{\gamma}{2*\pi}\right) \quad [7]$$

FIG. 11A shows a registration verification after an initial approximation whereby a computed position 125a of marker 20a is very close to a true position 125b of marker 20a due to an error in the twist.

In one embodiment of stage S100, the computed position is optimized using a least squares approach. For each ball bearing identified in the image, $b_i$; i=1 . . . n, a model corresponding to position $b^m i$; i=1 . . . n is computed and subsequently, using the approximate parameters $t_x$, $t_y$, $t_z$, $\Theta_{z1}$, $\Theta_x$, $\Theta_{z2}$ and C-arm geometry 115, virtual projections are computed in accordance with the following equations [8] and [9]:

$$b_i^{C-arm} = R_Z(\theta_{Z1})R_Z(\theta_x)R_Z(\theta_{Z2})b_i^m + (t_x t_y t_z)^T \equiv \begin{pmatrix} bx_i^{C-arm} \\ by_i^{C-arm} \\ bz_i^{C-arm} \end{pmatrix}; \quad [8]$$

$$i = 1 \ldots n$$

$$\tilde{b}_i = \begin{pmatrix} psz_x * x_s \\ psz_y * y_s \end{pmatrix} + \frac{z_s}{z_s - bz_i^{C-arm}} * \begin{pmatrix} psz_x * bx_i^{C-arm} \\ psz_y * by_i^{C-arm} \end{pmatrix}; i = 1 \ldots n \quad [9]$$

where $(x_s, y_s, z_s)^T$ is the position of the source 61 with respect to the detector 62 coordinate system, and $psz_x$ and $psz_y$ are the pixel sizes in x and y directions. It is assumed that the detector coordinate system coincides with the image coordinate system with only a difference in pixel size.

A cost function may then represented in accordance with the following equation [10]:

$$C(t_x,t_y,t_z,\theta_{z1},\theta_x,t\theta_{z2}) = \Sigma_{i=1}^n \|b_i - \tilde{b}_i\|_2^2 \quad [10]$$

The cost function is minimized using a "Nelder-Mead" algorithm.

FIG. 11B shows a registration verification after final optimization whereby a computed position 125c of marker 20a corresponds to true position 125b of marker 20a.

Figure 12A:
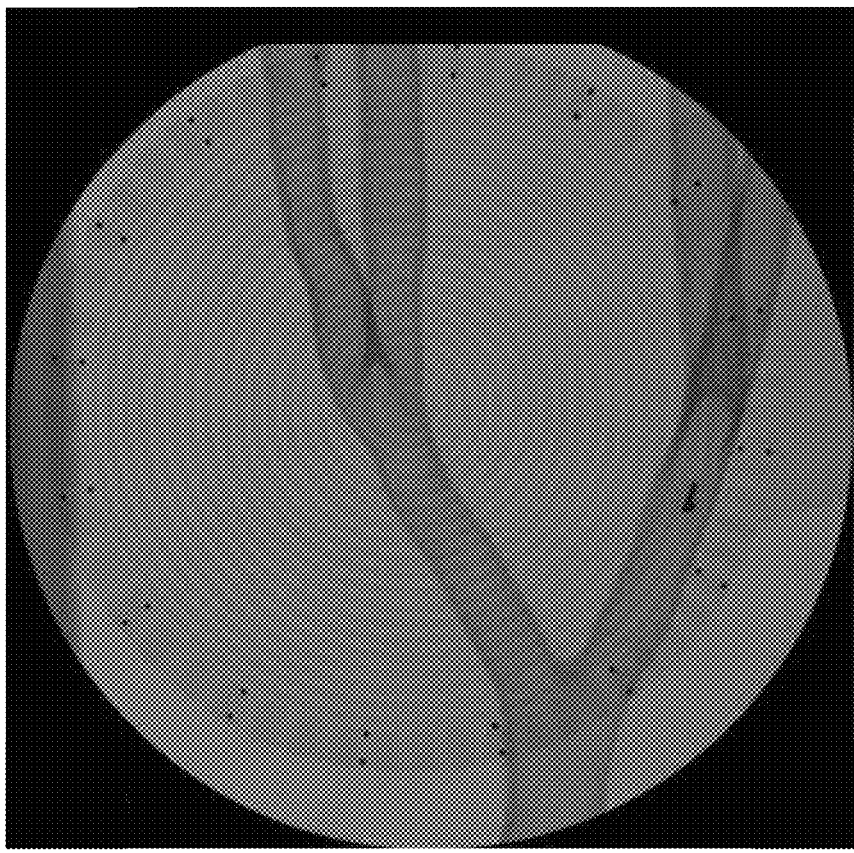
FIGS. 12A-12F illustrate an exemplary X-ray ripple marker image subtraction of FIG. 7 in accordance with various aspects of the present disclosure.
Figure 12B:
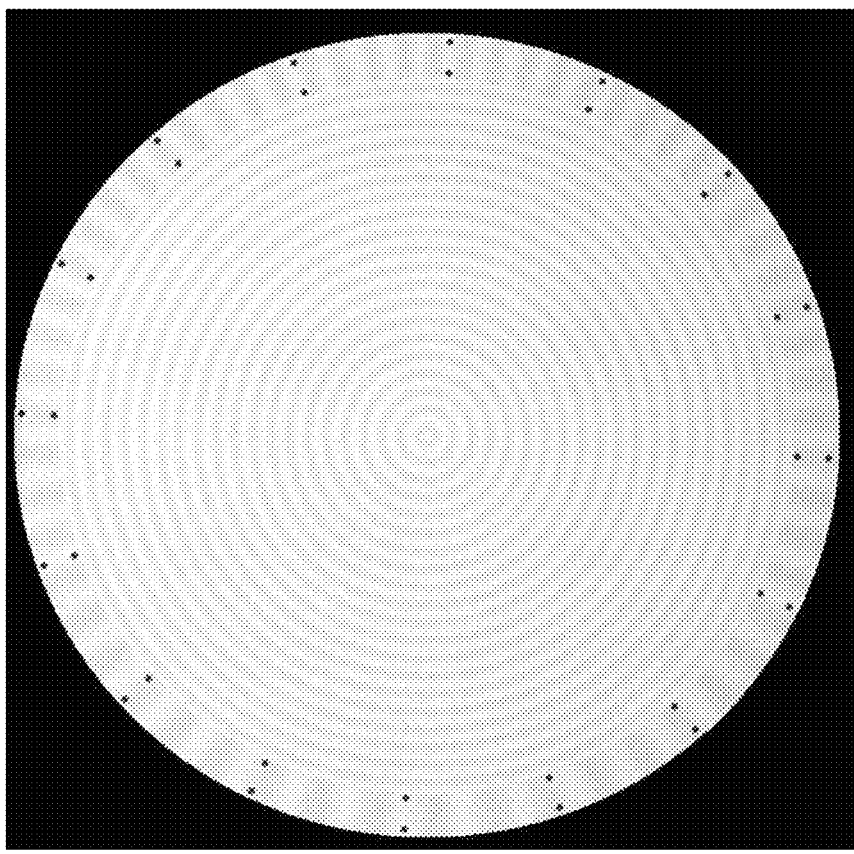
Figure 12C:
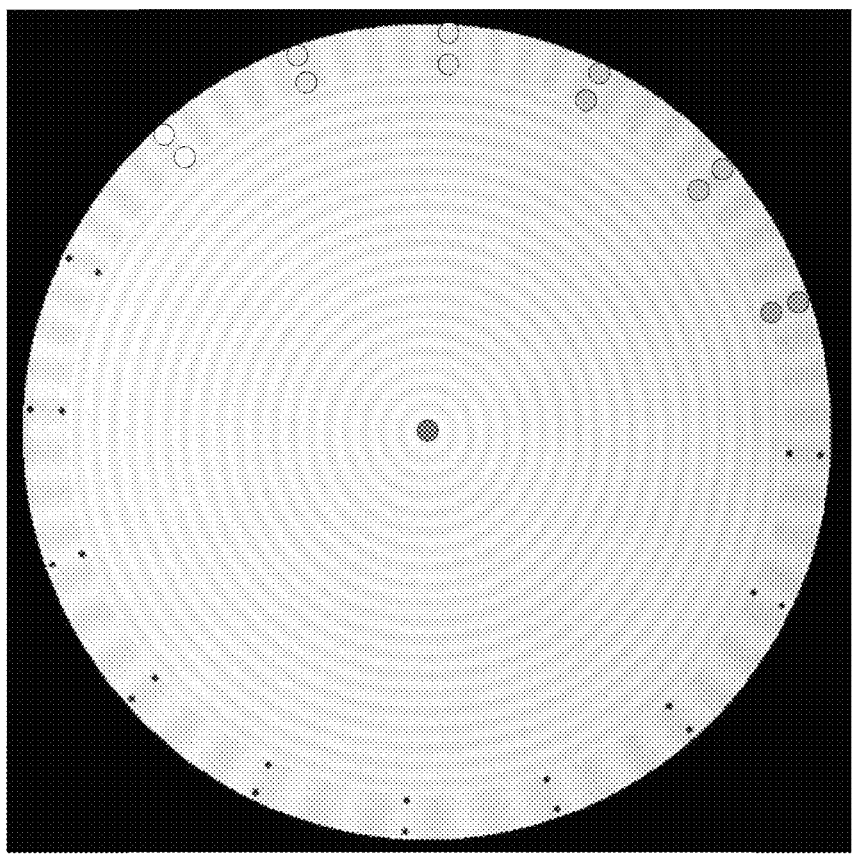

Referring back to FIG. 7, a subtraction embodiment of stage S88 for a patient image 65a of X-ripple marker 20a as shown in FIG. 12A utilizes a pre-acquired image 126a of X-ray image marker 20a alone in the field of view as shown in FIG. 12B, which will be referred to as the marker model. Additional interventional images can then be acquired that contain all or part of the marker at a variety of orientations. The marker model 20a is matched to an interventional image (e.g., interventional image 65a) using a point-to-point homographic transform based on the location of the ball bearings (for example, in OpenCV: cv2.findHomography ((Pts$_{model}$),(Pts$_{image}$))). Ball bearings were used for the point-to-point transform in this case because ball bearings are clear fiducials in each image, although any other points on the marker could be used instead of the ball bearings. In order to match the correct corresponding pairs of ball bearings in the marker model 126a with those in the interventional image 65a, the ball bearings are detected in order radially starting from the x-axis of the marker model 126b as shown in FIG. 12C.

Figure 12D:
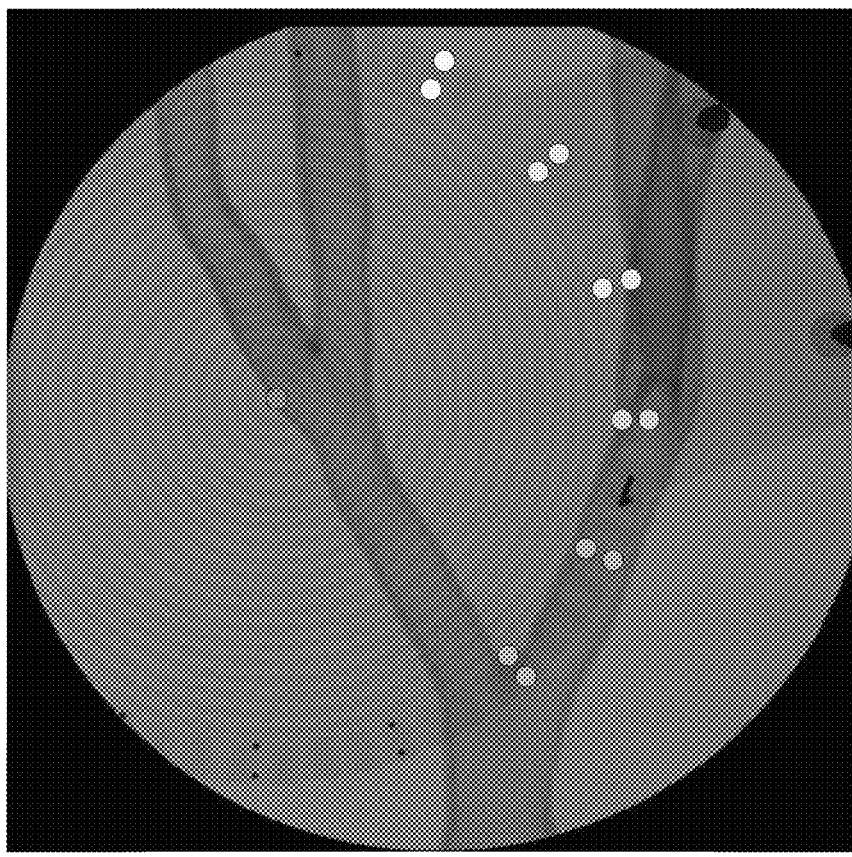
Figure 12E:
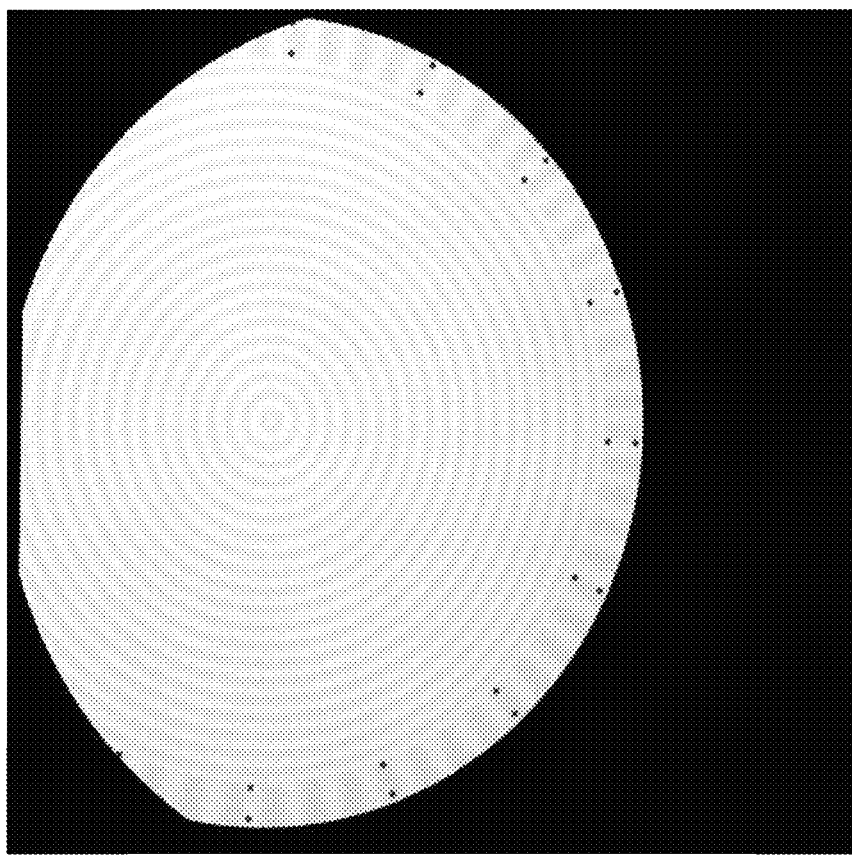
Figure 12F:
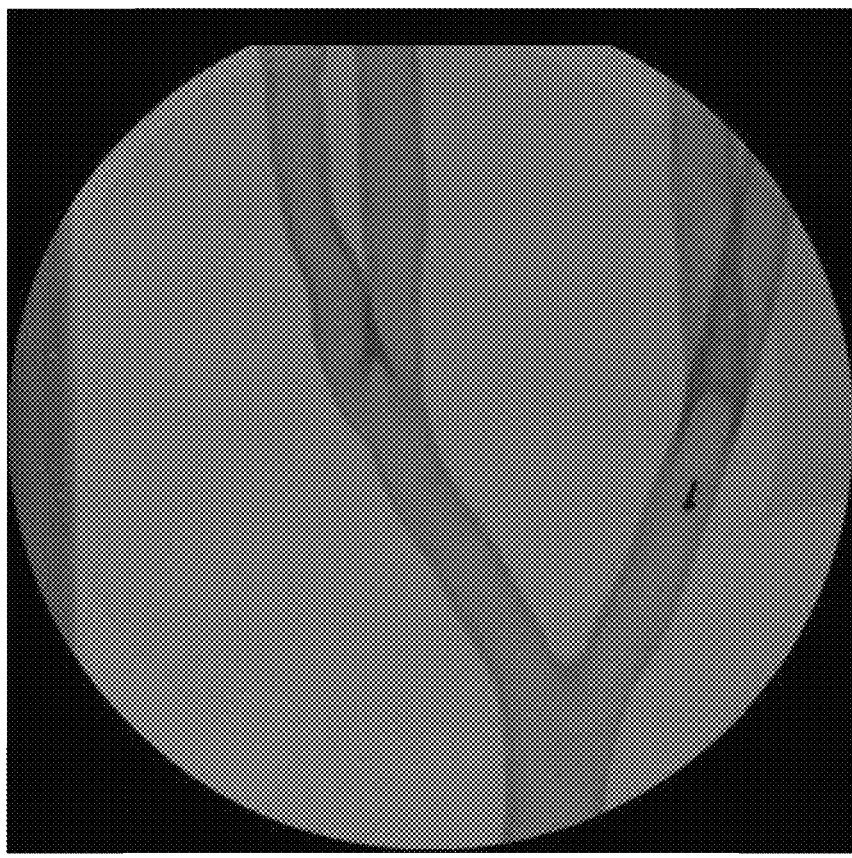

Once the point-to-point homographic transform has been applied to the marker model 126b to provide a rough registration 65c of FIG. 12D to the interventional marker in image space, the model alignment is fine-tuned using an enhanced correlation coefficient (ECC) optimization routine (e.g., iOpenCV: cv2.findTransformECC( )). Once optimal alignment between the marker model 126b and the image has been achieved, the aligned marker model 126c as shown in FIG. 12E is subtracted from the image to render image 65d of FIG. 12F, where the gray level of the subtracted model is optimized based on minimizing the power of the main frequency of the marker in the image. A uniform offset representing the mean gray level of the subtracted marker is added back into the image in the marker region.

The following Table I outlines the subtraction techniques

TABLE 1

| | Subtraction Technique |
|---|---|
| 1: | Compute model location in image space (Model) |
| 2: | Compute marker location in image space (Image) |
| 3: | Locate equivalent fiducial points in the model ($Pts_{image}$) and the image ($Pts_{model}$) |
| 4: | Compute point-to-point homographic transform ($Pts_{image} = T_{homography} * Pts_{model}$) |
| 5: | Transform model into marker space ($Model_{transformed} = T_{homography} * Model$) |
| 6: | Compute fine-tuned transformation ($T_{correlation}$) by optimizing image correlation |
| 7: | Make final model transform ($Model_{fineTuned} = T_{correlation} * Model_{transformed}$) |
| 8: | Subtract final model from image ($Image_{subtracted} = Image - Model_{finetuned}$) |
| 9: | Add mean value offset to subtracted marker region ($Image_{final} = Image_{subtracted} - Model_{mean}$) |

Figure 14:
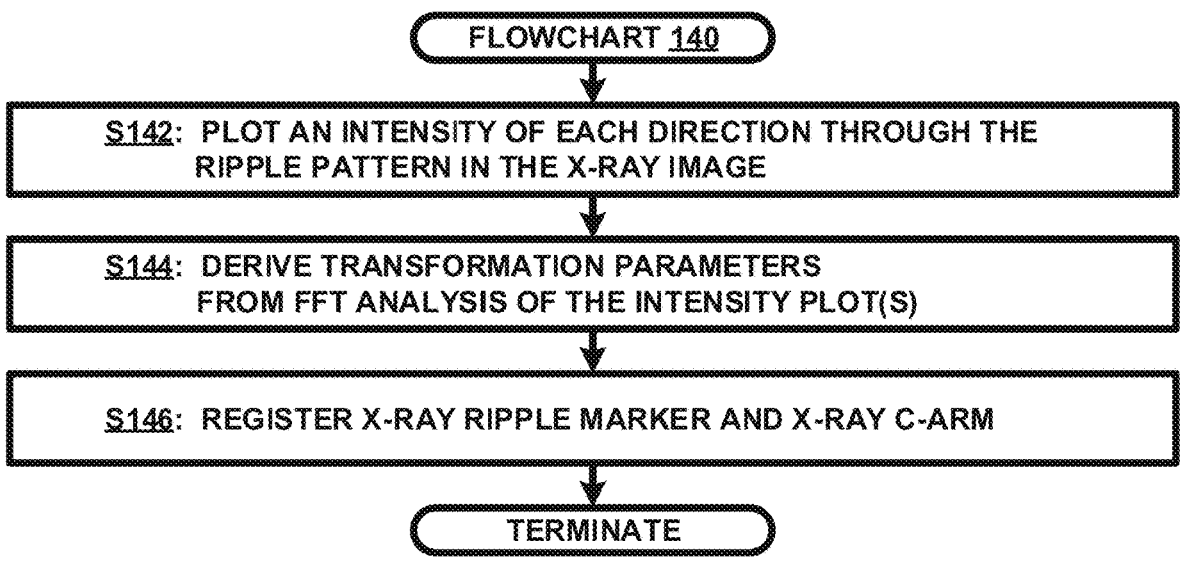
FIG. 14 illustrates a flowchart representative of a second exemplary embodiment of an C-arm registration of FIG. 5 in accordance with various aspects of the present disclosure.
Figure 15A:
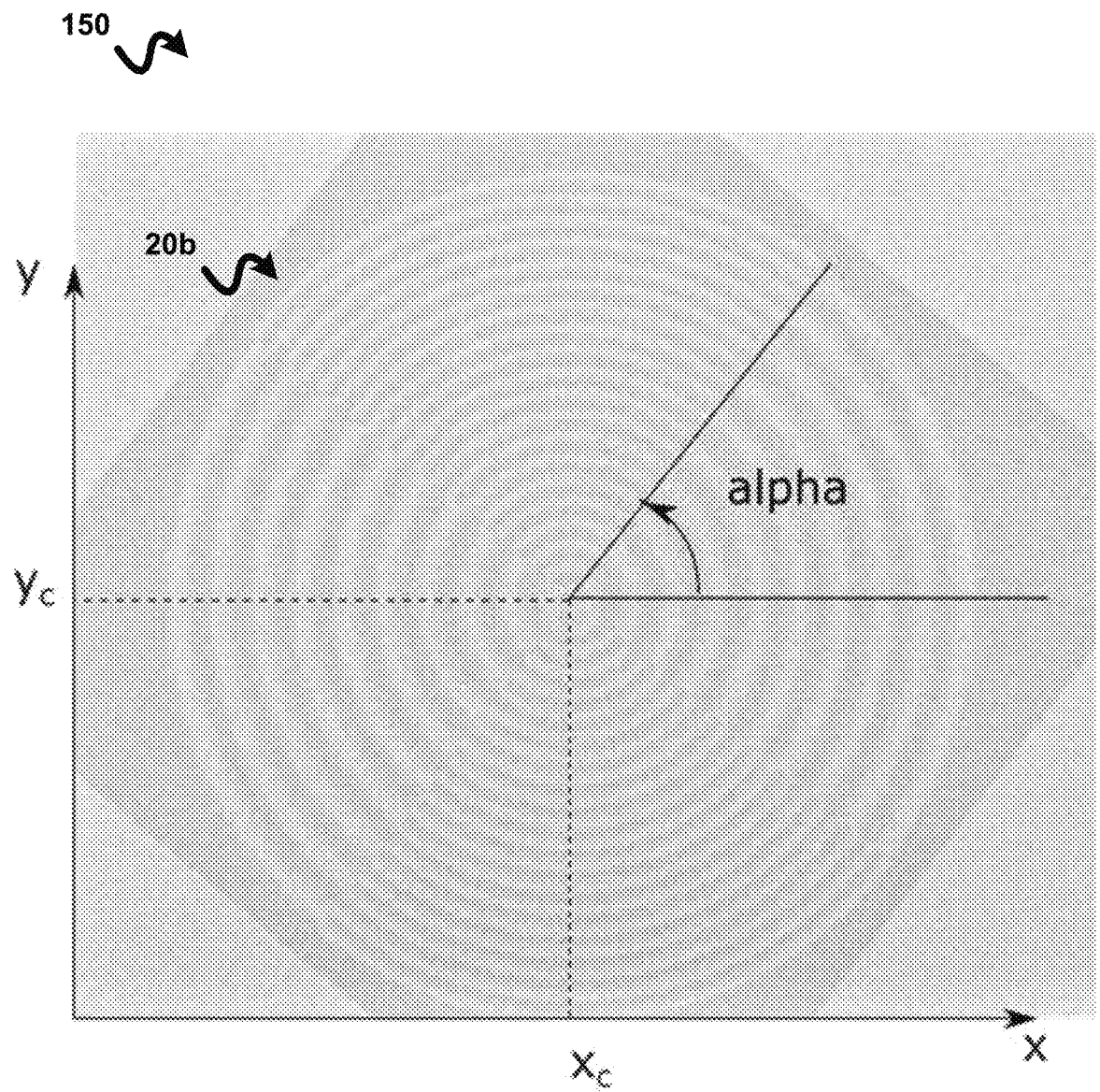
FIGS. 15A and 15B illustrate an exemplary C-arm registration in accordance with various aspects of the present disclosure.

FIG. 14 illustrates a flowchart 140 representative of a transformation generation method for X-ray ripple marker 20b shown in FIG. 15A.

Figure 13:
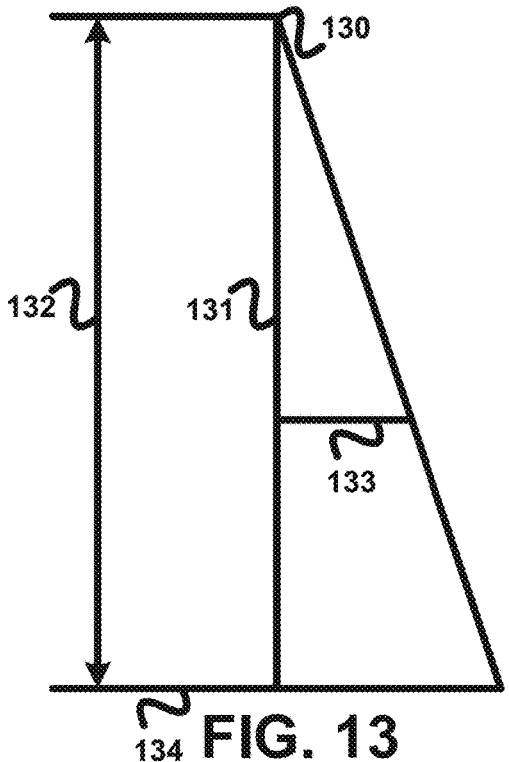
FIG. 13 illustrates an exemplary embodiment of the X-ray projection by a C-arm of FIG. 6 in accordance with the various aspects of the present disclosure.

More particularly to both the patient-less mode and the patient mode, as shown in FIG. 13, the C-arm to marker registration 71 involves projecting one period projecting through the perspective transformation of a distance 132 of an X-ray source 130 to an X-ray detector 134 into a distance 131 of X-ray source 130 to an X-ray ripple marker 133 in accordance with the following equation [11a]:

$$SM = SD \frac{T_M}{T_I} \quad [11a]$$

where SM is the distance 132 from X-ray source 130 to X-ray ripple marker 133, SD is the distance from X-ray source 130 to X-ray detector 134 (which is known from calibration or DICOM data), $T_M$ is the time period of the ripple pattern and Ti is image period (computed from image). Converting equation [11A] to frequencies yields the following equation [11b]:

$$SM = SD \frac{f_I}{f_{IM}} \quad [11b]$$

$f_M$ is the frequency of the known ripple pattern and $f_I$ is image frequency (computed from image).

Equation [11b] is for looking in one direction of the image. The following equation [11c] is for two directions suitable for X-ripple marker 20b (FIG. 15A):

$$SM = SD \left( \frac{f_H^I}{f_H^M} + \frac{f_L^I}{f_H^M} \right) \quad [11c]$$

where $f_H^M$ is the highest frequency of the known ripple pattern, $f_L^M$ is the highest frequency of the known ripple pattern, $f_H^I$ is highest image frequency (computed from image) and $f_L^I$ is lowest image frequency (computed from image).

In practice, more than two directions may be utilized. Also in practice, a simplest approach is by using fast Fourier transform (FFT) along lines going through the center of X-ray ripple marker 20b of FIG. 15A.

Referring to FIG. 14, a stage S142 of flowchart 140 encompasses controller 70 plotting an intensity of each direction through the ripple pattern of X-ray ripple marker 20b, and a stage S144 of flowchart 140 encompasses controller 70 deriving transformation parameter(s) from a FFT analysis of the intensity plot(s).

Figure 16A:
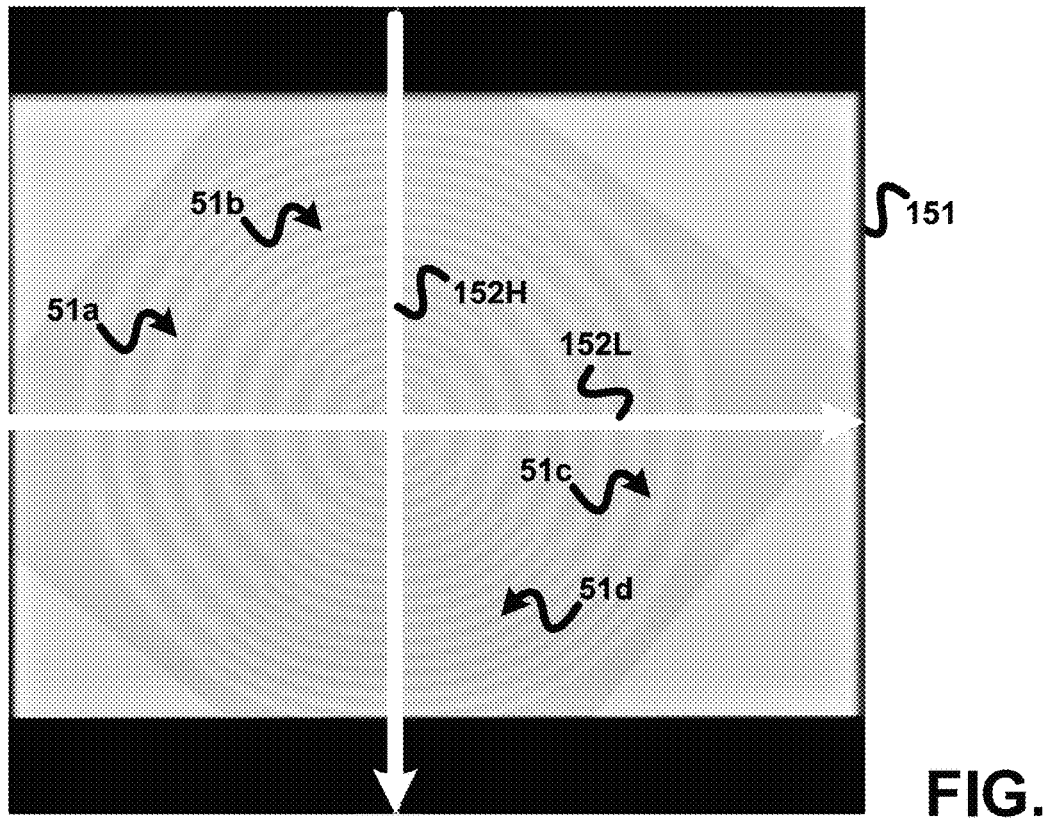

For example, FIG. 16A illustrates a scenario where the ripple pattern of X-ray ripple marker 20b is parallel with the X-ray detector at a first parallel position 151 with a line 152L traversing through low frequency radial ripple series 51a and low frequency radial ripple series 51c, and a line 152H traversing through high frequency radial ripple series 51b and high frequency radial ripple series 51d.

Figure 17A:
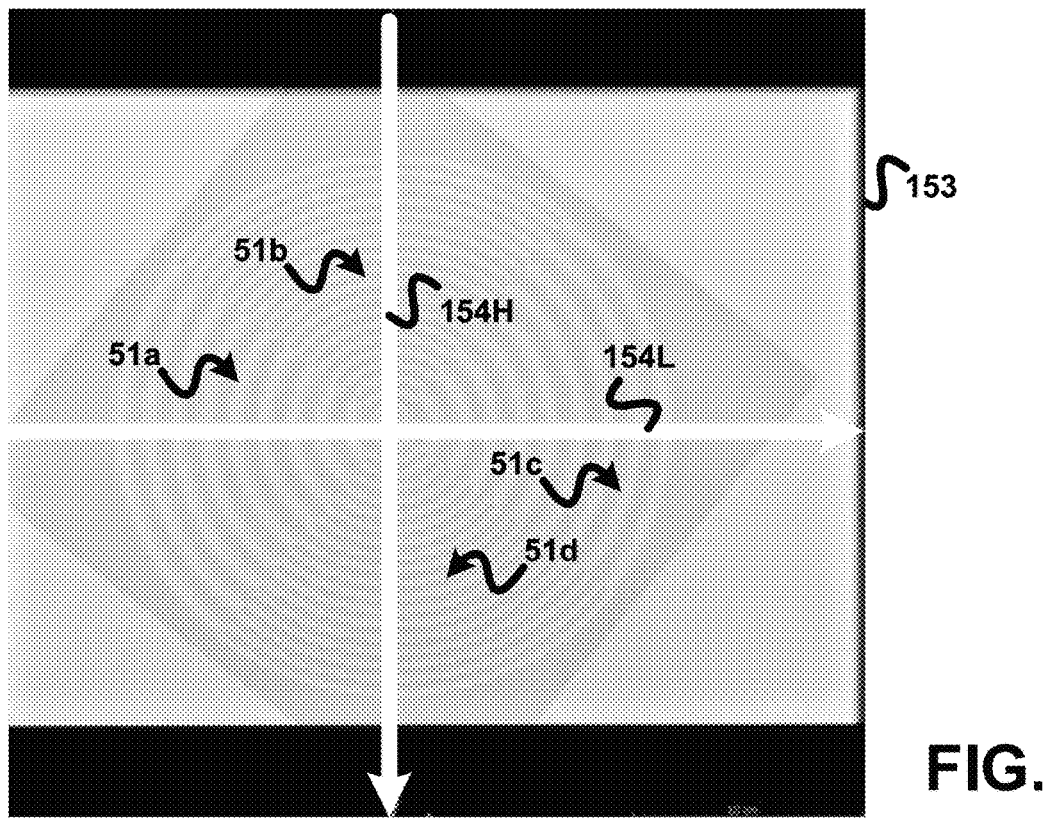

By further example, FIG. 17A illustrates a scenario where the ripple pattern of X-ray ripple marker 20b is parallel with the X-ray detector at a second parallel position 153 with a line 154L traversing through low frequency radial ripple series 51a and low frequency radial ripple series 51c, and a line 154H traversing through high frequency radial ripple series 51b and high frequency radial ripple series 51d.

For the first parallel position 151 (FIG. 16A) during stage S142, FIG. 16B shows an intensity plot 155L for low frequency radial ripple series 51a and low frequency radial ripple series 51c at the first position 151, and intensity plot 155H for high frequency radial ripple series 51b and high frequency radial ripple series 51d.

For the second parallel position 152 (FIG. 17A) during stage S142, FIG. 17B shows an intensity plot 156L for low frequency radial ripple series 51a and low frequency radial ripple series 51c at the first position 151, and intensity plot 156H for high frequency radial ripple series 51b and high frequency radial ripple series 51d.

Figure 15B:
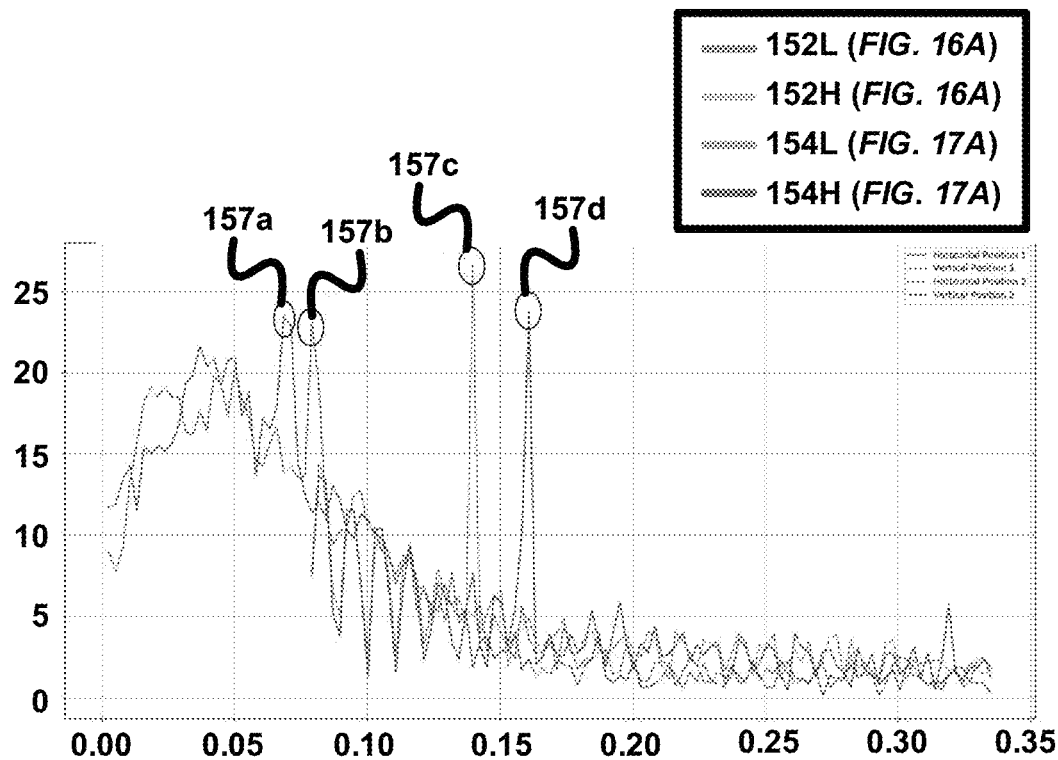

FIG. 15B shows a FFT analysis 157a of intensity plot 155L, a FFT analysis 157b of intensity plot 155H, a FFT analysis 157c of intensity plot 156L and a FFT analysis 157c of intensity plot 156H.

For the first position 151 of FIG. 16A, a peak of FFT analysis 157a is the lowest image frequency $f_L^I$ of equation [11c] and a peak of FFT analysis 157b is the highest image frequency $f_H^I$ of equation [11c].

For the second position 153 of FIG. 17A, a peak of FFT analysis 157c is the lowest image frequency $f_L^I$ of equation [11c] and a peak of FFT analysis 157d is the highest image frequency $f_H^I$ of equation [11c].

Referring back to FIG. 14, a stage S140 of flowchart S146 encompasses controller 70 registering X-ray ripple marker 20b and the X-ray C-arm.

In one embodiment of stage S140, xcd and ycd represent the center of the X-ray ripple marker 20b in detector coordinate system whereby the compute the translation of X-ray ripple marker 20b is computed in accordance with the following equations [12a]-[12c]:

$$tz = SD - SM \quad [12a]$$

$$tx = xcd * SD/SM \quad [12b]$$

$$ty = ycd * SD/SM \quad [12c]$$

By additional example illustrates a scenario where the ripple pattern of X-ray ripple marker 20b is titled with respect to the X-ray detector at a position 158 with a line 158L traversing through low frequency radial ripple series 51a and low frequency radial ripple series 51c, and a line 158H traversing through high frequency radial ripple series 51b and high frequency radial ripple series 51d.

Figure 18A:
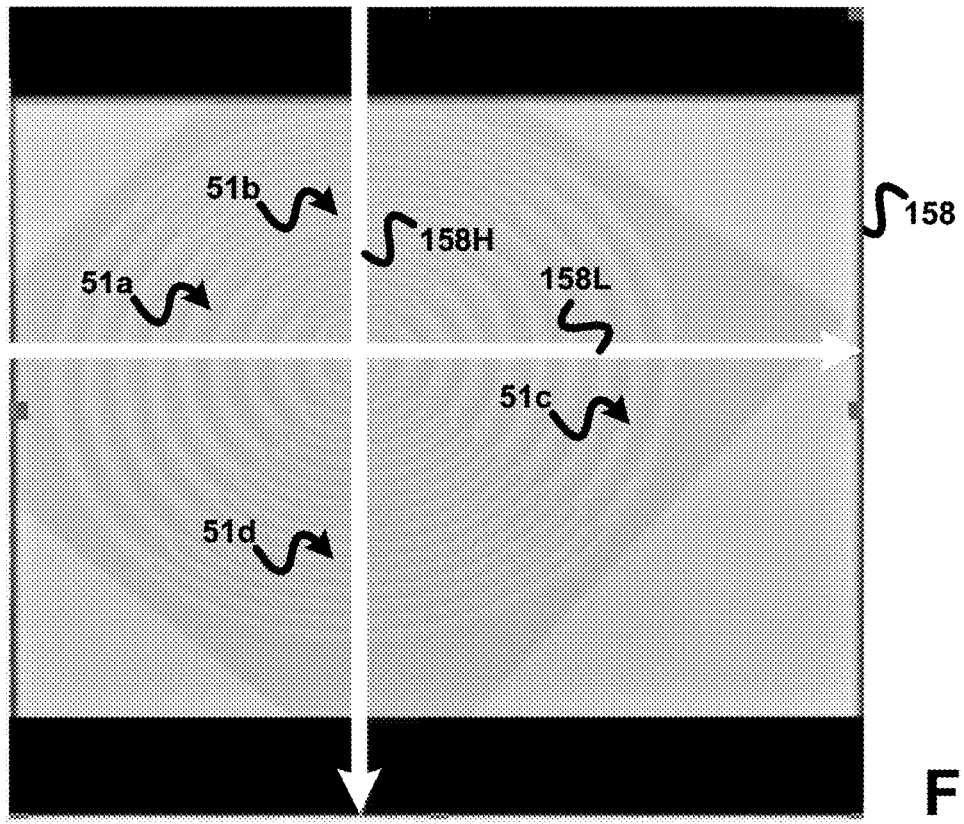
FIGS. 18A and 18B illustrate an exemplary C-arm registration of an X-ray ripple marker of FIG. 15A in a third position in accordance with various aspects of the present disclosure.
Figure 18B:
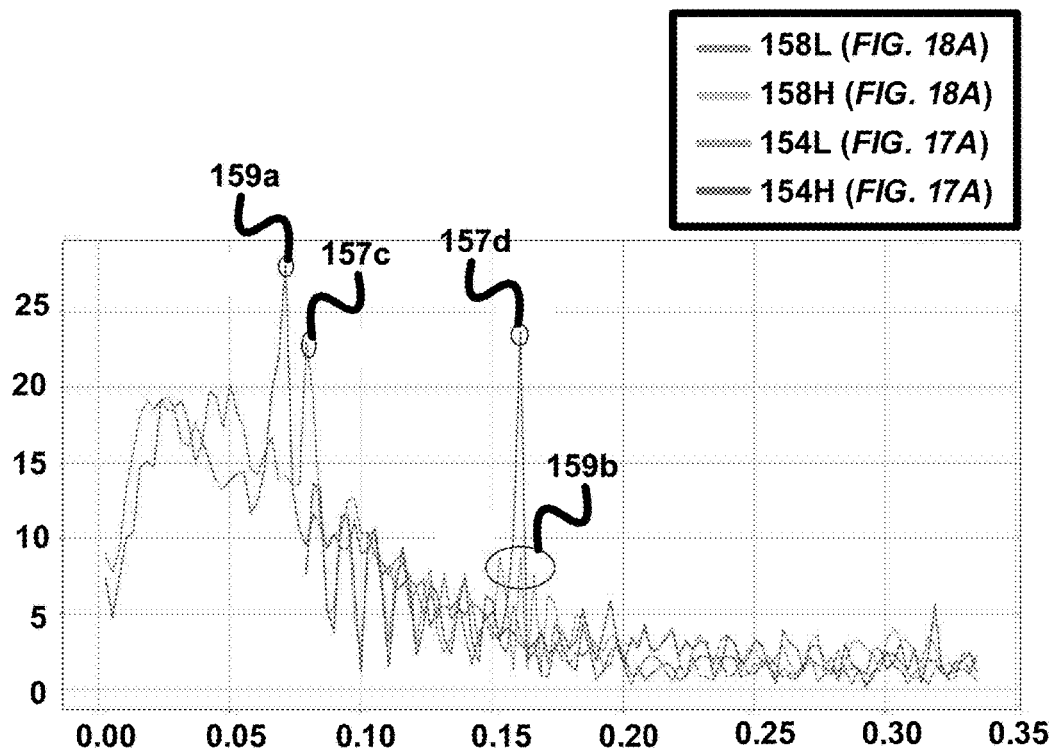

FIG. 18B shows a FFT analysis 159a of an intensity plot for line 158L and a FFT analysis 159b of an intensity plot for line 158H. The rotation axis of FFT analysis 159a is sharp as the rotation of the ripple pattern due to the tilt will not change the frequency of low frequency radial ripple series 51a and low frequency radial ripple series 51c, while the rotation axis of FFT analysis 159b is spread out as the rotation of the ripple pattern due to the tilt will change the frequency of high frequency radial ripple series 51b and high frequency radial ripple series 51d.

Figure 19:
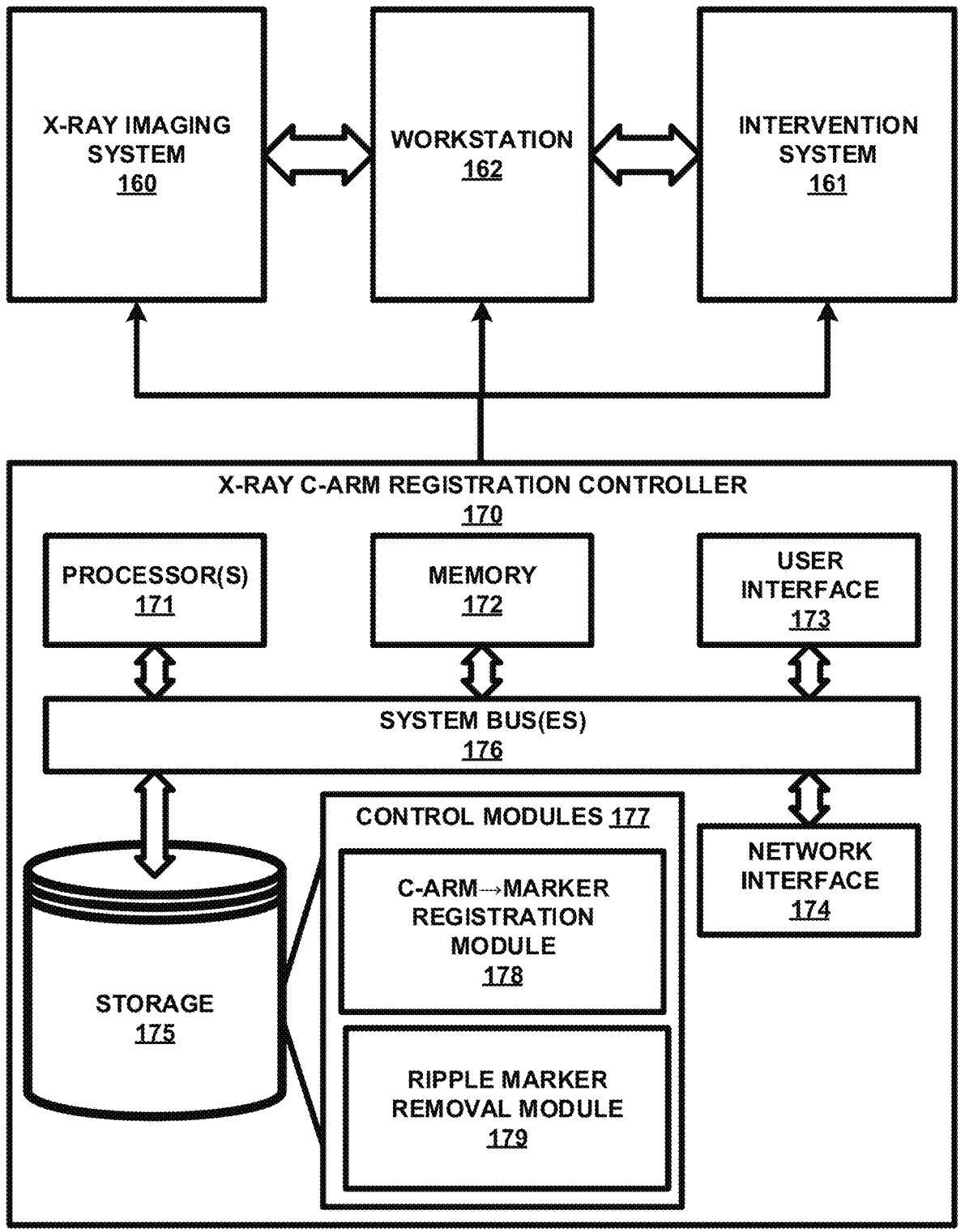
FIG. 19 illustrates an exemplary embodiment of a C-arm registration controller in accordance with various aspects of the present disclosure.

To facilitate a further understanding of the various inventions of the present disclosure, the following description of FIG. 19 teaches an exemplary embodiment of a C-arm registration controller of the present disclosure. From this description, those having ordinary skill in the art will appreciate how to apply various aspects of the present disclosure for making and using additional embodiments of C-arm registration controller of the present disclosure.

Referring to FIG. 19, a C-arm registration controller 170 includes one or more processor(s) 171, memory 172, a user interface 173, a network interface 174, and a storage 175 interconnected via one or more system buses 176.

Each processor 171 may be any hardware device, as known in the art of the present disclosure or hereinafter conceived, capable of executing instructions stored in memory 172 or storage or otherwise processing data. In a non-limiting example, the processor(s) 171 may include a microprocessor, field programmable gate array (FPGA), application-specific integrated circuit (ASIC), or other similar devices.

The memory 172 may include various memories, as known in the art of the present disclosure or hereinafter conceived, including, but not limited to, L1, L2, or L3 cache or system memory. In a non-limiting example, the memory 172 may include static random access memory (SRAM), dynamic RAM (DRAM), flash memory, read only memory (ROM), or other similar memory devices.

The user interface 173 may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface 174.

The network interface 174 may include one or more devices, as known in the art of the present disclosure or hereinafter conceived, for enabling communication with other hardware devices. In a non-limiting example, the network interface 174 may include a network interface card (NIC) configured to communicate according to the Ethernet protocol. Additionally, the network interface 174 may implement a TCP/IP stack for communication according to the TCP/IP protocols. Various alternative or additional hardware or configurations for the network interface 174 will be apparent.

The storage 175 may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage 175 may store instructions for execution by the processor(s) 171 or data upon with the processor(s) 171 may operate. For example, the storage 175 may store a base operating system for controlling various basic operations of the hardware. The storage 175 also stores application modules in the form of executable software/firmware for implementing the various functions of the controller 170a as previously described in the present disclosure including, but not limited to, a C-arm to marker registration module 178 and a ripple marker removal module 179 as previously described in the present disclosure.

In practice, controller 170 may be installed within an X-ray imaging system 160, an intervention system 161 (e.g., an intervention robot system), or a stand-alone workstation 162 in communication with X-ray imaging system 160 and/or intervention system 161 (e.g., a client workstation or a mobile device like a tablet). Alternatively, components of controller 170 may be distributed among X-ray imaging system 160, intervention system 161 and/or stand-alone workstation 162.

Figure 20:
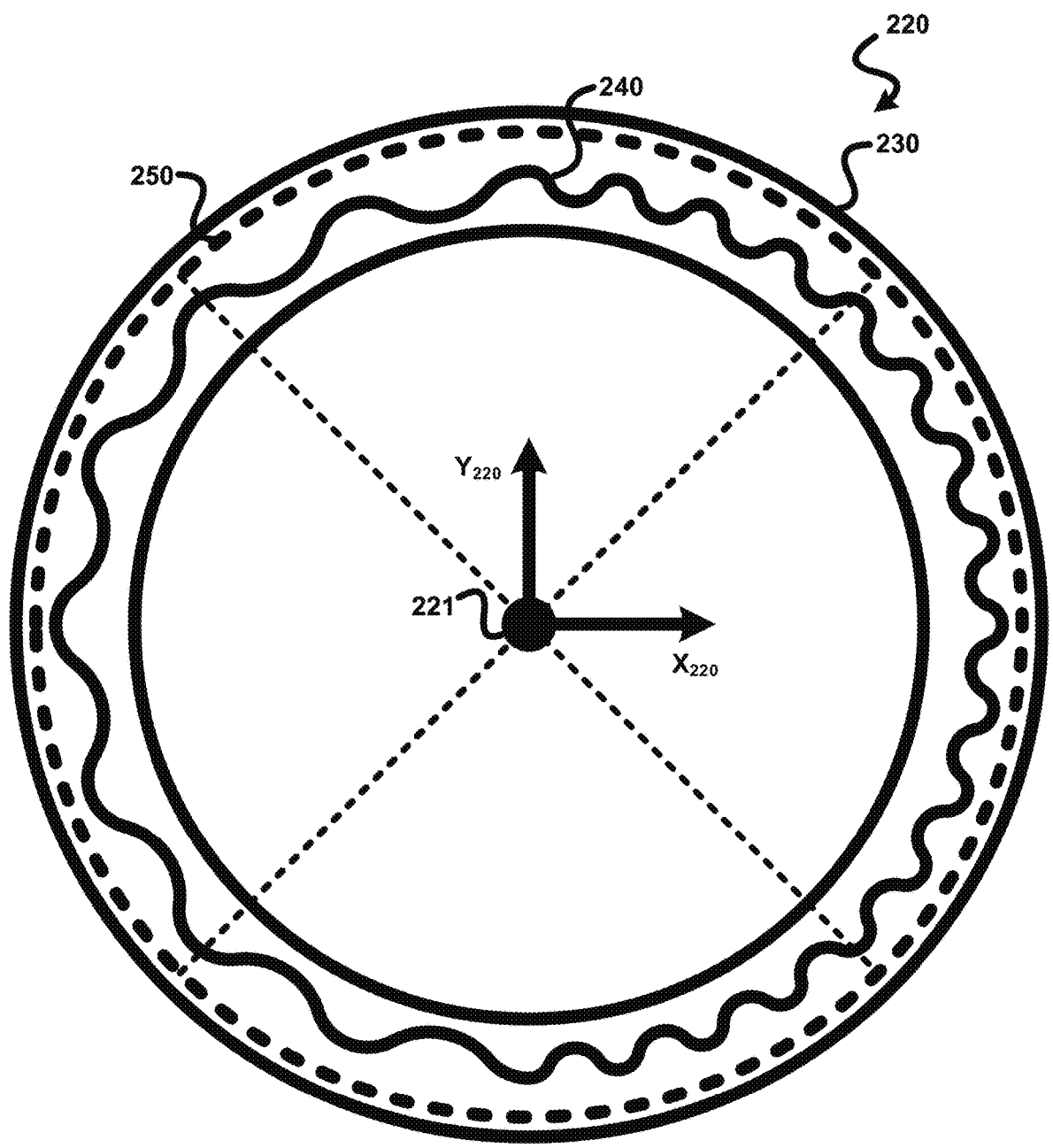
FIG. 20 illustrates an exemplary embodiment of a X-ray ring marker in accordance with various aspects of the present disclosure.

To facilitate a further understanding of various inventive aspects of the present disclosure, the following description of FIGS. 20-29 teaches embodiments of a X-ray ring marker of the present disclosure. From this description, those having ordinary skill in the art will appreciate how to apply the various aspects of the present disclosure for making and using additional embodiments of X-ray ring markers of the present disclosure. Referring to FIG. 20, a X-ray ring marker 220 of the present disclosure employs a coaxial construction of a chirp ring 240 and a centric ring 250 onto an annular base 230.

In practice, annular base 230 may have any annular shape suitable for a registration of C-arm to X-ray ring marker 240 including, but not limited to a circular shape and an elliptical shape.

Also in practice, annular base 230 may be constructed from material that is partially or entirely X-ray imagable.

Chirp ring 240 is a X-ray imagable annular structure embodying a chirp signal symbolically shown as a varying frequency waveform encircling annular base 230.

In one embodiment of chirp ring 240, the chirp signal is embodied as a varying spatial annular arrangement of protrusions formed in annular base 230.

In a second embodiment of chirp ring 240, the chirp signal is embodied as a varying spatial annular arrangement of indentations formed in annular base 230.

In a third embodiment of chirp ring 240, the chirp signal is embodied as a varying spatial annular arrangement of X-ray imagable objects disposed permanently or transiently onto/into annular base 230 (e.g., cooper balls, brass balls, etc.).

In practice, the chirp signal may have any amplitude, starting frequency and frequency shift suitable for an encoding of a twist of X-ray ring marker 220 around a Z-axis (not shown) of a C-arm coordinate system as will be further described in the present disclosure.

Still referring to FIG. 20, centric ring 250 is a X-ray imagable annular spatial structure embodying center intersection points as symbolically shown as a dashed ring encircling annular base 230. The center intersection points define a center point 221 of X-ray ring marker 220 as symbolically shown by the dashed lines extending from centric ring 250 to center point 221.

In one embodiment of centric ring 250, the center intersection points are embodied as a symmetrical annular spatial arrangement of protrusions formed in annular base 230.

In a second embodiment of centric ring 250, the center intersection points are embodied as a symmetrical annular spatial arrangement of indentations formed in annular base 230.

In a third embodiment of a centric ring 250, the center intersection points are embodied as a symmetrical annular spatial arrangement of X-ray imagable objects disposed permanently or transiently disposed onto/into annular base 230 (e.g., cooper balls, brass balls, etc.).

In practice, centers of the chirp ring 240 and centric ring 250 are concentrically or eccentrically co-axially aligned along the Z-axis (not shown) of a coordinate system $X_{220}$-$Y_{220}$-$Z_{220}$ of X-ray ring marker 220 with center point 221 serving as on origin of coordinate system $X_{220}$-$Y_{220}$-$Z_{220}$.

Figure 21:
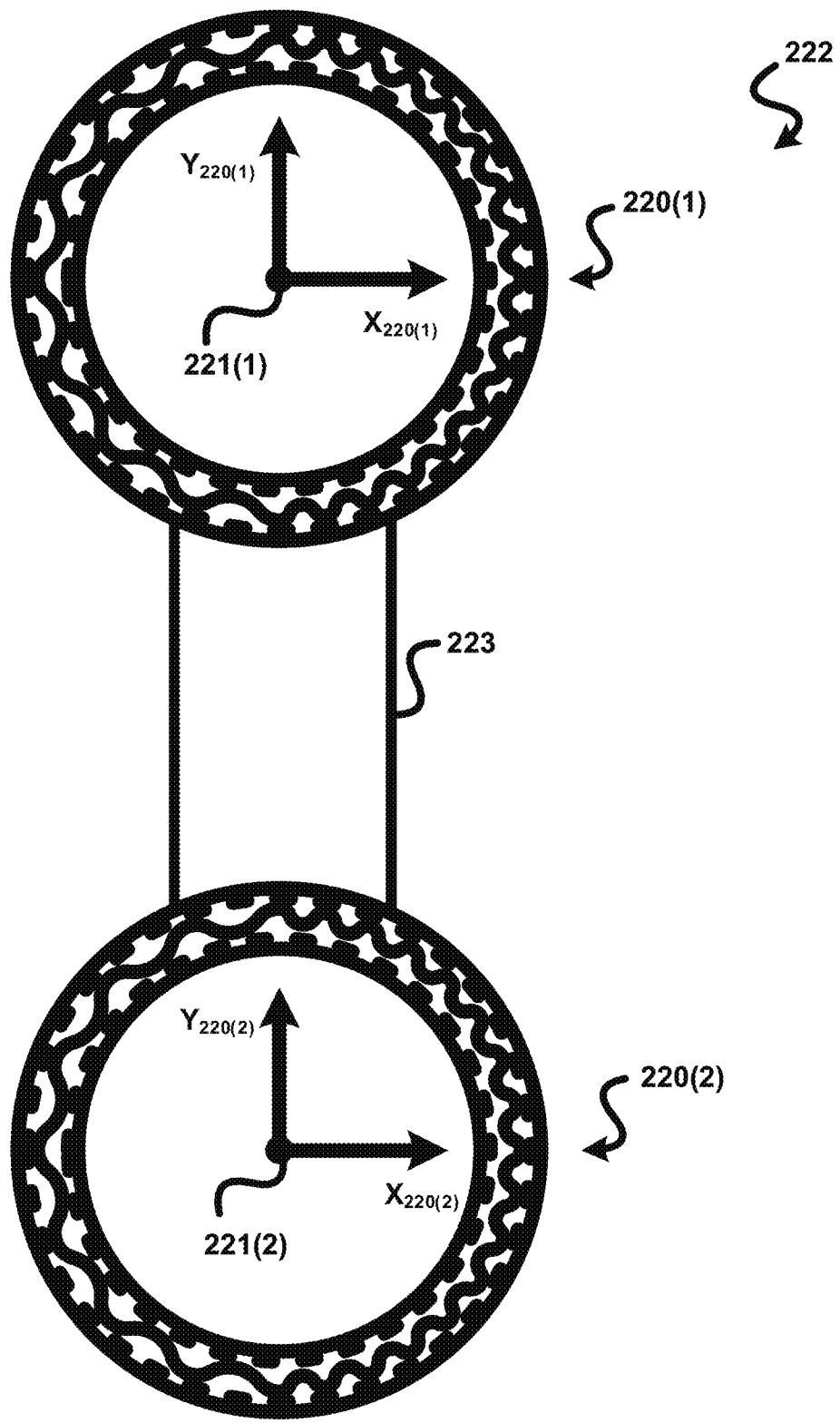
FIG. 21 illustrates an exemplary embodiment of a dual X-ray ring marker in accordance with various aspects of the present disclosure.

FIG. 21 illustrates a dual X-ray ring marker 222 of the present disclosure employing a pair of X-ray ring markers 220 of FIG. 20 of the present disclosure connected via a bridge 223. In practice, bridge 223 may be any shape suitable for a C-arm→X-ray ring marker registration involving a movement of C-arm from a baseline imaging pose to a target imaging pose as will be further described in the present disclosure, such as, for example, a prismatic shape of bridge 223 for establishing a co-planar alignment of the pair of X-ray ring markers 220 as shown in FIG. 21.

Figure 22A:
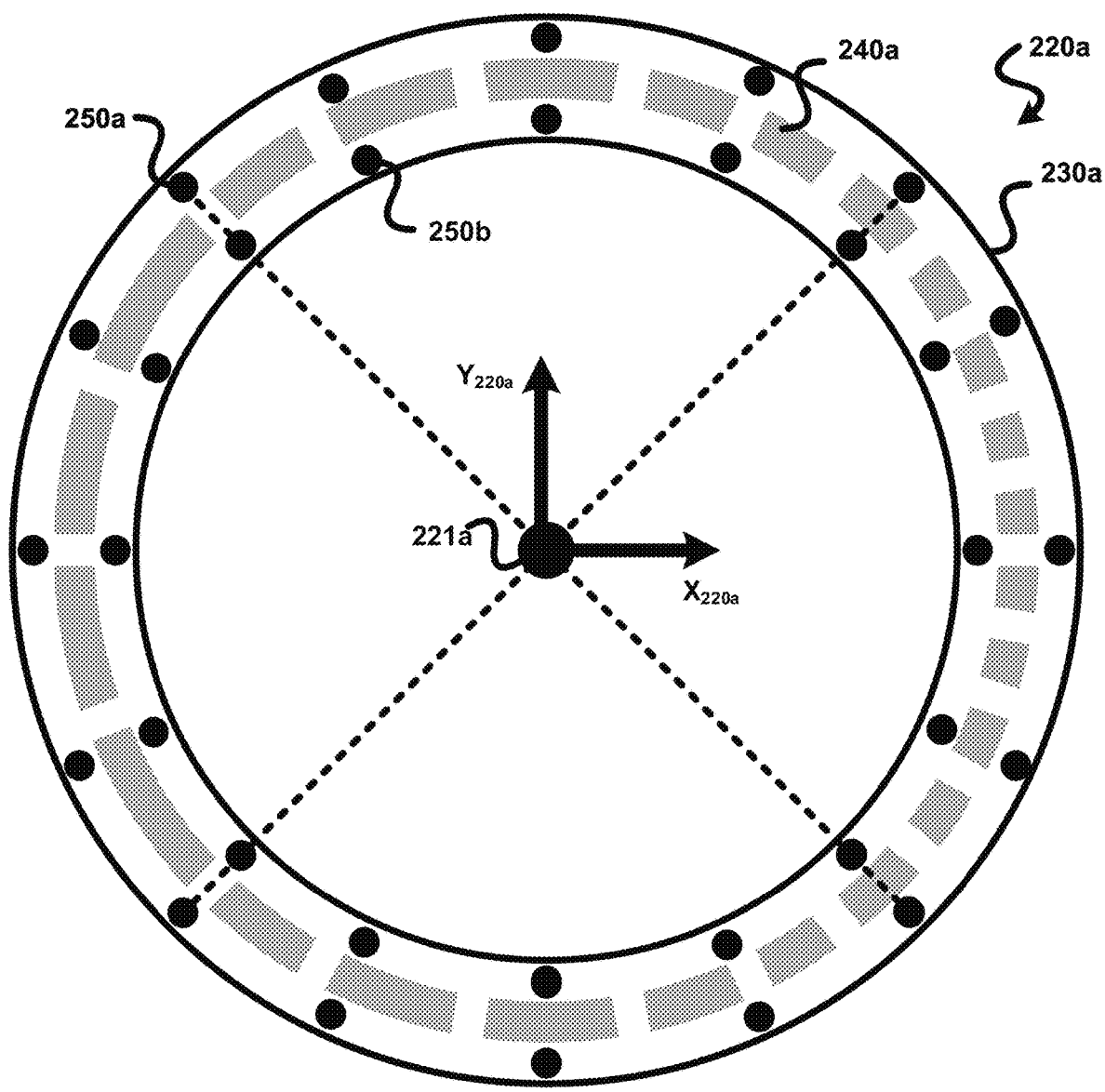
FIGS. 22A and 22B illustrate a first exemplary embodiment of the X-ray ring marker of FIG. 20 in accordance with various aspects of the present disclosure.
Figure 22B:
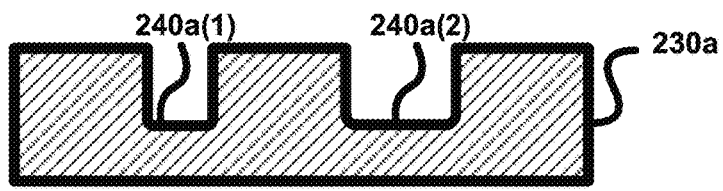

FIG. 22A illustrates an embodiment 220a of X-ray ring marker 220 of FIG. 20 of the present disclosure. X-ray ring marker 220a employs an annular base 230a having a chirp ring embodied as an annular spatial arrangement of indentations 240a formed in annular base 230a as exemplary shown in FIG. 22B. The dimensions of the indentations 240a vary along a 360° traversal of annular base 230a to define a chirp signal.

Still referring to FIG. 22A, centric ring 250 as shown in FIG. 20 of the present disclosure is embodied by an outer circle of uniformly spaced objects 250a (e.g., cooper balls, brass balls, etc.) affixed adjacent an outer perimeter of annular base 230a, and an inner circle of uniformly spaced objects 250b (e.g., cooper balls, brass balls, etc.) affixed adjacent an inner perimeter of annular base 230a. Each object 250a of the outer circle is paired with a corresponding object 250b of the inner circle to define an intersection line of a center point 221a of X-ray ring marker 220a serving as an origin of a coordinate system $X_{220a}$-$Y_{220a}$-$Z_{220a}$ of X-ray ring marker 220a (Z-axis not shown).

Figure 23:
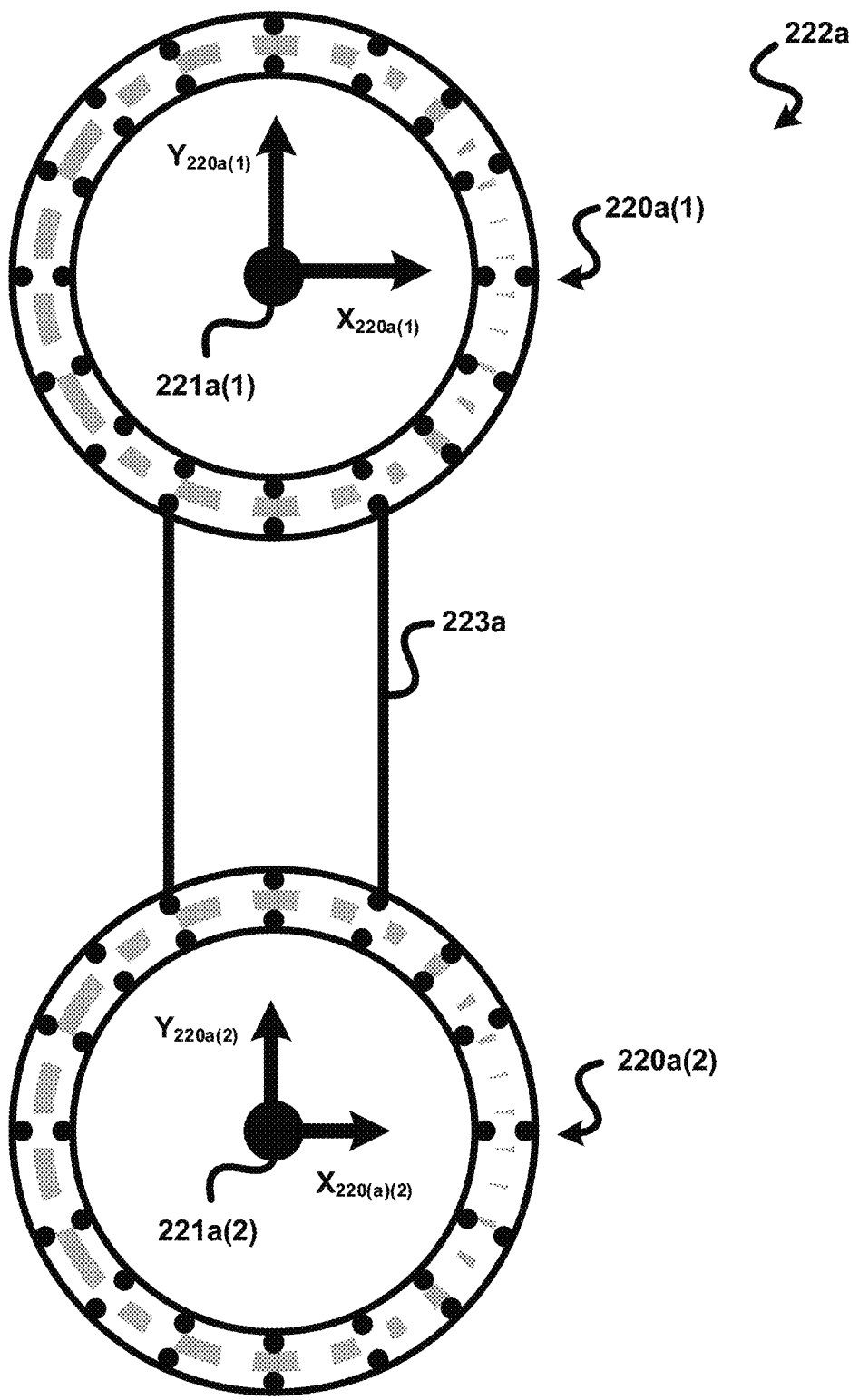
FIG. 23 illustrates a first exemplary embodiment of the dual X-ray ring marker of FIG. 2 in accordance with various aspects of the present disclosure.

FIG. 23 illustrates a dual X-ray ring marker 222a of the present disclosure employing a pair of X-ray ring markers 220a of FIG. 22A of the present disclosure connected via a bridge 223a. In practice, bridge 223a may be any shape suitable for a C-arm→X-ray ring marker 220a registration involving a movement of C-arm from a baseline imaging pose to a target imaging pose as will be further described in the present disclosure, such as, for example, a prismatic shape of bridge 223a for establishing a co-planar alignment of the pair of X-ray ring markers 220a as shown in FIG. 23.

Figure 24A:
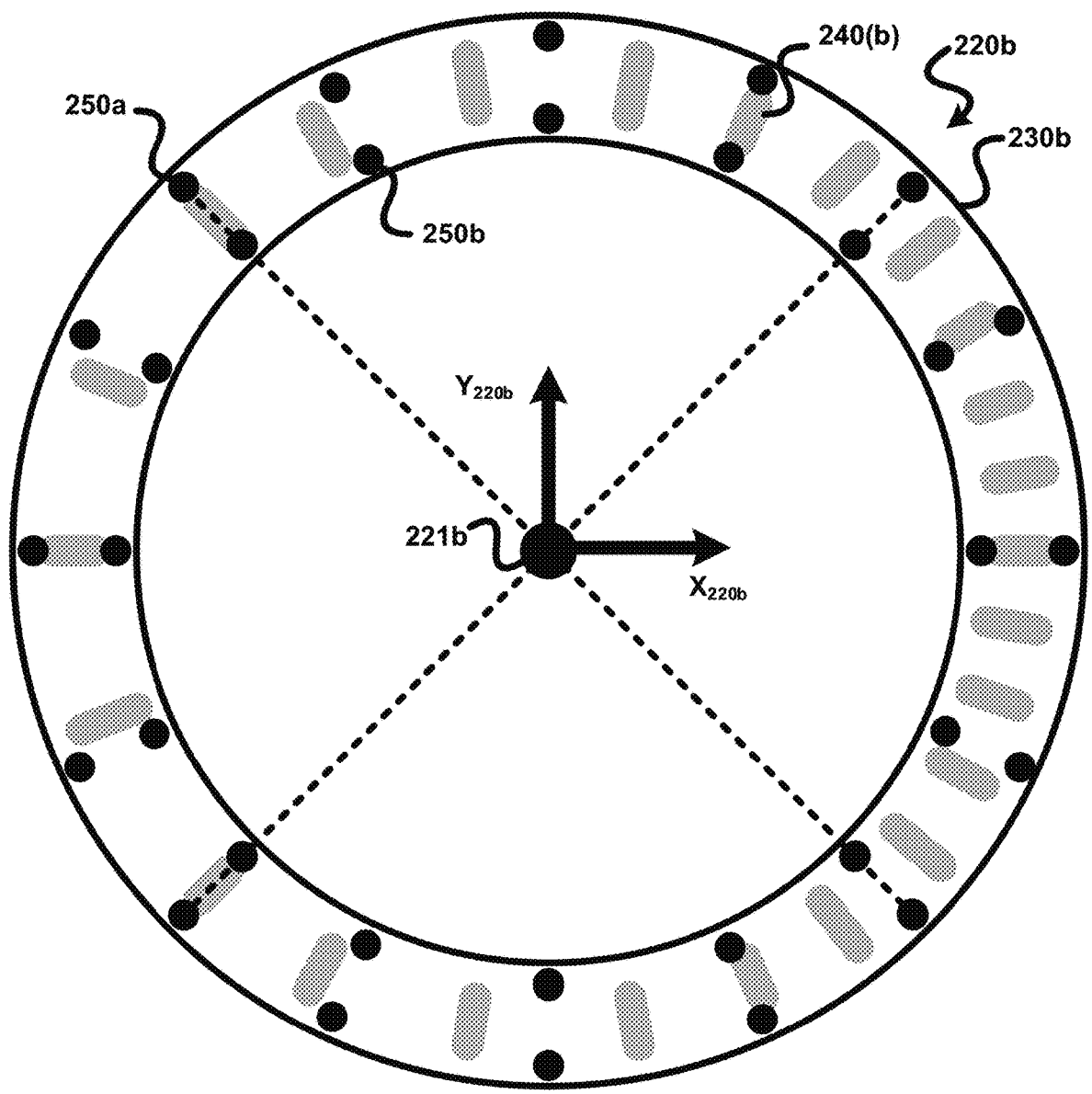
FIGS. 24A and 24B illustrate a second exemplary embodiment of the X-ray ring marker of FIG. 20 in accordance with various aspects of the present disclosure.
Figure 24B:
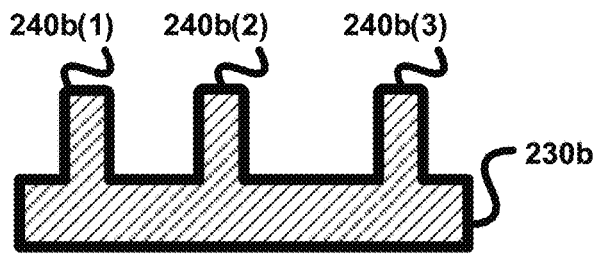

FIG. 24A illustrates an embodiment 220b of X-ray ring marker 220 of FIG. 20 of the present disclosure. X-ray ring marker 220b employs an annular base 230b having a chirp ring embodied as an annular spatial arrangement of protrusions 240b formed in annular base 230b as exemplary shown in FIG. 24B. The dimensions of protrusions 240b vary along a 360° traversal of annular base 230b to define a chirp signal.

Still referring to FIG. 24A, centric ring 250 as shown in FIG. 20 of the present disclosure is again embodied by an outer circle of uniformly spaced objects 250a (e.g., cooper balls, brass balls, etc.) affixed adjacent an outer perimeter of annular base 230b, and an inner circle of uniformly spaced objects 250b (e.g., cooper balls, brass balls, etc.) affixed adjacent an inner perimeter of annular base 230b. Each object 250a of the outer circle is paired with a corresponding object 250b of the inner circle to define an intersection line of a center point 221b of X-ray ring marker 220b serving as an origin of a coordinate system $X_{220b}$-$Y_{220b}$-$Z_{220b}$ of X-ray ring marker 220b (Z-axis not shown).

Figure 25:
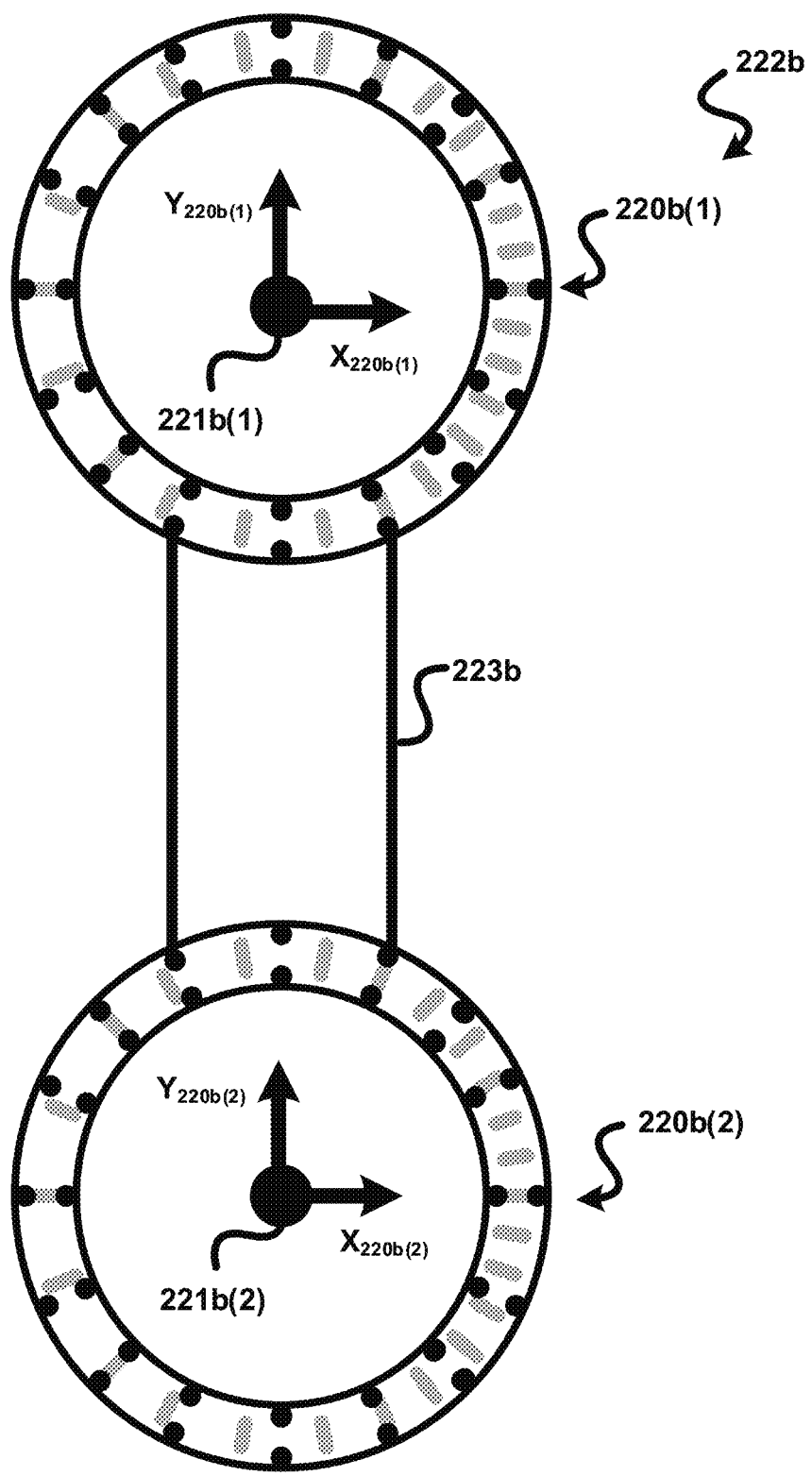
FIG. 25 illustrates a second exemplary embodiment of the dual X-ray ring marker of FIG. 20 in accordance with various aspects of the present disclosure.

FIG. 25 illustrates a dual X-ray ring marker 222b of the present disclosure employing a pair of X-ray ring markers 220b of FIG. 24A of the present disclosure connected via a bridge 223b. In practice, bridge 223b may be any shape suitable for a C-arm→X-ray ring marker registration involving a movement of C-arm from a baseline imaging pose to a target imaging pose as will be further described in the present disclosure, such as, for example, a prismatic shape of bridge 223b for establishing a co-planar alignment of the pair of X-ray ring markers 220b as shown in FIG. 25.

Figure 26:
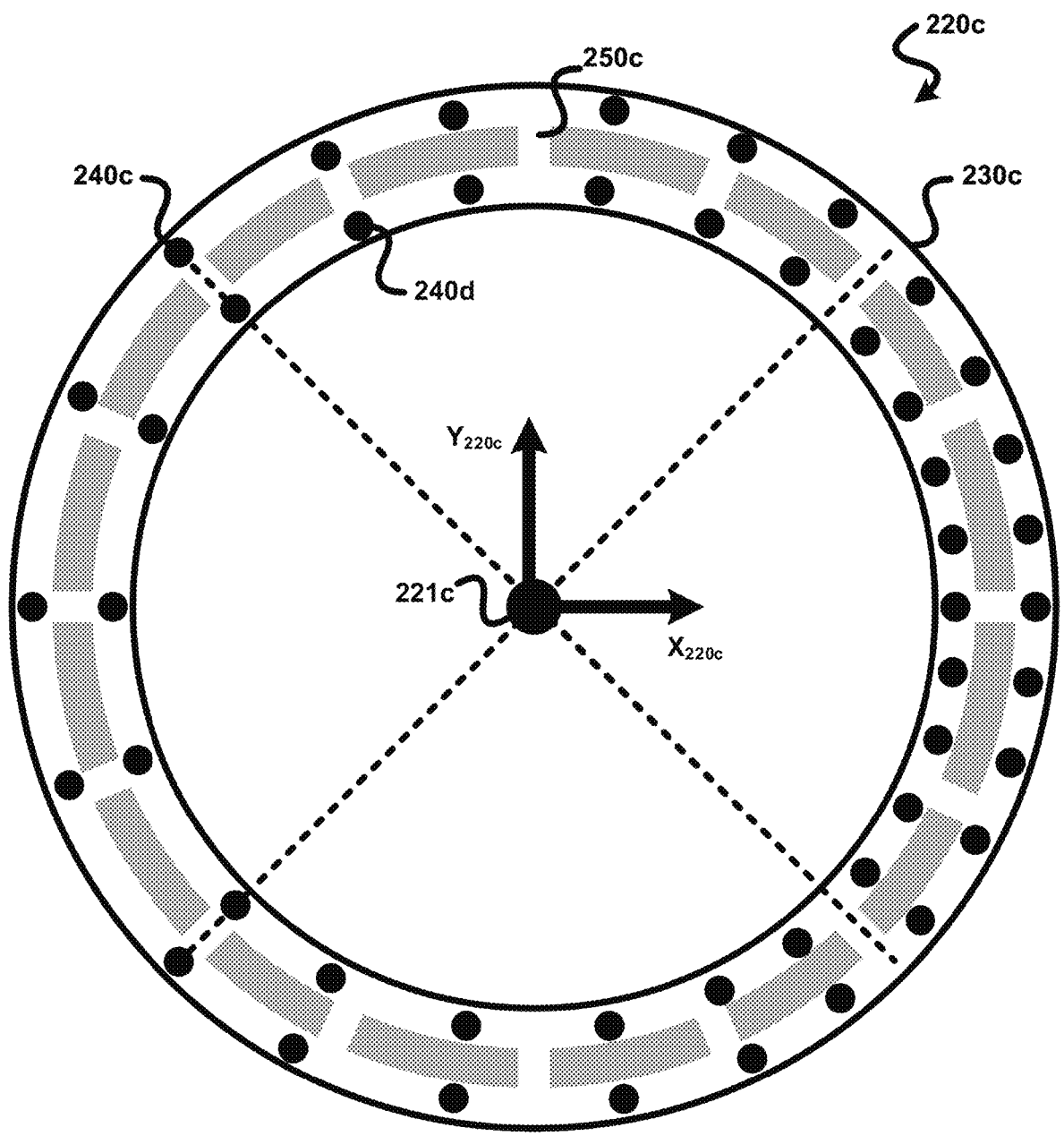
FIG. 26 illustrates a third exemplary embodiment of the X-ray ring marker of FIG. 1 in accordance with various aspects of the present disclosure.

FIG. 26 illustrates an embodiment 220c of X-ray ring marker 220 of FIG. 20 of the present disclosure. X-ray ring marker 220c employs an annular base 230c having a chirp ring embodied by an outer circle of varyingly spaced objects 240c (e.g., cooper balls, brass balls, etc.) affixed adjacent an outer perimeter of annular base 230c, and an inner circle of varyingly spaced objects 240d (e.g., cooper balls, brass balls, etc.) affixed adjacent an inner perimeter of annular base 230c. The spacing of the objects 240c and 240d vary along a 360° traversal of annular base 230c to define a chirp signal.

Still referring to FIG. 26, X-ray ring marker 220c further employs a centric ring embodied as uniformly spaced protrusions 250c formed into annular base 230c. Each protrusion 250c is paired with a corresponding 180° protrusion 250c to define intersection lines of a center point 221c of X-ray ring marker 220c serving as an origin of a coordinate system $X_{220c}$-$Y_{220c}$-$Z_{220c}$ of X-ray ring marker 220c (Z-axis not shown).

In an alternative embodiment, a centric ring may be embodied as uniformly spaced indentations formed into annular base 230c. Each indentations would be paired with a corresponding 180° indentation to define intersection lines of center point 221c of X-ray ring marker 220c.

Figure 27:
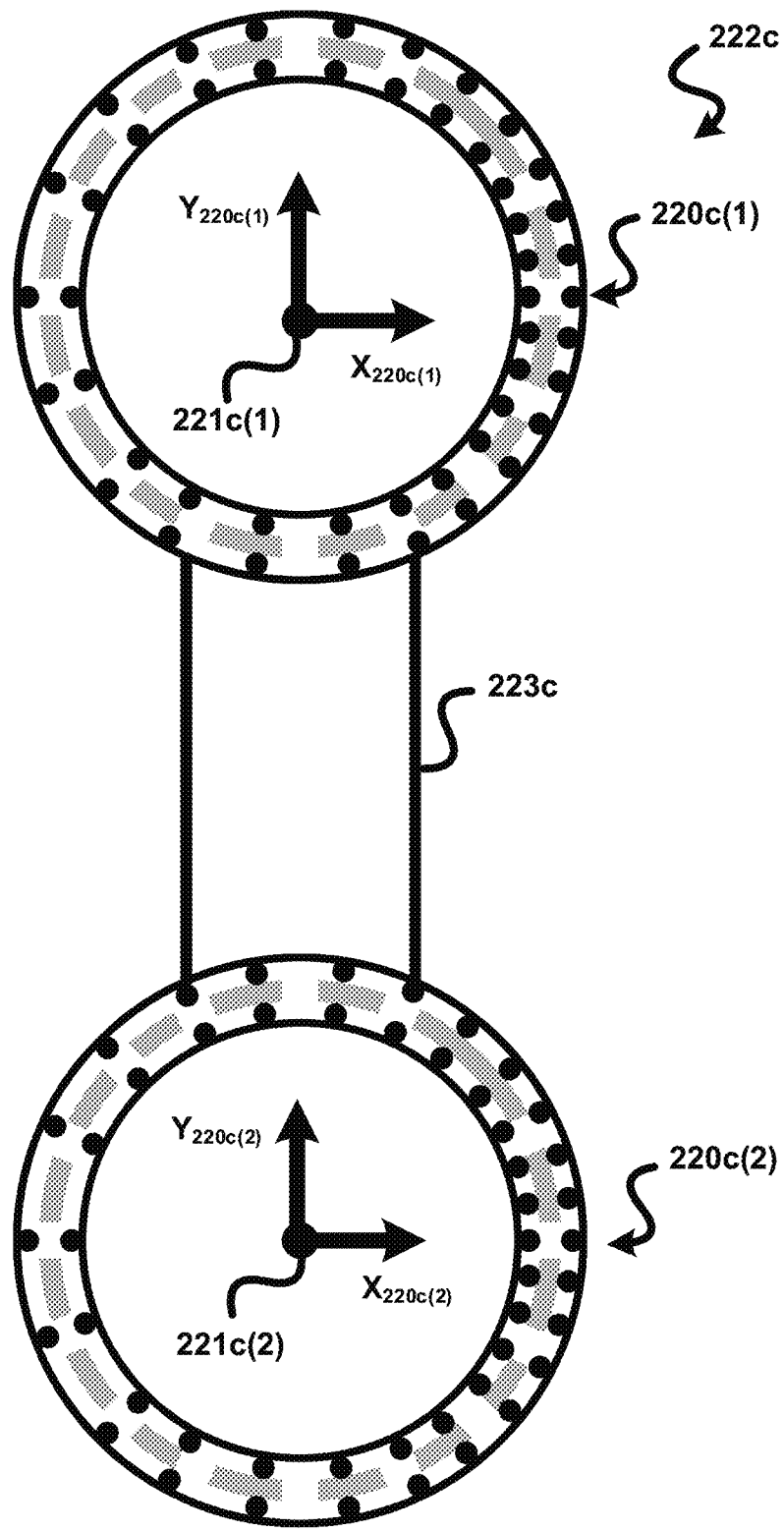
FIG. 27 illustrates a third exemplary embodiment of the dual X-ray ring marker of FIG. 2 in accordance with various aspects of the present disclosure.

FIG. 27 illustrates a dual X-ray ring marker 222c of the present disclosure employing a pair of X-ray ring markers 220c of FIG. 26 of the present disclosure connected via a bridge 223c. In practice, bridge 223c may be any shape suitable for a C-arm→X-ray ring marker registration involving a movement of C-arm from a baseline imaging pose to a target imaging pose as will be further described in the present disclosure, such as, for example, a prismatic shape of bridge 223c for establishing a co-planar alignment of the pair of X-ray ring markers 220c as shown in FIG. 27.

Figure 28:
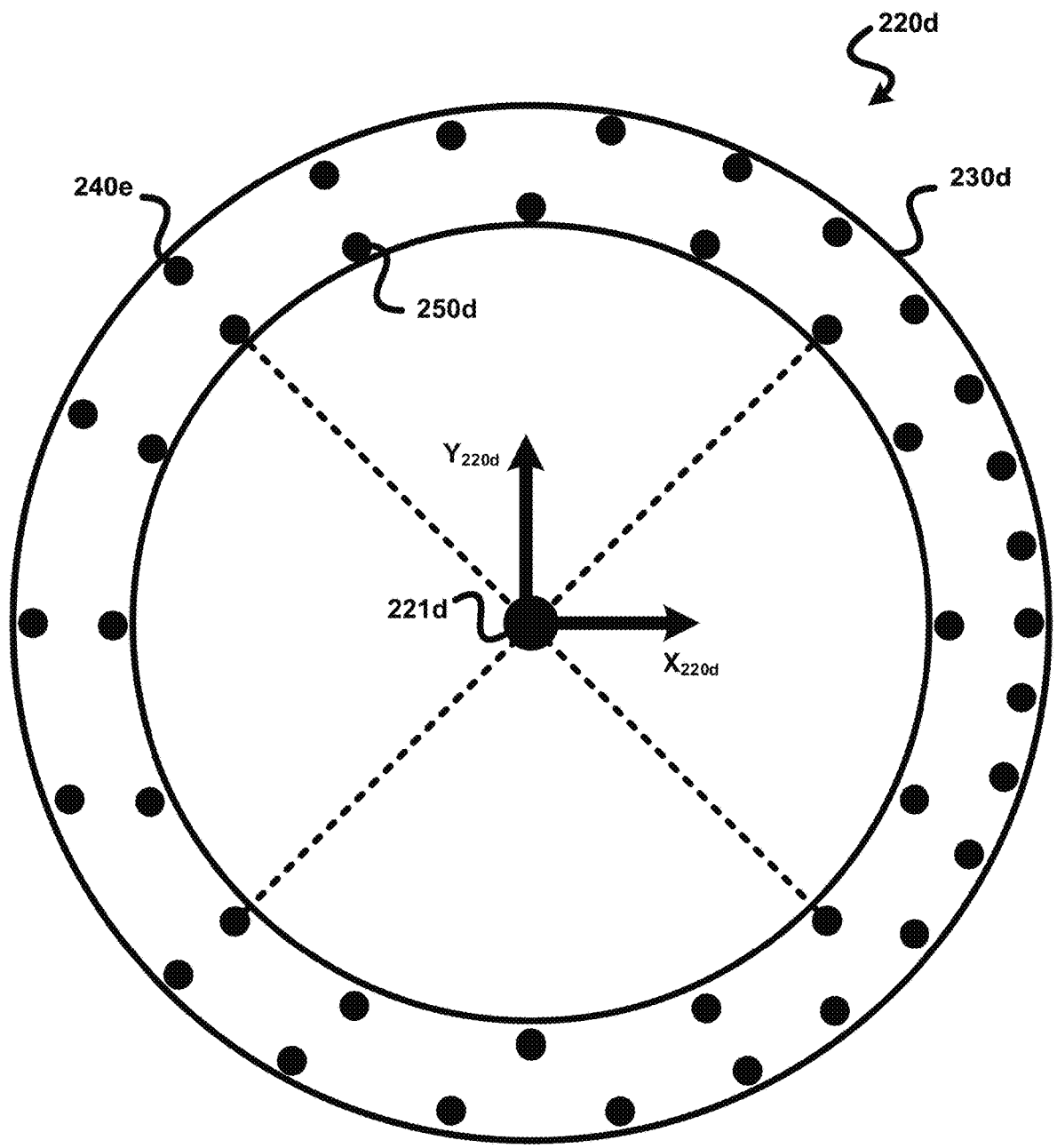
FIG. 28 illustrates a fourth exemplary embodiment of the X-ray ring marker of FIG. 1 in accordance with various aspects of the present disclosure.

FIG. 28 illustrates an embodiment 220d of X-ray ring marker 220 of FIG. 20 of the present disclosure. X-ray ring marker 220d employs an annular base 230d having a chirp ring embodied by an outer circle of varyingly spaced objects 240e (e.g., cooper balls, brass balls, etc.) affixed adjacent an outer perimeter of annular base 230d. The spacing of the objects 240e vary along a 360° traversal of annular base 230d to define a chirp signal.

Still referring to FIG. 28, X-ray ring marker 220d further employs a centric ring embodied an inner circle of varyingly spaced objects 250d (e.g., cooper balls, brass balls, etc.) affixed adjacent an inner perimeter of annular base 230d. Each object 250d is paired with a corresponding 180° object 250d to define intersection lines of a center point 221d of X-ray ring marker 220d serving as an origin of a coordinate system $X_{220d}$-$Y_{220d}$-$Z_{220d}$ of X-ray ring marker 220d (Z-axis not shown).

Figure 29:
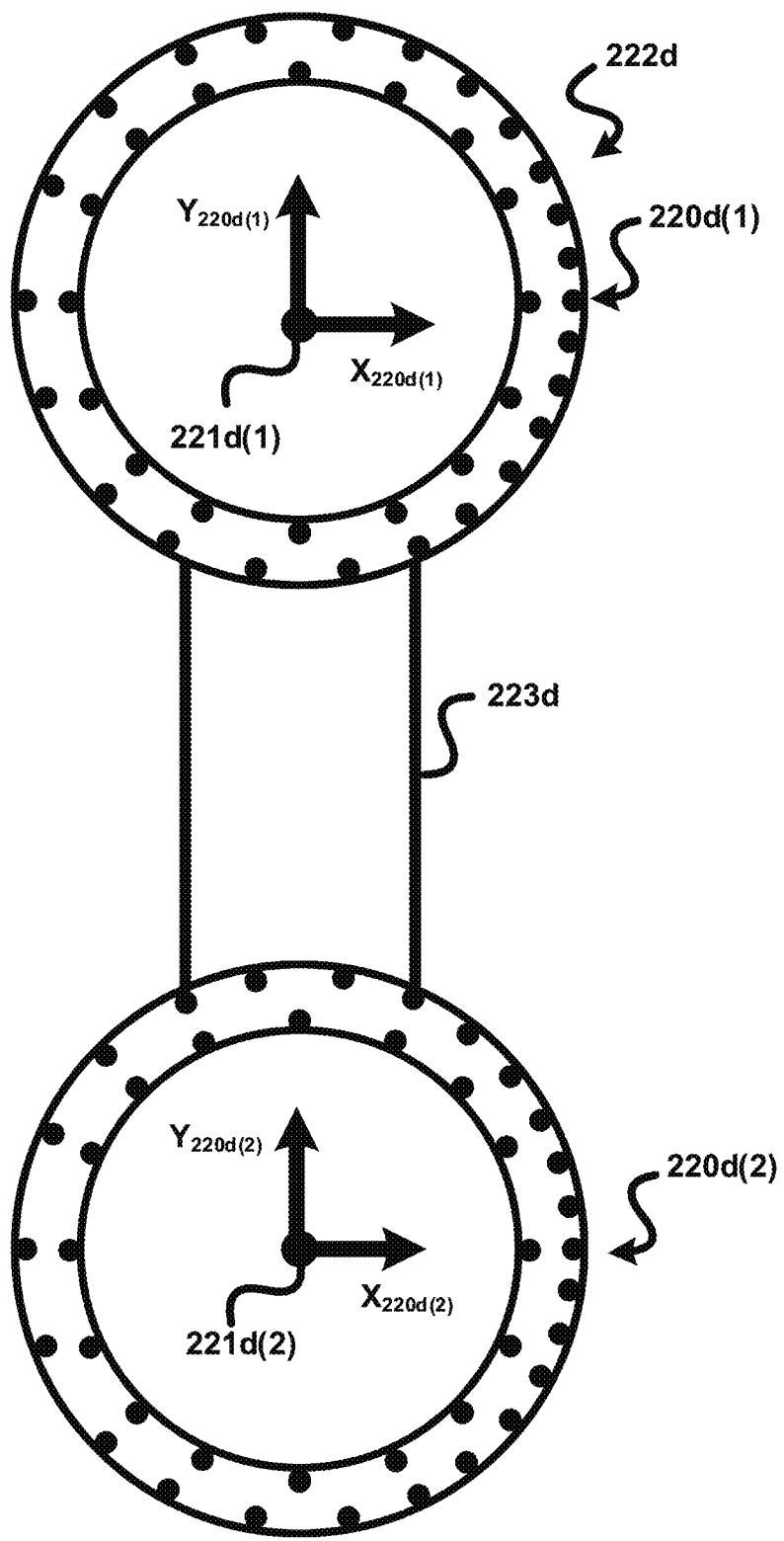
FIG. 29 illustrates a fourth exemplary embodiment of the dual X-ray ring marker of FIG. 21 in accordance with various aspects of the present disclosure.

FIG. 29 illustrates a dual X-ray ring marker 222d of the present disclosure employing a pair of X-ray ring markers 220d of FIG. 28 of the present disclosure connected via a bridge 223d. In practice, bridge 223d may be any shape suitable for a C-arm→X-ray ring marker registration involving a movement of C-arm from a baseline imaging pose to a target imaging pose as will be further described in the present disclosure, such as, for example, a prismatic shape of bridge 223d for establishing a co-planar alignment of the pair of X-ray ring markers 220d as shown in FIG. 29.

To further facilitate an understanding of various aspects of the present disclosure, the following description of FIGS. 30-37 teaches embodiments of a C-arm→X-ray ring maker registration of the present disclosure. From this description, those having ordinary skill in the art will appreciate how to apply various aspects of the present disclosure for making and using additional embodiments of C-arm→X-ray ring maker registration of the present disclosure.

In practice, a C-arm→X-ray ring maker registration of the present disclosure may be implemented in a baseline phase and a target phase for generating registration parameters to facilitate a wide range of C-arm intervention technologies including, but not limited to, robot three-dimensional measurements, anatomical/implant tracking, image stitching, pre-operative image overlay and first-time-right C-arm positioning.

Figure 30A:
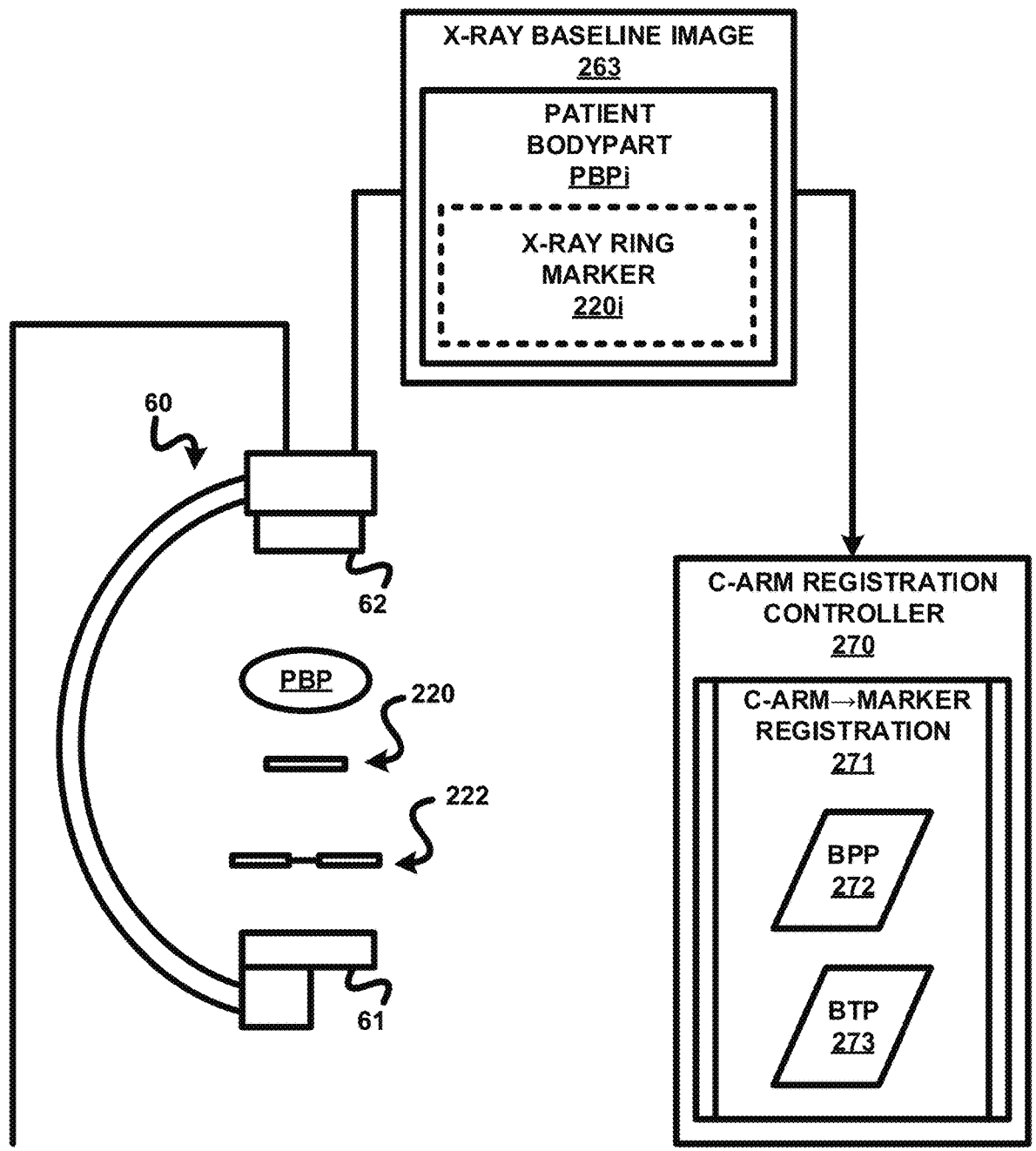
FIG. 30A illustrates an exemplary embodiment of a baseline phase of a C-arm→X-ray ring marker registration in accordance with various aspects of the present disclosure.

Referring to FIG. 30A, generally in the baseline phase, an embodiment of X-ray ring marker 220 as shown in FIG. 20 of the present disclosure or an embodiment of dual X-ray ring marker 222 shown in FIG. 21 of the present disclosure has a fixed position within an intervention space (e.g., an attachment to an operating table, a rail, a drape, or an intervention robot) and a body part of interest of a patient PBP is positioned above and adjacent X-ray ring marker 220 or dual X-ray ring marker 222.

A X-ray source 261 and a X-ray detector 262 of a C-arm 260 are positioned in a baseline imaging pose to generate a baseline X-ray image 263 illustrating an image of X-ray ring marker 220i below an image of patient body part PBPi.

A C-arm registration controller 270 acquires data of baseline X-ray image 263 and executes a C-arm→X-ray ring marker registration 271 of the present disclosure to derive baseline position parameters 272 and a baseline twist parameter 273 as a first subset of the registration parameters as will be further described in the present disclosure.

Figure 30B:
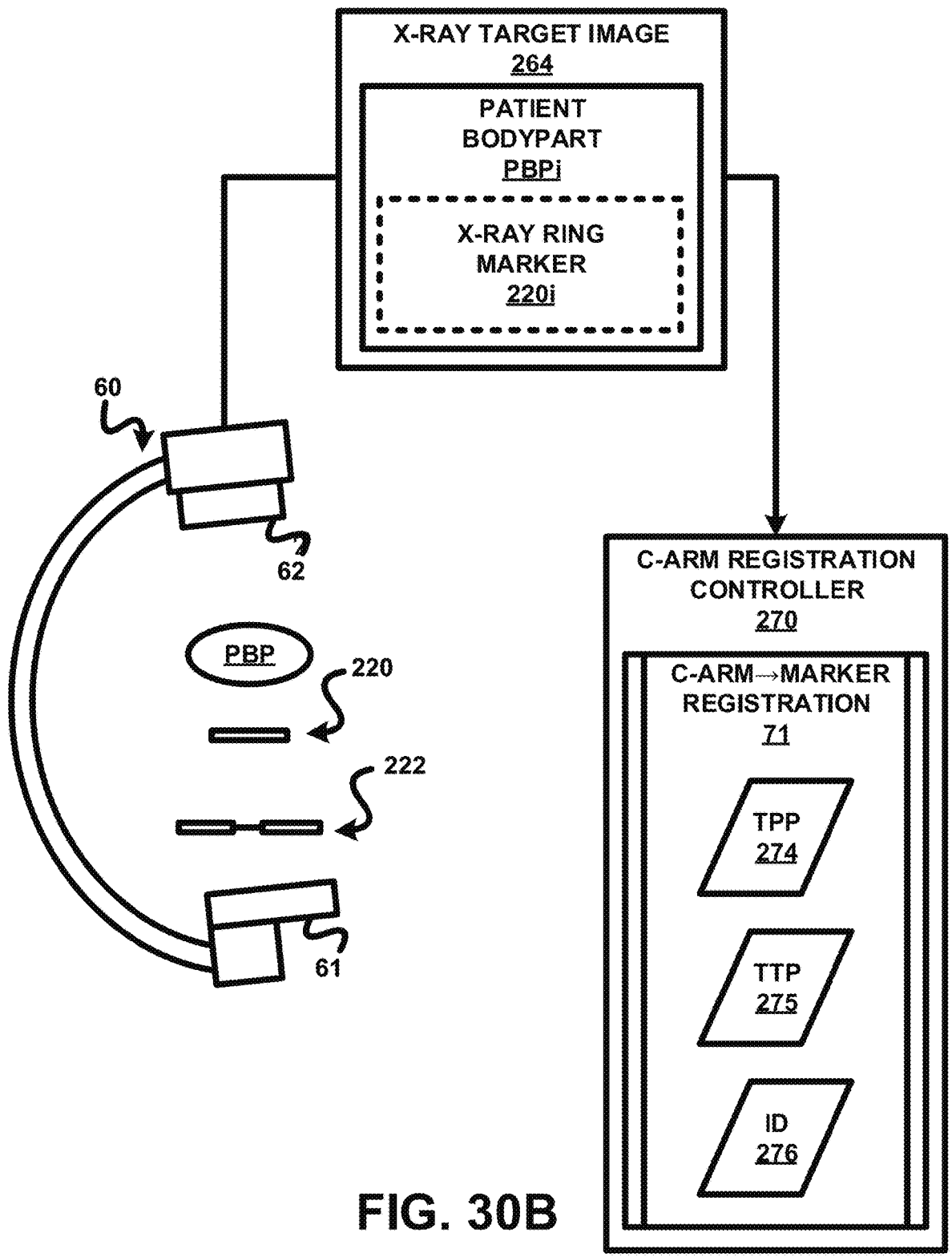
FIG. 30B illustrates an exemplary embodiment of a target phase of a C-arm→X-ray ring marker registration in accordance with various aspects of the present disclosure.

Referring to FIG. 30B, generally in the target phase, X-ray source 261 and X-ray detector 262 of C-arm 260 are moved from the baseline imaging pose to a target imaging pose, such as, for example, a rotation of C-arm 260 from the baseline imaging pose of FIG. 30A of the present disclosure to a target imaging pose of FIG. 30B. At the target imaging pose, X-ray source 261 and X-ray detector 262 of C-arm 260 are positioned to generate a target X-ray image 264 illustrating an image of X-ray ring marker 220i below an image of patient body part PBPi.

C-arm registration controller 270 acquires target X-ray image 264 and executes C-arm→X-ray ring marker registration 271 of the present disclosure to derive target position parameters 274 and a target twist parameter 275 as a second final subset of the registration parameters as will be further described in the present disclosure.

C-arm registration controller 270 may further execute C-arm→X-ray ring marker registration 271 to implement of one or more intervention steps to generate intervention data 276 based on the registration parameters.

In practice, any imaging pose of a C-arm may serve as a baseline imaging pose for one C-arm→X-ray ring marker registration during an intervention/diagnostic/imaging procedure, and may serve as a target imaging pose for another C-arm→X-ray ring marker registration during the same or different intervention/diagnostic/imaging procedure.

FIG. 31 illustrates a flowchart 280 representative of an embodiment of C-arm→X-ray ring marker registration 71. To facilitate an understanding of flowchart 280, FIG. 31 will be described in reference to FIGS. 30A, 30B, 33A and 33B. From this description, those having ordinary skill in the art will appreciate how to apply flowchart 280 to numerous and various additional embodiments of C-arm→X-ray ring marker registration 271.

Figure 33A:
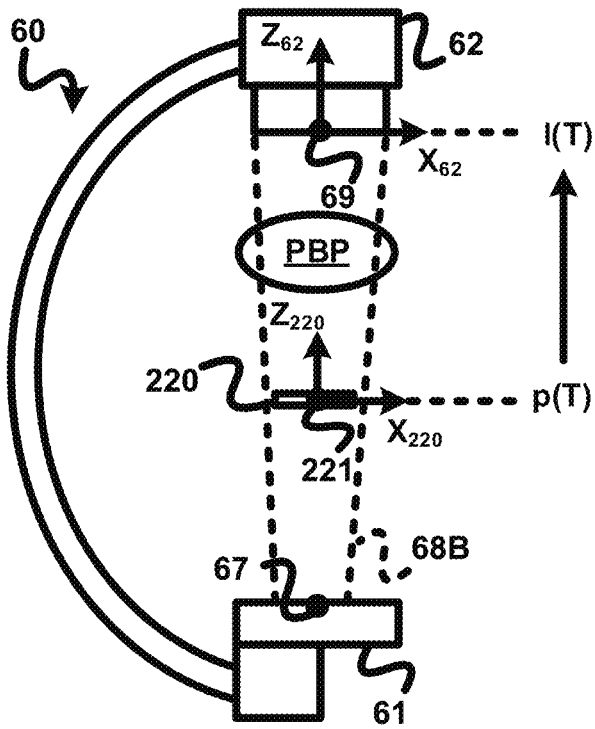
FIG. 33A illustrates an exemplary baseline imaging pose of a C-arm in accordance with the various aspects of the present disclosure.

Referring to FIGS. 30A and 31, during the baseline phase, a stage S282 of flowchart 280 encompasses an acquisition by controller 270 of baseline X-ray image 263 from C-arm 260 as known in the art of the present disclosure. More particularly during the baseline phase, as shown in FIG. 33A, the C-arm→X-ray ring marker registration 271 involves registering a position and a twist of X-ray ring marker 220 of the present disclosure within a X-ray projection 268B originating from a focal spot 267 of X-ray source 261 to X-ray detector 262.

In practice, a $X_{260}$-$Y_{260}$-$Z_{260}$ coordinate system of C-arm 260 may be defined on X-ray detector 262 whereby the X-axis and the Y-axis of the coordinate system of C-arm 260 may be aligned with a coordinate system of the baseline X-ray image, such as, for example a $X_{265a}$-$Y_{265a}$ coordinate system of baseline X-ray image 263 shown in FIG. 30A. An origin 269 of $X_{262}$-$Y_{262}$-$Z_{262}$ coordinate system of C-arm 260 may be delineated whereby X-ray source 262 is on a positive range of a $Z_{262}$ axis of $X_{262}$-$Y_{262}$-$Z_{262}$ coordinate system of C-arm 260 whereby focal spot 267 of X-ray source 261 has a (0, 0, +$Z_{262}$) coordinate within $X_{262}$-$Y_{262}$-$Z_{262}$ coordinate system of C-arm 260.

Referring back to FIGS. 30A and 31, a stage S284 of flowchart 280 encompasses controller 270 deriving baseline position parameters $t_x^B$, $t_y^B$, $t_z^B$, $\theta_{z1}^B$ and $\theta_x^B$ of X-ray ring marker 220 as a function of an illustration of the centric ring within the baseline X-ray image 263. The baseline position parameters $t_x^B$, $t_y^B$, $t_z^B$, $\theta_{z1}^B$ and $\theta_x^B$ are definitive of a position of X-ray ring marker 220 within the baseline X-ray projection 260B.

Stage S284 of flowchart 280 further encompasses controller 270 deriving a baseline twist parameter $\Theta_{z2}^B$ of X-ray ring marker 220 as a function of the baseline position parameters $t_x^B$, $t_y^B$, $t_z^B$, $\theta_{z1}^B$ and $\theta_x^B$ of an illustration of the chirp ring within the baseline X-ray image 263. The baseline twist parameter $\theta_{z2}^B$ is definitive of a twist of the X-ray ring marker 220 within the baseline X-ray projection 260B.

In one embodiment of stage S284, controller 270 executes a registration parameter computation method of the present disclosure represented by a flowchart 290 of FIG. 32.

Referring to FIGS. 32 and 33A, a stage S292 of flowchart 290 encompasses a computation of a center point 221 of X-ray ring marker 220 on X-ray detector 262.

In one embodiment of stage S292 with spherical objects (e.g., cooper balls or brass balls. etc.), an identification of the spherical objects as illustrated within baseline X-ray image 263 starts with an adaptive thresholding technique as known in the art of the present disclosure to identify imaging blobs within the baseline X-ray image 263 followed by a series of morphological operations to eliminate blobs having a smaller size relative to the size of the spherical objects.

From the remaining image blobs within the baseline X-ray image 263, image blobs having an aspect ratio close to round and areas between certain thresholds are selected as candidate spherical objects radial pairs whereby blob pairs with a distance therebetween within a certain range are selected as radial pairs whereby an intersection of all lines defined by radial pairs are computed using a least square approach providing a residual. A robustness of identification of the spherical objects as illustrated within a baseline X-ray image 263 is improved by iteratively eliminating candidate spherical objects that lead to large residual values.

The result of stage S292 is a following listing of an M number of paired objects in the C-arm coordinate system: $\{[(X_1^1,Y_1^1), (X_1^2,Y_1^2)] \ldots [(X_M^1,Y_M^1), (X_M^2,Y_M^2)]\}$, $M \geq 2$.

Still referring to FIGS. 32 and 33A, stage S292 further encompasses controller 270 delineating intersection lines between paired objects $\{[(X_1^1,Y_1^1), (X_1^2,Y_1^2)] \ldots [(X_M^1,Y_M^1), (X_M^2,Y_M^2)]\}$, $M \geq 2$, within the baseline X-ray image 263 to compute a projection $(X_C, Y_C)$ of a center of the X-ray ring marker 220 on the X-ray detector 262.

Figure 44:
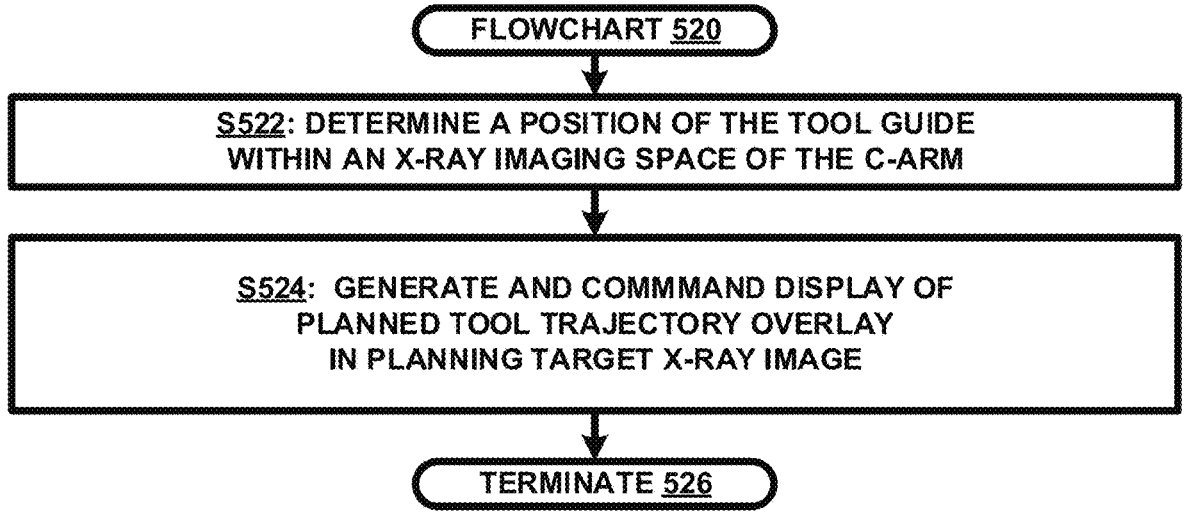
FIG. 44 illustrates a flowchart representative of a first exemplary embodiment of an interventional tool trajectory overlay display method in accordance the various aspects of the present disclosure

Referring back to FIGS. 32 and 44A, a stage S294 of flowchart 290 encompasses controller 270 utilizing the projection $(X_C, Y_C)$ of a center point 221 of the X-ray ring marker 220 on the X-ray detector 262 during stage S292 to compute baseline position parameters $t_x^B$, $t_y^B$, $t_z^B$, $\theta_{z1}^B$ and $\theta_x^B$.

In one embodiment of stage S294, based on the projection $(X_C, Y_C)$ of a center point 221 of the X-ray ring marker 220 on the X-ray detector 262, the projection ray defining the center point 221 of the X-ray ring marker 220 extend from source point $(0, 0, S_d^B)$ to detector point $(X_C, Y_C, 0)$. This means that the center point 221 of the X-ray ring marker 220 may be parameterized by the following equation [13]:

$$\begin{pmatrix} t_x^B \\ t_y^B \\ t_z^B \end{pmatrix} = \begin{pmatrix} X_C^B \dfrac{S_d^B - t_z^B}{S_d^B} \\ Y_C^B \dfrac{S_d^B - t_z^B}{S_d^B} \\ t_z^B \end{pmatrix}; t_z^B \in (0, S_d^B) \quad [13]$$

Assuming the listed object points $\{[(X_1^1,Y_1^1), (X_1^2,Y_1^2)] \ldots [(X_M^1,Y_M^1), (X_M^2,Y_M^2)]\}$ is such that the first point belongs to inner centering circle of a radius $R_I$ and the belongs to an the outer centering circle of a radius $R_O$, a cost function may be defined with parameters $t_z^B$, $\theta_{z1}^B$ and $\theta_x^B$ as a measure of how well the object points fit X-ray ring marker 220 placed at a location $(t_x^B, t_y^B, t_z^B)^T$ and angulation $\theta_{z1}^B$ and $\theta_x^B$.

In one embodiment, the cost function is constructed as follows.

First, a cost CF is initialized at a value of zero (0).

Second, for each landmark pair $\{[(X_i^1,Y_i^1), (X_i^2,Y_i^2)]\}$:

a. a computation of an intersection between segment $\{[(X_i^1,Y_i^1, 0), (0, 0, S_d^B)]\}$ and marker XY plane assuming that the X-ray ring marker 220 is at a location $(t_x^B, t_y^B, t_z^B)^T$ and angulation $\theta_{z1}^B$ and $\theta_x^B$. This point is $(Xsol_1, Ysol_1, 0)$ in the marker coordinate system;

b. a closest point on the circle to $(Xsol_1, Ysol_1, 0)$ is $(Xr_1, Yr_1, 0) = (R_1 \cos(\Phi_1), R_1 \sin(\Phi_1), 0)$, where $\Phi_1 = \text{atan}2(Ysol_1, Xsol_1)$;

c. the square distance between the two points is $dsq_1 = (Xsol_1 - xr_1)^2 + (Ysol_1 - yr_1)^2$ d. update cost function $CF += dsq_1$;

e. a computation of an intersection between segment $\{[(X_i^2, Y_i^2, 0), (0, 0, S_d^B)]\}$ and marker XY plane assuming that the X-ray ring marker 220 is at a location $(t_x^B, t_y^B, t_z^B)^T$ and angulation $\theta_{z1}^B$ and $\theta_x^B$. This point is $(xsol_2, ysol_2, 0)$ in the marker coordinate system;

f. a closest point on the circle to $(Xsol_2, Ysol_2, 0)$ is $(Xr_2, Yr_2, 0) = (R_2 \cos(\Phi_2), R_1 \sin(\Phi_2), 0)$, where $\Phi_2 = \text{atan}2(Ysol_2, Xsol_2)$;

g. the square distance between the two points is $dsq_2 = (Xsol_2 - Xr_2)^2 + (Ysol_2 - Yr_2)^2$ h. update cost function $CF += dsq_2$;

This is repeated for all M points and minimized using a Levenberg-Marquardt routine as known in the art of the present disclosure to find the optical values of position parameters $t_z^B$, $\theta_{z1}^B$ and $\theta_x^B$, and provide position parameters $t_x^B$ and $t_y^B$.

Still referring to FIGS. 32 and 33A, a stage S296 of flowchart 290 encompasses controller 270 utilizes baseline position parameters $t_x^B$, $t_y^B$, $t_z^B$, $\theta_{z1}^B$ and $\theta_x^B$ and the chirp signal to compute baseline twist parameter $\theta_{z2}^B$.

In one embodiment of stage S296, points on a rim of X-ray ring marker 220 may be parameterized in accordance with the following three equations [14]-[16]:

$$p(t) = R_z^B(\theta_{z1}^B) R_x^B(\theta_x^B) R_z^B(\theta_{z2}^B) \begin{pmatrix} \dfrac{R_i + R_0}{2} \cos(t) \\ \dfrac{R_i + R_0}{2} \sin(t) \\ 0 \end{pmatrix} + \begin{pmatrix} t_x^B \\ t_y^B \\ t_z^B \end{pmatrix}; t \in [0, 2\pi] \quad [14]$$

$$p(t) = R_z^B(\theta_{z1}^B) R_x^B(\theta_x^B) R_z^B(\theta_{z2}^B + t) \begin{pmatrix} \dfrac{R_i + R_0}{2} \\ 0 \\ 0 \end{pmatrix} + \begin{pmatrix} t_x^B \\ t_y^B \\ t_z^B \end{pmatrix}; t \in [0, 2\pi] \quad [15]$$

$$p(t_1) = R_z^B(\theta_{z1}^B) R_x^B(\theta_x^B) R_z^B(t_1) \begin{pmatrix} \dfrac{R_i + R_0}{2} \\ 0 \\ 0 \end{pmatrix} + \begin{pmatrix} t_x^B \\ t_y^B \\ t_z^B \end{pmatrix}; t_1 \in [0, 2\pi] \quad [16]$$

Thus, $p(t_1)$ is projected onto the X-ray detector 262 through a perspective transformation with known parameters and the pixel values are retrieved $I(t_1)$ as exemplary shown in FIG. 33A. The chip ring has a model in accordance with the following equation [17]:

$$c(t) = A e^{if_S t(1 + t f_{sh})}; t \in [0, 2\pi] \quad [17]$$

where $f_S$ is the start frequency (e.g., 40 Hz) and $f_{sh}$ is the frequency shift (e.g., $1/2\pi$).

Then, an offset $t_0$ is computed to maximize a normalized cross correlation between signals $I(t_1)$ and $c(t_1 + t_0)$. Since the intensity signal embeds the twist $\theta_{z2}^B$ through $t_1$ whereas $c(t)$ doesn't, then $t_0 \equiv \theta_{z2}^B$.

Referring back to FIGS. 30A and 32, a stage S298 of flowchart 290 controller 270 optimizing baseline position parameters $t_x^B$, $t_y^B$, $t_z^B$, $\theta_{z1}^B$ and $\theta_x^B$ and baseline twist parameter $\theta_{z2}^B$.

In one embodiment of stage S298, a final optimization matches the locations of the object points from the model of the X-ray ring marker 220 with the locations of the object points in the baseline X-ray image 263. This final optimization provides a measure of the Marker Registration Error (MRE) as a squared sum of the distances between the object points projected using the model of the X-ray ring marker 220 and the baseline parameters $t_x^B$, $t_y^B$, $t_z^B$, $\theta_{z1}^B$, $\theta_x^B$ and $\theta_{z2}^B$ the object point projections retrieved from the baseline X-ray image 263. An MRE of less than 1 pixel squared, where a pixel edge length is fixed (e.g., 0.64 mm of a source-detector distance and zoom remained constant across all images), is an indication of an accurate C-arm→X-ray ring marker registration.

Figure 33B:
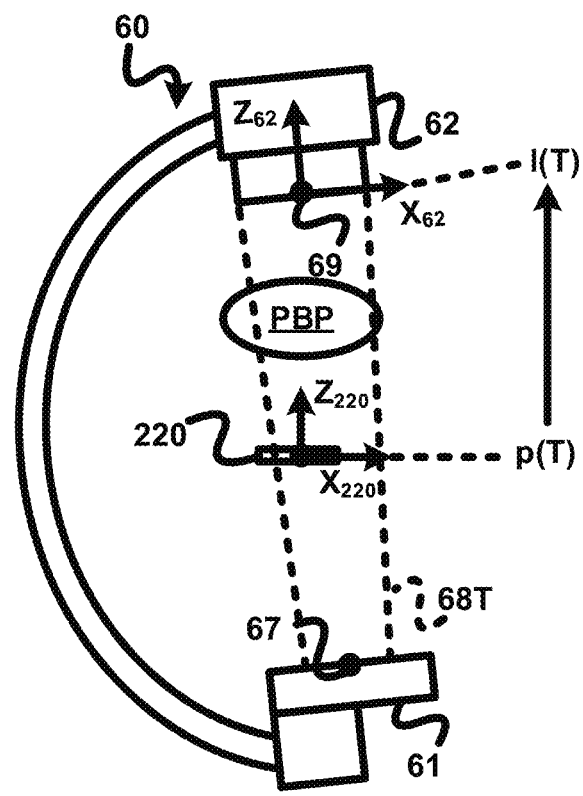
FIG. 33B illustrates an exemplary target imaging pose of a C-arm in accordance with the various aspects of the present disclosure.

Referring to FIGS. 30B and 31, during the target phase, a stage S286 of flowchart 280 encompasses an acquisition by controller 270 of target X-ray image 264 from C-arm 260 as known in the art of the present disclosure. More particularly, as shown in FIG. 33B, during the target phase the C-arm→X-ray ring marker registration 271 involves registering a position and a twist of X-ray ring marker 220 of the present disclosure within a target X-ray projection 68T originating from a focal spot 267 of X-ray source 261 to X-ray detector 262.

In practice, a $X_{260}$-$Y_{260}$-$Z_{260}$ coordinate system of C-arm 260 may be defined on X-ray detector 262 whereby the X-axis and the Y-axis of the coordinate system of C-arm 260 may be aligned with a coordinate system of the target X-ray image, such as, for example a $X_{65_a}$-$Y_{65_a}$ coordinate system of target X-ray image 264 shown in FIG. 30B. An origin 269 of $X_{62}$-$Y_{62}$-$Z_{62}$ coordinate system of C-arm 260 may be delineated whereby X-ray source 62 is on a positive range of a $Z_{62}$ axis of $X_{62}$-$Y_{62}$-$Z_{62}$ coordinate system of C-arm 260 whereby focal spot 267 of X-ray source 261 has a (0, 0, +$Z_{62}$) coordinate within $X_{62}$-$Y_{62}$-$Z_{62}$ coordinate system of C-arm 260.

Referring back to FIGS. 30B and 31, stage S288 of flowchart 280 encompasses controller 270 deriving target position parameters $t_x^T$, $t_y^T$, $t_z^T$ and $\theta_x^T$ of X-ray ring marker 220 as a function of an illustration of the centric ring within the target X-ray image 264. The target position parameters $t_x^T$, $t_y^T$, $t_z^T$, $\theta_{z1}^T$ and $\theta_x^T$ are definitive of a position of X-ray ring marker 220 within the target X-ray projection 268B.

Stage S288 of flowchart 280 further encompasses controller 270 deriving a target twist parameter $\theta_{z2}^T$ of X-ray ring marker 220 as a function of the target position parameters $t_x^T$, $t_y^T$, $t_z^T$, $\theta_{z1}^T$ and $\theta_x^T$ and of an illustration of the chirp ring within the target X-ray image 264. The target twist parameter $\theta_{z2}^T$ is definitive of a twist of the X-ray ring marker 220 within the target X-ray projection 268T.

In one embodiment of stage S288, controller 270 executes registration parameter computation method of the present disclosure as represented by flowchart 290 of FIG. 32.

Referring to FIGS. 32 and 33B, stage S292 of flowchart 290 encompasses a computation of a center point 221 of X-ray ring marker 220 on X-ray detector 262.

In one embodiment of stage S292 with spherical objects (e.g., cooper balls or brass balls. etc.), an identification of the spherical objects as illustrated within target X-ray image 264 starts with an adaptive thresholding technique as known in the art of the present disclosure to identify imaging blobs within the target X-ray image 264 followed by a series of morphological operations to eliminate blobs having a smaller size relative to the size of the spherical objects.

From the remaining image blobs within the target X-ray image, image blobs having an aspect ratio close to round and areas between certain thresholds are selected as candidate spherical objects radial pairs whereby blob pairs with a distance therebetween within a certain range are selected as radial pairs whereby an intersection of all lines defined by radial pairs are computed using a least square approach providing a residual. A robustness of identification of the spherical objects as illustrated within a target X-ray image 264 is improved by iteratively eliminating candidate spherical objects that lead to large residual values.

The result of stage S288 is a following listing of an M number of paired objects in the C-arm coordinate system: $\{[(X_1^1,Y_1^1), (X_1^2,Y_1^2)] \ldots [(X_M^1,Y_M^1), (X_M^2,Y_M^2)]\}$, M≥2.

Still referring to FIGS. 32 and 33B, stage S292 further encompasses controller 270 delineating intersection lines between paired objects $\{[(X_1^1,Y_1^1), (X_1^2,Y_1^2)] \ldots [(X_M^1, Y_M^1), (X_M^2,Y_M^2)]\}$, M≥2, within the target X-ray image 64 to compute a projection ($X_C$, $Y_C$) of a center of the X-ray ring marker 220 on the X-ray detector 262.

Referring back to FIGS. 32 and 33B, stage S294 of flowchart 290 encompasses controller 270 utilizing the projection ($X_C$, $Y_C$) of a center point 221 of the X-ray ring marker 220 on the X-ray detector 262 during stage S292 to compute target position parameters $t_x^T$, $t_y^T$, $t_z^T$, $\theta_{z1}^T$, and $\theta_x^T$.

In one embodiment of stage S294, based on the projection ($X_C$, $Y_C$) of a center point 221 of the X-ray ring marker 220 on the X-ray detector 262, the projection ray defining the center point 221 of the X-ray ring marker 220 extend from source point (0, 0, $S_d^T$) to detector point ($X_C$, $Y_C$, 0). This means that the center point 221 of the X-ray ring marker 220 may be parameterized by the following equation [17]:

$$\begin{pmatrix} t_x^T \\ t_y^T \\ t_z^T \end{pmatrix} = \begin{pmatrix} X_C^T \dfrac{S_d^T - t_z^T}{S_d^T} \\ Y_C^T \dfrac{S_d^T - t_z^T}{S_d^T} \\ t_z^T \end{pmatrix}; t_z^T \in (0, S_d^T) \quad [17]$$

Assuming the listed landmark points $\{[(X_1^1,Y_1^1), (X_1^2, Y_1^2)] \ldots [(X_M^1,Y_M^1), (X_M^2,Y_M^2)]\}$ is such that the first point belongs to inner centering circle of a radius $R_I$ and the belongs to an the outer centering circle of a radius $R_O$, a cost function may be defined with parameters $t_z^T$, $\theta_{z1}^T$, and $\theta_x^T$ as a measure of how well the object points fit X-ray ring marker 220 placed at a location $(t_x^T, t_y^T, t_z^T)^T$ and angulation $\theta_{z1}^T$ and $\theta_x^T$.

In one embodiment, the cost function is constructed as follows.

First, a cost CF is initialized at a value of zero (0).

Second, for each landmark pair $\{[(X_i^1,Y_i^1), (X_i^2,Y_i^2)]\}$:

a. a computation of an intersection between segment $\{[(X_i^1,X_i^1, 0), (0, 0, S_d)]\}$ and marker XY plane assuming that the X-ray ring marker 220 is at a location $(t_x^T, t_y^T, t_z^T)^T$ and angulation $\theta_{z1}^T$ and $\theta_x^T$. This point is (Xsol$_1$, Ysol$_1$, 0) in the marker coordinate system;

b. a closest point on the circle to (xsol$_1$, ysol$_1$, 0) is (Xr$_1$, Yr$_1$, 0)=($R_1$ cos($\Phi_1$), $R_1$ sin($\Phi_1$), 0), where $\Phi_1$=atan 2(Ysol$_1$, Xsol$_1$);

c. the square distance between the two points is dsq$_1$= (Xsol$_1$−Xr$_1$)$^2$+(Ysol$_1$−Yr$_1$)$^2$ d. update cost function CF+=dsq$_1$;

e. a computation of an intersection between segment $\{[(X_i^2, y_i^2, 0), (0, 0, S_d)]\}$ and marker XY plane assuming that the X-ray ring marker 220 is at a location $(t_x^T, t_y^T, t_z^T)^T$ and angulation $\theta_{z1}^T$ and $\theta_x^T$. This point is (Xsol$_2$, Ysol$_2$, 0) in the marker coordinate system;

f. a closest point on the circle to (Xsol$_2$, Ysol$_2$, 0) is (Xr$_2$, Yr$_2$, 0)=($R_2$ cos($\Phi_2$), $R_1$ sin($\Phi_2$), 0), where $\Phi_2$=atan 2(Ysol$_2$, Xsol$_2$);

g. the square distance between the two points is dsq$_2$= (Xsol$_2$−Xr$_2$)$^2$+(Ysol$_2$−Yr$_2$)$^2$ h. update cost function CF+=dsq$_2$;

This is repeated for all M points and minimized using a Levenberg-Marquardt routine as known in the art of the present disclosure to find the optical values of position parameters $t_z^T$, $\theta_{z1}^T$ and $\theta_x^T$, and provide position parameters $t_x^T$ and $t_y^T$.

Still referring to FIGS. 32 and 33B, a stage S296 of flowchart 290 encompasses controller 270 utilizes target position parameters $t_x^T$, $t_y^T$, $t_z^T$, $\theta_{z1}^T$ and $\theta_x^T$ and the chirp signal to compute target twist parameter $\theta_{z2}^T$.

In one embodiment of stage S296, points on a rim of X-ray ring marker 220 may be parameterized in accordance with the following three equations [18]-[20]:

$$p(t) = R_z^T(\theta_{z1}^T)R_x^T(\theta_x^T)R_z^T(\theta_{z2}^T)\begin{pmatrix}\frac{R_i+R_0}{2}\cos(t)\\ \frac{R_i+R_0}{2}\sin(t)\\ 0\end{pmatrix} + \begin{pmatrix}t_x^T\\ t_y^T\\ t_z^B\end{pmatrix}; t \in [0, 2\pi]$$

$$p(t) = R_z^T(\theta_{z1}^T)R_x^T(\theta_x^T)R_z^T(\theta_{z2}^T + t)\begin{pmatrix}\frac{R_i+R_0}{2}\cos(t)\\ \frac{R_i+R_0}{2}\sin(t)\\ 0\end{pmatrix} + \begin{pmatrix}t_x^T\\ t_y^T\\ t_z^T\end{pmatrix}; t \in [0, 2\pi]$$ [19]

$$p(t_1) = R_z^T(\theta_{z1}^T)R_x^T(\theta_x^T)R_z^T(t_1)\begin{pmatrix}\frac{R_i+R_0}{2}\cos(t)\\ \frac{R_i+R_0}{2}\sin(t)\\ 0\end{pmatrix} + \begin{pmatrix}t_x^T\\ t_y^T\\ t_z^T\end{pmatrix};$$ [20]

$$t_1 \in [0, 2\pi]$$

Thus, $p(t_1)$ is projected onto the X-ray detector 262 through a perspective transformation with known parameters and the pixel values are retrieved $I(t_1)$ as exemplary shown in FIG. 33B. The chip ring has a model in accordance with the following equation [21]:

$$c(t) = Ae^{jfs t(1 + tfsh)}; t \in [0, 2\pi]$$ [21]

where $f_S$ is the start frequency (e.g., 40 Hz) and $f_{sh}$ is the frequency shift (e.g., ½π).

Then, an offset $t_0$ is computed to maximize a normalized cross correlation between signals $I(t_1)$ and $c(t_1+t_0)$. Since the intensity signal embeds the twist $\theta_{z2}^T$ through $t_1$ whereas $c(t)$ doesn't, then $t_0 = \theta_{z2}^T$.

Referring back to FIGS. 30B and 32, stage S298 of flowchart 290 encompasses controller 270 optimizing target position parameters $t_x T$, $t_y^T$, $t_z^T$, $\theta_{z1}^T$ and $\theta_x^T$ and target twist parameter $\theta_{z2}^T$.

In one embodiment of stage S298, a final optimization matches the locations of the object points from the model of the X-ray ring marker 220 with the locations of the object points in the target X-ray image 264. This final optimization provides a measure of the Marker Registration Error (MRE) as a squared sum of the distances between the object points projected using the model of the X-ray ring marker 220 and the target parameters $t_x^T$, $t_y^T$, $t_z^T$, $\theta_{z1}^T$, $\theta_x^T$ and $\theta_{z2}^T$ and the object point projections retrieved from the target X-ray image 264. An MRE of less than 1 pixel squared, where a pixel edge length is fixed (e.g., 0.64 mm of a source-detector distance and zoom remained constant across all images), is an indication of an accurate C-arm→X-ray ring marker registration.

Referring back to FIG. 31, the generation of the registration parameters via flowchart 290 facilitates an implementation of a wide range of C-arm intervention technologies including, but not limited to, robot three-dimensional measurements, anatomical/implant tracking, image stitching, pre-operative image overlay and first-time-right C-arm positioning.

Figure 35:
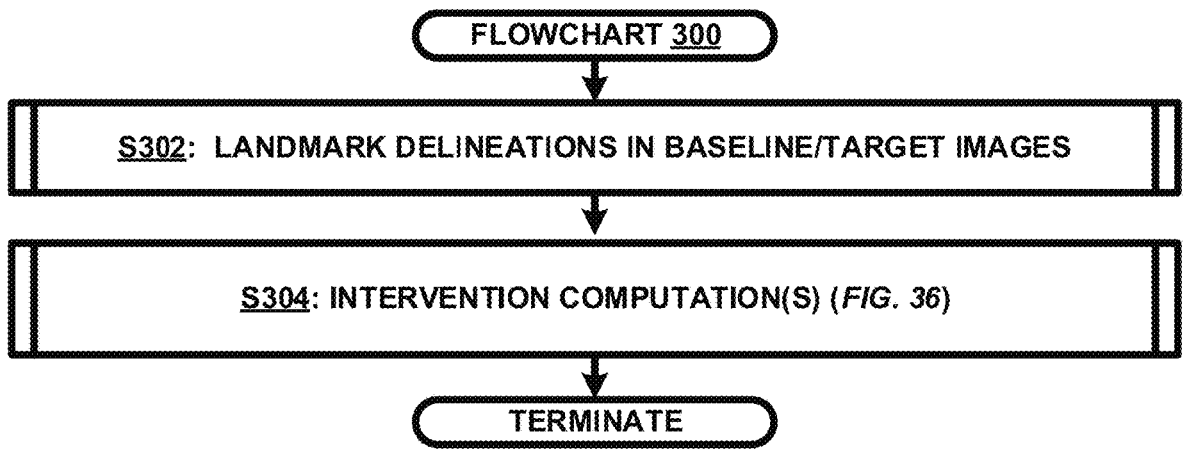
FIG. 35 illustrates a flowchart representative of an exemplary embodiment of an intervention step implementation method in accordance with various aspects of the present disclosure.
Figure 36:
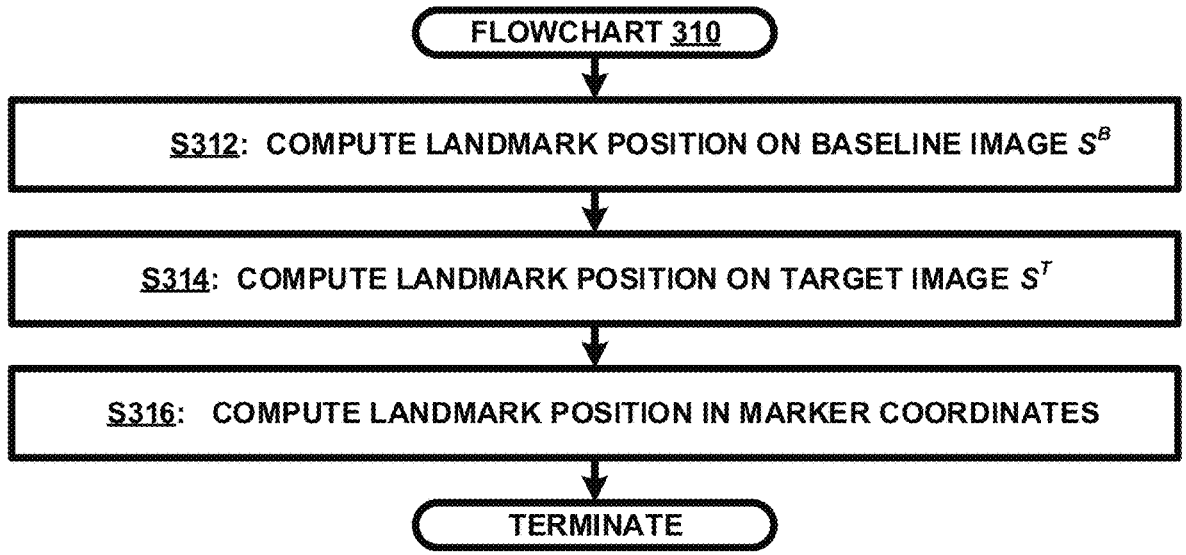
FIG. 36 illustrates a flowchart representative of an exemplary embodiment of an intervention computation method in accordance with various aspects of the present disclosure.

Referring to FIG. 35, a flowchart 300 is representative of an intervention step implementation method of the present disclosure in support of such C-arm intervention technologies.

Figure 37:
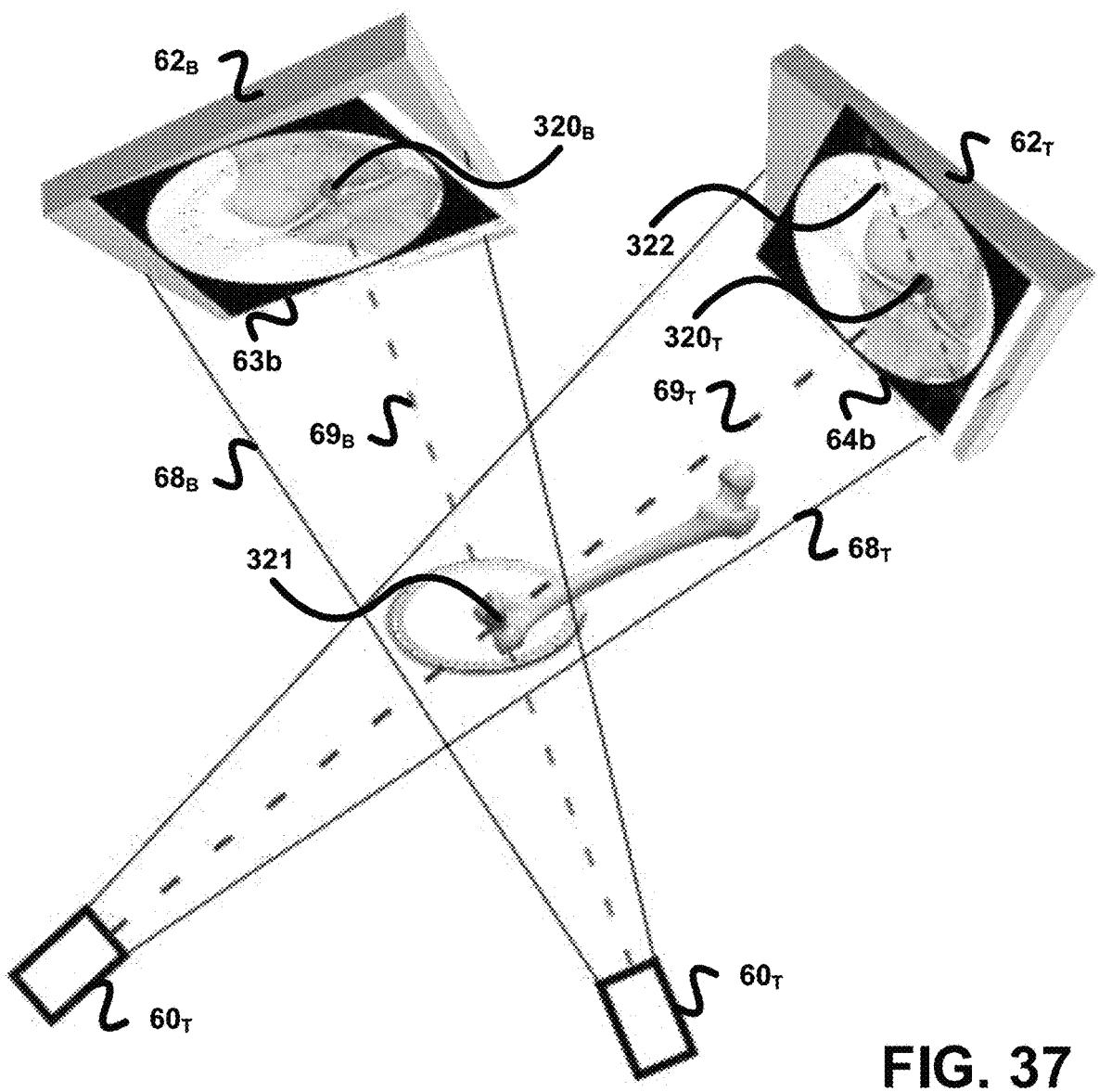
FIG. 37 illustrates an exemplary computation of landmark image delineation of in accordance with various aspects of the present disclosure.

A stage S302 of flowchart 300 encompasses controller 270 controlling a delineation of a landmark in both the baseline X-ray image and the target X-ray image. For example, as shown in FIG. 37, a point $320_B$ can be placed on a landmark of a baseline X-ray image 263B via and a projection 322 of this point $320_B$ may then be overlaid onto a target X-ray image 324T. The same landmark $320_T$ can be identified in target X-ray image 324B by sliding the point $320_T$ along the projection line 322.

Once the same landmark is defined in both images $263_B$ and $264_T$, controller 270 proceeds to a stage S304 of flowchart 300 to implement an intervention computation, such as, for example, a distance measurement between landmarks in the baseline/target images, a computation of three-dimensional angles between lines in the baseline/target images and three-dimensional reconstruction of linear or tree-like structures from the baseline/target images.

Figure 38:
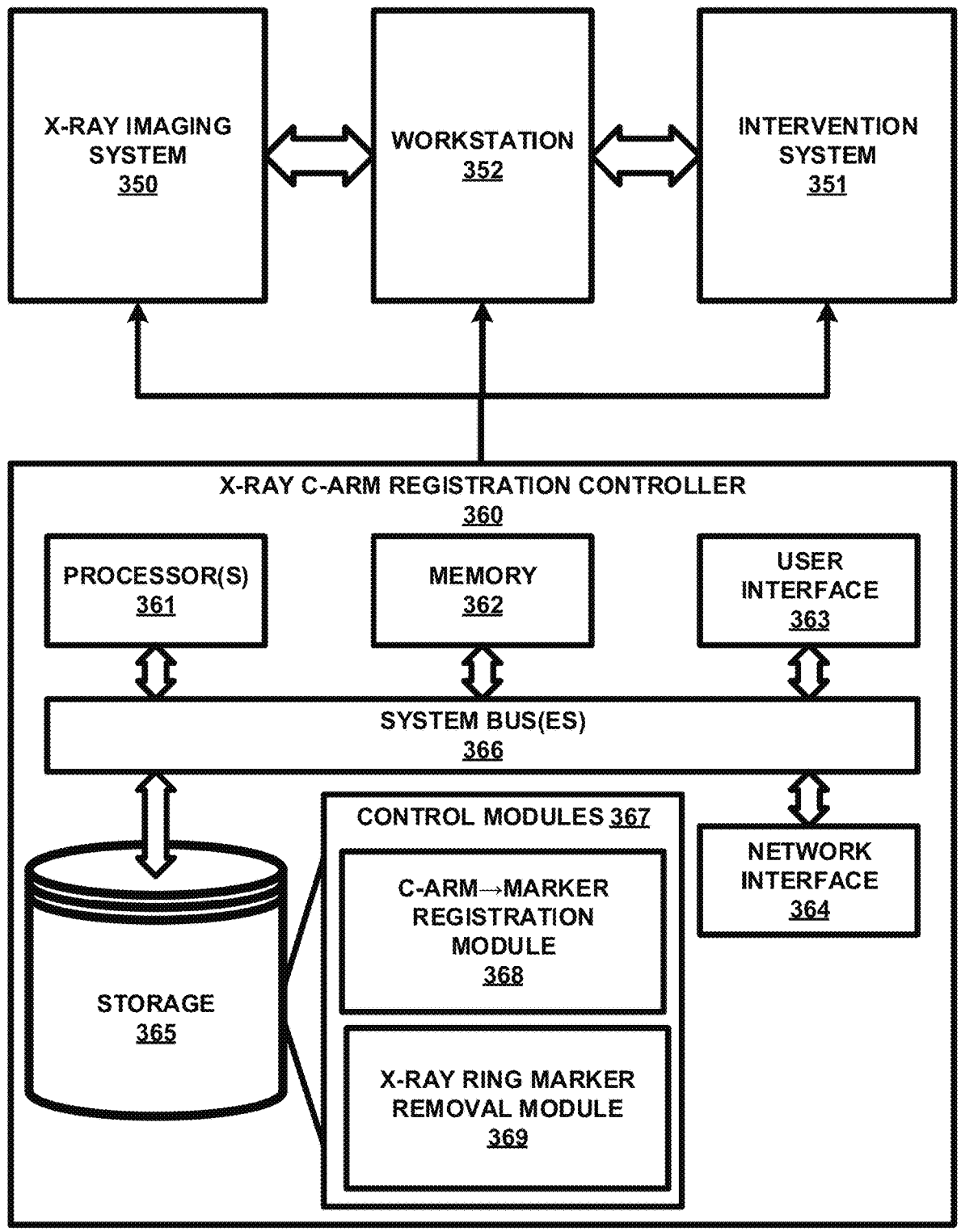
FIG. 38 illustrates an exemplary embodiment of a C-arm registration controller in accordance with various aspects of the present disclosure.

FIG. 38 illustrates a flowchart 310 as one embodiment of stage S304 of flowchart 300. Flowchart 310 uses the following TABLE 2 of previously computed registration parameters:

TABLE 2

| | Registration Parameters | | | | | | Detector Projection | |
|---|---|---|---|---|---|---|---|---|
| CArm Position | $t_x$ | $t_y$ | $t_z$ | $\theta_{z1}$ | $\theta_x$ | $\theta_{z2}$ | X | Y |
| Baseline | $t_x^B$ | $t_y^B$ | $t_z^B$ | $\theta_{z1}^B$ | $\theta_x^B$ | $\theta_{z2}^B$ | $X^B$ | $Y^B$ |
| Target | $t_x^T$ | $t_y^T$ | $t_z^T$ | $\theta_{z1}^T$ | $\theta_x^T$ | $\theta_{z2}^T$ | $X^T$ | $Y^T$ |

From TABLE 2, homogenous transformations may be computed from marker space to C-arm space in accordance with the following equations [22] and [23]:

$$H^B = \begin{pmatrix} R_z(\theta_{z1}^B)R_x(\theta_x^B)R_z(\theta_{z2}^B) & \begin{matrix}t_x^B\\ t_y^B\\ t_z^B\end{matrix} \\ 0_{1\times 3} & 1 \end{pmatrix}$$ [22]

$$H^T = \begin{pmatrix} R_z(\theta_{z1}^T)R_x(\theta_x^T)R_z(\theta_{z2}^T) & \begin{matrix}t_x^T\\ t_y^T\\ t_z^T\end{matrix} \\ 0_{1\times 3} & 1 \end{pmatrix}$$ [23]

where $Rz(.)$ and $Rx(.)$ are 3D rotations around the Z-axis and the A-axis, respectively.

Figure 34:
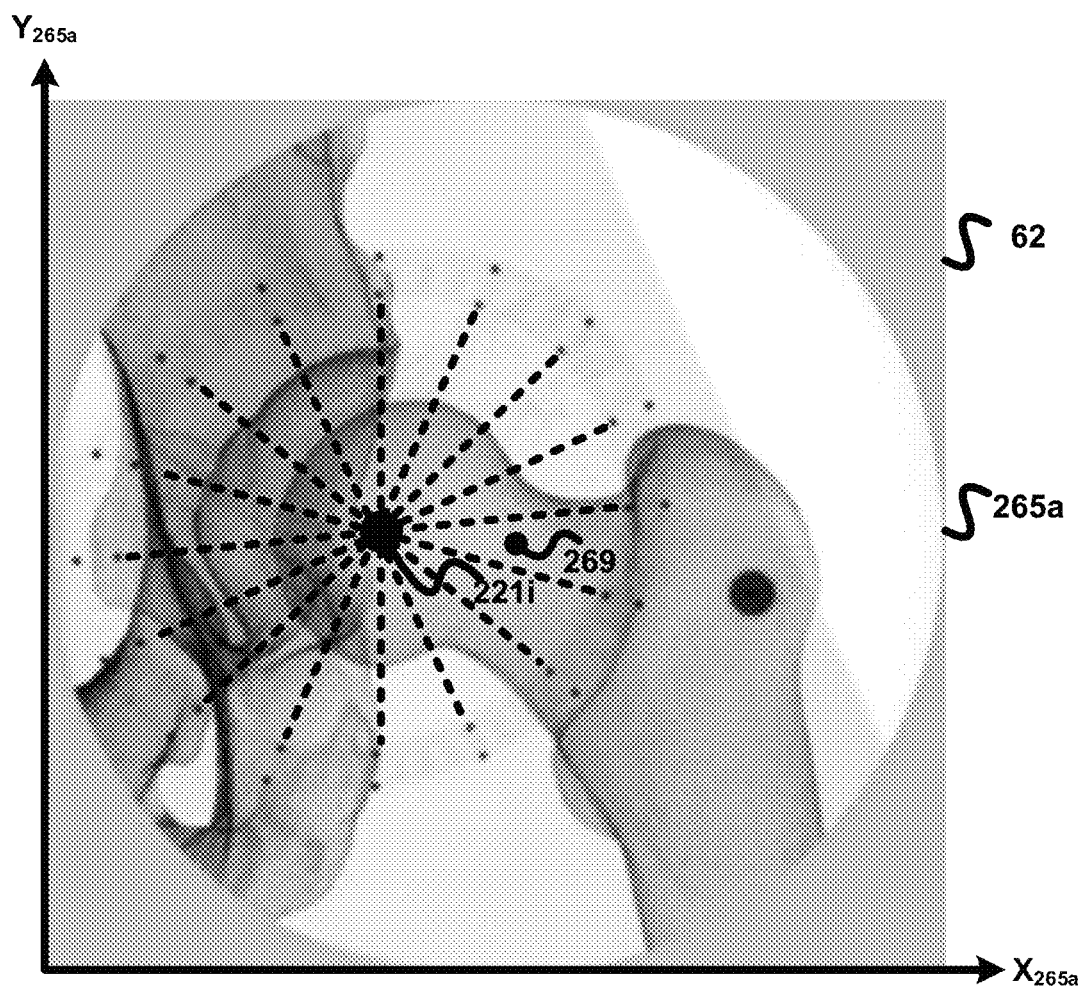
FIG. 34 illustrates an exemplary baseline X-ray image in accordance with the various aspects of the present disclosure.

For the baseline imaging pose, landmark 221 is on ray $269_B$ as shown in FIG. 34 that is defined by points in accordance with the following equations [24] and [25]:

$$S^B = (H^B)^{-1}\begin{pmatrix}0\\ 0\\ S_d^B\\ 1\end{pmatrix}$$ [24]

-continued $$p^B = (H^B)^{-1} \begin{pmatrix} x^B \\ y^B \\ 0 \\ 1 \end{pmatrix} \quad [25]$$

For the target imaging pose, landmark 221 is on ray 269$_T$ as shown in FIG. 34 that is defined by points in accordance with the following equations [25] and [27]:

$$S^T = (H^T)^{-1} \begin{pmatrix} 0 \\ 0 \\ S_d^B \\ 1 \end{pmatrix} \quad [26]$$

$$p^T = (H^T)^{-1} \begin{pmatrix} x^T \\ y^T \\ 0 \\ 1 \end{pmatrix} \quad [27]$$

Thus, the 3D position L of the landmark in the marker coordinates is computed by finding the intersection between the $\overline{S^B p^B}$ and $\overline{S^T p^{BT}}$. This embodiment may be extended to multiple points providing 3D landmark positions in marker space. With these it is easy to compute true distances between landmark, 3D angle between lines or to build approximate 3D reconstructions of linear or tree-like structures.

With the two images of the marker in the same position, the controller 270 may perform additional error checking by comparing the distances between known marker landmarks computed from the two views against the ones retrieved from the model.

To facilitate a further understanding of the various inventive aspects of the present disclosure, the following description of FIG. 38 teaches an exemplary embodiment of a C-arm registration controller of the present disclosure. From this description, those having ordinary skill in the art will appreciate how to apply various aspects of the present disclosure for making and using additional embodiments of C-arm registration controller of the present disclosure.

Referring to FIG. 38, a C-arm registration controller 360 includes one or more processor(s) 361, memory 362, a user interface 363, a network interface 364, and a storage 365 interconnected via one or more system buses 366.

Each processor 361 may be any hardware device, as known in the art of the present disclosure or hereinafter conceived, capable of executing instructions stored in memory 362 or storage or otherwise processing data. In a non-limiting example, the processor(s) 361 may include a microprocessor, field programmable gate array (FPGA), application-specific integrated circuit (ASIC), or other similar devices.

The memory 362 may include various memories, as known in the art of the present disclosure or hereinafter conceived, including, but not limited to, L1, L2, or L3 cache or system memory. In a non-limiting example, the memory 362 may include static random access memory (SRAM), dynamic RAM (DRAM), flash memory, read only memory (ROM), or other similar memory devices.

The user interface 363 may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface 364.

The network interface 364 may include one or more devices, as known in the art of the present disclosure or hereinafter conceived, for enabling communication with other hardware devices. In a non-limiting example, the network interface 364 may include a network interface card (NIC) configured to communicate according to the Ethernet protocol. Additionally, the network interface 364 may implement a TCP/IP stack for communication according to the TCP/IP protocols. Various alternative or additional hardware or configurations for the network interface 364 will be apparent.

The storage 365 may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage 365 may store instructions for execution by the processor(s) 361 or data upon with the processor(s) 361 may operate. For example, the storage 365 may store a base operating system for controlling various basic operations of the hardware. The storage 365 also stores application modules in the form of executable software/firmware for implementing the various functions of the controller 360 as previously described in the present disclosure including, but not limited to, a C-arm→X-ray ring marker registration module 368 as an embodiment of C-arm→X-ray ring marker registration 471 as previously described in the present disclosure, and a ring marker removal module 369 as known in the art of the present disclosure for removing X-ray ring marker from an X-ray image being displayed.

In practice, controller 360 may be installed within a X-ray imaging system 350, an intervention system 351 (e.g., an intervention robot system), or a stand-alone workstation 352 in communication with X-ray imaging 350 system and/or intervention system 351 (e.g., a client workstation or a mobile device like a tablet). Alternatively, components of controller 360 may be distributed among X-ray imaging system 350, intervention system 351 and/or stand-alone workstation 352.

To facilitate a further understanding of various inventive aspects of the present disclosure, the following description of FIGS. 39-42B teaches exemplary embodiments of a planning overlay mode by an X-ray overlay controller of the present disclosure. From this description, those having ordinary skill in the art of the present disclosure will appreciate how to apply the various aspects of the present disclosure for making and using additional embodiments of X-ray overlay controller of the present disclosure for executing additional embodiments of a planning overlay mode of the present disclosure.

Generally, the planning overlay mode applies to any X-ray imaging based interventional procedure as known in the art of the present disclosure or conceived hereafter that requires multiple C-arm orientations relative to an anatomical region AR to properly visualize an alignment of any interventional tool as known in the art of the present disclosure to a target location within the anatomical region AR.

For example, mobile x-ray fluoroscopy is widely used in minimally invasive interventions in fields such as orthopedics, trauma, vascular and spine. Mobile x-ray systems are commonly used because of their relatively small footprint compared to fixed x-ray systems, their maneuverability and reduced cost. However, given that mobile X-ray systems are typically not position-encoded, it can be difficult to implement advanced tools that rely on the precise orientation of the C-arm. For example, mobile X-ray systems have a limited field of view, and given that the translational position is not encoded, it is not trivial to stitch images together to increase the field of view.

For mobile x-ray fluoroscopy, many mobile C-arm procedures require precise positioning of tools or anatomy. In ortho-trauma, for example, fracture reduction is common, which requires clinicians to realign bone fragments and deploy nails or screws at specific locations and angles. In pelvic fracture reduction, a screw may be placed through the sacroiliac joint. The placement of the sacroiliac screw is particularly challenging, given that there is a small target area for the screw to land and it is important to avoid damaging critical structures in the spine. Furthermore, the target landing area for the screw may not be visible in the same field of view as the starting point.

More particularly, sacroiliac screw placement remains a challenge, even for experienced surgeons. Given the complexity of the anatomy and difficulty of properly visualizing the position of the tool relative to the anatomy, sacroiliac screw misplacement is not uncommon. The challenge comes from the fact that multiple sequential C-arm orientations are needed to properly align the screw/tool. Since the motion of the tool is not constrained, there is the possibility that the surgeon may misalign the screw placement in old views when aligning the tool in the current view.

The planning overlay mode of the present disclosure localizes an interventional tool in 3D space to show its trajectory and/or position both inside and outside of the field of view of a live X-ray image in order to improve device insertion outcomes with minimal effect on procedure time.

Figure 39:
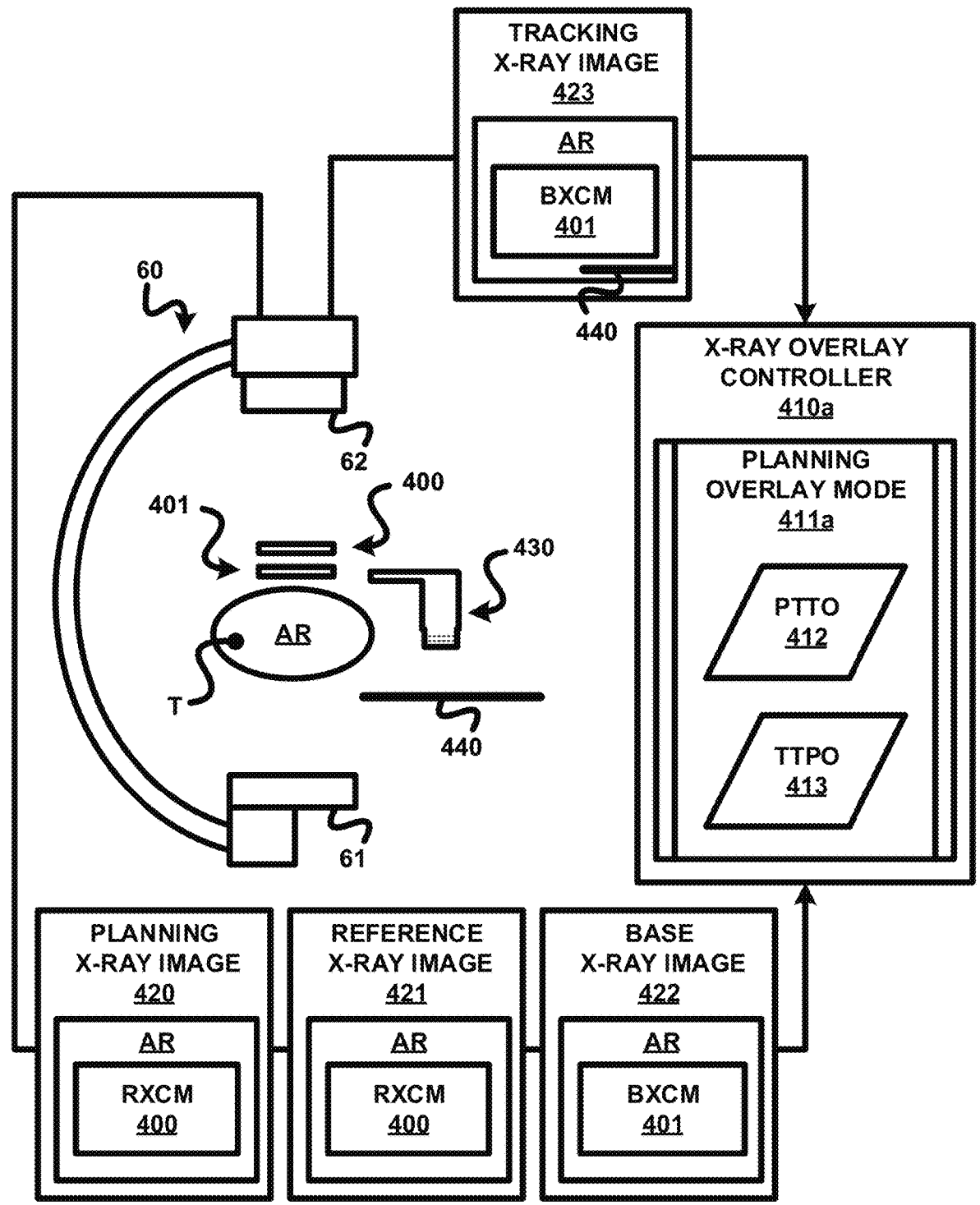
FIG. 39 illustrates an exemplary embodiment of a X-ray imaging system for implementing a planning overlay display mode in accordance with the various aspects of present disclosure.

Referring to FIG. 39, generally, a planning overlay mode 411a of the present disclosure will initially encompass an acquisition of at least two (2) planning X-ray images 420, 421 at different imaging poses of a C-arm 60 with each planning X-ray image 420 being illustrative of different views of an anatomical region AR required for the succeeding interventional procedure. Each planning X-ray image 420, 421 is illustrative of a planning X-ray calibration device 400 relative to the anatomical region AR and non-illustrative of an interventional tool 440 to be navigated within the anatomical region AR during the succeeding interventional procedure. The planning X-ray images 420, 421 facilitate a planning of a trajectory of the interventional tool 440 within the anatomical region AR.

For a preparation phase of the interventional procedure, a base X-ray image 422 is acquired at a same imaging pose of the C-arm 60 as one of the acquired planning X-ray imaging pose 420, 421 that is serving as a reference, and the base X-ray image 422 is illustrative of a base X-ray calibration device 401 relative to the anatomical region AR. As will be further described in the present disclosure, the base X-ray image 422 is registered to a tool guide 430 positioned and aligned at a planned entry location of the anatomical region AR to facilitate a generation of a planned tool trajectory overlay 412 on one or more of the planning X-ray images 420, 421 and optionally onto the base X-ray image 422. Thereafter, as the interventional tool 440 is navigated through the entry location into the anatomical region AR via the tool guide 430, a tracking of the interventional tool 440 relative to the tool guide 430 facilitates a generation of a tracked tool position overlay 413 onto the base X-ray image 422 and one or more of the planning X-ray images 420, 421. Alternatively, a tracking X-ray image 423 may be acquired as the interventional tool is navigated through the entry location into the anatomical region AR via the tool guide whereby the acquisition of the tracking X-ray image 423 is at the same X-ray imaging pose of the C-arm 60 as the base X-ray image 422 and the tracking X-ray image 423 is illustrative of the interventional tool 400 within the anatomical region AR. A tracking of the interventional tool 440 relative to the tool guide 430 in this alternative embodiment facilitates a generation of the tracked tool position overlay 413 onto one or more of the planning X-ray images 420, 421 with the interventional tool 440 being illustrated in the tracking image 423.

From the description of FIGS. 39-42B, those having ordinary skill in the art of the present disclosure will appreciate and understand the planning overlay mode 411a constitutes an image-based method to register a position and/or a trajectory of an interventional tool relative to an anatomical region AR as illustrated in a base X-ray image 422 to planning X-ray images 420, 421 to thereby provide a simultaneous display of a planned trajectory and/or a position of the interventional tool 400 within anatomical region AR in the base X-ray image 422/tracking X-ray image 423 and an overlay of the planned trajectory and/or the position of the interventional tool within anatomical region onto the planning X-ray images 420, 421.

An X-ray image as shown in FIGS. 39-42B and claimed herein is labelled as either a "planning X-ray image", a "base X-ray image" or a "tracking X-ray image" as a basis for specifying what is being illustrated by that X-ray image as described in the present disclosure. Nonetheless, these labels do not change the definition of these images as X-ray images as known in the art of the present disclosure.

In practice, one planning X-ray image or multiple planning X-ray images at different X-ray imaging poses of C-arm 60 may be acquired prior to the interventional procedure and/or multiple tracking X-ray images at the same X-ray imaging pose or different X-ray imaging poses of C-arm 60 may be acquired during different stages of the interventional procedure. Nonetheless, to provide a concise exemplary description of planning overlay mode 410a, FIGS. 39-42B will be described in the context of an acquisition of two planning X-ray images 420, 421 at different X-ray imaging poses of C-arm 60 prior to the interventional procedure and an acquisition of single tracking X-ray image 423 at the same X-ray imaging pose of C-arm 60 of base X-ray imaging pose 422.

Additionally, an X-ray calibration device as shown in FIGS. 39-42B and claimed herein may be embodied as one or more X-ray ripple markers as previously described in the present disclosure and shown in FIGS. 1-19 of the present disclosure and/or one or more X-ray ring markers as previously described in the present disclosure and shown in FIGS. 20-38 of the present disclosure.

Further, an X-ray calibration device as shown in FIGS. 39-42B and claimed herein is labelled as either a "planning X-ray calibration device" or a "base X-ray calibration device" as a basis for distinguishing a purpose of that X-ray calibration device. Nonetheless, these labels do not change the definition of a X-ray calibration device as previously set forth in the present disclosure. Further, in practice, a planning X-ray calibration device and a base X-ray calibration device may be the physically embodied as the same X-ray calibration device or physically embodied as two different X-ray calibration devices.

Also in practice, a X-ray calibration device as illustrated in an acquired X-ray image may be removed (unillustrated) in a display of the acquired X-ray image as previously described in the present disclosure.

Further, the exemplary embodiments of tool guide 430 and interventional tool 440 as shown in FIGS. 39-46C are to facilitate a description of planning overlay mode 411. In practice, a tool guide and an interventional tool for purposes of the present disclosure may be embodied as known in the art of the present disclosure or herein after conceived.

Still referring to FIG. 39, an X-ray calibration device will have be mounted relative to an anatomical region AR within an X-ray imaging space of C-arm 60 (mobile or fixed) during an acquisition of X-ray images as known in the art of the present disclosure. The X-ray source 61 and an the X-ray detector 62 of the C-arm 60 are translatable and/or rotatable to various imaging poses for acquiring the X-ray images illustrative of an X-ray calibration device relative to the anatomical region AR as exemplarily described herein.

More particularly, an X-ray overlay controller 410a processes the X-ray images generated by C-arm 60 to execute a planning overlay mode 411a of the present disclosure for controlling a display of a planned tool trajectory overlay 412 of an interventional tool 440 and/or a tracked tool position overlay 413 of interventional tool 440 onto planning X-ray image(s).

For purposes of the description and claims herein, a planned tool trajectory overlay is a virtual representation of a planned trajectory of an interventional tool within anatomical region that is superimposed onto an X-ray image, and a tracked tool position overlay is a virtual representation of a tracked position of an interventional tool within an anatomical region that is superimposed onto an X-ray image.

Figure 40A:
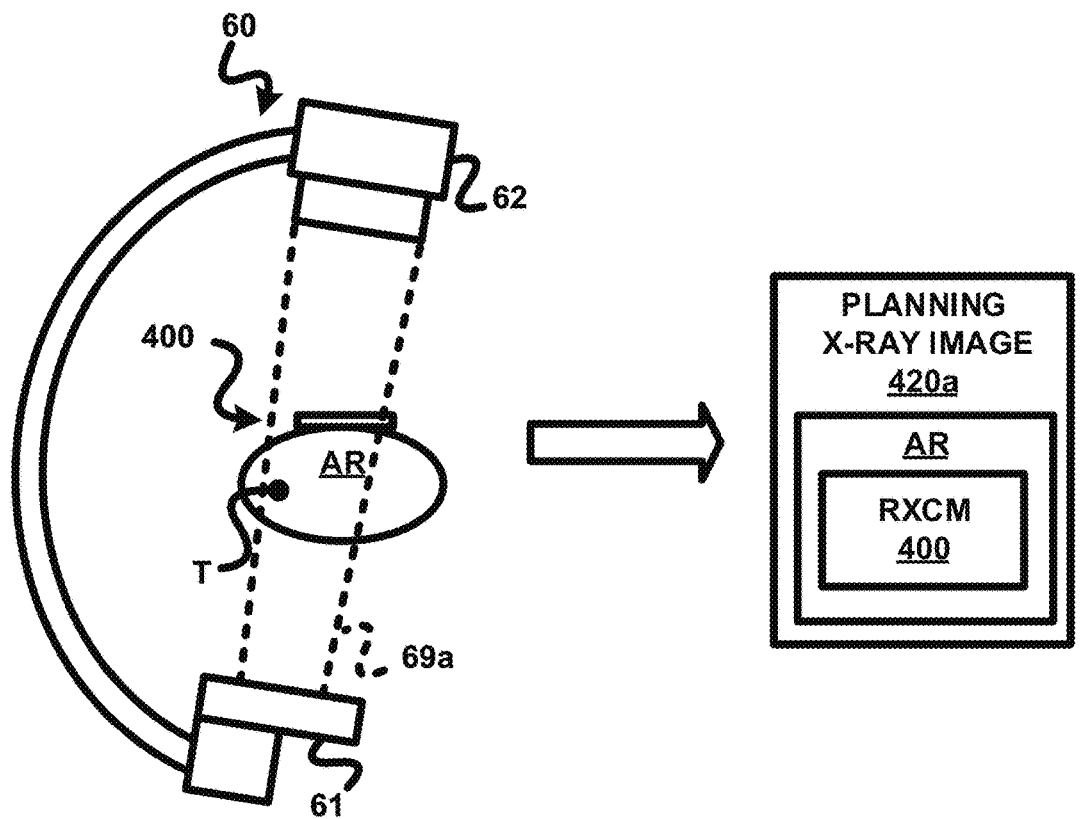
FIGS. 40A-40D illustrate exemplary planned overlay display of X-ray images in accordance the various aspects of the planned overlay display mode of the present disclosure.

Still referring to FIG. 39, in a preparation phase of planning overlay mode 411a, C-arm 60 is operated at a designated planning X-ray imaging pose to acquire a planning X-ray image 420 illustrative of planning X-ray calibration device 400 and non-illustrative of interventional tool 440. For example, FIG. 40A shows an X-ray projection 69a of C-arm 60 at a designated planning X-ray imaging pose to acquire a planning X-ray image 420a illustrative of planning X-ray calibration device 400 and non-illustrative of interventional tool 440. X-ray overlay controller 410a processes planning X-ray image 420a to calculate a rigid body transformation F1 of planning X-ray calibration device 400 to the X-ray detector 62 of C-arm 60 at the planning X-ray imaging pose 450 as exemplary shown in FIGS. 41A and 41B.

Figure 40B:
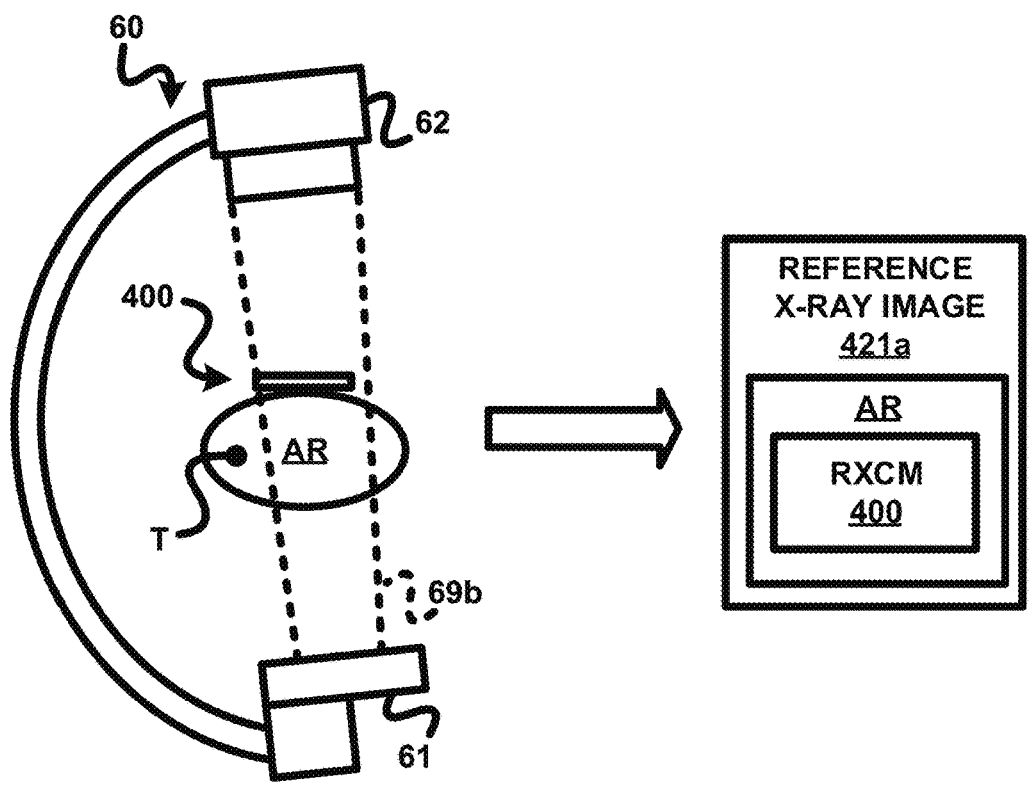

Referring back to FIG. 39, also in the preparation phase of planning overlay mode 411a, C-arm 60 is operated at a designated reference X-ray imaging pose to acquire a reference planning X-ray image 421 illustrative of planning X-ray calibration device 400 and non-illustrative of interventional tool 440. For example, FIG. 40B shows an X-ray projection 69b of C-arm 60 at a designated reference X-ray imaging pose to acquire a reference planning X-ray image 421a illustrative of planning X-ray calibration device 400 and non-illustrative of interventional tool 440. X-ray overlay controller 410a processes reference planning X-ray image 421b to calculate a rigid body transformation F2 of planning X-ray calibration device 400 to the X-ray detector 62 of C-arm 60 at a reference X-ray imaging pose 451 as exemplary shown in FIGS. 41A and 41B.

In practice of the preparation phase of planning overlay mode 411a, planning X-ray calibration device 400 may be fixed relative to anatomical region AR by any suitable means as known in the art of the present disclosure (e.g., an attachment to an operating table, a rail, a drape, or an intervention robot).

Figure 40C:
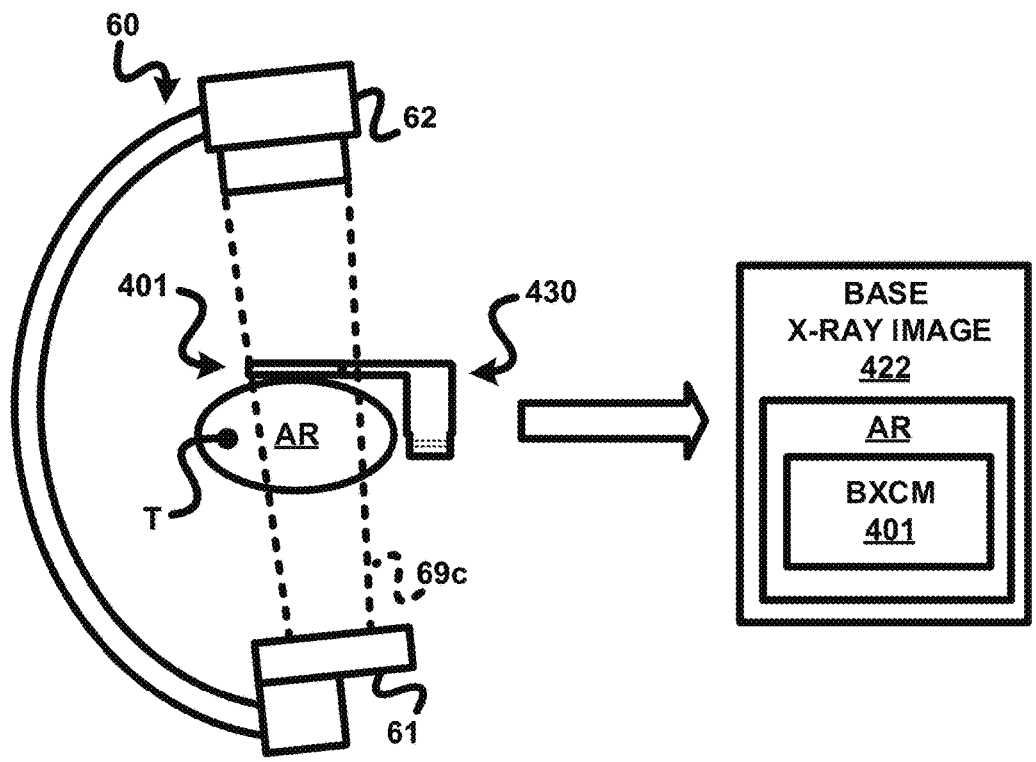

In an interventional phase of planning overlay mode 411a, C-arm 60 is operated at the designated reference X-ray imaging pose to acquire a base X-ray image 422 illustrative of a base X-ray calibration device 401 as supported by a tool guide 430 relative to the anatomical region AR. For example, FIG. 40C shows an X-ray projection 69c of C-arm 60 at the designated reference X-ray imaging pose to acquire a base X-ray image 422a illustrative of base X-ray calibration device 401. X-ray overlay controller 410a processes base X-ray image 422a to calculate a rigid body transformation F3 of base X-ray calibration device 401 to the X-ray detector 62 of C-arm 60 at the reference X-ray imaging pose 451 as exemplary shown in FIGS. 41A and 41B.

Further, a rigid body transformation F4 from tool guide 430 to base X-ray calibration device 401 as shown in FIGS. 4A and 4B is known prior to planning overlay mode 411a or calculated during planning overlay mode 411a. In practice, rigid body transformation F4 may be derived from embodiments of a tool guide manufactured/assembled to support a base X-ray calibration device as shown in FIGS. 40A-40D, or may be derived utilizing a known registration technique based on a fixed spatial relationship between a tool guide and a base X-ray calibration device.

Figure 40D:
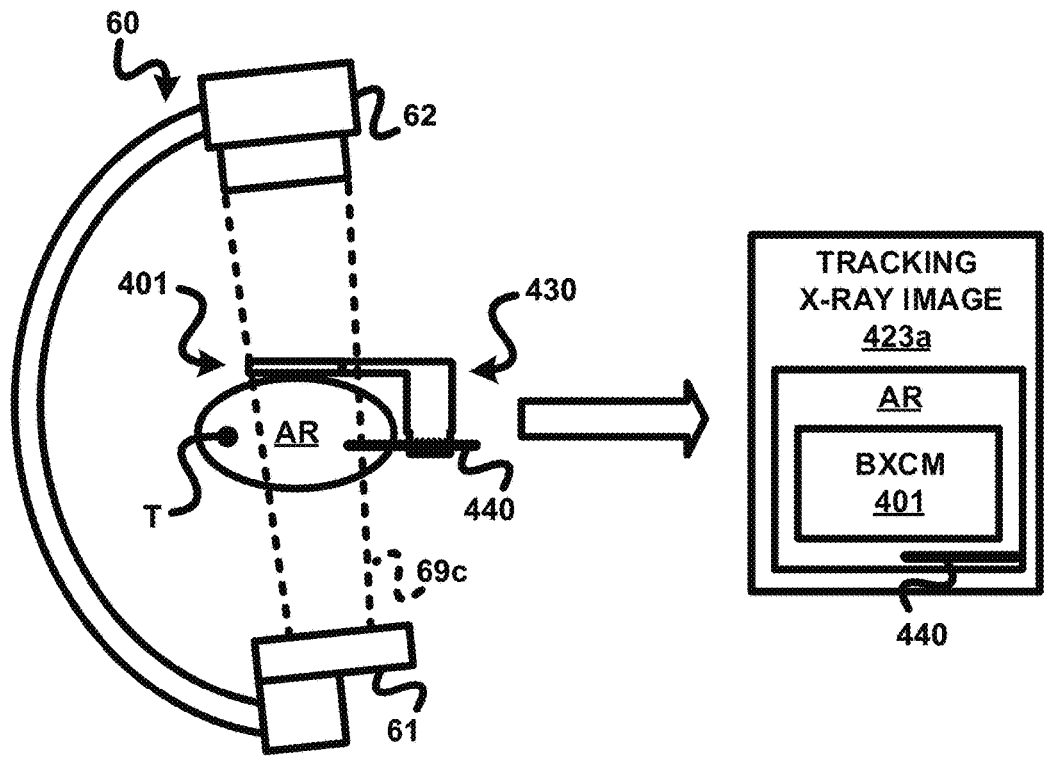

Referring back to FIG. 39, subsequently during the interventional phase of planning overlay mode 411a, C-arm 60 is operated at the designated reference X-ray imaging pose to acquire a tracking X-ray image 423 illustrative of base X-ray calibration device 401 as exemplarily supported by a tool guide 430 relative to the anatomical region AR and further illustrative of interventional tool 440 navigated within the anatomical region AR. For example, FIG. 40D shows an X-ray projection 69c of C-arm 60 at the designated reference X-ray imaging pose to acquire a tracking X-ray image 423a illustrative of both base X-ray calibration device 401 and interventional tool 440. X-ray overlay controller 410a processes tracking X-ray image 423a to calculate a rigid body transformation F3 of base X-ray calibration device 401 to the X-ray detector 62 of C-arm 60 at the reference X-ray imaging pose 451 as exemplary shown in FIGS. 41A and 41B.

Figure 41A:
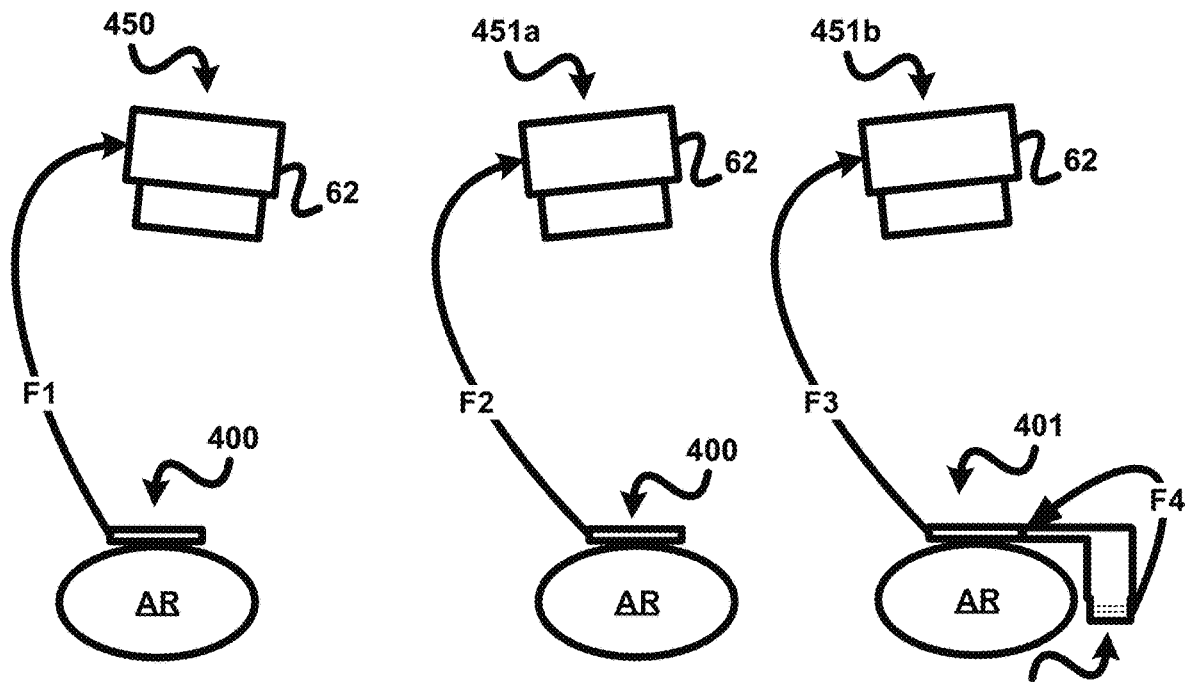
FIGS. 41A and 41B illustrate exemplary X-ray source→calibration marker transformations in accordance the various aspects of the planned overlay display mode of the present disclosure.
Figure 41B:
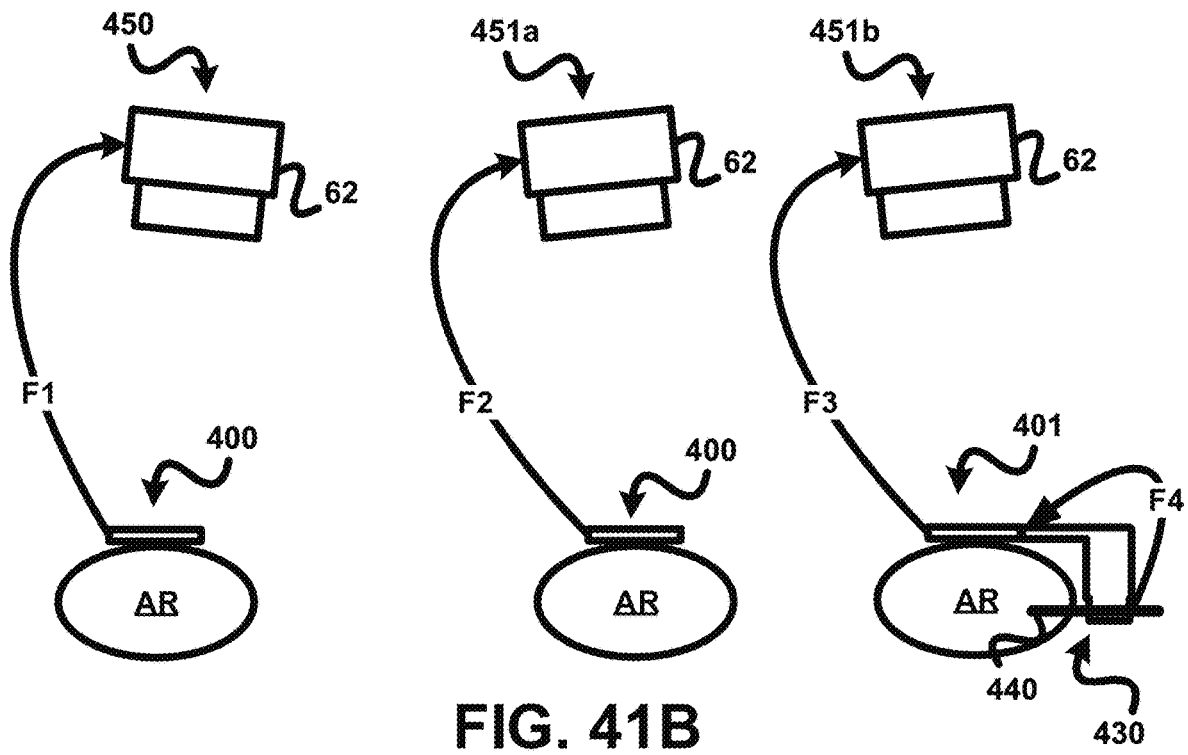

Referring to FIGS. 41A and 41B, as will be further described in the present disclosure, transformations F1-F4 facilitate a generation and a display of planned tool trajectory overlay 312 and tracked tool position overlay 413 onto the various X-ray images.

For example, prior to an entry of interventional tool 440 within anatomical region AR, FIG. 42A shows a display of a base X-ray image 422b illustrating a planned tool trajectory overlay 412a of interventional tool 400 within the anatomical region AR via tool guide 430, and further shows a planned tool trajectory overlay 412b of interventional tool 440 onto a planning X-ray image 420b as derived from transformations F1-F4 of FIGS. 41A and 41B.

By further example, upon interventional tool 440 approaching the target location T, FIG. 42B shows a display of a tracking X-ray image 422b illustrating interventional tool 400 positioned along a planned tool trajectory of interventional tool 400 within the anatomical region AR via tool guide 430, and further shows a display of a planned tool trajectory overlay 412b and a tracking tool position overlay 413a onto planning X-ray image 420b as derived from transformations F1-F4 of FIG. 41.

To facilitate a further understanding of various inventive aspects of the present disclosure, the following description of FIGS. 43-47C teaches exemplary embodiments of a planning overlay mode of the present disclosure. From this description, those having ordinary skill in the art of the present disclosure will appreciate how to apply the various aspects of the present disclosure for making and using additional embodiments of a planning overlay mode of the present disclosure.

Figure 43:
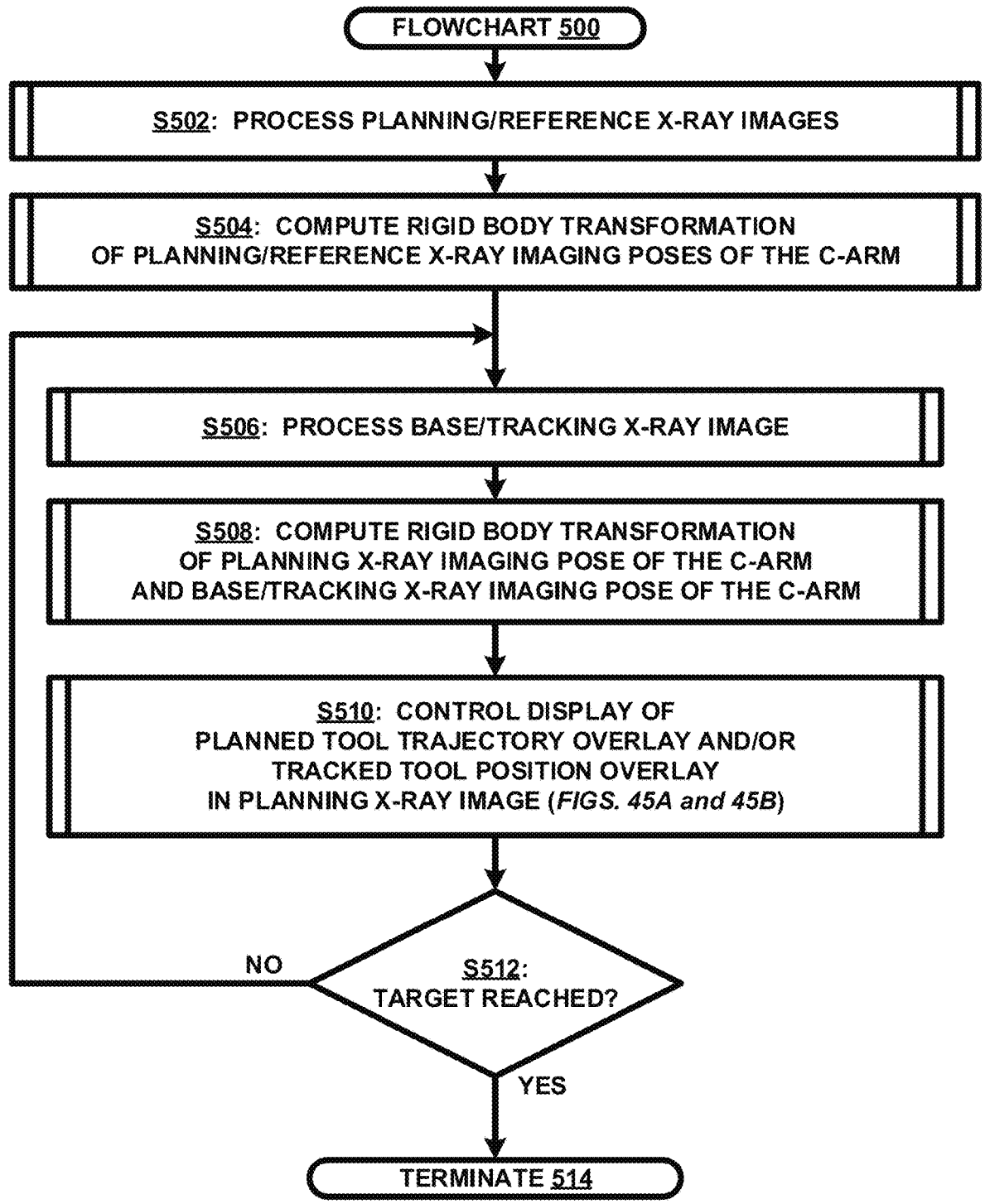
FIG. 43 illustrates a flowchart representative of an exemplary embodiment of a planned overlay display method in accordance the various aspects of the present disclosure

FIG. 43 illustrates a flowchart 500 representative of an exemplary embodiment of planning overlay mode 411a of FIG. 39.

Figure 47A:
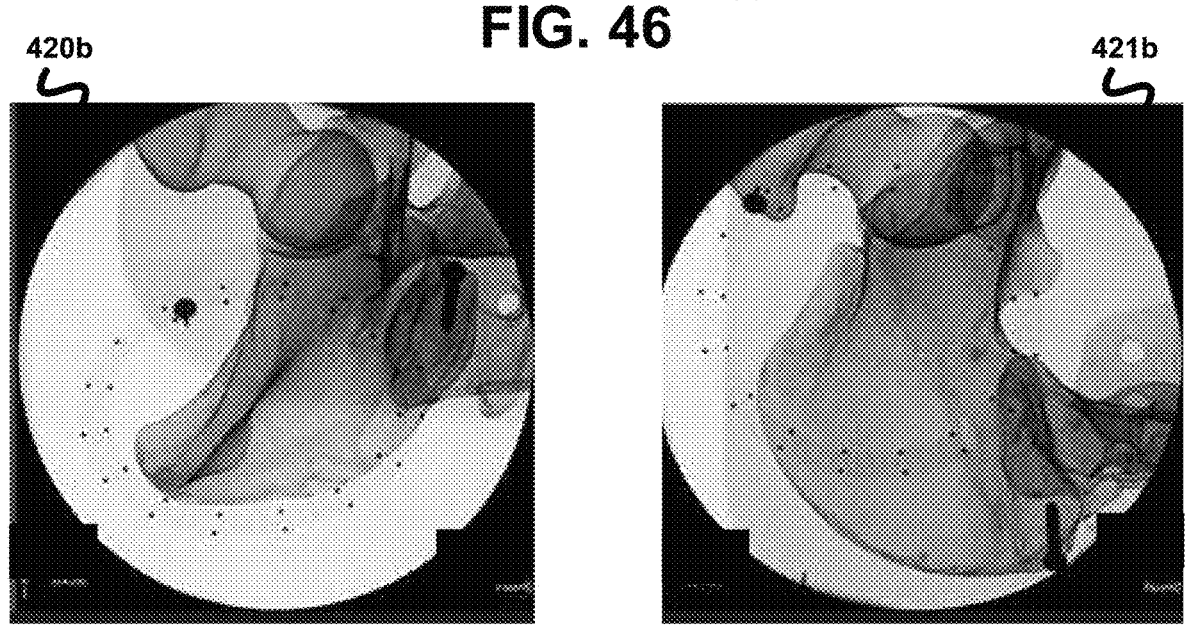
FIGS. 47A-47C illustrate a second exemplary displayed navigation of an interventional tool in accordance the various aspects of the planned overlay display mode of the present disclosure.

Referring to FIG. 43, a stage S502 of flowchart 500 encompasses X-ray overlay controller 410a processing planning X-ray images acquired at different imaging poses of the C-arm 60 whereby the planning X-ray images are illustrative of different views of a planning X-ray calibration device (e.g., X-ray rippler marker(s) or X-ray ring marker(s)) relative to anatomical region AR and non-illustrative of an interventional tool, such as, for example, a planning X-ray image 420b and reference planning X-ray image 421b as shown in FIG. 47A.

The processing of the planning X-ray images by X-ray overlay controller 410a may encompass one or more techniques as known in the art of the present disclosure or hereinafter conceived for facilitating a planning of the interventional procedure and a display of the planning X-ray images.

In one exemplary embodiment of stage S502, X-ray overlay controller 410a processes the DICOM data associated with the acquired planning X-ray images as needed to support a planning of a tool trajectory through the anatomical region.

In a second exemplary embodiment of stage S502, the acquired planning X-ray images may be duplicated whereby the planning X-ray calibration device may be removed from the duplicated planning X-ray images as previously described in the present disclosure to facilitate a clear view of the anatomical region AR from a display of the markerless duplicated planning X-ray images.

In a third exemplary embodiment of stage S502, a target depth estimation technique as known in the art of the present disclosure may be implemented to select a target in the inputted/duplicated planning X-ray images and to estimate a desired insertion depth of the interventional tool into the patient body part.

In a fourth exemplary embodiment of stage S502, a trajectory planning technique as known in the art of the present disclosure may be implemented to delineate a trajectory of the interventional tool through the anatomical region AR to the target that avoids critical structures within the anatomical region AR.

In a fifth exemplary embodiment of stage S502, the planning X-ray images may be fused to other imaging modalities of the anatomical region AR (e.g., 3D CT imaging or 3D MRI imaging).

Referring back to FIG. 43, a stage S504 of flowchart 500 encompasses X-ray overlay controller 410a executing a rigid body transformation of the X-ray imaging poses of C-arm 50 during the acquisition of the planning X-ray images that is based on the illustration of the reference X-ray calibration marker 400 in the planning X-ray images.

In one embodiment of stage S504, the X-ray overlay controller 410a calculates the following equation [28]:

$$F_{D1}^{D2} = (F_M^{D1})^{-1} F_M^{D2} \quad [28]$$

where $F_M^{D1}$ is a rigid body transformation F1 of planning X-ray calibration device 400 as illustrated in the planning X-ray image 420b to the planning imaging pose 450 (FIG. 41) of C-arm 60 during the acquisition of planning X-ray image 421a, where $F_M^{D2}$ is a rigid body transformation F2 of planning X-ray calibration device 400 as illustrated in the reference planning X-ray image 421b to the reference planning imaging pose 451a (FIG. 41) of C-arm 60 during the acquisition of reference planning X-ray image 421a, and where $F_{D1}^{D2}$ is a transformation of the reference planning imaging pose 451a (FIG. 41) of C-arm 60 during the acquisition of reference planning X-ray image 421a to the planning imaging pose 451 (FIG. 41) of C-arm 60 during the acquisition of planning X-ray image 421a.

Figure 47B:
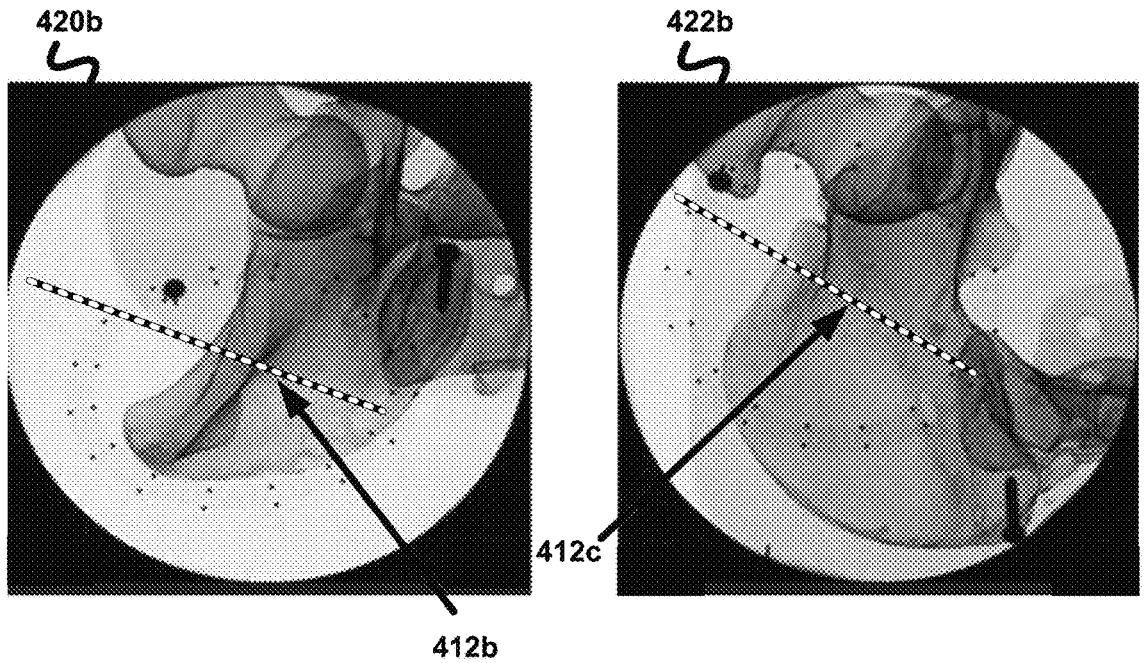

Still referring to FIG. 43, a stage S506 of flowchart 500 encompasses X-ray overlay controller 410a processing base X-ray image acquired at the reference imaging pose of C-arm 60, whereby the base X-ray image is illustrative of a base X-ray calibration device (e.g., X-ray rippler marker(s) or X-ray ring marker(s)) relative to an anatomical region AR, such as, for example, a base X-ray image 422b as shown in FIG. 47B.

Figure 46:
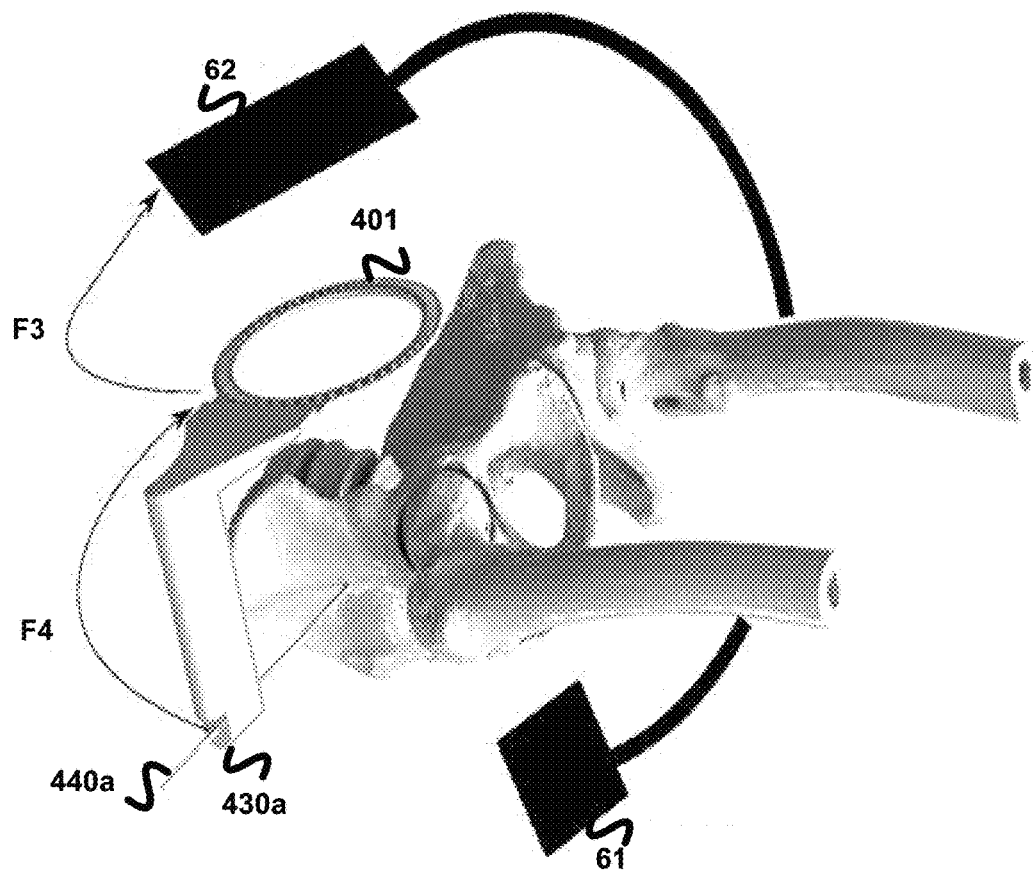
FIG. 46 illustrates a tool guide positioned relative to an anatomical region in accordance the various aspects of the present disclosure.

More particularly, in practice the base X-ray calibration device may be supported by a tool guide relative to the anatomical region AR, such as, for example, a tool guide 430a supporting a base X-ray calibration device 401 relative to an anatomical region AR as shown in FIG. 46.

Alternatively in practice, the base X-ray calibration device may be fixed relative to a tool guide by any suitable means as known in the art of the present disclosure (e.g., an attachment to an operating table or an intervention robot).

Referring back to FIG. 43, the processing of the base X-ray image by X-ray overlay controller 410a may encompass one or more techniques as known in the art of the present disclosure or hereinafter conceived for facilitating a visualization of a navigation of an interventional tool through an anatomical region AR.

In one exemplary embodiment of stage S504, X-ray overlay controller 410a processes the DICOM data associated with the base X-ray image as needed to support an entry of an interventional tool into the anatomical region.

In a second exemplary embodiment of stage S506, the acquired base X-ray image may be duplicated whereby the base X-ray calibration device (e.g., X-ray ripple marker(s) of the present disclosure or X-ray ring marker(s) of the present disclosure) may be removed from the duplicated base X-ray image as previously described in the present disclosure to facilitate a clear view of the anatomical region AR from a display of the marker-less duplicated base X-ray image.

In a third exemplary embodiment of stage S506, a target depth estimation technique as known in the art of the present disclosure may be implemented to estimate an insertion depth of the interventional tool relative to the target of the anatomical region AR.

In a fourth exemplary embodiment of stage S506, the base X-ray image may be fused other imaging modalities of the anatomical region AR (e.g., 3D CT imaging or 3D MRI imaging).

Still referring to FIG. 43, a stage S508 of flowchart 500 encompasses X-ray overlay controller 410a computing a rigid body transformation between the C-arm 60 at the planning X-ray imaging pose 420 and tool guide 430 based on a computation of the rigid body transformation between the C-arm 60 at the planning X-ray imaging pose 450 and the C-arm 60 at the reference X-ray imaging pose 451 and further based on a registration between the base X-ray calibration device 401 and tool guide 430. In one embodiment of stage S508, the X-ray overlay controller 410a calculates the following equations [29] and [30]:

$$F_{D2}{}^N = (F_N{}^M F_M{}^{D3})^{-1} \qquad [29]$$

$$F_{D1}{}^N = F_{D2}{}^{D1} F_{D2}{}^N \qquad [30]$$

whereby is $F_N{}^M$ is a transformation of the tool guide 430a to the base X-ray calibration device 401 also labelled F4 in FIG. 46, whereby is $F_M{}^{D3}$ is a transformation of the base X-ray calibration device 401 as illustrated in the base X-ray image 422a to the reference imaging pose 451 (FIG. 41) of C-arm 60 during the acquisition of base X-ray image 422b, where $F_{D2}{}^N$ is a transformation of the tool guide 430a to the reference planning imaging pose 451 (FIG. 41) of C-arm 60 during the acquisition of reference planning X-ray image 421a, where $F_{D1}{}^{D2}$ is a transformation of the reference planning imaging pose 451 (FIG. 41) of C-arm 60 during the acquisition of reference planning X-ray image 421a to the reference planning imaging pose 451a (FIG. 41) of C-arm 60 during the acquisition of reference planning X-ray image 421a, and where $F_{D1}{}^N$ is a transformation of the tool guide 430a to the planning imaging pose 450 (FIG. 41) of C-arm 60 during the acquisition of planning X-ray image 420a.

Since the direction of the tool on the planning image is provided by the transformation $F_{D1}{}^N$, this trajectory may be easily displayed on the planning image by projecting this trajectory on the X-ray image. Assuming that the tool direction in the coordinate frame associated with the tool-guide is aligned with the z axis of transformation $F_N{}^M$, then the tool position with respect to reference planning imaging pose 451 (FIG. 41) of C-arm 60 during the acquisition of reference planning X-ray image 421a is completely described by the following equations [31]:

$$(N_{dir}, N_{offset}) = (F_{D2}{}^N (0,0,1,0)^T F_{D2}{}^N (0,0,0,1)^T) \qquad [31]$$

where $N_{dir}$ is a unit vector providing the direction of the tool/needle, and where $N_{offset}$ is the offset of the tool/needle with respect to the origin of the coordinate system.

It is also further assumed that all transformations are represented as 4×4 homogeneous matrices of the form $$\begin{pmatrix} R_{3\times 3} & t_{3\times 1} \\ 0_{1\times 3} & 1 \end{pmatrix}$$

where R is 3×3 rotation matrix and t is a 3×1 translation vector.

Still referring to FIG. 42, a stage S510 of flowchart 500 encompasses the X-ray overlay controller 410a controlling a display of a planned tool trajectory overlay and/or a tracked tool position overlay on the planning X-ray image(s).

In one embodiment of stage S510, prior to a X-ray imaging of a positioning of the interventional tool into the anatomical region AR, X-ray overlay controller 410a executes a flowchart 520 representative of one embodiment of an overlay generation/display method of the present disclosure as shown in FIG. 44A.

Referring to FIG. 44A, a stage S522 of flowchart 520 encompasses X-ray overlay controller 410a determining a position of the tool guide 430 within an X-ray imaging space of C-arm 60.

In one embodiment of stage S522, X-ray overlay controller 410a utilizes transformations $F_N{}^M$ and $F_M{}^{D3}$ as previously described in the present disclosure to determine a position $\delta_1$ within the X-ray imaging space of C-arm 60 of a distal exit of tool guide 430 that will be abutting or adjacent the anatomical region AR upon a placement of tool guide 430 during the intraoperative X-ray imaging of the anatomical region AR.

Still referring to FIG. 44A, a stage S524 of flowchart 520 encompasses X-ray overlay controller 410a generating and commanding a display of tracked tool position overlay 413b onto planning X-ray image 420b and base X-ray image 422b.

In one embodiment of stage S524, X-ray overlay controller 410a first delineates tracked tool position overlay 413b as an extension of a longitudinal axis of tool guide 430 from the distal exit of tool guide 430 into the X-ray imaging space of C-arm.

Next, for planning X-ray image 420b as shown in FIG. 47B, X-ray overlay controller 410a converts the position $TG^{image}$ within the X-ray imaging space of C-arm 60 of the distal exit of tool guide 430 into a position of the distal exit of tool guide 430 relative to the X-ray projection associated with planning X-ray image 420b as follows:

Step 1 Compute the projection line of the distal point of the tool guide $\delta_{TG}$ using C-arm/X-ray projection geometry and $TG^{image}$ Step 2 Compute 3D tip position in accordance the following equations [32] and [33]:

$$TG^{D2} = \delta_{TG} \cap (N_{dir}, N_{offset}) \qquad [32]$$

$$TG^{D1} = F_{D1}{}^{D2} TG^{D2} \qquad [32]$$

wherein $TG^{D2}$ is the position of the distal point of the tool guide 430 relative to the X-ray projection associated with reference planning X-ray image 421b/base X-ray image 422b as shown in FIG. 47B, and wherein $TG^{D1}$ is the position of the distal point of the tool guide 430 relative to the X-ray projection associated with planning X-ray image 420b as shown in FIG. 47B.

The orientation of the distal exit of tool guide 430 relative to the X-ray projection associated with planning X-ray image 420b is derived from the rigid body transformations, and the delineated extension of the longitudinal axis of tool guide 430 from the distal exit of tool guide 430 into the X-ray imaging space of C-arm extending and oriented from position $TG^{D1}$ will be projected as planned tool trajectory overlay 412b onto planning X-ray image 420b as shown in FIG. 47B.

For base X-ray image 422b, the orientation of the distal exit of tool guide 430 relative to the X-ray projection associated with base X-ray image 422b is derived from transformations $F_N{}^M$ and $F_M{}^{D3}$ as previously described in the present disclosure, and the delineated extension of the longitudinal axis of tool guide 430 from the distal exit of tool guide 430 into the X-ray imaging space of C-arm extending and oriented from position $TG^{D1}$ will be projected as planned tool trajectory overlay 412b onto planning X-ray image 422b as shown in FIG. 47B.

Upon generating the planned tool trajectory overlays, X-ray overlay controller 410a will command the display of the overlays onto a display of the X-ray images on a X-ray workstation monitor, a monitoring array, an augmented reality headset, a virtual reality headset, a mixed reality headset or any other platform for displaying the X-ray images and overlays.

Additionally, in practice, the X-ray images with overlays may be displayed with co-registered or fused 3D images, such as, for example, a CT scan or a MRI scan.

Referring back to FIG. 43, after the completion of the first iteration of stages S506-S510, the navigation of the interventional tool into the anatomical region AR via the tool guide is commenced whereby, for numerous subsequent iterations of stages S506-S510, X-ray overlay controller 410a reiterates flowchart 520 to thereby control a processing of a target X-ray image 423 and a continual display of a tracked tool position overlay and simultaneously executes a flowchart 530 representative of a second embodiment of an overlay generation/display method of the present disclosure as shown in FIG. 44B.

Figure 45:
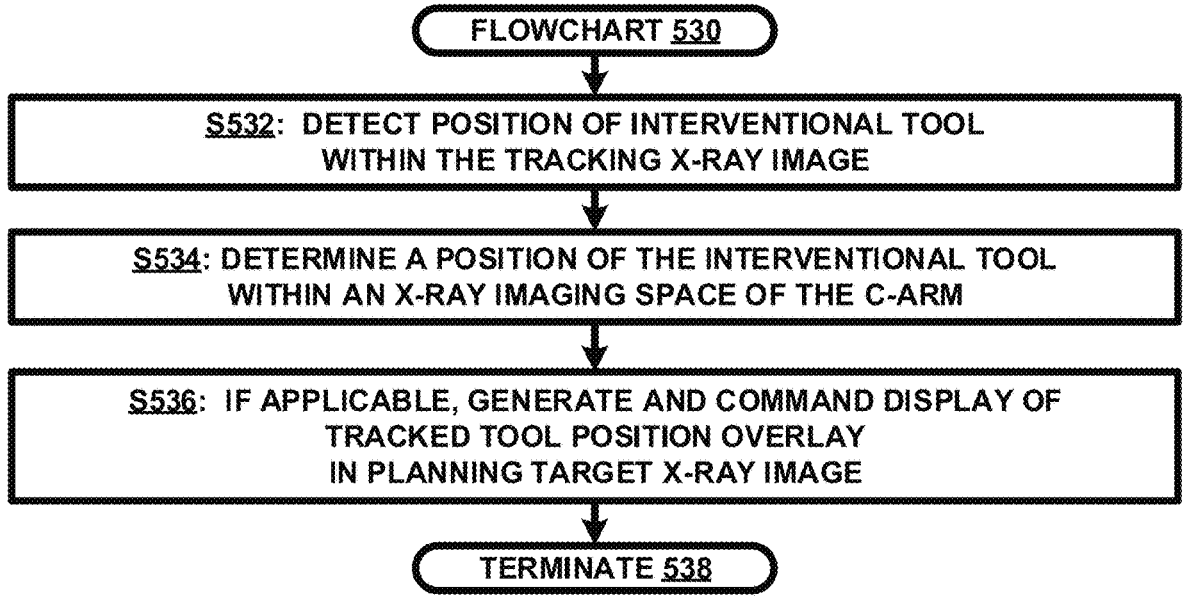
FIG. 45 illustrates a flowchart representative of a second exemplary embodiment of an interventional tool position overlay display method in accordance the various aspects of the present disclosure.

Referring to FIG. 45, a stage S532 of flowchart 530 encompasses X-ray controller implementing imaging techniques as known in the art of the present disclosure for detecting an illustration of the interventional tool within the target X-ray image 423b, particularly an illustration of a distal tip of the interventional tool within the target X-ray image 423b.

Upon detecting the illustration of the interventional tool within the target X-ray image 423b, X-ray overlay controller 410a converts a detected position $Tip^{image}$ within the X-ray imaging space of C-arm 60 of the tip of the interventional tool into a position of the tip of the interventional tool relative to the X-ray projection associated with planning X-ray image 420b in accordance to the following algorithm:

Step 1 Compute the projection line of the tool tip $\delta_{Tip}$ using C-arm/X-ray projection geometry and $Tip^{image}$ and Step 2 Compute 3D tip position in accordance the following equations [34] and [35]:

$$Tip^{D2} = \delta_{Tip} \cap (N_{dir}, N_{offset}) \quad [34]$$

$$TG^{D1} = F_{D1}{}^{D2}Tip^{D2} \quad [35]$$

wherein $Tip^{D2}$ is the position of a tip of the interventional tool 440a relative to the X-ray projection associated with reference planning X-ray image 421b/the target X-ray image 423b, and wherein $Tip^{D1}$ is the position a tip of the interventional tool 440a relative to the X-ray projection associated with planning X-ray image 420b.

The orientation of the tip of the interventional tool relative to the X-ray projection associated with planning X-ray image 420b is derived from the co-registration of the images, and a segment of tracked tool position overlay 413b corresponding to the interventional tool extending from the distal exit of the tool guide will serve as a planned tool trajectory overlay 412b projected onto tracked tool position overlay 413b, which is projected onto planning X-ray image 420b as exemplarily shown in FIG. 47B.

Figure 47C:
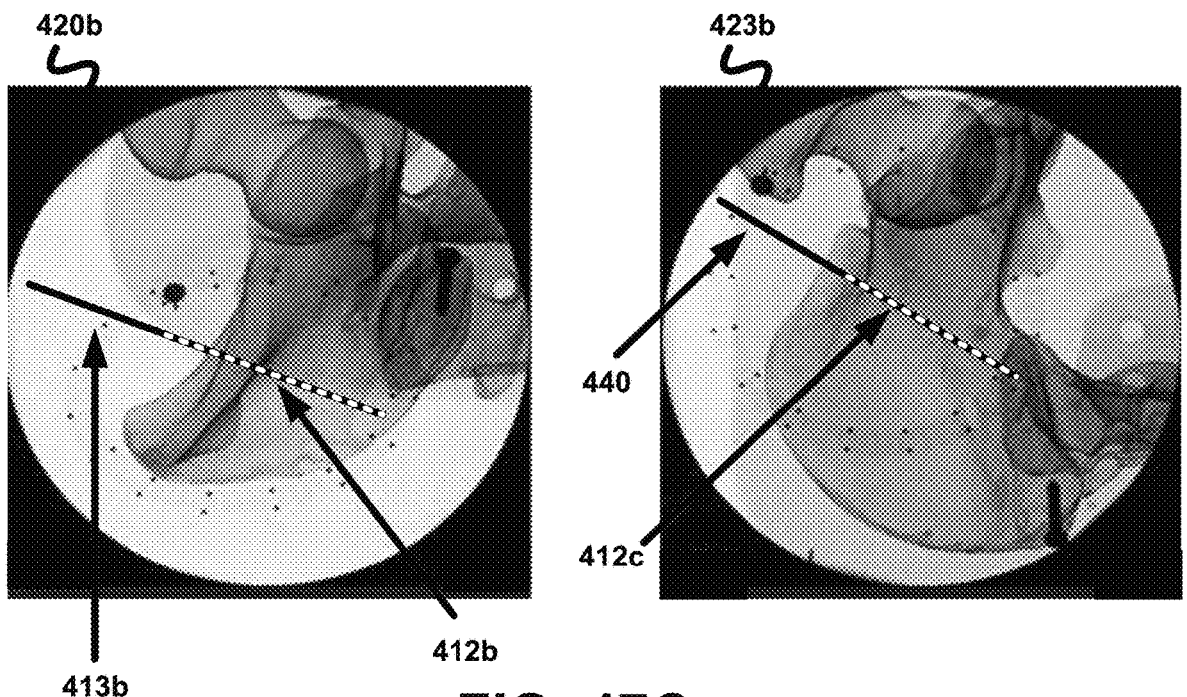

For numerous subsequent reiterations of stages S532-S536, (1) the interventional tool 401 as navigated within the anatomical region AR will be illustrated within the target X-ray image 423b as exemplarily shown in FIG. 47C, (2) tracked tool position overlay 413c will be projected onto planning X-ray image 420b and the target X-ray image 423b as exemplarily shown in FIG. 47C and (3) the planned tool trajectory overlay 412b, corresponding to the interventional tool as illustrated within the target X-ray image 423b, is projected onto a corresponding segment of tracked tool position overlay 413c as projected onto planning X-ray image 420b.

Referring back to FIG. 43, flowchart 500 will loop through stages S506-S510 until such time the target is reached whereby (1) the interventional tool 401 as navigated within the anatomical region AR to the target will be illustrated within the target X-ray image 423b, and (2) the tracked tool position overlay 413c, corresponding to the interventional tool as illustrated within base X-ray image 422b, is fully projected onto the planned tool trajectory overlay 412b as projected unto planning X-ray image 420b.

Those skilled in the art of the present disclosure will appreciate and understand, that upon completion, the planning overlay mode of the present disclosure provides a proper visualization of a target alignment of an interventional tool within the anatomical region AR.

For example, additional planning images may be acquired at different imaging poses of the C-arm corresponding to necessary views of the anatomical region AR during the intervention procedures. These additional images will also be co-registered with the reference images whereby the overlay(s) may be projected the additional images for a more comprehensive visualization of a target alignment of an interventional tool within the anatomical region AR.

By further example, a selection of the target in two or more of the co-registered images will facilitate an estimation of the desired insertion depth. More particularly, if the interventional tool had imagable markings, then the surgeon can control the instrument insertion depth. This can be augmented by tip tracking to display distance to target.

Also be example, when the interventional tool is illustrated in one or more of the co-registered images, then controller 410a may compare the instrument trajectory from the base X-ray image with the tracked tool position overlay for error checking.

Referring back to FIG. 39, an alternative embodiment of flowchart 500, planning X-ray image(s) 420 and a base X-ray image 422 may all be illustrative of a base X-ray calibration device 401 at different X-ray imaging poses of C-arm 60.

In one exemplary operation of this embodiment, X-ray overlay controller 410 process a planning X-ray image 420 acquired by the C-arm 60 at a planning X-ray imaging pose 450 of the C-arm with planning X-ray image being illustrative of base X-ray calibration device 401 and non-illustrative of interventional tool 440.

X-ray overlay controller 410 then processes a base X-ray image 422 acquired by the C-arm 60 at the reference X-ray imaging pose 451 of the C-arm 60 with the base X-ray image 422 being illustrative of a base X-ray calibration device 401 and non-illustrative of the interventional tool 440 and the base X-ray calibration device 401 being registered to tool guide 430.

Next, X-ray overlay controller 410 computes a rigid body transformation between the C-arm 60 at the planning X-ray imaging pose 450 and the C-arm 60 at the reference X-ray imaging pose 451 based on the illustrations of the base X-ray calibration device 401 in the planning X-ray image 420 and in the base X-ray image 422.

Next, X-ray overlay controller 410 computes a rigid body transformation between the C-arm 60 at the planning X-ray imaging pose 450 and a tool guide 430 based on a computation of the rigid body transformation between the C-arm 60 at the planning X-ray imaging pose 450 and the C-arm 60 at the reference X-ray imaging pose 451 and further based on the registration of the base X-ray calibration device 401 to the tool guide 430.

Thereafter, X-ray controller 410 controls a display of a planned tool trajectory overlay 412 and a tracked tool position overlay 413 onto the planning X-ray image 420 based on a computation of the rigid body transformation between the C-arm 60 at the planning X-ray imaging pose 450 and a tool guide 430.

To facilitate a further understanding of various inventive aspects of the present disclosure, the following description of FIGS. 48-55B teaches exemplary embodiments of a guiding overlay display mode by an X-ray overlay controller of the present disclosure. From this description, those having ordinary skill in the art of the present disclosure will appreciate how to apply the various aspects of the present disclosure for making and using additional embodiments of X-ray overlay controller of the present disclosure for executing additional embodiments of a guiding overlay display mode of the present disclosure.

Generally, the guiding overlay display mode applies to any X-ray imaging based interventional procedure as known in the art of the present disclosure or conceived hereafter that requires multiple C-arm orientations relative to an anatomical region to proper visualize an alignment of an interventional tool within the anatomical region.

For example, as previously set forth, mobile x-ray fluoroscopy is widely used in minimally invasive interventions in fields such as orthopedics, trauma, vascular and spine. Mobile x-ray systems are commonly used because of their relatively small footprint compared to fixed x-ray systems, their maneuverability and reduced cost. However, given that mobile X-ray systems are typically not position-encoded, it can be difficult to implement advanced tools that rely on the precise orientation of the C-arm. For example, mobile X-ray systems have a limited field of view, and given that the translational position is not encoded, it is not trivial to stitch images together to increase the field of view.

For mobile x-ray fluoroscopy, many mobile C-arm procedures require precise positioning of tools or anatomy. In ortho-trauma, for example, fracture reduction is common, which requires clinicians to realign bone fragments and deploy nails or screws at specific locations and angles. In pelvic fracture reduction, a screw may be placed through the sacroiliac joint. The placement of the sacroiliac screw is particularly challenging, given that there is a small target area for the screw to land and it is important to avoid damaging critical structures in the spine. Furthermore, the target landing area for the screw may not be visible in the same field of view as the starting point.

More particularly, sacroiliac screw placement remains a challenge, even for experienced surgeons. Given the complexity of the anatomy and difficulty of properly visualizing the position of the tool relative to the anatomy, sacroiliac screw misplacement is not uncommon. The challenge comes from the fact that multiple sequential C-arm orientations are needed to properly align the screw/tool. Since the motion of the tool is not constrained, there is the possibility that the surgeon may misalign the screw placement in old views when he is aligning the tool in the current view.

The guiding overlay display mode of the present disclosure localizes an interventional tool in 3D space to show its trajectory both inside and outside of the field of view of a live X-ray image in order to improve device insertion outcomes with minimal effect on procedure time.

In practice, generally, the guiding overlay display mode of the present disclosure will initially encompass an acquisition of a pair of interventional X-ray images at different imaging poses of a C-arm with each interventional X-ray image being illustrative of different views of an interventional tool positioned within an anatomical region. Each interventional X-ray image is illustrative of a guiding X-ray calibration device relative to the anatomical region. For the procedure, guiding X-ray image(s) may be acquired at different imaging poses of the C-arm. The guiding X-ray image(s) are non-illustrative of the interventional tool and are illustrative of a planned path to a target in the anatomical region. From the description of FIGS. 48-55B, those having ordinary skill in the art of the present disclosure will appreciate and understand the guiding overlay display mode constitutes an image-based method to register a position of an interventional tool relative to an anatomical region as illustrated in a pair of interventional X-ray images to guiding X-ray image(s) illustrative of a planned path to a target to thereby provide a simultaneous display of the position and/or the trajectory of the interventional tool in the X-ray image(s).

For purposes of describing the guiding overlay display mode of the present disclosure, the term "intraoperative" encompasses X-ray imaging of an interventional tool positioned within an anatomical region AR as will be further described in the present disclosure.

Various X-ray images as shown in FIGS. 48-55B and claimed herein are labelled as either "interventional" and "guiding" as a means for distinguishing between the X-ray images of acquired during various aspects of the present disclosure. Nonetheless, these labels do not change the definition of these images as X-ray images.

Additionally, a guiding X-ray calibration device as shown in FIGS. 48-55B and claimed herein may be embodied as one or more X-ray ripple markers as previously described in the present disclosure and shown in FIGS. 1-19 of the present disclosure and/or one or more X-ray ring markers as previously described in the present disclosure and shown in FIGS. 20-38 of the present disclosure.

Figure 48:
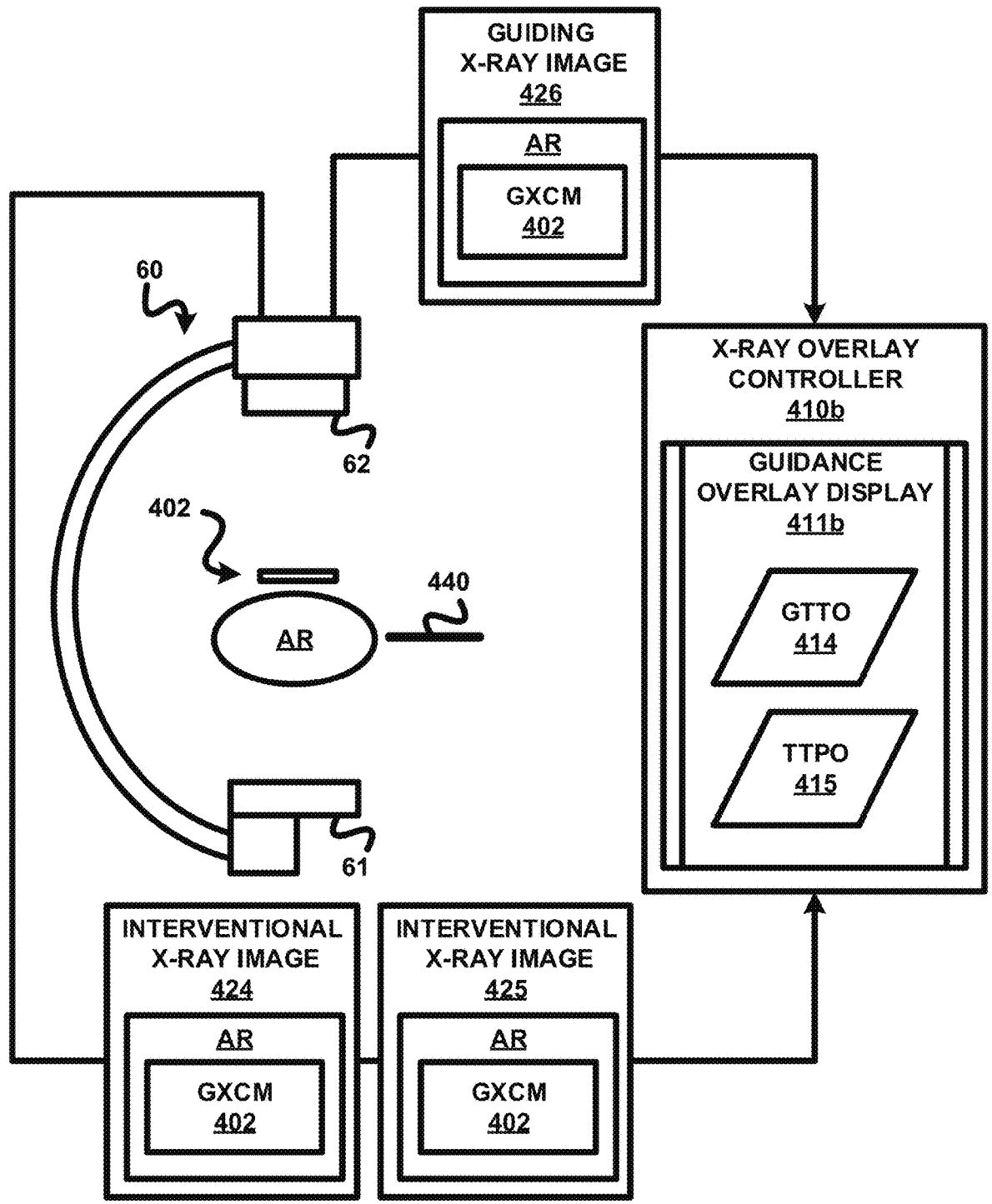
FIG. 48 illustrates an exemplary embodiment of an X-ray imaging system for implementing a guidance overlay display mode in accordance with the various aspects of present disclosure.

Referring to FIG. 48, in practice of the guiding overlay display mode, a guiding X-ray calibration device 402 will be mounted relative to an anatomical region AR within an X-ray imaging space of C-arm 60 (mobile or fixed) during an acquisition of an interventional X-ray image. The X-ray source 61 and the X-ray detector 62 of the C-arm 60 are translatable and/or rotatable to various imaging poses for generating various interventional X-ray images of guiding X-ray calibration device 402 relative to the anatomical region AR.

An X-ray overlay controller 410b processes a pair of interventional X-ray images illustrative of interventional tool 440 relative to the anatomical region AR to execute a guiding overlay display mode 411b of the present disclosure for controlling a display of an guided tool trajectory overlay 414 onto guiding X-ray image(s) illustrative of a planned path to a target within the anatomical region AR and/or a tracked tool position overlay 415 onto guiding X-ray image(s) illustrative of a tracked position of an interventional tool within the anatomical region AR.

Guiding overlay display mode 411b will now be exemplary described in the context of an acquisition of a pair of interventional X-ray images 424 and 425 illustrative of interventional tool 440 at different imaging poses of the C-arm 60 and an acquisition of one (1) guiding X-ray image 426 non-illustrative of interventional tool 440 at an additional different imaging pose of the C-arm 60. Nonetheless, in practice, a guiding overlay display mode of the present disclosure may encompass an acquisition of one or more interventional X-ray images illustrative of an interventional tool at different imaging poses of a C-arm and an acquisition of one or more guiding X-ray images non-illustrative of an interventional tool at an additional different imaging pose of the C-arm.

Figure 49A:
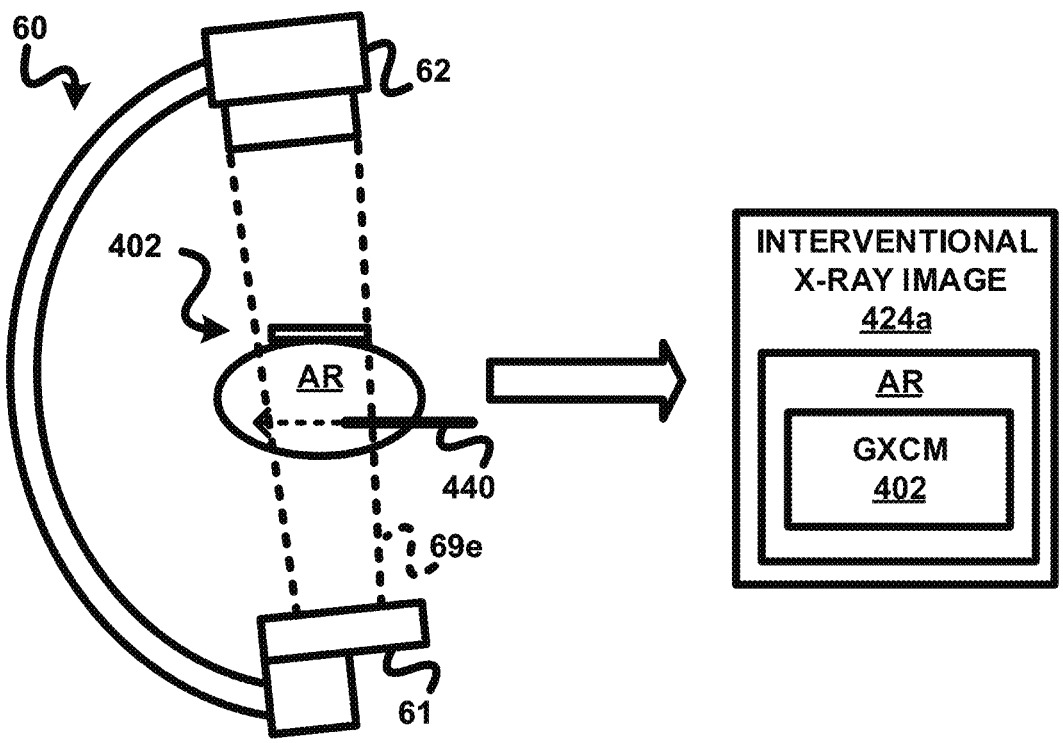
FIGS. 49A-49C illustrate exemplary a guidance overlay display of X-ray images in accordance the various aspects of the guidance overlay display mode of the present disclosure.

Still referring to FIG. 48, in an initial navigation phase of guiding overlay display mode 411b, C-arm 60 is operated at a designated interventional X-ray imaging pose to acquire an interventional X-ray image 424 illustrative of a guiding X-ray calibration device 402 and illustrative of interventional tool 440. For example, FIG. 49A shows an X-ray projection 69e of C-arm 60 at a designated interventional X-ray imaging pose to acquire an interventional X-ray image 424a illustrative of guiding X-ray calibration device 402 and illustrative of interventional tool 440. X-ray overlay controller 410b processes interventional X-ray image 424a to calculate a rigid-body transformation F5 of guiding X-ray calibration device 402 to the X-ray detector 62 of C-arm 60 at the interventional X-ray imaging pose 460 as exemplary shown in FIG. 50.

The display of guiding X-ray image 426b may include guided tool trajectory overlay 414c as shown in FIG. 51A that is generated and overlaid on guiding X-ray image 426b as known in the art of the present disclosure.

Figure 49B:
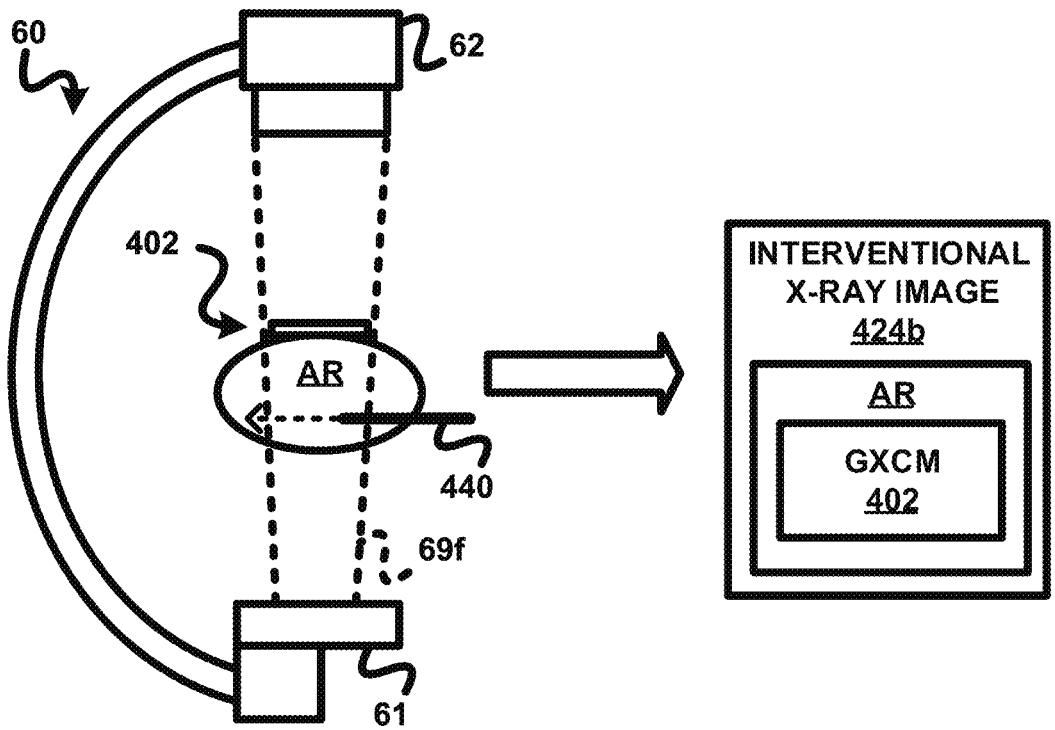

Referring back to FIG. 48, also in the initial navigation phase of guiding overlay display mode 411b, C-arm 60 is operated at a designated interventional X-ray imaging pose to acquire an interventional X-ray image 425 illustrative of a guiding X-ray calibration device 402 and illustrative of interventional tool 440. For example, FIG. 49B shows an X-ray projection 69f of C-arm 60 at a designated interventional X-ray imaging pose to acquire an interventional X-ray image 425a illustrative of guiding X-ray calibration device 402 and illustrative of interventional tool 440. X-ray overlay controller 410b processes interventional X-ray image 425a to calculate a rigid-body transformation F6 of guiding X-ray calibration device 402 to the X-ray detector 62 of C-arm 60 at the interventional X-ray imaging pose 461 as exemplary shown in FIG. 50.

The display of interventional X-ray image 424b may include guided tool trajectory overlay 414b as shown in FIG. 51B that is generated and overlaid on interventional X-ray image 424b as known in the art of the present disclosure.

In practice of guiding overlay display mode 411b, guiding X-ray calibration device 402 may be fixed relative to the patient body part by any suitable means (e.g., an attachment to tool guide, an operating table, a rail, a drape, or an intervention robot).

Figure 49C:
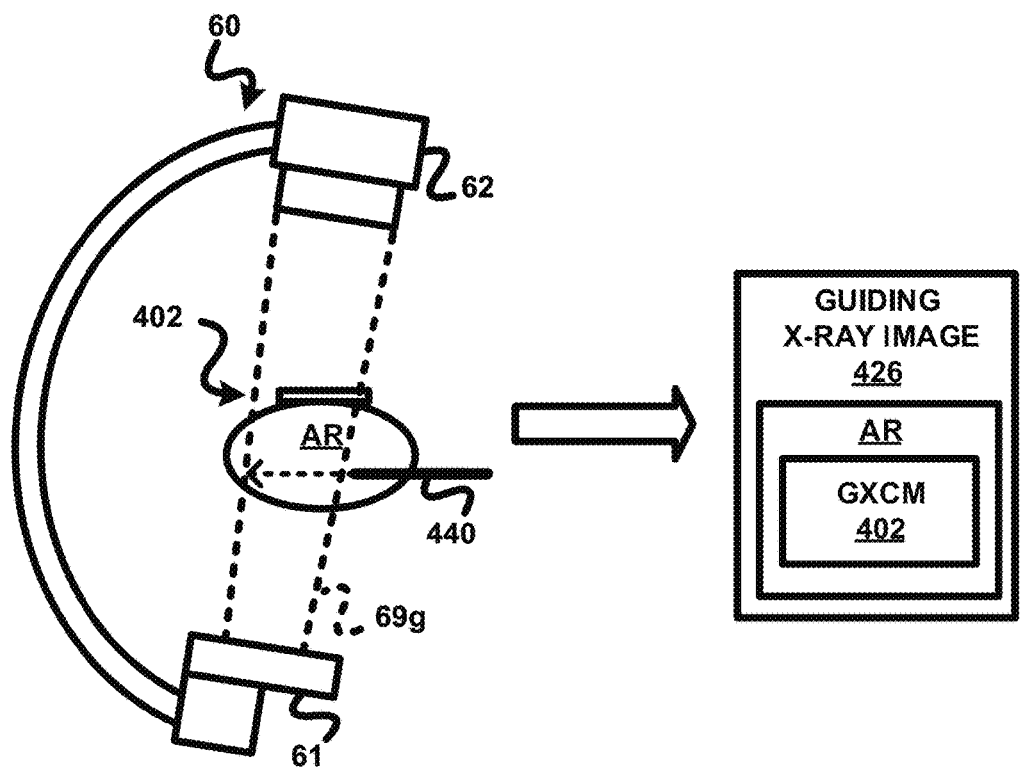

In a targeted navigation phase of guiding overlay display mode 411b, C-arm 60 is operated at a designated guiding X-ray imaging pose to acquire a guiding X-ray image 426 illustrative of guiding X-ray calibration device 402 and of a target within the anatomical region AR. For example, FIG. 49C shows an X-ray projection 69g of C-arm 60 at the designated guiding X-ray imaging pose to acquire a guiding X-ray image 426a illustrative of guiding X-ray calibration device 402 and an anatomical target 415. X-ray overlay controller 410b processes guiding X-ray image 426a to calculate a rigid-body transformation F7 of guiding X-ray calibration device 402 to the X-ray detector 62 of C-arm 60 at the guiding X-ray imaging pose 462 as exemplary shown in FIG. 50.

Figure 50:
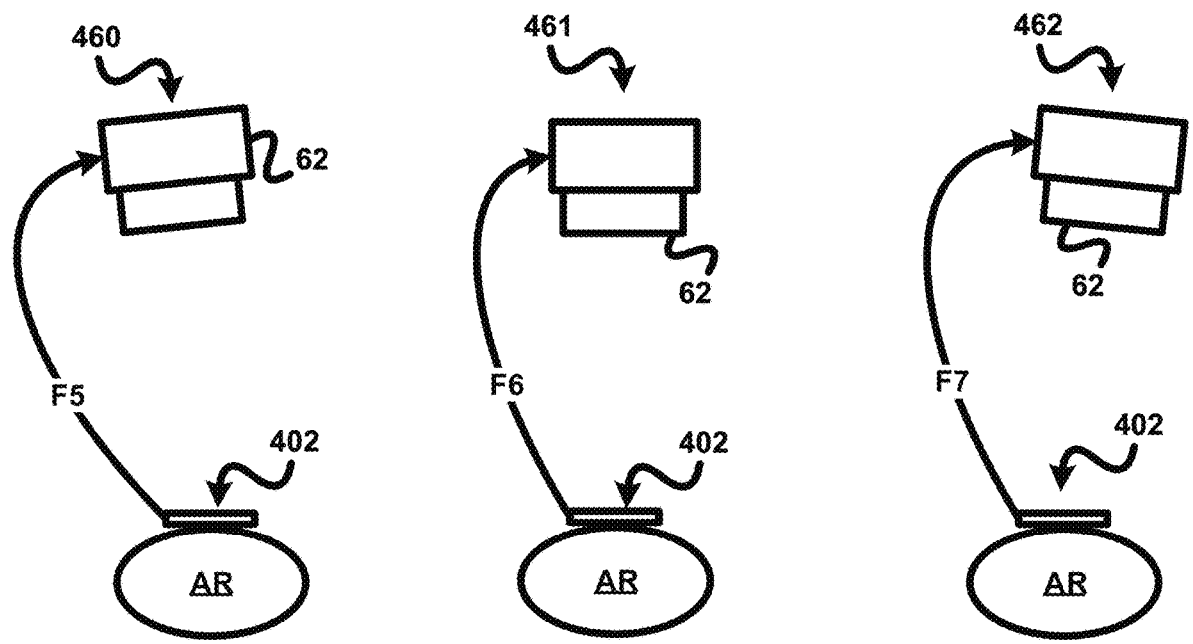
FIG. 50 illustrates exemplary X-ray source→calibration marker transformations in accordance the various aspects of the guidance overlay display mode of the present disclosure.

Referring to FIGS. 49B and 50, as will be further described in the present disclosure, rigid-body transformations F5-F7 facilitate a generation and a display of guided tool trajectory overlay 414 and tracked tool position overlay 415 of interventional tool 440 onto guiding X-ray image 426a.

Figure 52:
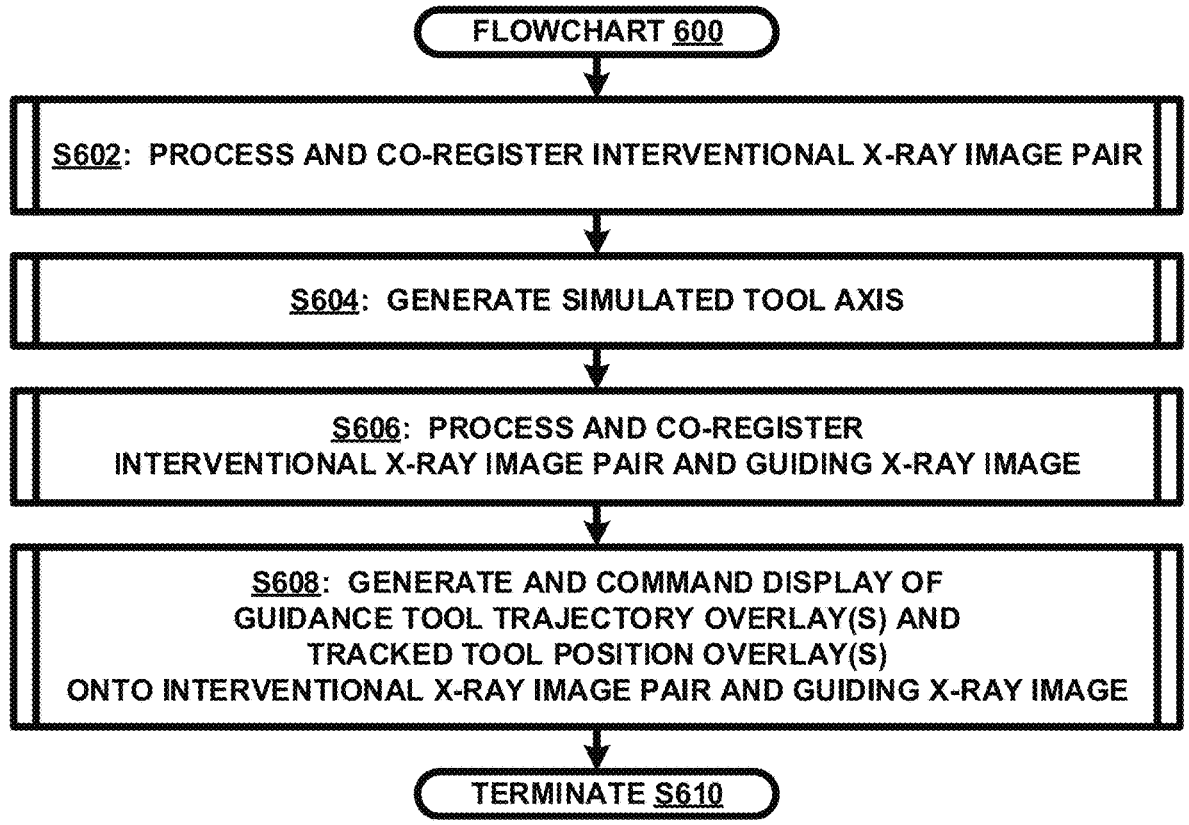
FIG. 52 illustrates a flowchart representative of an exemplary embodiment of a guidance overlay display method in accordance the various aspects of the present disclosure

FIG. 52 illustrates a flowchart 600 representative of an exemplary embodiment of guiding overlay display mode 411b of FIG. 48.

Referring to FIG. 52, a stage S602 of flowchart 600 encompasses X-ray overlay controller 410b processing a pair of interventional X-ray images acquired at different imaging poses of the C-arm 60 whereby the interventional X-ray images are illustrative of different views of a guiding X-ray calibration device (e.g., X-ray rippler marker(s) and/or X-ray ring markers) relative to an anatomical region AR and further illustrative of an interventional tool, such as, for example, an interventional X-ray image 424b as shown in FIG. 54A and an interventional X-ray image 425b as shown in FIG. 54A that are illustrative of a guiding X-ray calibration device and an interventional tool 440b different imaging poses 460 and 461, respectively, of the C-arm 60 as shown in FIG. 50.

The processing of the interventional X-ray images by X-ray overlay controller 410b may encompass one or more techniques as known in the art of the present disclosure or hereinafter conceived for facilitating a navigation of the interventional tool through the anatomical region AR and a display of the interventional X-ray images.

In one exemplary embodiment of stage S602, the inputted interventional X-ray image may be duplicated whereby the guiding X-ray calibration device may be removed from the duplicated interventional X-ray images as previously described in the present disclosure to facilitate a clear view of the patient body part from a display of the marker-less duplicated interventional X-ray images.

In a second exemplary embodiment of stage S602, a trajectory delineation technique as known in the art of the present disclosure may be implemented to delineate a trajectory of the interventional tool through the anatomical region AR as illustrated by each interventional X-ray image.

In a third exemplary embodiment of stage S602, the interventional X-ray images may be fused with other imaging modalities of the anatomical region AR (e.g., 3D CT imaging or 3D MRI imaging).

Still referring to FIG. 51, stage S602 of flowchart 600 further encompasses X-ray overlay controller 410b co-registering guiding X-ray calibration device 402 as illustrated in the interventional X-ray images in accordance within any co-registering technique as known in the art of the present disclosure or hereinafter conceived.

In one embodiment of stage S604, the X-ray overlay controller 410b calculates the following equation [36]:

$$F_{D3}^{D4} = (F_M^{D3})^{-1} F_M^{D4} \qquad [36]$$

where $F_M^{D3}$ is a rigid-body transformation F5 of guiding X-ray calibration device 402 as illustrated in the interventional X-ray image 424b to the interventional imaging pose 460 (FIG. 50) of C-arm 60 during the acquisition of interventional X-ray image 424b, where $F_M^{D4}$ is a rigid-body transformation F6 of guiding X-ray calibration device 402 as illustrated in the interventional X-ray image 425b to the interventional imaging pose 461 (FIG. 50) of C-arm 60 during the acquisition of interventional X-ray image 425b, and where $F_{D3}^{D4}$ is a rigid-body transformation of the interventional imaging pose 461 (FIG. 50) of C-arm 60 during the acquisition of interventional X-ray image 425b to the interventional imaging pose 460 (FIG. 50) of C-arm 60 during the acquisition of interventional X-ray image 425b.

Still referring to FIG. 51, a stage S604 of flowchart 600 encompasses X-ray overlay controller 410b generating a simulated virtual axis of interventional tool 440 in accordance with the present disclosure.

Figure 53:
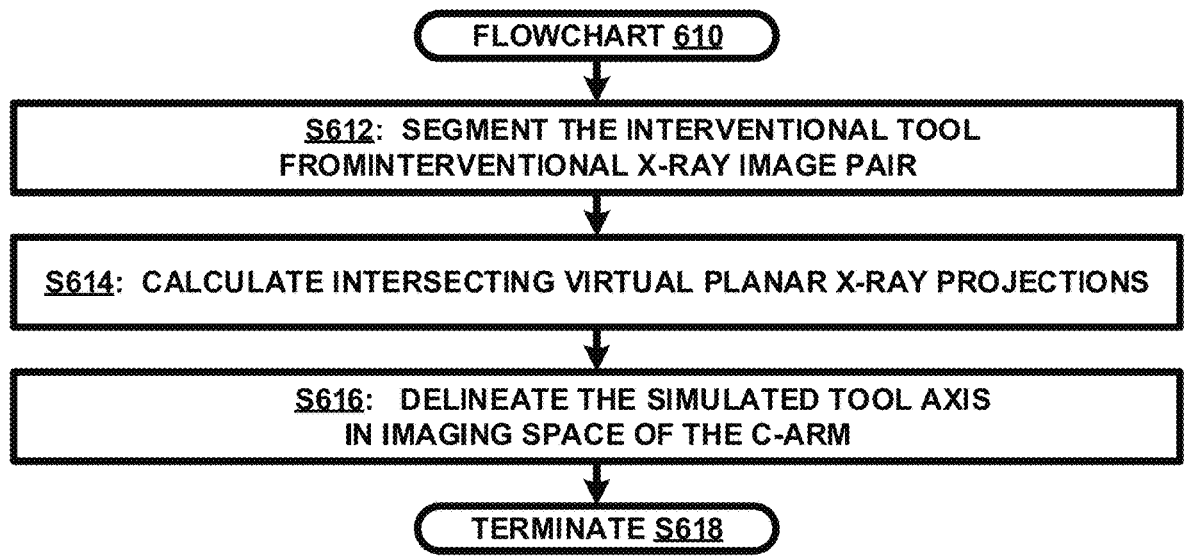
FIG. 53 illustrates a flowchart representative of an exemplary embodiment of a simulated tool axis generation method in accordance the various aspects of the present disclosure.

In one embodiment of stage S604, X-ray overlay controller 410b executes a flowchart 610 as shown in FIG. 53 that is representative of an exemplary embodiment of simulated tool axis generation method of the present disclosure.

Referring to FIG. 53, a stage S612 of flowchart 610 encompasses X-ray overlay controller 410b segmenting interventional tool 440b from interventional X-ray images 424b and 425b.

In one exemplary embodiment of stage S612, X-ray overlay controller 410b may implement any image segmentation technique as known in the art of the present disclosure or hereinafter conceived, particularly image segmentation techniques applying filters and geometric constraints.

In a second exemplary embodiment of stage S612, X-ray overlay controller 410b may implement any machine learning method or deep learning method as known in the art of the present disclosure or hereinafter conceived, that is configured to detect interventional tools within X-ray images.

Still referring to FIG. 53, a stage S614 of flowchart 610 encompasses X-ray overlay controller 410b calculating a pair of intersecting virtual planar X-ray projections based on the image segmentation of interventional tool 440b from interventional X-ray images 424b and 425b.

In one embodiment of stage S614, as shown in FIG. 55A, X-ray overlay controller 410b calculates a virtual planar X-ray plane projection 632a from a virtual X-ray detector surface 630a having a width of the segmented interventional tool of interventional X-ray image 424b to an emission point of a virtual X-ray source 634a. The distance between virtual X-ray detector surface 630a and virtual X-ray source 634a equals the distance between a surface of X-ray detector 62 and an emission point of X-ray source 61 during the acquisition of interventional X-ray image 424a. Further an X-ray imaging pose of virtual X-ray detector surface 630a and virtual X-ray source 634a match the X-ray imaging pose 460 of detector 62 and X-ray source 61 during the acquisition of interventional X-ray image 424b.

Additionally as shown in FIG. 55A, X-ray overlay controller 410b calculates a virtual planar X-ray plane projection 632b from a virtual X-ray detector surface 630b having a width of the segmented interventional tool of interventional X-ray image 425b to the emission point of a virtual X-ray source 634b. The distance between virtual X-ray detector surface 630b and virtual X-ray source 634b equals the distance between a surface of X-ray detector 62 and an emission point of X-ray source 61 during the acquisition of interventional X-ray image 424b. Further an X-ray imaging pose of virtual X-ray detector surface 630b and virtual X-ray source 634b match the X-ray imaging pose 461 of detector 62 and X-ray source 61 during the acquisition of interventional X-ray image 424b.

Referring back to FIG. 53, a stage S616 of flowchart 610 encompasses X-ray overlay controller 410b delineating a simulated tool axis as an intersection of the pair of intersecting virtual planar X-ray projections calculated during stage S614.

In one embodiment of stage S616 as shown in FIG. 55A, X-ray overlay controller 410b delineates a simulated tool axis 635 extending across the full width of the intersection between virtual planar X-ray projections 632a and 632b. X-ray overlay controller 410b further generates a simulated tool trajectory 636 extending from the simulated tool axis 635 to a target based on a registration of the anatomical region AR to C-arm 60 as known in the art of the present disclosure or hereinafter conceived.

Figure 54B:
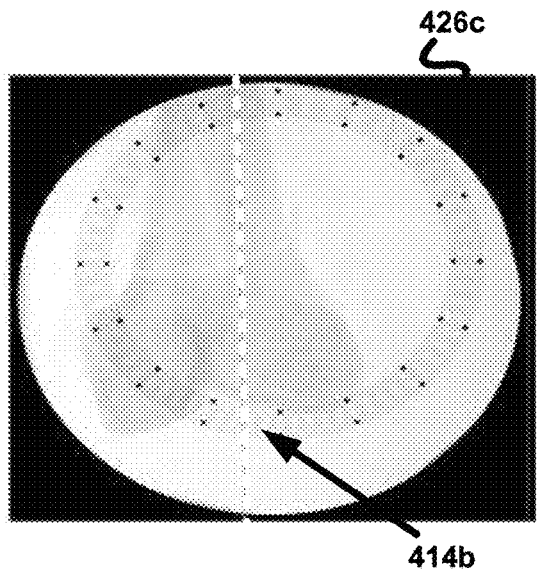

Referring back to FIG. 52, a stage S606 of flowchart 600 encompasses X-ray overlay controller 410b processing guiding X-ray image acquired at guiding imaging pose of the C-arm 60 whereby the guiding X-ray image is illustrative of different views of guiding X-ray calibration device 402 (e.g., X-ray rippler marker(s) and/or X-ray ring marker(s)) relative to an anatomical region AR and are non-illustrative of an interventional tool, such as, for example, an guiding X-ray image 426b as shown in FIG. 54B that is illustrative of a guiding X-ray calibration device 402 and non-illustrative of interventional tool 440b at a guiding imaging pose 462 of the C-arm 60 as shown in FIG. 50.

The processing of the guiding X-ray image 426b by X-ray overlay controller 410b may encompass one or more techniques as known in the art of the present disclosure or hereinafter conceived for facilitating a navigation of the interventional tool through the anatomical region AR and a display of the guiding X-ray image.

In one exemplary embodiment of stage S606, the inputted guiding X-ray image may be duplicated whereby the guiding X-ray calibration device may be removed from the duplicated guiding X-ray image as previously described in the present disclosure to facilitate a clear view of the patient body part from a display of the marker-less duplicated guiding X-ray image.

In a second exemplary embodiment of stage S606, the guiding X-ray images may be fused with other imaging modalities of the anatomical region AR (e.g., 3D CT imaging or 3D MRI imaging).

Still referring to FIG. 51, a stage S606 of flowchart 600 further encompasses X-ray overlay controller 410b co-registering guiding X-ray calibration device as illustrated in one of the pair of interventional X-ray images and as illustrated in the guiding X-ray image in accordance within any co-registering technique as known in the art of the present disclosure or hereinafter conceived.

In one embodiment of stage S606, the X-ray overlay controller 410b calculates the following equation [37]:

$$F_{D3}^{D5} = (F_M^{D3})^{-1} F_M^{D5} \qquad [37]$$

where $F_M^{D3}$ is a rigid-body transformation F5 of guiding X-ray calibration device 402 as illustrated in the interventional X-ray image 424b to the interventional imaging pose 460 (FIG. 50) of C-arm 60 during the acquisition of interventional X-ray image 424b, where $F_M^{D5}$ is a rigid-body transformation F7 of guiding X-ray calibration device 402 as illustrated in the guiding X-ray image 426b to the interventional imaging pose 461 (FIG. 50) of C-arm 60 during the acquisition of guiding X-ray image 426b, and where $F_{D3}^{D5}$ is a rigid-body transformation of the interventional imaging pose 461 (FIG. 50) of C-arm 60 during the acquisition of guiding X-ray image 426b to the interventional imaging pose 460 (FIG. 50) of C-arm 60 during the acquisition of interventional X-ray image 425b.

Still referring to FIG. 51, a stage S608 of flowchart 600 encompasses X-ray overlay controller 410b generating and commanding a display of an guided tool trajectory overlay 414b onto the guiding image 426b.

Figure 55B:
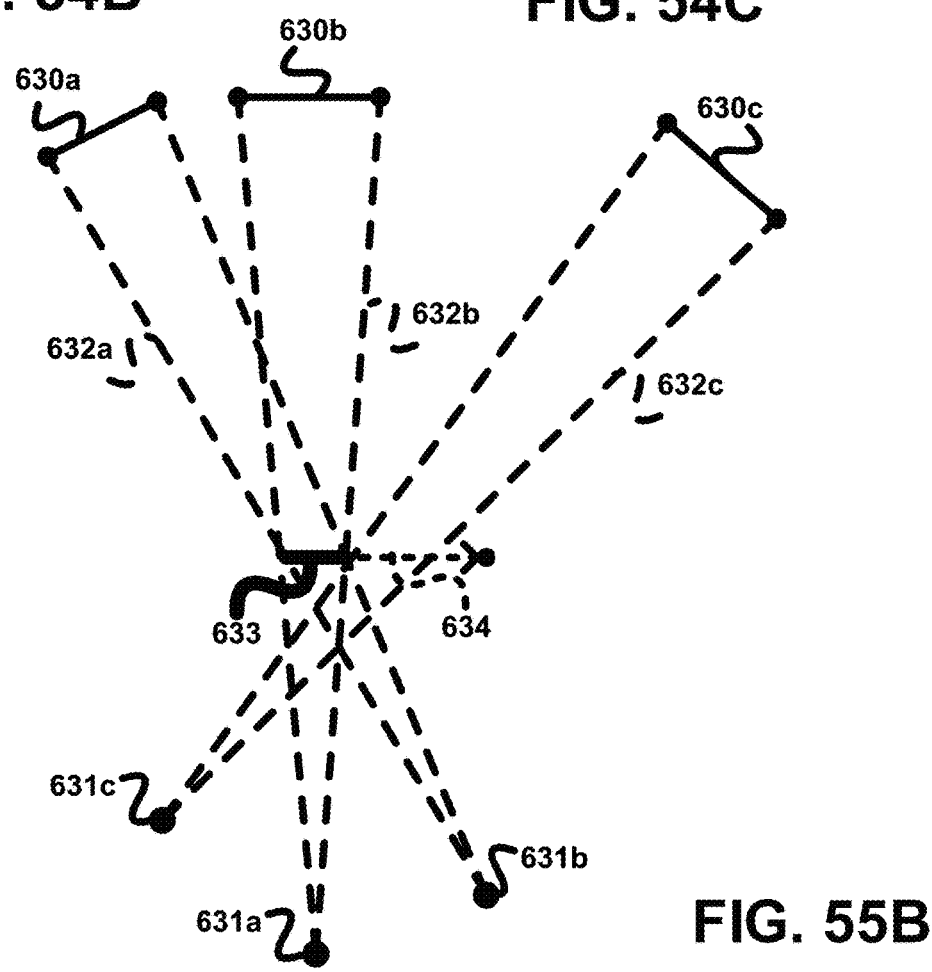

In one embodiment of stage S608 as shown in FIG. 55B, X-ray overlay controller 410b calculates a virtual planar X-ray plane projection 632c from a virtual X-ray detector surface 630c having a width of a surface of X-ray detector 62 to an emission point of a virtual X-ray source 634c. The distance between virtual X-ray detector surface 630c and virtual X-ray source 634c equals the distance between a surface of X-ray detector 62 and an emission point of X-ray source 61 during the acquisition of guiding X-ray image 426b. Further an X-ray imaging pose of virtual X-ray detector surface 630c and virtual X-ray source 63c match the X-ray imaging pose 462 of X-ray detector 62 and X-ray source 61 during the acquisition of guiding X-ray image 426b.

Based on the co-registration, the X-ray overlay controller 410b positions and orients the virtual planar X-ray plane projection 632c relative to the simulated tool axis 635 to delineate a portion or an entirety of simulated tool trajectory 636, which serves as the guided tool trajectory overlay 414b as shown in FIG. 54B.

Figure 54C:
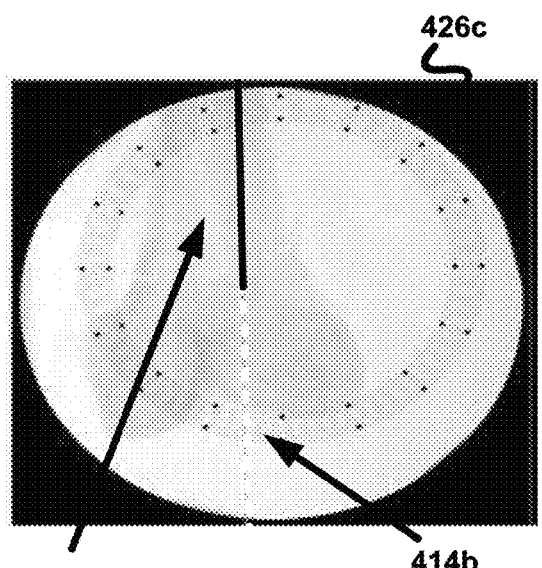

As the interventional tool 440 is navigated within the anatomical region AR, the X-ray overlay controller 410b tracks the position of the interventional tool within the anatomical region to generate and superimpose tracked tool position overlay 415a as shown in FIG. 54C.

Referring back to FIG. 52, X-ray overlay controller 410b may be operated to re-execute flowchart 600 for a different set of X-ray images or guiding X-ray images as the procedure is being conducted.

Those having one skilled in the art of the present disclosure will appreciate and understand, that upon completion, the guiding overlay display mode of the present disclosure provides a proper visualization of a target alignment of an interventional tool within the anatomical region AR.

For example, interventional images may be acquired at different imaging poses of the C-arm corresponding to necessary views of the anatomical region AR during the intervention procedures. These additional images will also be co-registered with the reference images whereby the overlay(s) may be projected the additional images for a more comprehensive visualization of a target alignment of an interventional tool within the anatomical region AR.

By further example, a selection of the target in two or more of the co-registered X-ray images will facilitate an estimation of the desired insertion depth. More particularly, if the interventional tool had imagable markings, then the surgeon can control the instrument insertion depth. This can augmented by tip tracking to display distance to target.

Also be example, when the interventional tool is illustrated in one or more of the co-registered X-ray images, then the controller may compare the instrument trajectory from the pair of interventional X-ray images with the guided tool trajectory overlay in the guiding X-ray images for error checking.

To facilitate a further understanding of various inventive aspects of the present disclosure, the following description of FIGS. 48-55B teaches exemplary embodiments of a guiding overlay display mode by an X-ray overlay controller of the present disclosure. From this description, those having ordinary skill in the art of the present disclosure will appreciate how to apply the various aspects of the present disclosure for making and using additional embodiments of X-ray overlay controller of the present disclosure for executing additional embodiments of a guiding overlay display mode of the present disclosure.

Generally, the guiding overlay display mode applies to any X-ray imaging based interventional procedure as known in the art of the present disclosure or conceived hereafter that requires multiple C-arm orientations relative to an anatomical region to proper visualize an alignment of an interventional tool within the anatomical region.

For example, as previously set forth, mobile x-ray fluoroscopy is widely used in minimally invasive interventions in fields such as orthopedics, trauma, vascular and spine. Mobile x-ray systems are commonly used because of their relatively small footprint compared to fixed x-ray systems, their maneuverability and reduced cost. However, given that mobile X-ray systems are typically not position-encoded, it can be difficult to implement advanced tools that rely on the precise orientation of the C-arm. For example, mobile X-ray systems have a limited field of view, and given that the translational position is not encoded, it is not trivial to stitch images together to increase the field of view.

For mobile x-ray fluoroscopy, many mobile C-arm procedures require precise positioning of tools or anatomy. In ortho-trauma, for example, fracture reduction is common, which requires clinicians to realign bone fragments and deploy nails or screws at specific locations and angles. In pelvic fracture reduction, a screw may be placed through the sacroiliac joint. The placement of the sacroiliac screw is particularly challenging, given that there is a small target area for the screw to land and it is important to avoid damaging critical structures in the spine. Furthermore, the target landing area for the screw may not be visible in the same field of view as the starting point.

More particularly, sacroiliac screw placement remains a challenge, even for experienced surgeons. Given the complexity of the anatomy and difficulty of properly visualizing the position of the tool relative to the anatomy, sacroiliac screw misplacement is not uncommon. The challenge comes from the fact that multiple sequential C-arm orientations are needed to properly align the screw/tool. Since the motion of the tool is not constrained, there is the possibility that the surgeon may misalign the screw placement in old views when he is aligning the tool in the current view.

The guiding overlay display mode of the present disclosure localizes an interventional tool in 3D space to show its trajectory both inside and outside of the field of view of a live X-ray image in order to improve device insertion outcomes with minimal effect on procedure time.

In practice, generally, the guiding overlay display mode of the present disclosure will initially encompass an acquisition of a pair of interventional X-ray images at different imaging poses of a C-arm with each interventional X-ray image being illustrative of different views of an interventional tool positioned within an anatomical region. Each interventional X-ray image is illustrative of a guiding X-ray calibration device relative to the anatomical region. For the procedure, guiding X-ray image(s) may be acquired at different imaging poses of the C-arm. The guiding X-ray image(s) are non-illustrative of the interventional tool and are illustrative of a planned path to a target in the anatomical region. From the description of FIGS. 48-55B, those having ordinary skill in the art of the present disclosure will appreciate and understand the guiding overlay display mode constitutes an image-based method to register a position of an interventional tool relative to an anatomical region as illustrated in a pair of interventional X-ray images to guiding X-ray image(s) illustrative of a planned path to a target to thereby provide a simultaneous display of the position and/or the trajectory of the interventional tool in the X-ray image(s).

For purposes of describing the guiding overlay display mode of the present disclosure, the term "intraoperative" encompasses X-ray imaging of an interventional tool positioned within an anatomical region AR as will be further described in the present disclosure.

Various X-ray images as shown in FIGS. 48-55B and claimed herein are labelled as either "interventional" and "guiding" as a means for distinguishing between the X-ray images of acquired during various aspects of the present disclosure. Nonetheless, these labels do not change the definition of these images as X-ray images.

Additionally, a guiding X-ray calibration device as shown in FIGS. 48-55B and claimed herein may be embodied as one or more X-ray ripple markers as previously described in the present disclosure and shown in FIGS. 1-19 of the present disclosure and/or one or more X-ray ring markers as previously described in the present disclosure and shown in FIGS. 20-38 of the present disclosure.

Referring to FIG. 48, in practice of the guiding overlay display mode, a guiding X-ray calibration device 402 will be mounted relative to an anatomical region AR within an X-ray imaging space of C-arm 60 (mobile or fixed) during an acquisition of an interventional X-ray image. The X-ray source 61 and the X-ray detector 62 of the C-arm 60 are translatable and/or rotatable to various imaging poses for generating various interventional X-ray images of guiding X-ray calibration device 402 relative to the anatomical region AR.

An X-ray overlay controller 410b processes a pair of interventional X-ray images illustrative of interventional tool 440 relative to the anatomical region AR to execute a guiding overlay display mode 411b of the present disclosure for controlling a display of an guided tool trajectory overlay 414 onto guiding X-ray image(s) illustrative of a planned path to a target within the anatomical region AR and/or a tracked tool position overlay 415 onto guiding X-ray image(s) illustrative of a tracked position of an interventional tool within the anatomical region AR.

Guiding overlay display mode 411b will now be exemplary described in the context of an acquisition of a pair of interventional X-ray images 424 and 425 illustrative of interventional tool 440 at different imaging poses of the C-arm 60 and an acquisition of one (1) guiding X-ray image 426 non-illustrative of interventional tool 440 at an additional different imaging pose of the C-arm 60. Nonetheless, in practice, a guiding overlay display mode of the present disclosure may encompass an acquisition of one or more interventional X-ray images illustrative of an interventional tool at different imaging poses of a C-arm and an acquisition of one or more guiding X-ray images non-illustrative of an interventional tool at an additional different imaging pose of the C-arm.

Still referring to FIG. 48, in an initial navigation phase of guiding overlay display mode 411b, C-arm 60 is operated at a designated interventional X-ray imaging pose to acquire an interventional X-ray image 424 illustrative of a guiding X-ray calibration device 402 and illustrative of interventional tool 440. For example, FIG. 49A shows an X-ray projection 69e of C-arm 60 at a designated interventional X-ray imaging pose to acquire an interventional X-ray image 424a illustrative of guiding X-ray calibration device 402 and illustrative of interventional tool 440. X-ray overlay controller 410b processes interventional X-ray image 424a to calculate a rigid-body transformation F5 of guiding X-ray calibration device 402 to the X-ray detector 62 of C-arm 60 at the interventional X-ray imaging pose 460 as exemplary shown in FIG. 50.

The display of guiding X-ray image 426b may include guided tool trajectory overlay 414c as shown in FIG. 51A that is generated and overlaid on guiding X-ray image 426b as known in the art of the present disclosure.

Referring back to FIG. 48, also in the initial navigation phase of guiding overlay display mode 411b, C-arm 60 is operated at a designated interventional X-ray imaging pose to acquire an interventional X-ray image 425 illustrative of a guiding X-ray calibration device 402 and illustrative of interventional tool 440. For example, FIG. 49B shows an X-ray projection 69f of C-arm 60 at a designated interventional X-ray imaging pose to acquire an interventional X-ray image 425a illustrative of guiding X-ray calibration device 402 and illustrative of interventional tool 440. X-ray overlay controller 410b processes interventional X-ray image 425a to calculate a rigid-body transformation F6 of guiding X-ray calibration device 402 to the X-ray detector 62 of C-arm 60 at the interventional X-ray imaging pose 461 as exemplary shown in FIG. 50.

The display of interventional X-ray image 424b may include guided tool trajectory overlay 414b as shown in FIG. 51B that is generated and overlaid on interventional X-ray image 424b as known in the art of the present disclosure.

In practice of guiding overlay display mode 411b, guiding X-ray calibration device 402 may be fixed relative to the patient body part by any suitable means (e.g., an attachment to tool guide, an operating table, a rail, a drape, or an intervention robot). In a targeted navigation phase of guiding overlay display mode 411b, C-arm 60 is operated at a designated guiding X-ray imaging pose to acquire a guiding X-ray image 426 illustrative of guiding X-ray calibration device 402 and of a target within the anatomical region AR. For example, FIG. 49C shows an X-ray projection 69g of C-arm 60 at the designated guiding X-ray imaging pose to acquire a guiding X-ray image 426a illustrative of guiding X-ray calibration device 402 and an anatomical target 415. X-ray overlay controller 410b processes guiding X-ray image 426a to calculate a rigid-body transformation F7 of guiding X-ray calibration device 402 to the X-ray detector 62 of C-arm 60 at the guiding X-ray imaging pose 462 as exemplary shown in FIG. 50.

Referring to FIGS. 49B and 50, as will be further described in the present disclosure, rigid-body transformations F5-F7 facilitate a generation and a display of guided tool trajectory overlay 414 and tracked tool position overlay 415 of interventional tool 440 onto guiding X-ray image 426a.

FIG. 52 illustrates a flowchart 600 representative of an exemplary embodiment of guiding overlay display mode 411b of FIG. 48.

Referring to FIG. 52, a stage S602 of flowchart 600 encompasses X-ray overlay controller 410b processing a pair of interventional X-ray images acquired at different imaging poses of the C-arm 60 whereby the interventional X-ray images are illustrative of different views of a guiding X-ray calibration device (e.g., X-ray rippler marker(s) and/or X-ray ring markers) relative to an anatomical region AR and further illustrative of an interventional tool, such as, for example, an interventional X-ray image 424b as shown in FIG. 54A and an interventional X-ray image 425b as shown in FIG. 54A that are illustrative of a guiding X-ray calibration device and an interventional tool 440b different imaging poses 460 and 461, respectively, of the C-arm 60 as shown in FIG. 50.

The processing of the interventional X-ray images by X-ray overlay controller 410b may encompass one or more techniques as known in the art of the present disclosure or hereinafter conceived for facilitating a navigation of the interventional tool through the anatomical region AR and a display of the interventional X-ray images.

In one exemplary embodiment of stage S602, the inputted interventional X-ray image may be duplicated whereby the guiding X-ray calibration device may be removed from the duplicated interventional X-ray images as previously described in the present disclosure to facilitate a clear view of the patient body part from a display of the marker-less duplicated interventional X-ray images.

In a second exemplary embodiment of stage S602, a trajectory delineation technique as known in the art of the present disclosure may be implemented to delineate a trajectory of the interventional tool through the anatomical region AR as illustrated by each interventional X-ray image.

In a third exemplary embodiment of stage S602, the interventional X-ray images may be fused with other imaging modalities of the anatomical region AR (e.g., 3D CT imaging or 3D MRI imaging).

Still referring to FIG. 51, stage S602 of flowchart 600 further encompasses X-ray overlay controller 410b co-registering guiding X-ray calibration device 402 as illustrated in the interventional X-ray images in accordance within any co-registering technique as known in the art of the present disclosure or hereinafter conceived.

In one embodiment of stage S604, the X-ray overlay controller 410b calculates the following equation [36]:

$$F_{D3}^{D4}=(F_M^{D3})^{-1}F_M^{D4} \qquad [36]$$

where $F_M^{D3}$ is a rigid-body transformation F5 of guiding X-ray calibration device 402 as illustrated in the interventional X-ray image 424b to the interventional imaging pose 460 (FIG. 50) of C-arm 60 during the acquisition of interventional X-ray image 424b, where $F_M^{D4}$ is a rigid-body transformation F6 of guiding X-ray calibration device 402 as illustrated in the interventional X-ray image 425b to the interventional imaging pose 461 (FIG. 50) of C-arm 60 during the acquisition of interventional X-ray image 425b, and where $F_{D3}^{D4}$ is a rigid-body transformation of the interventional imaging pose 461 (FIG. 50) of C-arm 60 during the acquisition of interventional X-ray image 425b to the interventional imaging pose 460 (FIG. 50) of C-arm 60 during the acquisition of interventional X-ray image 425b.

Still referring to FIG. 51, a stage S604 of flowchart 600 encompasses X-ray overlay controller 410b generating a simulated virtual axis of interventional tool 440 in accordance with the present disclosure.

In one embodiment of stage S604 of flowchart 600, X-ray overlay controller 410b executes a flowchart 610 as shown in FIG. 53 that is representative of an exemplary embodiment of simulated tool axis generation method of the present disclosure.

Referring to FIG. 53, a stage S612 of flowchart 610 encompasses X-ray overlay controller 410b segmenting interventional tool 440b from interventional X-ray images 424b and 425b.

In one exemplary embodiment of stage S612, X-ray overlay controller 410b may implement any image segmentation technique as known in the art of the present disclosure or hereinafter conceived, particularly image segmentation techniques applying filters and geometric constraints.

In a second exemplary embodiment of stage S612, X-ray overlay controller 410b may implement any machine learning method or deep learning method as known in the art of the present disclosure or hereinafter conceived, that is configured to detect interventional tools within X-ray images.

Still referring to FIG. 53, a stage S614 of flowchart 610 encompasses X-ray overlay controller 410b calculating a pair of intersecting virtual planar X-ray projections based on the image segmentation of interventional tool 440b from interventional X-ray images 424b and 425b.

In one embodiment of stage S614, as shown in FIG. 55A, X-ray overlay controller 410b calculates a virtual planar X-ray plane projection 632a from a virtual X-ray detector surface 630a having a width of the segmented interventional tool of interventional X-ray image 424b to an emission point of a virtual X-ray source 634a. The distance between virtual X-ray detector surface 630a and virtual X-ray source 634a equals the distance between a surface of X-ray detector 62 and an emission point of X-ray source 61 during the acquisition of interventional X-ray image 424a. Further an X-ray imaging pose of virtual X-ray detector surface 630a and virtual X-ray source 634a match the X-ray imaging pose 460 of detector 62 and X-ray source 61 during the acquisition of interventional X-ray image 424b.

Additionally as shown in FIG. 55A, X-ray overlay controller 410b calculates a virtual planar X-ray plane projection 632b from a virtual X-ray detector surface 630b having a width of the segmented interventional tool of interventional X-ray image 425b to the emission point of a virtual X-ray source 634b. The distance between virtual X-ray detector surface 630b and virtual X-ray source 634b equals the distance between a surface of X-ray detector 62 and an emission point of X-ray source 61 during the acquisition of interventional X-ray image 424b. Further an X-ray imaging pose of virtual X-ray detector surface 630b and virtual X-ray source 634b match the X-ray imaging pose 461 of detector 62 and X-ray source 61 during the acquisition of interventional X-ray image 424b.

Referring back to FIG. 53, a stage S616 of flowchart 610 encompasses X-ray overlay controller 410b delineating a simulated tool axis as an intersection of the pair of intersecting virtual planar X-ray projections calculated during stage S614.

In one embodiment of stage S616 as shown in FIG. 55A, X-ray overlay controller 410b delineates a simulated tool axis 635 extending across the full width of the intersection between virtual planar X-ray projections 632a and 632b. X-ray overlay controller 410b further generates a simulated tool trajectory 636 extending from the simulated tool axis 635 to a target based on a registration of the anatomical region AR to C-arm 60 as known in the art of the present disclosure or hereinafter conceived.

Referring back to FIG. 52, a stage S606 of flowchart 600 encompasses X-ray overlay controller 410b processing guiding X-ray image acquired at guiding imaging pose of the C-arm 60 whereby the guiding X-ray image is illustrative of different views of guiding X-ray calibration device 402 (e.g., X-ray rippler marker(s) and/or X-ray ring marker(s)) relative to an anatomical region AR and are non-illustrative of an interventional tool, such as, for example, an guiding X-ray image 426b as shown in FIG. 54B that is illustrative of a guiding X-ray calibration device 402 and non-illustrative of interventional tool 440b at a guiding imaging pose 462 of the C-arm 60 as shown in FIG. 50.

The processing of the guiding X-ray image 426b by X-ray overlay controller 410b may encompass one or more techniques as known in the art of the present disclosure or hereinafter conceived for facilitating a navigation of the interventional tool through the anatomical region AR and a display of the guiding X-ray image.

In one exemplary embodiment of stage S606, the inputted guiding X-ray image may be duplicated whereby the guiding X-ray calibration device may be removed from the duplicated guiding X-ray image as previously described in the present disclosure to facilitate a clear view of the patient body part from a display of the marker-less duplicated guiding X-ray image.

In a second exemplary embodiment of stage S606, the guiding X-ray images may be fused with other imaging modalities of the anatomical region AR (e.g., 3D CT imaging or 3D MRI imaging).

Still referring to FIG. 51, a stage S606 of flowchart 600 further encompasses X-ray overlay controller 410b co-registering guiding X-ray calibration device as illustrated in one of the pair of interventional X-ray images and as illustrated in the guiding X-ray image in accordance within any co-registering technique as known in the art of the present disclosure or hereinafter conceived.

In one embodiment of stage S606, the X-ray overlay controller 410b calculates the following equation [37]:

$$F_{D3}^{D5} = (F_M^{D3})^{-1} F_M^{D5} \qquad [37]$$

where $F_M^{D3}$ is a rigid-body transformation F5 of guiding X-ray calibration device 402 as illustrated in the interventional X-ray image 424b to the interventional imaging pose 460 (FIG. 50) of C-arm 60 during the acquisition of interventional X-ray image 424b, where $F_M^{D5}$ is a rigid-body transformation F7 of guiding X-ray calibration device 402 as illustrated in the guiding X-ray image 426b to the interventional imaging pose 461 (FIG. 50) of C-arm 60 during the acquisition of guiding X-ray image 426b, and where $F_{D3}^{D5}$ is a rigid-body transformation of the interventional imaging pose 461 (FIG. 50) of C-arm 60 during the acquisition of guiding X-ray image 426b to the interventional imaging pose 460 (FIG. 50) of C-arm 60 during the acquisition of interventional X-ray image 425b.

Still referring to FIG. 51, a stage S608 of flowchart 600 encompasses X-ray overlay controller 410b generating and commanding a display of an guided tool trajectory overlay 414b onto the guiding image 426b.

In one embodiment of stage S608 as shown in FIG. 55B, X-ray overlay controller 410b calculates a virtual planar X-ray plane projection 632c from a virtual X-ray detector surface 630c having a width of a surface of X-ray detector 62 to an emission point of a virtual X-ray source 634c. The distance between virtual X-ray detector surface 630c and virtual X-ray source 634c equals the distance between a surface of X-ray detector 62 and an emission point of X-ray source 61 during the acquisition of guiding X-ray image 426b. Further an X-ray imaging pose of virtual X-ray detector surface 630c and virtual X-ray source 63c match the X-ray imaging pose 462 of X-ray detector 62 and X-ray source 61 during the acquisition of guiding X-ray image 426b.

Based on the co-registration, the X-ray overlay controller 410b positions and orients the virtual planar X-ray plane projection 632c relative to the simulated tool axis 635 to delineate a portion or an entirety of simulated tool trajectory 636, which serves as the guided tool trajectory overlay 414b as shown in FIG. 54B.

As the interventional tool 440 is navigated within the anatomical region AR, the X-ray overlay controller 410b tracks the position of the interventional tool within the anatomical region to generate and superimpose tracked tool position overlay 415a as shown in FIG. 54C.

Referring back to FIG. 52, X-ray overlay controller 410b may be operated to re-execute flowchart 600 for a different set of X-ray images or guiding X-ray images as the procedure is being conducted.

Those having one skilled in the art of the present disclosure will appreciate and understand, that upon completion, the guiding overlay display mode of the present disclosure provides a proper visualization of a target alignment of an interventional tool within the anatomical region AR.

For example, interventional images may be acquired at different imaging poses of the C-arm corresponding to necessary views of the anatomical region AR during the intervention procedures. These additional images will also be co-registered with the reference images whereby the overlay(s) may be projected the additional images for a more comprehensive visualization of a target alignment of an interventional tool within the anatomical region AR.

By further example, a selection of the target in two or more of the co-registered X-ray images will facilitate an estimation of the desired insertion depth. More particularly, if the interventional tool had imagable markings, then the surgeon can control the instrument insertion depth. This can augmented by tip tracking to display distance to target.

Also be example, when the interventional tool is illustrated in one or more of the co-registered X-ray images, then the controller may compare the instrument trajectory from the pair of interventional X-ray images with the guided tool trajectory overlay in the guiding X-ray images for error checking.

Figure 56:
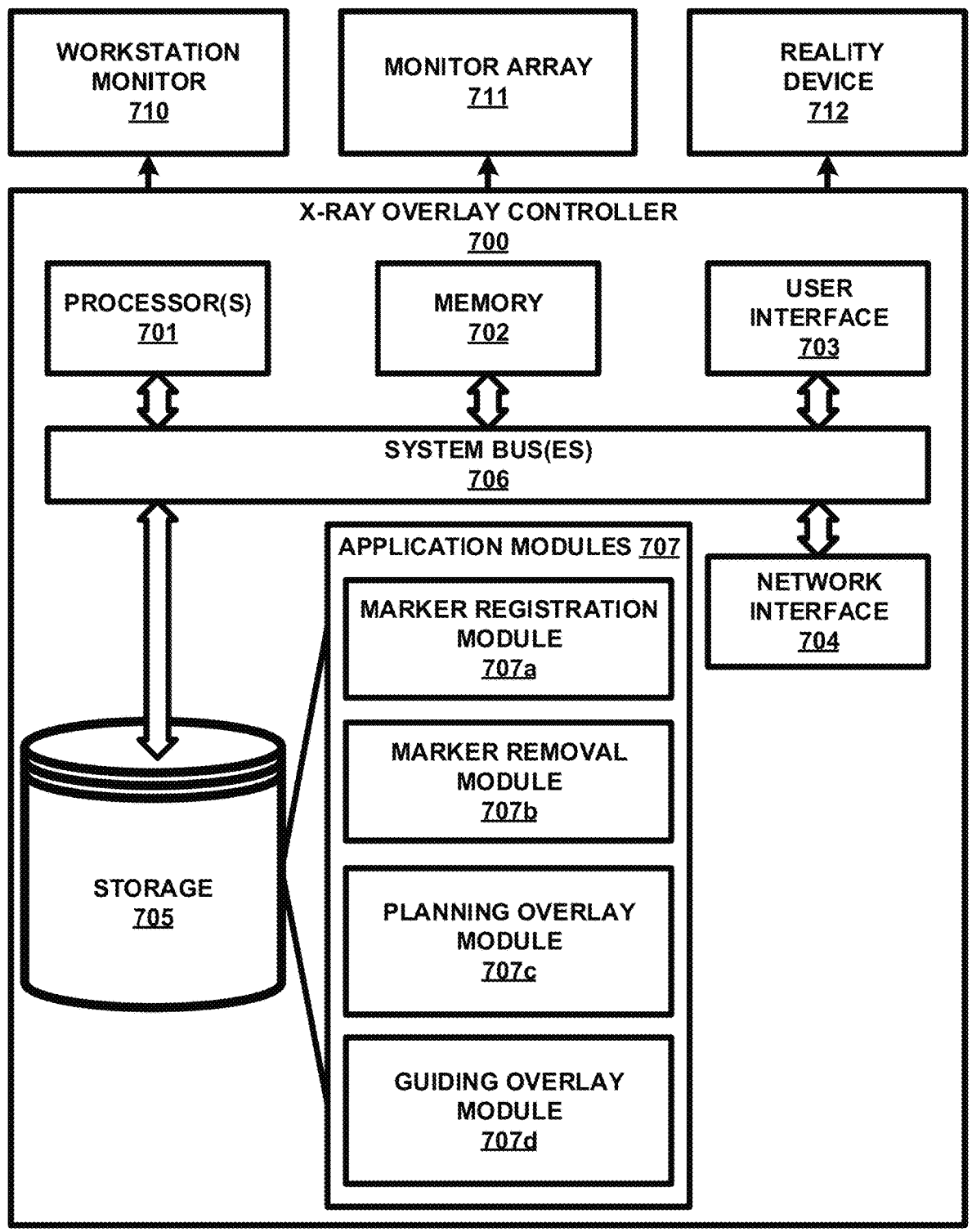
FIG. 56 illustrates an exemplary embodiment of an X-ray overlay controller in accordance with various aspects of the present disclosure.

To facilitate a further understanding of the various inventions of the present disclosure, the following description of FIG. 56 teaches an exemplary embodiment of a X-ray overlay controller of the present disclosure. From this description, those having ordinary skill in the art will appreciate how to apply various aspects of the present disclosure for making and using additional embodiments of X-ray overlay controller of the present disclosure.

Referring to FIG. 56, a X-ray overlay controller 700 includes one or more processor(s) 701, memory 702, a user interface 703, a network interface 704, and a storage 705 interconnected via one or more system buses 706.

Each processor 701 may be any hardware device, as known in the art of the present disclosure or hereinafter conceived, capable of executing instructions stored in memory 702 or storage or otherwise processing data. In a non-limiting example, the processor(s) 701 may include a microprocessor, field programmable gate array (FPGA), application-specific integrated circuit (ASIC), or other similar devices.

The memory 702 may include various memories, as known in the art of the present disclosure or hereinafter conceived, including, but not limited to, L1, L2, or L3 cache or system memory. In a non-limiting example, the memory 702 may include static random access memory (SRAM), dynamic RAM (DRAM), flash memory, read only memory (ROM), or other similar memory devices.

The user interface 703 may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface 704.

The network interface 704 may include one or more devices, as known in the art of the present disclosure or hereinafter conceived, for enabling communication with other hardware devices. In a non-limiting example, the network interface 704 may include a network interface card (NIC) configured to communicate according to the Ethernet protocol. Additionally, the network interface 704 may implement a TCP/IP stack for communication according to the TCP/IP protocols. Various alternative or additional hardware or configurations for the network interface 704 will be apparent.

The storage 705 may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage 705 may store instructions for execution by the processor(s) 701 or data upon with the processor(s) 701 may operate. For example, the storage 705 may store a base operating system for controlling various basic operations of the hardware.

The storage 705 also stores application modules 707 in the form of executable software/firmware for implementing the various functions of the controller 700 as previously described in the present disclosure including, but not limited to, preoperative overlay display module 707a, intraoperative overlay display module 707b, a C-arm to marker registration module 707c and a marker removal module 707d.

In practice, X-ray overlay controller 700 may be (1) installed within an X-ray imaging system (e.g., a fixed or mobile C-arm), (2) installed within an intervention system (e.g., an intervention robot system), or (3) a stand-alone workstation in communication with (a) an X-ray imaging system and/or (b) intervention system (e.g., a client workstation or a mobile device like a tablet).

Alternatively, components of controller 700 may be distributed among the X-ray imaging system, the intervention system and/or the stand-alone workstation.

More particularly, the application modules 707 are implemented by controller 700 during an intervention procedure utilizing a workstation monitor 710, a monitor array 711, an augmented reality headset/glasses 712, virtual reality headset/glasses (not shown), mixed reality headset/glasses (not shown) and/or any other means for displaying interventional tool overlays onto X-images as described in the present disclosure.

Also in practice, X-ray controller 700 may be integrated within an X-ray imaging controller for controlling operations of a C-arm as known in the art of the present disclosure whereby the X-ray imaging controller executes one or more the various overlay methods of the present disclosure.

Alternatively, X-ray controller 700 may be segregated from such an X-ray imaging controller whereby X-ray images may be transmitted from the C-arm or a Picture Archiving and Communication System (PACS) to the X-ray overlay controller 700 using protocol known in the art of the present disclosure (e.g. DICOM).

Referring to FIGS. 1-56, those having ordinary skill in the art of the present disclosure will appreciate numerous benefits of the inventions of the present disclosure including, but not limited to, a localization of an interventional tool in three-dimensional (3D) space that facilitates a display of a tool position and/or a tool trajectory both inside and outside of the field of view of the X-ray imaging system to thereby improve tool insertion outcomes with minimal effect on procedure time.

Further, as one having ordinary skill in the art will appreciate in view of the teachings provided herein, structures, elements, components, etc. described in the present disclosure/specification and/or depicted in the Figures may be implemented in various combinations of hardware and software, and provide functions which may be combined in a single element or multiple elements. For example, the functions of the various structures, elements, components, etc. shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of the various and numerous inventions of the present disclosure (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. An X-ray imaging system, comprising:
   a C-arm configured to acquire a plurality of X-ray images at different X-ray imaging poses of the C-arm; and
   an X-ray overlay controller configured in a planning overlay display mode to:
   process a planning X-ray image acquired by the C-arm at a planning X-ray imaging pose of the C-arm, the planning X-ray image being illustrative of a planning X-ray calibration device and non-illustrative of an interventional tool;
   process a reference planning X-ray image acquired by the C-arm at a reference X-ray imaging pose (451) of the C-arm, the reference planning X-ray image being illustrative of the planning X-ray calibration device and non-illustrative of the interventional tool;
   compute a rigid body transformation between the C-arm at the planning X-ray imaging pose and the C-arm at the reference X-ray imaging pose based on the illustrations of the planning X-ray calibration device in the planning X-ray image and in the reference planning X-ray image;

process a base X-ray image acquired by the C-arm at the reference X-ray imaging pose of the C-arm, the base X-ray image being illustrative of a base X-ray calibration device and non-illustrative of the interventional tool, the base X-ray calibration device being registered to a tool guide;

compute a rigid body transformation between the C-arm at the planning X-ray imaging pose and a tool guide based on a computation of the rigid body transformation between the C-arm at the planning X-ray imaging pose and the C-arm at the reference X-ray imaging pose and further based on the registration of the base X-ray calibration device to the tool guide; and control a display of a planned tool trajectory overlay onto the planning X-ray image based on a computation of the rigid body transformation between the C-arm at the planning X-ray imaging pose and a tool guide.

2. The X-ray imaging system of claim 1, wherein the X-ray overlay controller is further configured in the planning overlay display mode to:

process a tracking X-ray image acquired by the C-arm at the reference X-ray imaging pose of the C-arm, the tracking X-ray image being illustrative of the base X-ray calibration device and illustrative of the interventional tool; and control a display of a tracked tool position overlay onto the planning X-ray image based on a computation of the rigid body transformation between the C-arm at the planning X-ray imaging pose and a tool guide and the illustration of the interventional tool in the tracking X-ray image.

3. The X-ray imaging system of claim 1, wherein the X-ray overlay controller (410) is configured in a guiding overlay display mode to:

process a pair of interventional X-ray images acquired by the C-arm at different interventional X-ray imaging poses of the C-arm, each interventional X-ray image being illustrative of a guiding X-ray calibration device and illustrative of the interventional tool;

co-register the pair of interventional X-ray images based on the illustrations of the guiding X-ray calibration device in the pair of interventional X-ray images;

generate a simulated tool axis virtually positioned within the X-ray imaging space of the C-arm based on a co-registration of the pair of interventional X-ray images;

process a guiding X-ray image acquired by the C-arm at a guiding X-ray imaging pose of the C-arm, the guiding X-ray image being illustrative of the guiding X-ray calibration device and non-illustrative of the interventional tool;

co-register the pair of interventional X-ray images and the guiding X-ray image based on the illustration of the guiding X-ray calibration device in the pair of interventional X-ray images and in the guiding X-ray image;

derive a guidance tool trajectory overlay from the simulated tool axis based on a co-registration of the pair of interventional X-ray images and the guiding X-ray image; and control a display of the guidance tool trajectory overlay onto the guiding X-ray image.

4. The X-ray imaging system of claim 3, wherein the X-ray overlay controller being configured to generate the simulated tool axis includes the X-ray overlay controller configured to:

segment the interventional tool as illustrated in the pair of interventional X-ray images;

calculate a pair of intersecting virtual planar X-ray projections based on a delineation of at least two points on a segmentation of the interventional tool as illustrated in the pair of interventional X-ray images; and delineate the simulated tool axis within the X-ray imaging space of the C-arm from an intersection of the pair of intersecting virtual planar X-ray projections.

5. The X-ray imaging system of claim 3, wherein the X-ray overlay controller is further configured in the guiding overlay display mode to:

control a display of a tracked tool position overlay onto the guiding X-ray image based on a tracking of the interventional tool within the X-ray imaging space of the C-arm.

6. An X-ray overlay controller, comprising:

at least one processor operable in a planning overlay display mode; and a non-transitory machine-readable storage medium encoded in the planning overlay display mode with instructions executable by the at least one processor to:

process a planning X-ray image acquired by the C-arm at a planning X-ray imaging pose of the C-arm, the planning X-ray image being illustrative of a planning X-ray calibration device and non-illustrative of an interventional tool;

process a reference planning X-ray image acquired by the C-arm at a reference X-ray imaging pose of the C-arm, the reference planning X-ray image being illustrative of the planning X-ray calibration device and non-illustrative of the interventional tool;

compute a rigid body transformation between the C-arm at the planning X-ray imaging pose and the C-arm at the reference X-ray imaging pose based on the illustrations of the planning X-ray calibration device in the planning X-ray image and in the reference planning X-ray image;

process a base X-ray image acquired by the C-arm at the reference X-ray imaging pose of the C-arm, the base X-ray image being illustrative of a base X-ray calibration device and non-illustrative of the interventional tool, the base X-ray calibration device being registered to a tool guide;

compute a rigid body transformation between the C-arm at the planning X-ray imaging pose and a tool guide based on a computation of the rigid body transformation between the C-arm at the planning X-ray imaging pose and the C-arm at the reference X-ray imaging pose and further based on the registration of the base X-ray calibration device to the tool guide; and control a display of a planned tool trajectory overlay onto the planning X-ray image based on a computation of the rigid body transformation between the C-arm at the planning X-ray imaging pose and a tool guide.

7. The X-ray overlay controller of claim 6, wherein the non-transitory machine-readable storage medium is further encoded in the planning overlay display mode with instructions executable by the at least one processor to:

process a tracking X-ray image acquired by the C-arm at the reference X-ray imaging pose of the C-arm, the tracking X-ray image being illustrative of the base X-ray calibration device and illustrative of the interventional tool; and control a display of a tracked tool position overlay onto the planning X-ray image based on a computation of the rigid body transformation between the C-arm at the planning X-ray imaging pose and a tool guide and the illustration of the interventional tool in the tracking X-ray image.

8. The X-ray overlay controller of claim 6,
wherein the at least one processor is further operable in a guiding overlay display mode; and
wherein the non-transitory machine-readable storage medium is further encoded in the guiding overlay display mode with instructions executable by the at least one processor to:
process a pair of interventional X-ray images acquired by the C-arm at different interventional X-ray imaging poses of the C-arm, each interventional X-ray image being illustrative of a guiding X-ray calibration device and illustrative of the interventional tool;
co-register the pair of interventional X-ray images based on the illustration of the guiding X-ray calibration device in the pair of interventional X-ray images;
generate a simulated tool axis positioned within an X-ray imaging space of the C-arm based on a co-registration of the pair of interventional X-ray images;
process a guiding X-ray image acquired by the C-arm at a guiding X-ray imaging pose of the C-arm, the guiding X-ray image being illustrative of the guiding X-ray calibration device and non-illustrative of the interventional tool;
co-register the pair of interventional X-ray images and the guiding X-ray image based on the illustration of the guiding X-ray calibration device in the pair of interventional X-ray images and in the guiding X-ray image;
derive a guidance tool trajectory overlay from the simulated tool axis based on a co-registration of the pair of interventional X-ray images and the guiding X-ray image; and
control a display of the guidance tool trajectory overlay onto the guiding X-ray image.

9. The X-ray overlay controller of claim 8, wherein the non-transitory machine-readable storage medium being further encoded with instructions executable by the at least one processor to generate the simulated tool axis includes instructions:
segment the interventional tool as illustrated in the pair of interventional X-ray images;
calculate a pair of intersecting virtual planar X-ray projections based on a delineation of at least two points on a segmentation of the interventional tool as illustrated in the pair of interventional X-ray images; and
delineate the simulated tool axis within the X-ray imaging space of the C-arm from an intersection of the pair of intersecting virtual planar X-ray projections.

10. The X-ray overlay controller of claim 6, wherein the non-transitory machine-readable storage medium is further encoded in the guiding overlay display mode with instructions executable by the at least one processor to:
control a display of a tracked tool position overlay onto the guiding X-ray image based on a tracking of the interventional tool within the X-ray imaging space of the C-arm.

11. An X-ray overlay display method, comprising:
executing, by an X-ray overlay controller, a planning overlay display mode including:
processing, by the X-ray overlay controller, a planning X-ray image acquired by the C-arm at a planning X-ray imaging pose of the C-arm, the planning X-ray image being illustrative of a planning X-ray calibration device and non-illustrative of an interventional tool;
processing, by the X-ray overlay controller, reference planning X-ray image acquired by the C-arm at a reference X-ray imaging pose of the C-arm, the reference planning X-ray image being illustrative of the planning X-ray calibration device and non-illustrative of the interventional tool;
computing, by the X-ray overlay controller, a rigid body transformation between the C-arm at the planning X-ray imaging pose and the C-arm at the reference X-ray imaging pose based on the illustrations of the planning X-ray calibration device in the planning X-ray image and in the reference planning X-ray image;
processing, by the X-ray overlay controller, a base X-ray image acquired by the C-arm at the reference X-ray imaging pose of the C-arm, the planning X-ray image being illustrative of a base X-ray calibration device and non-illustrative of the interventional tool, the base X-ray calibration device being registered to a tool guide;
computing, by the X-ray overlay controller, a rigid body transformation between the C-arm at the planning X-ray imaging pose and a tool guide based on a computation of the rigid body transformation between the C-arm at the planning X-ray imaging pose and the C-arm at the reference X-ray imaging pose and further based on the registration of the base X-ray calibration device to the tool guide; and
controlling, by the X-ray overlay controller, a display of a planned tool trajectory overlay onto the planning X-ray image based on a computation of the rigid body transformation between the C-arm at the planning X-ray imaging pose and a tool guide.

12. The X-ray overlay display method of claim 11, wherein the executing, by the X-ray overlay controller, of the planning overlay display mode further includes:
processing, by the X-ray overlay controller, a tracking X-ray image acquired by the C-arm at the reference X-ray imaging pose of the C-arm, the tracking X-ray image being illustrative of the base X-ray calibration device and illustrative of the interventional tool; and
controlling, by the X-ray overlay controller, a display of a tracked tool position overlay onto the planning X-ray image based on a computation of the rigid body transformation between the C-arm at the planning X-ray imaging pose and a tool guide and the illustration of the interventional tool in the tracking X-ray image.

13. The X-ray overlay display method of claim 11, further comprising:
executing, by the X-ray overlay controller, a guiding overlay display mode including:
processing, by the X-ray overlay controller, a pair of interventional X-ray images acquired by the C-arm at different interventional X-ray imaging poses of the C-arm, each interventional X-ray image being illustrative of a guiding X-ray calibration device and illustrative of the interventional tool;

co-registering, by the X-ray overlay controller, the pair of interventional X-ray images based on the illustration of the guiding X-ray calibration device in the pair of interventional X-ray images;

generating, by the X-ray overlay controller, a simulated tool axis positioned within an X-ray imaging space of the C-arm based on a co-registration of the pair of interventional X-ray images;

processing, by the X-ray overlay controller, a guiding X-ray image acquired by the C-arm at a guiding X-ray imaging pose of the C-arm, the guiding X-ray image being illustrative of the guiding X-ray calibration device and non-illustrative of the interventional tool;

co-registering, by the X-ray overlay controller, the pair of interventional X-ray images and the guiding X-ray image based on the illustration of the guiding X-ray calibration device in the pair of interventional X-ray images and in the guiding X-ray image;

deriving, by the X-ray overlay controller, a guidance took trajectory overlay from the simulated tool axis based on a co-registration of the pair of interventional X-ray images and the guiding X-ray image; and controlling, by the X-ray overlay controller, a display of the guidance took trajectory overlay onto the guiding X-ray image.

14. The X-ray overlay display method of claim 13, wherein the generating, by the X-ray overlay controller, of the simulated tool axis includes:

segmenting, by the X-ray overlay controller, the interventional tool as illustrated in the pair of interventional X-ray images;

calculating, by the X-ray overlay controller, a pair of intersecting virtual planar X-ray projections based on a delineation of at least two points on a segmentation of the interventional tool as illustrated in the pair of interventional X-ray images; and delineating, by the X-ray overlay controller, the simulated tool axis within the X-ray imaging space of the C-arm from an intersection of the pair of intersecting virtual planar X-ray projections.

15. The X-ray overlay display method of claim 11, wherein the executing, by the X-ray overlay controller, of the guiding overlay display mode further includes:

controlling, by the X-ray overlay controller, a display of a tracked tool position overlay onto the guiding X-ray image based on a tracking of the interventional tool within the X-ray imaging space of the C-arm.

* * * * *